(12) United States Patent
Pfizenmaier et al.

(10) Patent No.: US 10,570,206 B2
(45) Date of Patent: Feb. 25, 2020

(54) RECOMBINANT TNF LIGAND FAMILY MEMBER POLYPEPTIDES WITH ANTIBODY BINDING DOMAIN AND USES THEREOF

(71) Applicant: UNIVERSITAT STUTTGART, Stuttgart (DE)

(72) Inventors: Klaus Pfizenmaier, Tiefenbronn (DE); Roland Kontermann, Nurtingen (DE); Martin Siegemund, Stuttgart (DE)

(73) Assignee: UNIVERSITAT STUTTGART, Stuttgart (DE)

( * ) Notice: Subject to any disclaimer, the term of this patent is extended or adjusted under 35 U.S.C. 154(b) by 0 days.

(21) Appl. No.: 15/797,059

(22) Filed: Oct. 30, 2017

(65) Prior Publication Data

US 2018/0072807 A1    Mar. 15, 2018

Related U.S. Application Data

(63) Continuation of application No. 14/009,186, filed as application No. PCT/EP2012/001426 on Mar. 30, 2012, now Pat. No. 9,822,179.

(30) Foreign Application Priority Data

Apr. 1, 2011    (EP) .................... 11002745

(51) Int. Cl.

| | |
|---|---|
| *C07K 14/525* | (2006.01) |
| *C07K 16/28* | (2006.01) |
| *C07K 16/30* | (2006.01) |
| *C07K 19/00* | (2006.01) |
| *A61K 38/19* | (2006.01) |
| *A61K 39/395* | (2006.01) |
| *C07K 14/705* | (2006.01) |
| *A61K 39/00* | (2006.01) |

(52) U.S. Cl.
CPC ........ *C07K 16/2863* (2013.01); *A61K 38/191* (2013.01); *A61K 39/3955* (2013.01); *C07K 14/525* (2013.01); *C07K 14/70575* (2013.01); *C07K 16/28* (2013.01); *C07K 19/00* (2013.01); *A61K 39/001102* (2018.08); *A61K 2039/505* (2013.01); *C07K 16/30* (2013.01); *C07K 2317/34* (2013.01); *C07K 2317/56* (2013.01); *C07K 2317/622* (2013.01); *C07K 2317/73* (2013.01); *C07K 2317/76* (2013.01); *C07K 2317/92* (2013.01); *C07K 2319/00* (2013.01); *C07K 2319/31* (2013.01); *C07K 2319/33* (2013.01); *C07K 2319/43* (2013.01); *C07K 2319/74* (2013.01)

(58) Field of Classification Search
CPC .............. C07K 16/00; C07K 2317/622; C07K 2319/00; C07K 14/525; C07K 2317/56; C07K 14/52; C07K 2317/569; C07K 16/18; C07K 16/28; C07K 16/30; C07K 2319/30; A61K 39/3955; A61K 2039/505; A61K 38/191; A61K 39/39558; A61K 38/19

See application file for complete search history.

(56) References Cited

U.S. PATENT DOCUMENTS

| | | |
|---|---|---|
| 4,588,585 A | 5/1986 | Mark et al. |
| 4,737,462 A | 4/1988 | Mark et al. |
| 4,879,111 A | 11/1989 | Chong |
| 4,959,314 A | 9/1990 | Mark et al. |
| 5,017,691 A | 5/1991 | Lee et al. |
| 5,116,943 A | 5/1992 | Koths et al. |
| 6,730,303 B1 | 5/2004 | Feng et al. |
| 8,927,205 B2 | 1/2015 | Pfizenmaier et al. |
| 2003/0069395 A1 | 4/2003 | Sato et al. |
| 2005/0152872 A1* | 7/2005 | Gaide .............. C07K 14/70578 424/85.1 |
| 2007/0286843 A1 | 12/2007 | Pfizenmaier et al. |
| 2011/0162095 A1* | 6/2011 | Hill ...................... C07K 14/525 800/13 |
| 2012/0134984 A1 | 5/2012 | Lubman et al. |

FOREIGN PATENT DOCUMENTS

| | | |
|---|---|---|
| DE | 102 47 755 | 4/2004 |
| DE | 10 2004 014983 | 10/2005 |
| WO | 2001/025277 | 4/2001 |

(Continued)

OTHER PUBLICATIONS

Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*
Genbank Accession No. NM_00311, www.ncbi.nlm.nih.gov/nuccore/NM_003811.1; Aug. 9, 2001.*

(Continued)

*Primary Examiner* — Bridget E Bunner
(74) *Attorney, Agent, or Firm* — McDonnell Boehnen Hulbert & Berghoff LLP

(57) ABSTRACT

The present invention relates in general to the field of TNF ligand family members. In more detail the present invention relates to polypeptides comprising at least three components A, each of which comprises the sequence of a TNF homology domain (THD) of a TNF ligand family member, or a functional derivative thereof, and comprising at least one component B consisting of a $V_L$ region and a $V_H$ region linked directly to each other with a linker sequence L which has a length of <12 amino acids. Furthermore, the present invention also relates to nucleic acids encoding such polypeptides and pharmaceutical compositions thereof.

18 Claims, 43 Drawing Sheets

Figure 1:
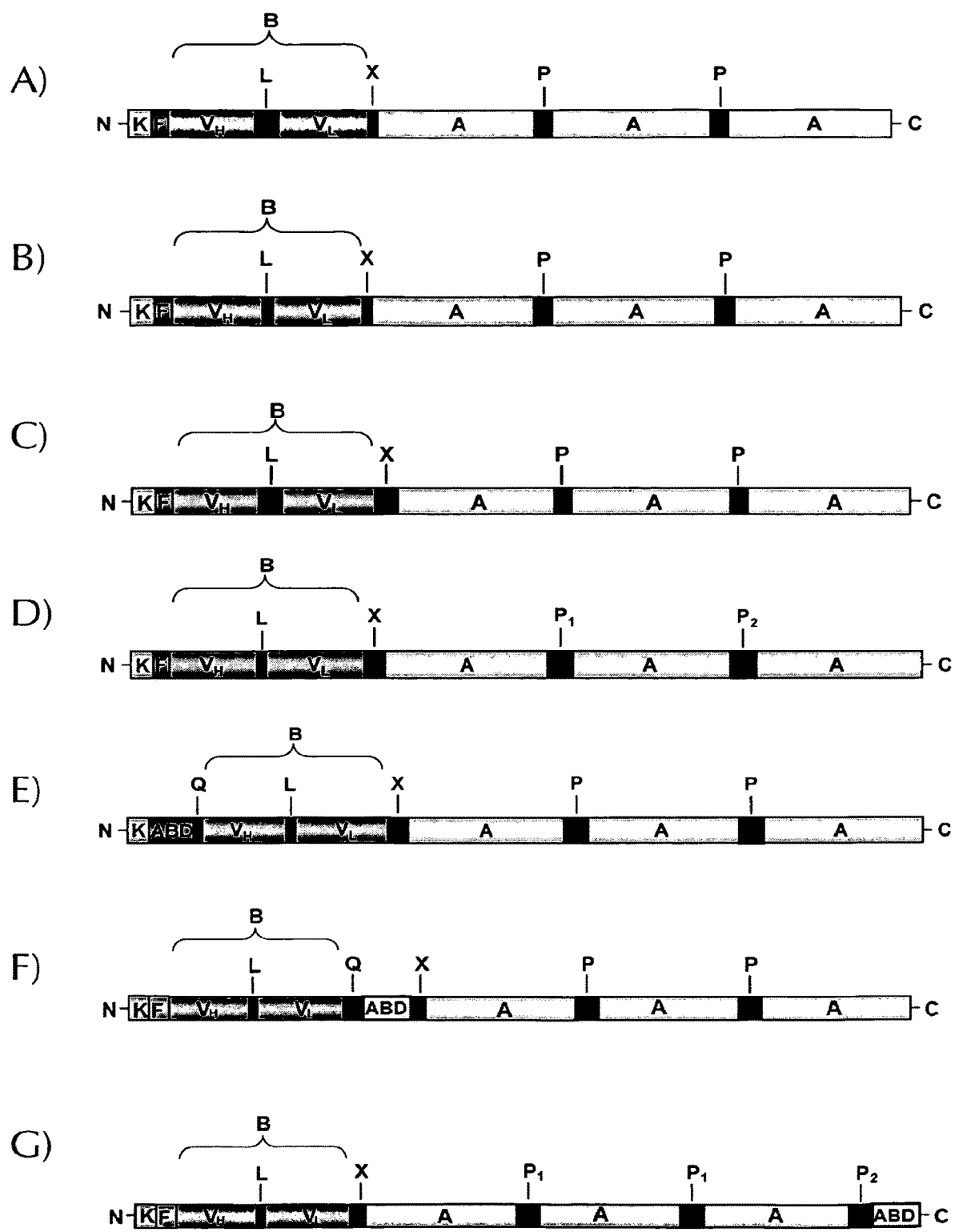

Specification includes a Sequence Listing.

(56) References Cited

FOREIGN PATENT DOCUMENTS

| WO | 2002/022680 | | 3/2002 |
|---|---|---|---|
| WO | 2005/103077 | | 11/2005 |
| WO | 2006/115800 | | 11/2006 |
| WO | 2007/014744 | | 2/2007 |
| WO | 2010/051502 | | 5/2010 |
| WO | WO-2011109789 | A2 * | 9/2011 |

OTHER PUBLICATIONS

Muller et al. A novel antibody-4-1BBL fusion protein for targeted costimulation in cancer immunotherapy. J Immunother 31: 714-722, 2008.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*
Zhang et al. Targeted and untargeted CD137L fusion proteins for the immunotherapy of experimental solid tumors. Clin Cancer Res 13(9): 2758-2767, 2007.*
Kortt, et al. (2001) "Dimeric and trimeric antibodies: high avidity scFvs for cancer targeting," Biomolecular Engineering, 18(3):95-108.
Wajant, et al. (2005) "Tumor therapeutics by design: targeting and activation of death receptors," Cytokine and Growth Factor Reviews, 16(1):55-76.
Wyzgol, et al. (2009) "Trimer stabilization, oligomerization, and antibody-mediated cell surface immobliization improve the activity of soluble trimers of CD27L, CD40L, 41BBL, and glucocorticoid-induced TNF receptor ligand," The Journal of Immunology, 183(3): 1851-1861.
Muller, et al., (2008) "activity of soluble OX40 ligand is enhanced by oligomerization and cell surface immobilization," FEBS Journal, 275(9): 2296-2304.
Schneider, et al. (2010) "Potent antitumoral activity of TRAIL trhough generation of tumor-targeted single-chain fusion proteins," Cell Death and Disease, 1(8): E68.
Cuesta, et al. (2010) "Multivalent antibodies: when design surpasses evolution" Trends in Biotechnology, 28(7): 355-362.
International Search Report for PCT/EP2012/001426, dated Jul. 18, 2012.
Bodmer et al. (2002) "The molecular architecture of the TNF superfamily." Trends Biochem Sci, 27(1):19-26 (Jan. 2002).
Valliere-Douglass et al., (2010) "Glutamine-linked and non-consensus asparagine-linked oligosaccharides present in human recombinant antibodies define novel protein glycosylation motifs." J Biol Chem. 285(21):16012-22 (Epub Mar. 16, 2010).
Fibroblast activation protein alpha, in MeSH Database, National Center for Biotechnology Information, Bethesda, Maryland, USA [online], [retrieved on Mar. 2, 2016]. (Date introduced: Jul. 1, 1994). One page. Retrieved from the Internet: <URL: http://www.ncbi.nlm.nih.gov/mesh/67087522>.

* cited by examiner

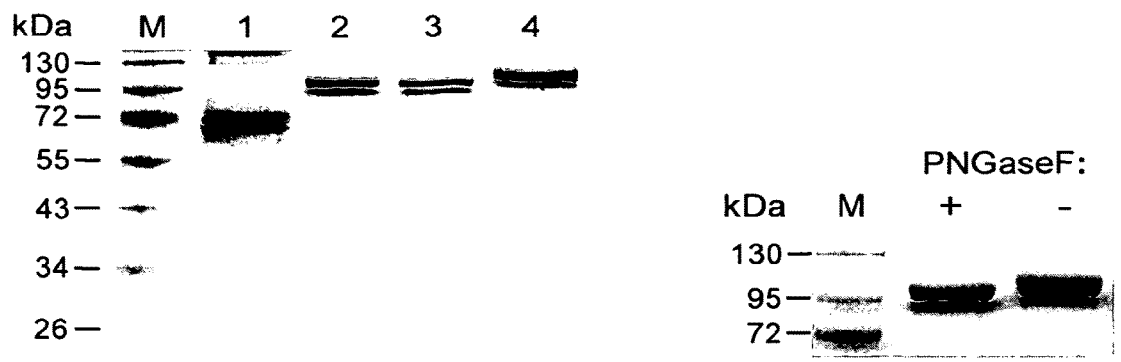
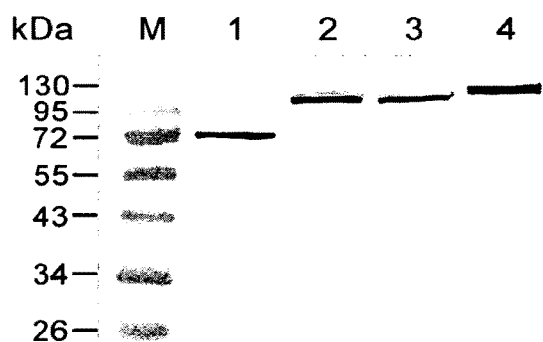
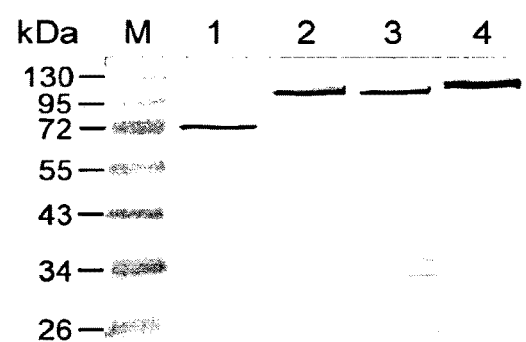
Fig.2

A
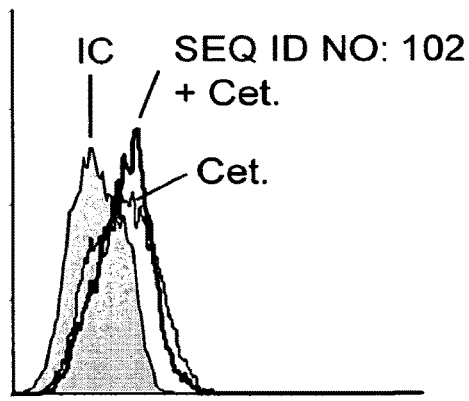
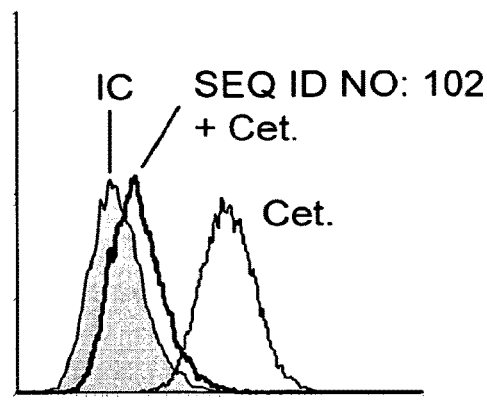
B
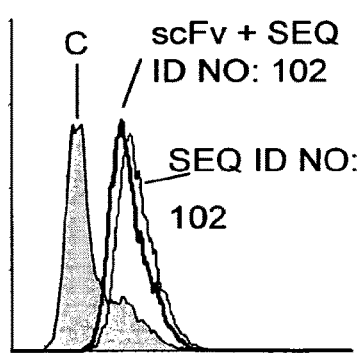
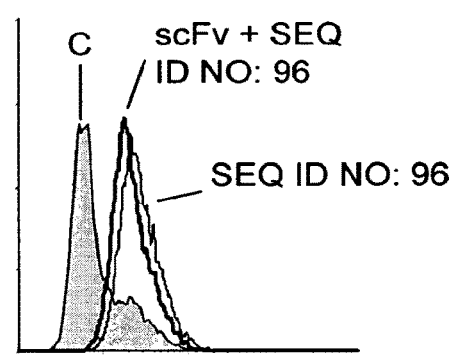
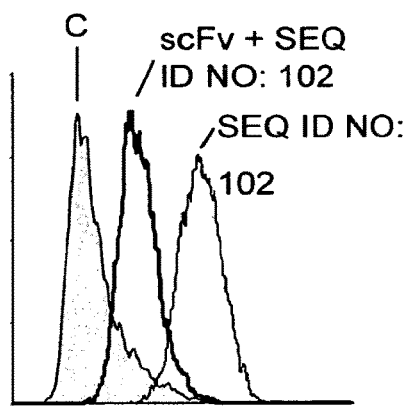
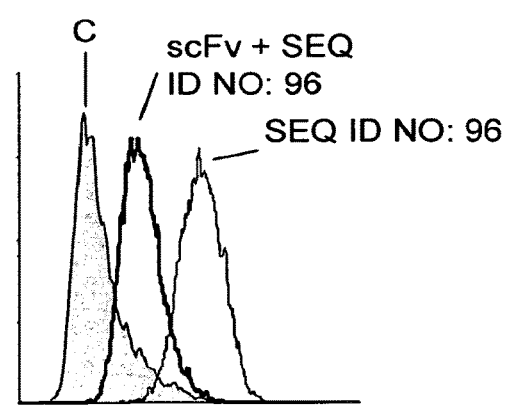
Fig.5

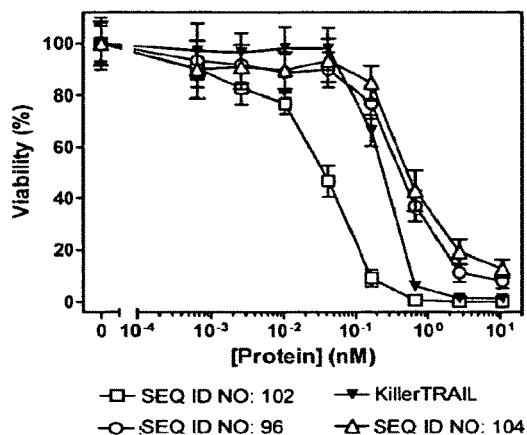
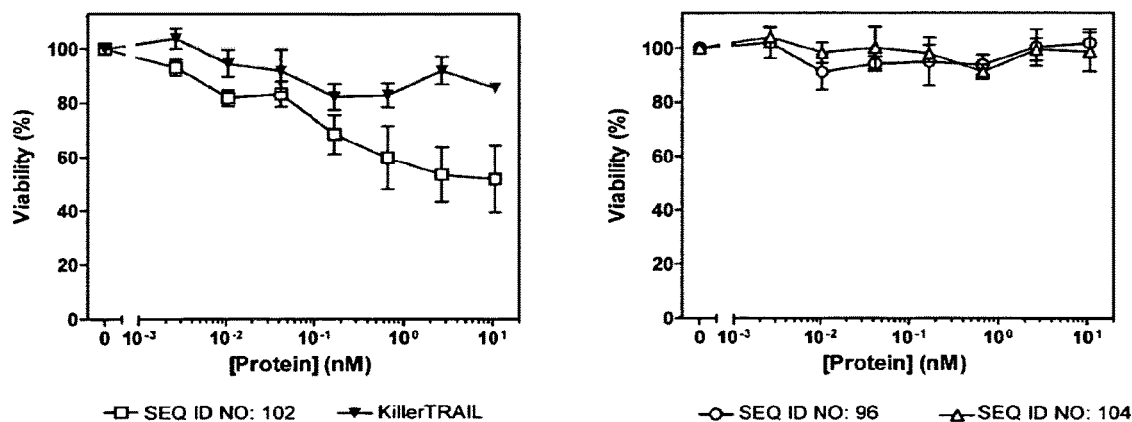
Fig.6

Fig.7
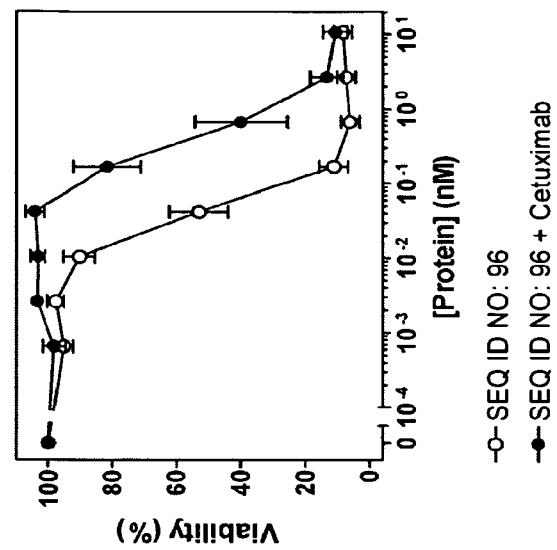
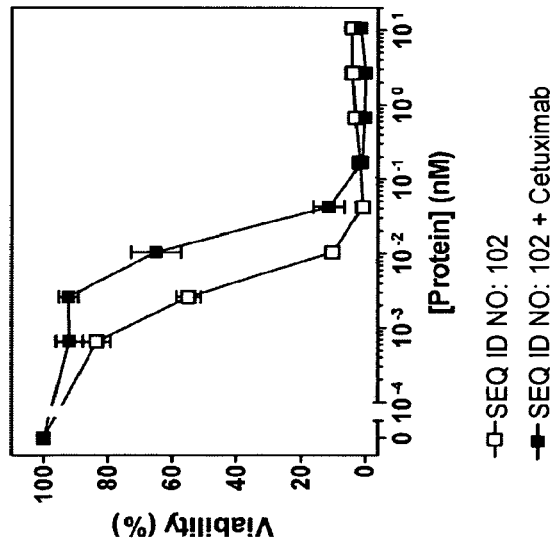
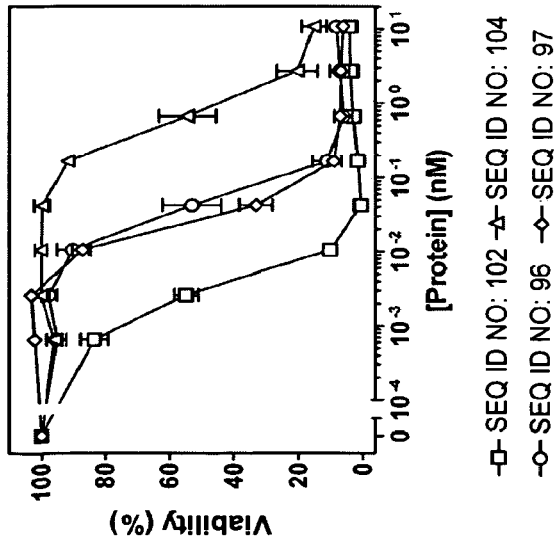

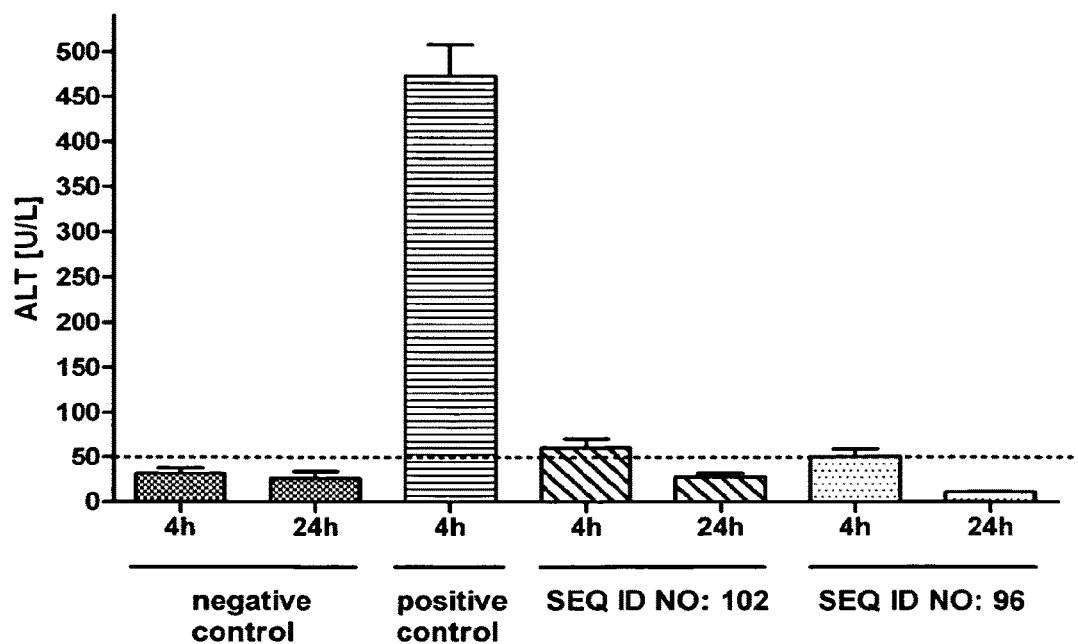
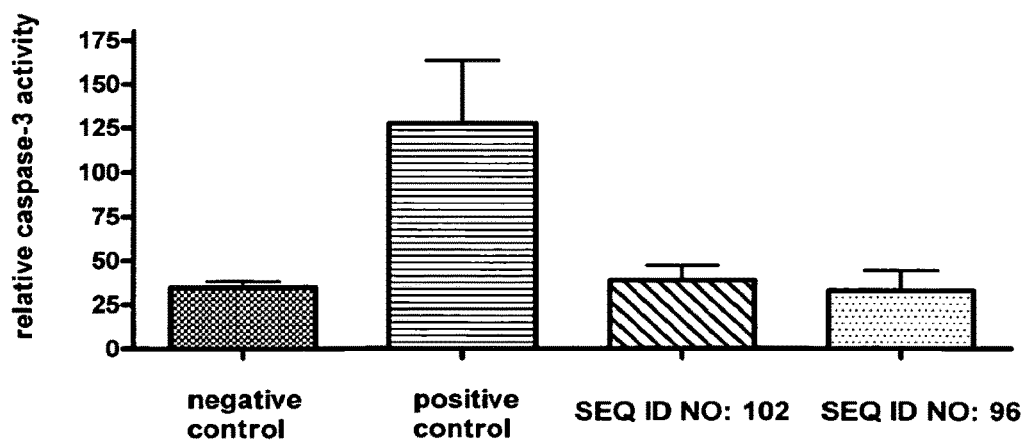
Fig.9

A
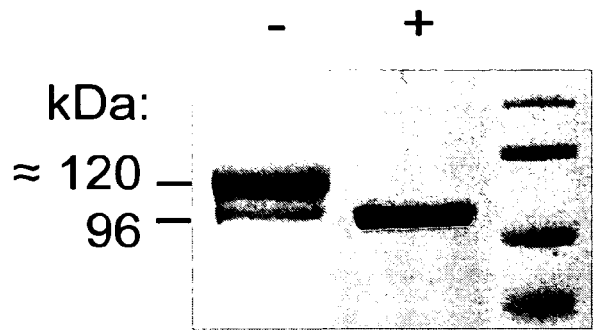
B
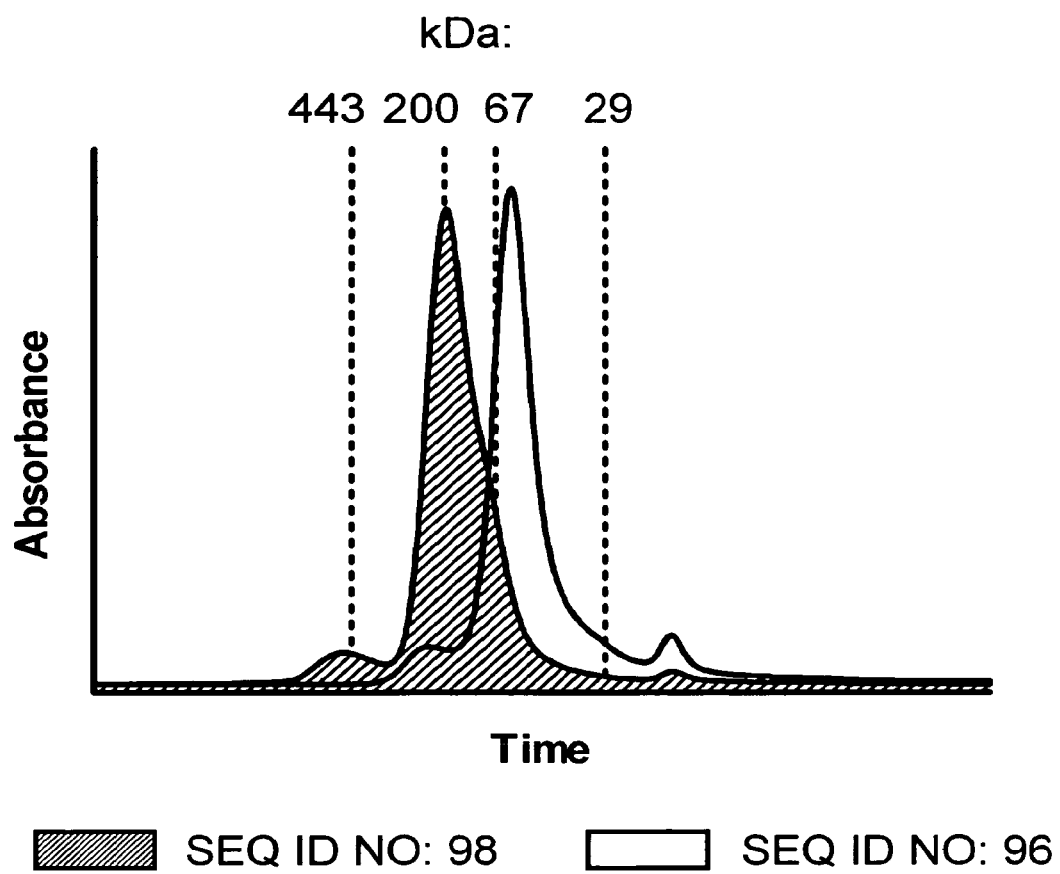
Fig.11

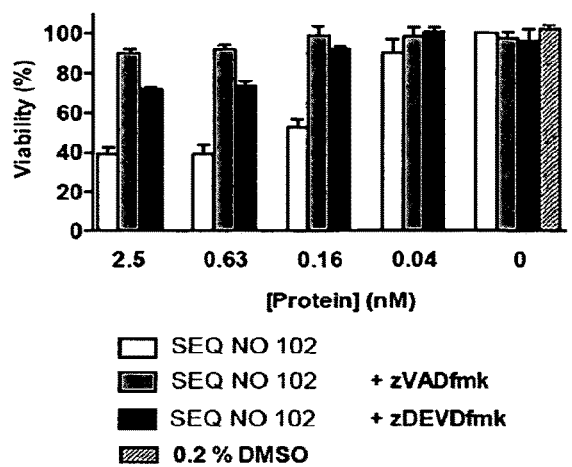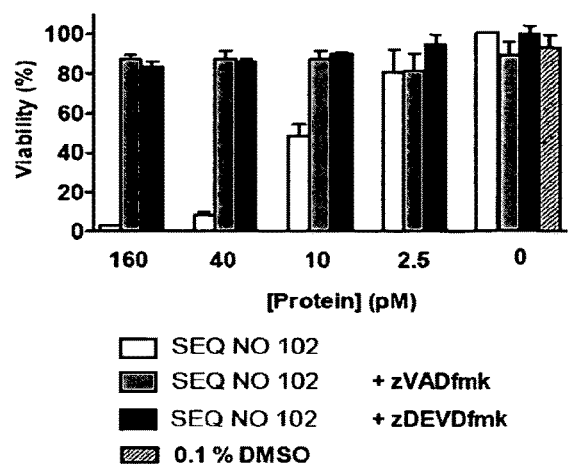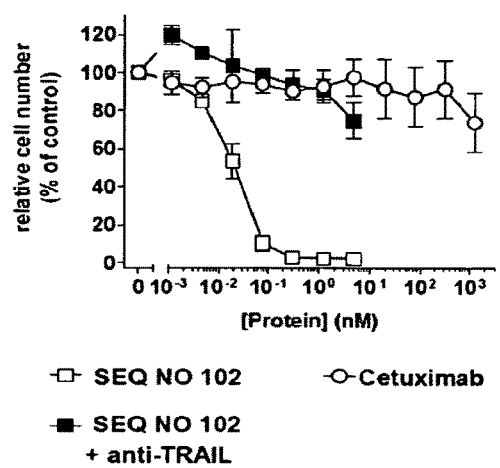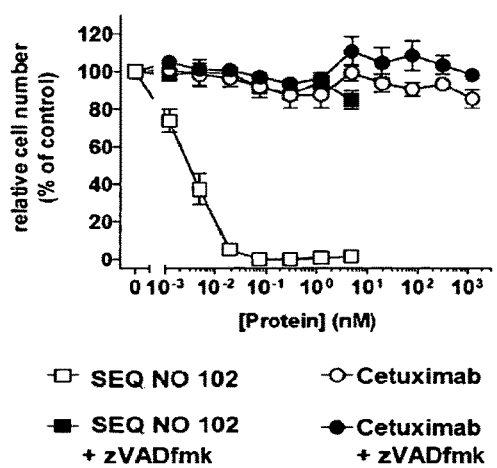
Fig.13

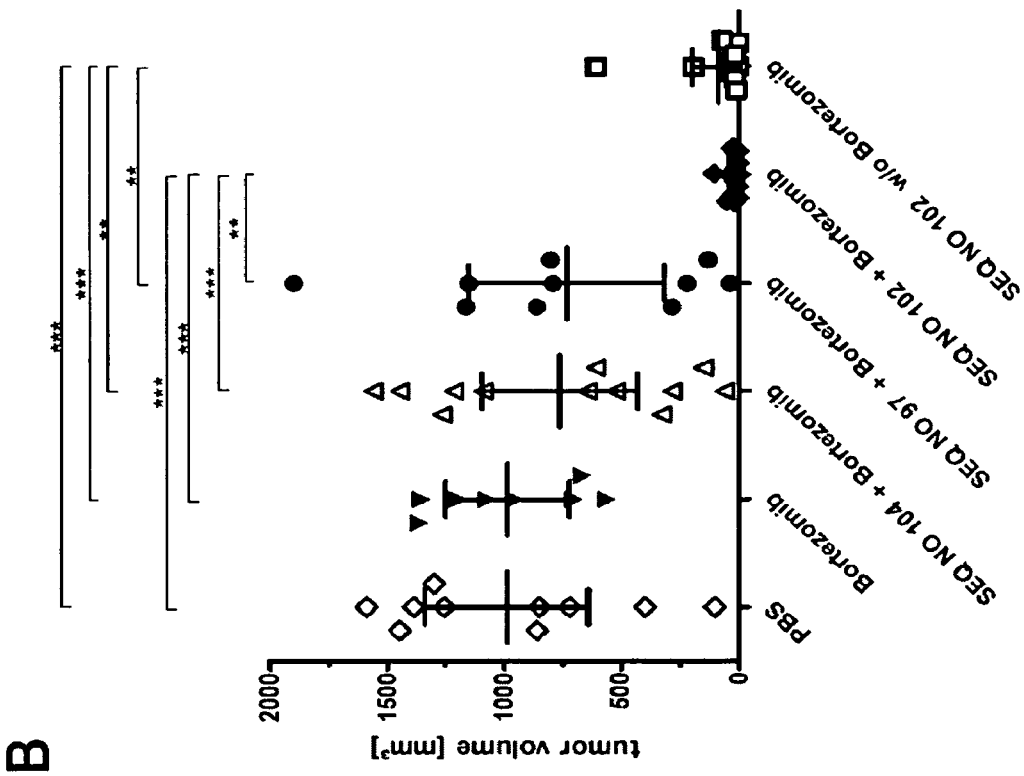
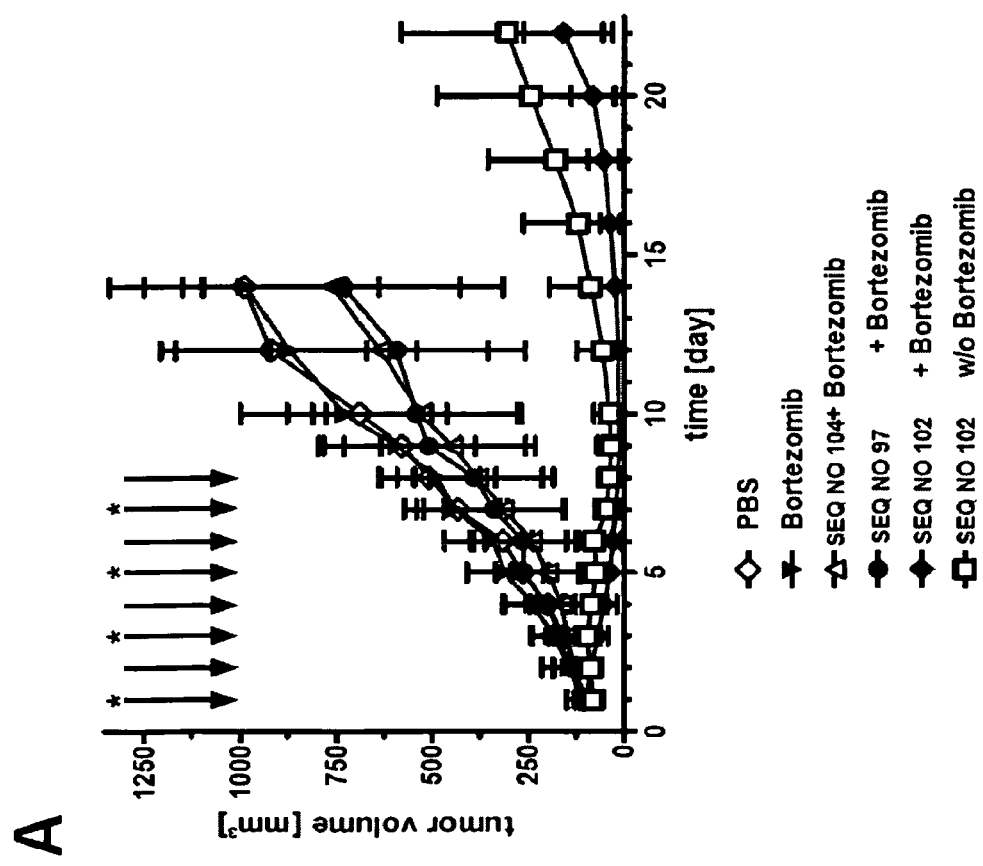
Fig. 15

1) SEQ ID NO. 102
2) SEQ ID NO. 125
3) SEQ ID NO. 126

Fig. 17
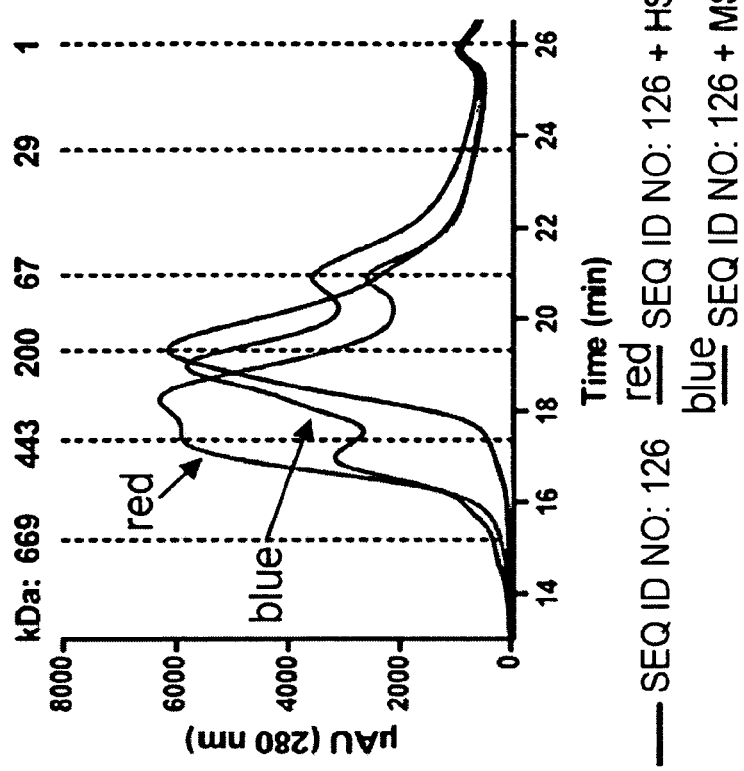
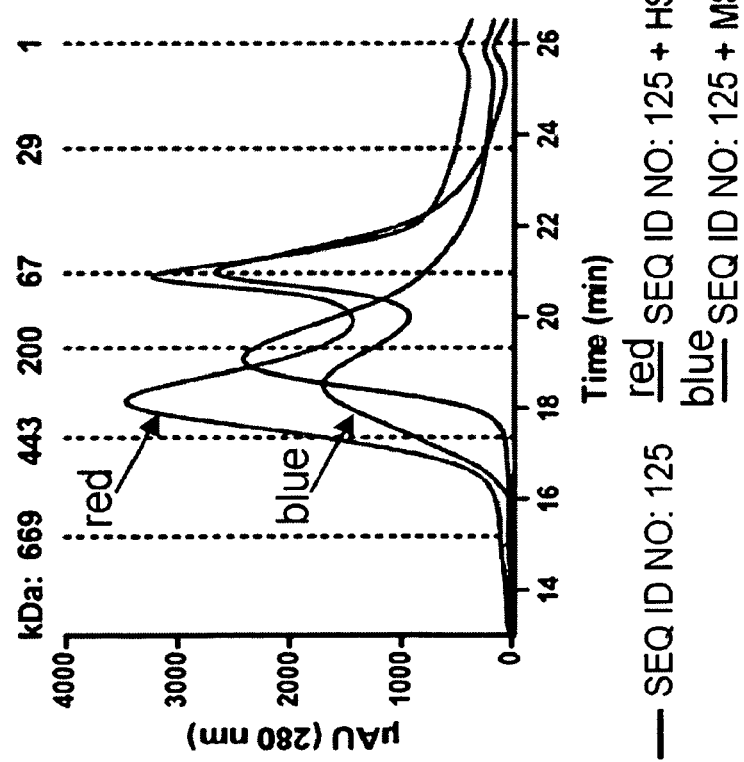

A
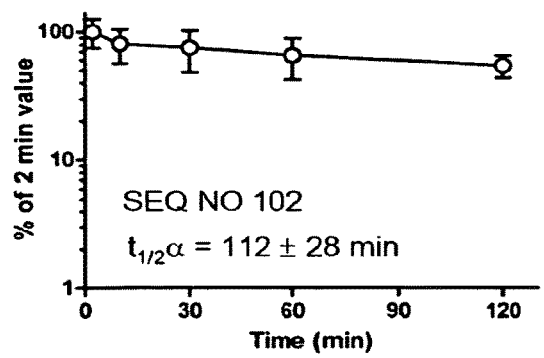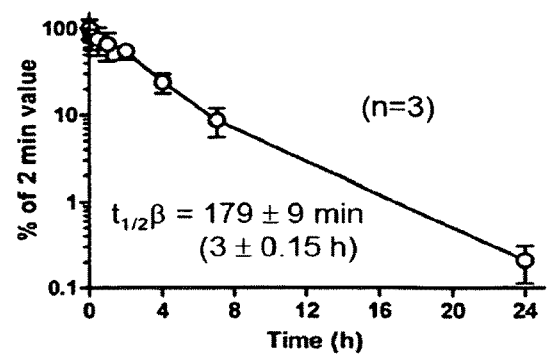
B
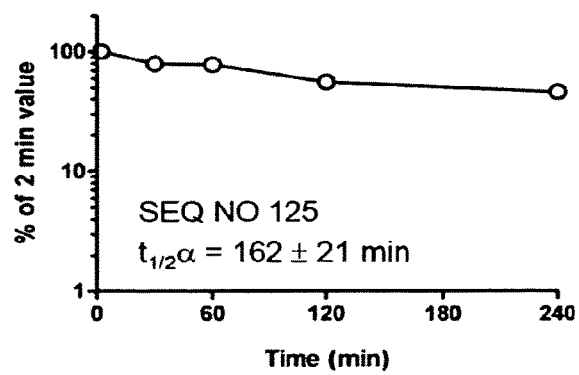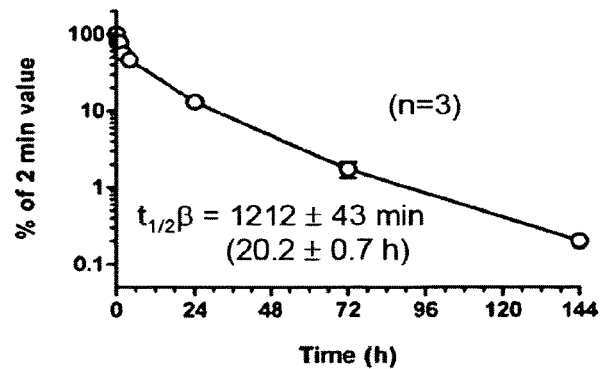
Fig.19

Leader: aa res. 1-19
FLAG tag with linkers: 20-33
VH: 34-152
Linker: 153-167
VL: 168-275
Linker: 276-283
TRAIL: 284-470
Linker: 471-478
TRAIL: 479-665
Linker: 666-673
TRAIL: 674-860

```
  1  atg gac tgg acc tgg cgc gtg ttt tgc ctg ctc gcc gtg gct cct ggg gcc cac
  1   M   D   W   T   W   R   V   F   C   L   L   A   V   A   P   G   A   H 55  agc ctc gag gcc agc gac tac aaa gac gat gac gat aaa gga gcc gag gtg cag
 19   S   L   E   A   S   D   Y   K   D   D   D   D   K   G   A   E   V   Q 109  ctg gtc gag tct ggc ggc gga ctg gtg cag cct ggc ggc tcc ctg aga ctg tct
 37   L   V   E   S   G   G   G   L   V   Q   P   G   G   S   L   R   L   S 163  tgc gct gcc tcc ggc ttc tcc ctg acc aac tac ggc gtg cac tgg gtc cgg cag
 55   C   A   A   S   G   F   S   L   T   N   Y   G   V   H   W   V   R   Q 217  gct ccc ggc aag gga ctg gaa tgg ctg ggc gtg att tgg tcc ggc ggc aac acc
 73   A   P   G   K   G   L   E   W   L   G   V   I   W   S   G   G   N   T 271  gac tac aac acc cct ttc acc tcc cgg ttc acc atc tcc cgg gac aac tcc aag
 91   D   Y   N   T   P   F   T   S   R   F   T   I   S   R   D   N   S   K 325  aac acc ctg tac ctg cag atg aac tcc ctg cgg gcc gag gac acc gcc gtg tac
109   N   T   L   Y   L   Q   M   N   S   L   R   A   E   D   T   A   V   Y 379  tac tgc gcc agg gct ctg acc tac tac gac tac gag ttc gcc tac tgg ggc cag
127   Y   C   A   R   A   L   T   Y   Y   D   Y   E   F   A   Y   W   G   Q 433  ggc acc aca gtg acc gtg tct agt ggc ggt ggc ggc tct ggt ggc gga gga agt
145   G   T   T   V   T   V   S   S   G   G   G   G   S   G   G   G   G   S 487  ggc gga ggg ggc tcc gat att cag ctg acc cag tcc ccc tcc ttc ctg tcc gcc
163   G   G   G   G   S   D   I   Q   L   T   Q   S   P   S   F   L   S   A 541  tcc gtg ggc gac aga gtg acc atc acc tgc cgg gcc tcc cag tcc atc ggc acc
181   S   V   G   D   R   V   T   I   T   C   R   A   S   Q   S   I   G   T 595  aac atc cac tgg tat cag cag aag cct ggc aag gcc cct aag ctg ctg atc aag
199   N   I   H   W   Y   Q   Q   K   P   G   K   A   P   K   L   L   I   K 649  tac gcc tcc gag tct atc tcc ggc gtg cct tcc cgg ttc tcc ggc tcc ggc tct
217   Y   A   S   E   S   I   S   G   V   P   S   R   F   S   G   S   G   S 703  gga acc gag ttc acc ctg acc atc tcc agc ctg cag cct gag gac ttc gcc acc
235   G   T   E   F   T   L   T   I   S   S   L   Q   P   E   D   F   A   T 757  tac tac tgc cag cag aac aac aac tgg cct acc acc ttc ggc gct ggc acc aag
253   Y   Y   C   Q   Q   N   N   N   W   P   T   T   F   G   A   G   T   K 811  ctg gaa atc aag aga gcg gcc gca gaa ttc acg cgt ggc acc agc gag gaa acc
271   L   E   I   K   R   A   A   A   E   F   T   R   G   T   S   E   E   T
```

Fig. 20A

```
865  att agc acc gtc cag gaa aag cag cag aac atc agc ccc ctg gtc cgg gag aga
289   I   S   T   V   Q   E   K   Q   Q   N   I   S   P   L   V   R   E   R 919  ggc ccc cag aga gtc gcc gcc cac atc acc ggc acc cgg ggc aga agc aac acc
307   G   P   Q   R   V   A   A   H   I   T   G   T   R   G   R   S   N   T 973  ctg agc agc ccc aac agc aag aac gag aag gcc ctg ggc cgg aag atc aac agc
325   L   S   S   P   N   S   K   N   E   K   A   L   G   R   K   I   N   S 1027 tgg gag agc agc aga agc ggc cac agc ttt ctg agc aac ctg cac ctg cgg aac
343   W   E   S   S   R   S   G   H   S   F   L   S   N   L   H   L   R   N 1081 ggc gag ctg gtc atc cac gag aag ggc ttc tac tac atc tac agc cag acc tac
361   G   E   L   V   I   H   E   K   G   F   Y   Y   I   Y   S   Q   T   Y 1135 ttc aga ttc caa gaa gag atc aaa gag aac acc aag aac gac aag cag atg gtg
379   F   R   F   Q   E   E   I   K   E   N   T   K   N   D   K   Q   M   V 1189 cag tac atc tac aag tac acc agc tac ccc gac ccc atc ctg ctg atg aag tcc
397   Q   Y   I   Y   K   Y   T   S   Y   P   D   P   I   L   L   M   K   S 1243 gcc cgg aac agc tgc tgg tcc aag gac gcc gag tac ggc ctg tac agc atc tac
415   A   R   N   S   C   W   S   K   D   A   E   Y   G   L   Y   S   I   Y 1297 cag ggc ggc atc ttc gag ctg aaa gag aac gac cgg atc ttc gtg agc gtg acc
433   Q   G   G   I   F   E   L   K   E   N   D   R   I   F   V   S   V   T 1351 aac gag cac ctg atc gac atg gac cac gag gcc agc ttt ttc ggc gca ttc ctg
451   N   E   H   L   I   D   M   D   H   E   A   S   F   F   G   A   F   L 1405 gtc ggc gga ggg gga tcc ggc gga gga agc acc tcc gaa gag act atc tct aca
469   V   G   G   G   G   S   G   G   G   S   T   S   E   E   T   I   S   T 1459 gtc cag gaa aaa cag cag aat atc tcc cct ctc gtg cgg gag cgg gga cct cag
487   V   Q   E   K   Q   Q   N   I   S   P   L   V   R   E   R   G   P   Q 1513 cgg gtg gcc gcc cat att aca ggc aca aga ggc cgg tcc aac acc ctg tcc tcc
505   R   V   A   A   H   I   T   G   T   R   G   R   S   N   T   L   S   S 1567 ccc aac tct aag aat gaa aag gcc ctc ggg aga aag atc aac tcc tgg gag tcc
523   P   N   S   K   N   E   K   A   L   G   R   K   I   N   S   W   E   S 1621 agc cgc tcc ggc cac tcc ttt ctg tcc aat ctg cac ctg aga aat ggg gag ctg
541   S   R   S   G   H   S   F   L   S   N   L   H   L   R   N   G   E   L 1675 gtc att cac gaa aag ggg ttt tac tat atc tac tct cag aca tac ttt agg ttt
559   V   I   H   E   K   G   F   Y   Y   I   Y   S   Q   T   Y   F   R   F 1729 cag gaa gaa att aaa gaa aat aca aag aat gat aaa cag atg gtc cag tat atc
577   Q   E   E   I   K   E   N   T   K   N   D   K   Q   M   V   Q   Y   I 1783 tat aaa tac act tcc tac cct gat cct att ctg ctg atg aaa agc gcc aga aac
595   Y   K   Y   T   S   Y   P   D   P   I   L   L   M   K   S   A   R   N 1837 agc tgt tgg agc aag gat gcc gaa tat ggg ctc tac tct atc tac cag ggg ggg
613   S   C   W   S   K   D   A   E   Y   G   L   Y   S   I   Y   Q   G   G 1891 att ttt gaa ctt aag gag aat gac aga atc ttt gtg tct gtg aca aat gag cat
631   I   F   E   L   K   E   N   D   R   I   F   V   S   V   T   N   E   H 1945 ctg att gat atg gat cac gaa gcc tca ttc ttt gga gcc ttt ctt gtg gga ggg
649   L   I   D   M   D   H   E   A   S   F   F   G   A   F   L   V   G   G
```

Fig. 20B

```
1999  ggc gga tct ggt ggc gga tcc acc tct gag gaa aca ata tcc acc gtc cag gag
 667   G   G   S   G   G   G   S   T   S   E   E   T   I   S   T   V   Q   E 2053  aag caa caa aac att tcc ccc ctc gtg cgc gaa cgg ggc cca cag agg gtc gcc
 685   K   Q   Q   N   I   S   P   L   V   R   E   R   G   P   Q   R   V   A 2107  gct cac att aca ggg acc agg ggc cgc agc aat acc ctg tcc agc ccg aac tcc
 703   A   H   I   T   G   T   R   G   R   S   N   T   L   S   S   P   N   S 2161  aaa aat gag aaa gcg ctg ggg cgg aag att aat tcc tgg gaa agc tcc aga agc
 721   K   N   E   K   A   L   G   R   K   I   N   S   W   E   S   S   R   S 2215  ggg cac tcc ttc ctc agc aat ctg cat ctg cgc aac ggg gaa ctc gtg att cat
 739   G   H   S   F   L   S   N   L   H   L   R   N   G   E   L   V   I   H 2269  gag aag gga ttc tat tat atc tat tcc cag aca tac ttc cgc ttc caa gag gaa
 757   E   K   G   F   Y   Y   I   Y   S   Q   T   Y   F   R   F   Q   E   E 2323  att aaa gag aac act aaa aac gat aaa caa atg gtt caa tac atc tac aaa tat
 775   I   K   E   N   T   K   N   D   K   Q   M   V   Q   Y   I   Y   K   Y 2377  acc tct tac cca gat ccc atc ctc ctc atg aag agt gcc aga aac tcc tgc tgg
 793   T   S   Y   P   D   P   I   L   L   M   K   S   A   R   N   S   C   W 2431  tct aag gat gcg gaa tac gga ttg tac tcc atc tat caa ggg gga atc ttt gag
 811   S   K   D   A   E   Y   G   L   Y   S   I   Y   Q   G   G   I   F   E 2485  ttg aaa gaa aat gat cgc att ttc gtg tcc gtc acg aat gag cac ctc ata gac
 829   L   K   E   N   D   R   I   F   V   S   V   T   N   E   H   L   I   D 2539  atg gat cat gaa gcg agt ttc ttc ggg gct ttc ctc gtg ggt tga
 847   M   D   H   E   A   S   F   F   G   A   F   L   V   G   -
```

Fig. 20C

Leader: aa res. 1-19
FLAG tag with linkers: 20-33
VH: 34-152
Linker: 153-157
VL: 158-265
Linker: 266-273
TRAIL: 274-460
Linker: 461-468
TRAIL: 469-655
Linker: 656-663
TRAIL: 664-850

```
  1  atg gac tgg acc tgg cgc gtg ttt tgc ctg ctc gcc gtg gct cct ggg gcc cac
  1   M   D   W   T   W   R   V   F   C   L   L   A   V   A   P   G   A   H 55  agc ctc gag gcc agc gac tac aaa gac gat gac gat aaa gga gcc gag gtg cag
 19   S   L   E   A   S   D   Y   K   D   D   D   D   K   G   A   E   V   Q 109  ctg gtc gag tct ggc ggc gga ctg gtg cag cct ggc ggc tcc ctg aga ctg tct
 37   L   V   E   S   G   G   G   L   V   Q   P   G   G   S   L   R   L   S 163  tgc gct gcc tcc ggc ttc tcc ctg acc aac tac ggc gtg cac tgg gtc cgg cag
 55   C   A   A   S   G   F   S   L   T   N   Y   G   V   H   W   V   R   Q 217  gct ccc ggc aag gga ctg gaa tgg ctg ggc gtg att tgg tcc ggc ggc aac acc
 73   A   P   G   K   G   L   E   W   L   G   V   I   W   S   G   G   N   T 271  gac tac aac acc cct ttc acc tcc cgg ttc acc atc tcc cgg gac aac tcc aag
 91   D   Y   N   T   P   F   T   S   R   F   T   I   S   R   D   N   S   K 325  aac acc ctg tac ctg cag atg aac tcc ctg cgg gcc gag gac acc gcc gtg tac
109   N   T   L   Y   L   Q   M   N   S   L   R   A   E   D   T   A   V   Y 379  tac tgc gcc agg gct ctg acc tac tac gac tac gag ttc gcc tac tgg ggc cag
127   Y   C   A   R   A   L   T   Y   Y   D   Y   E   F   A   Y   W   G   Q 433  ggc acc aca gtg acc gtg tct agt ggc ggt ggc ggc tct gat att cag ctg acc
145   G   T   T   V   T   V   S   S   G   G   G   G   S   D   I   Q   L   T 487  cag tcc ccc tcc ttc ctg tcc gcc tcc gtg ggc gac aga gtg acc atc acc tgc
163   Q   S   P   S   F   L   S   A   S   V   G   D   R   V   T   I   T   C 541  cgg gcc tcc cag tcc atc ggc acc aac atc cac tgg tat cag cag aag cct ggc
181   R   A   S   Q   S   I   G   T   N   I   H   W   Y   Q   Q   K   P   G 595  aag gcc cct aag ctg ctg atc aag tac gcc tcc gag tct atc tcc ggc gtg cct
199   K   A   P   K   L   L   I   K   Y   A   S   E   S   I   S   G   V   P 649  tcc cgg ttc tcc ggc tcc ggc tct gga acc gag ttc acc ctg acc atc tcc agc
217   S   R   F   S   G   S   G   S   G   T   E   F   T   L   T   I   S   S 703  ctg cag cct gag gac ttc gcc acc tac tac tgc cag cag aac aac aac tgg cct
235   L   Q   P   E   D   F   A   T   Y   Y   C   Q   Q   N   N   N   W   P 757  acc acc ttc ggc gct ggc acc aag ctg gaa atc aag aga gcg gcc gca gaa ttc
253   T   T   F   G   A   G   T   K   L   E   I   K   R   A   A   A   E   F 811  acg cgt ggc acc agc gag gaa acc att agc acc gtc cag gaa aag cag cag aac
271   T   R   G   T   S   E   E   T   I   S   T   V   Q   E   K   Q   Q   N
```

Fig. 21A

```
865  atc agc ccc ctg gtc cgg gag aga ggc ccc cag aga gtc gcc gcc cac atc acc
289   I   S   P   L   V   R   E   R   G   P   Q   R   V   A   A   H   I   T 919  ggc acc cgg ggc aga agc aac acc ctg agc agc ccc aac agc aag aac gag aag
307   G   T   R   G   R   S   N   T   L   S   S   P   N   S   K   N   E   K 973  gcc ctg ggc cgg aag atc aac agc tgg gag agc agc aga agc ggc cac agc ttt
325   A   L   G   R   K   I   N   S   W   E   S   S   R   S   G   H   S   F 1027 ctg agc aac ctg cac ctg cgg aac ggc gag ctg gtc atc cac gag aag ggc ttc
343   L   S   N   L   H   L   R   N   G   E   L   V   I   H   E   K   G   F 1081 tac tac atc tac agc cag acc tac ttc aga ttc caa gaa gag atc aaa gag aac
361   Y   Y   I   Y   S   Q   T   Y   F   R   F   Q   E   E   I   K   E   N 1135 acc aag aac gac aag cag atg gtg cag tac atc tac aag tac acc agc tac ccc
379   T   K   N   D   K   Q   M   V   Q   Y   I   Y   K   Y   T   S   Y   P 1189 gac ccc atc ctg ctg atg aag tcc gcc cgg aac agc tgc tgg tcc aag gac gcc
397   D   P   I   L   L   M   K   S   A   R   N   S   C   W   S   K   D   A 1243 gag tac ggc ctg tac agc atc tac cag ggc ggc atc ttc gag ctg aaa gag aac
415   E   Y   G   L   Y   S   I   Y   Q   G   G   I   F   E   L   K   E   N 1297 gac cgg atc ttc gtg agc gtg acc aac gag cac ctg atc gac atg gac cac gag
433   D   R   I   F   V   S   V   T   N   E   H   L   I   D   M   D   H   E 1351 gcc agc ttt ttc ggc gca ttc ctg gtc ggc gga ggg gga tcc ggc gga gga agc
451   A   S   F   F   G   A   F   L   V   G   G   G   G   S   G   G   G   S 1405 acc tcc gaa gag act atc tct aca gtc cag gaa aaa cag cag aat atc tcc cct
469   T   S   E   E   T   I   S   T   V   Q   E   K   Q   Q   N   I   S   P 1459 ctc gtg cgg gag cgg gga cct cag cgg gtg gcc gcc cat att aca ggc aca aga
487   L   V   R   E   R   G   P   Q   R   V   A   A   H   I   T   G   T   R 1513 ggc cgg tcc aac acc ctg tcc tcc ccc aac tct aag aat gaa aag gcc ctc ggg
505   G   R   S   N   T   L   S   S   P   N   S   K   N   E   K   A   L   G 1567 aga aag atc aac tcc tgg gag tcc agc cgc tcc ggc cac tcc ttt ctg tcc aat
523   R   K   I   N   S   W   E   S   S   R   S   G   H   S   F   L   S   N 1621 ctg cac ctg aga aat ggg gag ctg gtc att cac gaa aag ggg ttt tac tat atc
541   L   H   L   R   N   G   E   L   V   I   H   E   K   G   F   Y   Y   I 1675 tac tct cag aca tac ttt agg ttt cag gaa gaa att aaa gaa aat aca aag aat
559   Y   S   Q   T   Y   F   R   F   Q   E   E   I   K   E   N   T   K   N 1729 gat aaa cag atg gtc cag tat atc tat aaa tac act tcc tac cct gat cct att
577   D   K   Q   M   V   Q   Y   I   Y   K   Y   T   S   Y   P   D   P   I 1783 ctg ctg atg aaa agc gcc aga aac agc tgt tgg agc aag gat gcc gaa tat ggg
595   L   L   M   K   S   A   R   N   S   C   W   S   K   D   A   E   Y   G 1837 ctc tac tct atc tac cag ggg ggg att ttt gaa ctt aag gag aat gac aga atc
613   L   Y   S   I   Y   Q   G   G   I   F   E   L   K   E   N   D   R   I 1891 ttt gtg tct gtg aca aat gag cat ctg att gat atg gat cac gaa gcc tca ttc
631   F   V   S   V   T   N   E   H   L   I   D   M   D   H   E   A   S   F 1945 ttt gga gcc ttt ctt gtg gga ggg ggc gga tct ggt ggc gga tcc acc tct gag
649   F   G   A   F   L   V   G   G   G   G   S   G   G   G   S   T   S   E
```

Fig. 21B

```
1999 gaa aca ata tcc acc gtc cag gag aag caa caa aac att tcc ccc ctc gtg cgc
 667  E   T   I   S   T   V   Q   E   K   Q   Q   N   I   S   P   L   V   R 2053 gaa cgg ggc cca cag agg gtc gcc gct cac att aca ggg acc agg ggc cgc agc
 685  E   R   G   P   Q   R   V   A   A   H   I   T   G   T   R   G   R   S 2107 aat acc ctg tcc agc ccg aac tcc aaa aat gag aaa gcg ctg ggg cgg aag att
 703  N   T   L   S   S   P   N   S   K   N   E   K   A   L   G   R   K   I 2161 aat tcc tgg gaa agc tcc aga agc ggg cac tcc ttc ctc agc aat ctg cat ctg
 721  N   S   W   E   S   S   R   S   G   H   S   F   L   S   N   L   H   L 2215 cgc aac ggg gaa ctc gtg att cat gag aag gga ttc tat tat atc tat tcc cag
 739  R   N   G   E   L   V   I   H   E   K   G   F   Y   Y   I   Y   S   Q 2269 aca tac ttc cgc ttc caa gag gaa att aaa gag aac act aaa aac gat aaa caa
 757  T   Y   F   R   F   Q   E   E   I   K   E   N   T   K   N   D   K   Q 2323 atg gtt caa tac atc tac aaa tat acc tct tac cca gat ccc atc ctc ctc atg
 775  M   V   Q   Y   I   Y   K   Y   T   S   Y   P   D   P   I   L   L   M 2377 aag agt gcc aga aac tcc tgc tgg tct aag gat gcg gaa tac gga ttg tac tcc
 793  K   S   A   R   N   S   C   W   S   K   D   A   E   Y   G   L   Y   S 2431 atc tat caa ggg gga atc ttt gag ttg aaa gaa aat gat cgc att ttc gtg tcc
 811  I   Y   Q   G   G   I   F   E   L   K   E   N   D   R   I   F   V   S 2485 gtc acg aat gag cac ctc ata gac atg gat cat gaa gcg agt ttc ttc ggg gct
 829  V   T   N   E   H   L   I   D   M   D   H   E   A   S   F   F   G   A 2539 ttc ctc gtg ggt tga
 847  F   L   V   G   -
```

Fig. 21C

Leader: aa res. 1-19
FLAG tag with linkers: 20-33
VH: 34-152
Linker: 153-167
VL: 168-275
Linker: 276-292
TRAIL: 293-479
Linker: 480-487
TRAIL: 488-674
Linker: 675-682
TRAIL: 683-869

```
  1   atg gac tgg acc tgg cgc gtg ttt tgc ctg ctc gcc gtg gct cct ggg gcc cac
  1    M   D   W   T   W   R   V   F   C   L   L   A   V   A   P   G   A   H 55   agc ctc gag gcc agc gac tac aaa gac gat gac gat aaa gga gcc gag gtg cag
 19    S   L   E   A   S   D   Y   K   D   D   D   D   K   G   A   E   V   Q 109   ctg gtc gag tct ggc ggc gga ctg gtg cag cct ggc ggc tcc ctg aga ctg tct
 37    L   V   E   S   G   G   G   L   V   Q   P   G   G   S   L   R   L   S 163   tgc gct gcc tcc ggc ttc tcc ctg acc aac tac ggc gtg cac tgg gtc cgg cag
 55    C   A   A   S   G   F   S   L   T   N   Y   G   V   H   W   V   R   Q 217   gct ccc ggc aag gga ctg gaa tgg ctg ggc gtg att tgg tcc ggc ggc aac acc
 73    A   P   G   K   G   L   E   W   L   G   V   I   W   S   G   G   N   T 271   gac tac aac acc cct ttc acc tcc cgg ttc acc atc tcc cgg gac aac tcc aag
 91    D   Y   N   T   P   F   T   S   R   F   T   I   S   R   D   N   S   K 325   aac acc ctg tac ctg cag atg aac tcc ctg cgg gcc gag gac acc gcc gtg tac
109    N   T   L   Y   L   Q   M   N   S   L   R   A   E   D   T   A   V   Y 379   tac tgc gcc agg gct ctg acc tac tac gac tac gag ttc gcc tac tgg ggc cag
127    Y   C   A   R   A   L   T   Y   Y   D   Y   E   F   A   Y   W   G   Q 433   ggc acc aca gtg acc gtg tct agt ggc ggt ggc ggc tct ggt ggc gga gga agt
145    G   T   T   V   T   V   S   S   G   G   G   G   S   G   G   G   G   S 487   ggc gga ggg ggc tcc gat att cag ctg acc cag tcc ccc tcc ttc ctg tcc gcc
163    G   G   G   G   S   D   I   Q   L   T   Q   S   P   S   F   L   S   A 541   tcc gtg ggc gac aga gtg acc atc acc tgc cgg gcc tcc cag tcc atc ggc acc
181    S   V   G   D   R   V   T   I   T   C   R   A   S   Q   S   I   G   T 595   aac atc cac tgg tat cag cag aag cct ggc aag gcc cct aag ctg ctg atc aag
199    N   I   H   W   Y   Q   Q   K   P   G   K   A   P   K   L   L   I   K 649   tac gcc tcc gag tct atc tcc ggc gtg cct tcc cgg ttc tcc ggc tcc ggc tct
217    Y   A   S   E   S   I   S   G   V   P   S   R   F   S   G   S   G   S 703   gga acc gag ttc acc ctg acc atc tcc agc ctg cag cct gag gac ttc gcc acc
235    G   T   E   F   T   L   T   I   S   S   L   Q   P   E   D   F   A   T 757   tac tac tgc cag cag aac aac aac tgg cct acc acc ttc ggc gct ggc acc aag
253    Y   Y   C   Q   Q   N   N   N   W   P   T   T   F   G   A   G   T   K 811   ctg gaa atc aag aga gcg gcc gca ggc aac ggc acc agc aac ggg aca tcc gaa
271    L   E   I   K   R   A   A   A   G   N   G   T   S   N   G   T   S   E
```

Fig. 22A

```
 865 ttc acg cgt ggc acc agc gag gaa acc att agc acc gtc cag gaa aag cag cag
 289  F   T   R   G   T   S   E   E   T   I   S   T   V   Q   E   K   Q   Q 919 aac atc agc ccc ctg gtc cgg gag aga ggc ccc cag aga gtc gcc gcc cac atc
 307  N   I   S   P   L   V   R   E   R   G   P   Q   R   V   A   A   H   I 973 acc ggc acc cgg ggc aga agc aac acc ctg agc agc ccc aac agc aag aac gag
 325  T   G   T   R   G   R   S   N   T   L   S   S   P   N   S   K   N   E 1027 aag gcc ctg ggc cgg aag atc aac agc tgg gag agc agc aga agc ggc cac agc
 343  K   A   L   G   R   K   I   N   S   W   E   S   S   R   S   G   H   S 1081 ttt ctg agc aac ctg cac ctg cgg aac ggc gag ctg gtc atc cac gag aag ggc
 361  F   L   S   N   L   H   L   R   N   G   E   L   V   I   H   E   K   G 1135 ttc tac tac atc tac agc cag acc tac ttc aga ttc caa gaa gag atc aaa gag
 379  F   Y   Y   I   Y   S   Q   T   Y   F   R   F   Q   E   E   I   K   E 1189 aac acc aag aac gac aag cag atg gtg cag tac atc tac aag tac acc agc tac
 397  N   T   K   N   D   K   Q   M   V   Q   Y   I   Y   K   Y   T   S   Y 1243 ccc gac ccc atc ctg ctg atg aag tcc gcc cgg aac agc tgc tgg tcc aag gac
 415  P   D   P   I   L   L   M   K   S   A   R   N   S   C   W   S   K   D 1297 gcc gag tac ggc ctg tac agc atc tac cag ggc ggc atc ttc gag ctg aaa gag
 433  A   E   Y   G   L   Y   S   I   Y   Q   G   G   I   F   E   L   K   E 1351 aac gac cgg atc ttc gtg agc gtg acc aac gag cac ctg atc gac atg gac cac
 451  N   D   R   I   F   V   S   V   T   N   E   H   L   I   D   M   D   H 1405 gag gcc agc ttt ttc ggc gca ttc ctg gtc ggc gga ggg gga tcc ggc gga gga
 469  E   A   S   F   F   G   A   F   L   V   G   G   G   S   G   G   G 1459 agc acc tcc gaa gag act atc tct aca gtc cag gaa aaa cag cag aat atc tcc
 487  S   T   S   E   E   T   I   S   T   V   Q   E   K   Q   Q   N   I   S 1513 cct ctc gtg cgg gag cgg gga cct cag cgg gtg gcc gcc cat att aca ggc aca
 505  P   L   V   R   E   R   G   P   Q   R   V   A   A   H   I   T   G   T 1567 aga ggc cgg tcc aac acc ctg tcc tcc ccc aac tct aag aat gaa aag gcc ctc
 523  R   G   R   S   N   T   L   S   S   P   N   S   K   N   E   K   A   L 1621 ggg aga aag atc aac tcc tgg gag tcc agc cgc tcc ggc cac tcc ttt ctg tcc
 541  G   R   K   I   N   S   W   E   S   S   R   S   G   H   S   F   L   S 1675 aat ctg cac ctg aga aat ggg gag ctg gtc att cac gaa aag ggg ttt tac tat
 559  N   L   H   L   R   N   G   E   L   V   I   H   E   K   G   F   Y   Y 1729 atc tac tct cag aca tac ttt agg ttt cag gaa gaa att aaa gaa aat aca aag
 577  I   Y   S   Q   T   Y   F   R   F   Q   E   E   I   K   E   N   T   K 1783 aat gat aaa cag atg gtc cag tat atc tat aaa tac act tcc tac cct gat cct
 595  N   D   K   Q   M   V   Q   Y   I   Y   K   Y   T   S   Y   P   D   P 1837 att ctg ctg atg aaa agc gcc aga aac agc tgt tgg agc aag gat gcc gaa tat
 613  I   L   L   M   K   S   A   R   N   S   C   W   S   K   D   A   E   Y 1891 ggg ctc tac tct atc tac cag ggg ggg att ttt gaa ctt aag gag aat gac aga
 631  G   L   Y   S   I   Y   Q   G   G   I   F   E   L   K   E   N   D   R 1945 atc ttt gtg tct gtg aca aat gag cat ctg att gat atg gat cac gaa gcc tca
 649  I   F   V   S   V   T   N   E   H   L   I   D   M   D   H   E   A   S
```

Fig. 22B

```
1999  ttc ttt gga gcc ttt ctt gtg gga ggg ggc gga tct ggt ggc gga tcc acc tct
667    F   F   G   A   F   L   V   G   G   G   G   S   G   G   G   S   T   S 2053  gag gaa aca ata tcc acc gtc cag gag aag caa caa aac att tcc ccc ctc gtg
685    E   E   T   I   S   T   V   Q   E   K   Q   Q   N   I   S   P   L   V 2107  cgc gaa cgg ggc cca cag agg gtc gcc gct cac att aca ggg acc agg ggc cgc
703    R   E   R   G   P   Q   R   V   A   A   H   I   T   G   T   R   G   R 2161  agc aat acc ctg tcc agc ccg aac tcc aaa aat gag aaa gcg ctg ggg cgg aag
721    S   N   T   L   S   S   P   N   S   K   N   E   K   A   L   G   R   K 2215  att aat tcc tgg gaa agc tcc aga agc ggg cac tcc ttc ctc agc aat ctg cat
739    I   N   S   W   E   S   S   R   S   G   H   S   F   L   S   N   L   H 2269  ctg cgc aac ggg gaa ctc gtg att cat gag aag gga ttc tat tat atc tat tcc
757    L   R   N   G   E   L   V   I   H   E   K   G   F   Y   Y   I   Y   S 2323  cag aca tac ttc cgc ttc caa gag gaa att aaa gag aac act aaa aac gat aaa
775    Q   T   Y   F   R   F   Q   E   E   I   K   E   N   T   K   N   D   K 2377  caa atg gtt caa tac atc tac aaa tat acc tct tac cca gat ccc atc ctc ctc
793    Q   M   V   Q   Y   I   Y   K   Y   T   S   Y   P   D   P   I   L   L 2431  atg aag agt gcc aga aac tcc tgc tgg tct aag gat gcg gaa tac gga ttg tac
811    M   K   S   A   R   N   S   C   W   S   K   D   A   E   Y   G   L   Y 2485  tcc atc tat caa ggg gga atc ttt gag ttg aaa gaa aat gat cgc att ttc gtg
829    S   I   Y   Q   G   G   I   F   E   L   K   E   N   D   R   I   F   V 2539  tcc gtc acg aat gag cac ctc ata gac atg gat cat gaa gcg agt ttc ttc ggg
847    S   V   T   N   E   H   L   I   D   M   D   H   E   A   S   F   F   G 2593  gct ttc ctc gtg ggt tga
865    A   F   L   V   G   -
```

Fig. 22C

Leader: aa res. 1-19
FLAG tag with linkers: 20-33
VH: 34-152
Linker: 153-167
VL: 168-275
Linker: 276-292
TRAIL: 293-479
Linker: 480-493
TRAIL: 494-680
Linker: 681-694
TRAIL: 695-881

```
  1  atg gac tgg acc tgg cgc gtg ttt tgc ctg ctc gcc gtg gct cct ggg gcc cac
  1   M   D   W   T   W   R   V   F   C   L   L   A   V   A   P   G   A   H 55  agc ctc gag gcc agc gac tac aaa gac gat gac gat aaa gga gcc gag gtg cag
 19   S   L   E   A   S   D   Y   K   D   D   D   D   K   G   A   E   V   Q 109  ctg gtc gag tct ggc ggc gga ctg gtg cag cct ggc ggc tcc ctg aga ctg tct
 37   L   V   E   S   G   G   G   L   V   Q   P   G   G   S   L   R   L   S 163  tgc gct gcc tcc ggc ttc tcc ctg acc aac tac ggc gtg cac tgg gtc cgg cag
 55   C   A   A   S   G   F   S   L   T   N   Y   G   V   H   W   V   R   Q 217  gct ccc ggc aag gga ctg gaa tgg ctg ggc gtg att tgg tcc ggc ggc aac acc
 73   A   P   G   K   G   L   E   W   L   G   V   I   W   S   G   G   N   T 271  gac tac aac acc cct ttc acc tcc cgg ttc acc atc tcc cgg gac aac tcc aag
 91   D   Y   N   T   P   F   T   S   R   F   T   I   S   R   D   N   S   K 325  aac acc ctg tac ctg cag atg aac tcc ctg cgg gcc gag gac acc gcc gtg tac
109   N   T   L   Y   L   Q   M   N   S   L   R   A   E   D   T   A   V   Y 379  tac tgc gcc agg gct ctg acc tac tac gac tac gag ttc gcc tac tgg ggc cag
127   Y   C   A   R   A   L   T   Y   Y   D   Y   E   F   A   Y   W   G   Q 433  ggc acc aca gtg acc gtg tct agt ggc ggt ggc ggc tct ggt ggc gga gga agt
145   G   T   T   V   T   V   S   S   G   G   G   G   S   G   G   G   G   S 487  ggc gga ggg ggc tcc gat att cag ctg acc cag tcc ccc tcc ttc ctg tcc gcc
163   G   G   G   G   S   D   I   Q   L   T   Q   S   P   S   F   L   S   A 541  tcc gtg ggc gac aga gtg acc atc acc tgc cgg gcc tcc cag tcc atc ggc acc
181   S   V   G   D   R   V   T   I   T   C   R   A   S   Q   S   I   G   T 595  aac atc cac tgg tat cag cag aag cct ggc aag gcc cct aag ctg ctg atc aag
199   N   I   H   W   Y   Q   Q   K   P   G   K   A   P   K   L   L   I   K 649  tac gcc tcc gag tct atc tcc ggc gtg cct tcc cgg ttc tcc ggc tcc ggc tct
217   Y   A   S   E   S   I   S   G   V   P   S   R   F   S   G   S   G   S 703  gga acc gag ttc acc ctg acc atc tcc agc ctg cag cct gag gac ttc gcc acc
235   G   T   E   F   T   L   T   I   S   S   L   Q   P   E   D   F   A   T 757  tac tac tgc cag cag aac aac aac tgg cct acc acc ttc ggc gct ggc acc aag
253   Y   Y   C   Q   Q   N   N   N   W   P   T   T   F   G   A   G   T   K 811  ctg gaa atc aag aga gcg gcc gca ggc aac ggc acc agc aac ggg aca tcc gaa
271   L   E   I   K   R   A   A   A   G   N   G   T   S   N   G   T   S   E
```

Fig. 23A

```
865  ttc acg cgt ggc acc agc gag gaa acc att agc acc gtc cag gaa aag cag cag
289   F   T   R   G   T   S   E   E   T   I   S   T   V   Q   E   K   Q   Q 919  aac atc agc ccc ctg gtc cgg gag aga ggc ccc cag aga gtc gcc gcc cac atc
307   N   I   S   P   L   V   R   E   R   G   P   Q   R   V   A   A   H   I 973  acc ggc acc cgg ggc aga agc aac acc ctg agc agc ccc aac agc aag aac gag
325   T   G   T   R   G   R   S   N   T   L   S   S   P   N   S   K   N   E 1027 aag gcc ctg ggc cgg aag atc aac agc tgg gag agc agc aga agc ggc cac agc
343   K   A   L   G   R   K   I   N   S   W   E   S   S   R   S   G   H   S 1081 ttt ctg agc aac ctg cac ctg cgg aac ggc gag ctg gtc atc cac gag aag ggc
361   F   L   S   N   L   H   L   R   N   G   E   L   V   I   H   E   K   G 1135 ttc tac tac atc tac agc cag acc tac ttc aga ttc caa gaa gag atc aaa gag
379   F   Y   Y   I   Y   S   Q   T   Y   F   R   F   Q   E   E   I   K   E 1189 aac acc aag aac gac aag cag atg gtg cag tac atc tac aag tac acc agc tac
397   N   T   K   N   D   K   Q   M   V   Q   Y   I   Y   K   Y   T   S   Y 1243 ccc gac ccc atc ctg ctg atg aag tcc gcc cgg aac agc tgc tgg tcc aag gac
415   P   D   P   I   L   L   M   K   S   A   R   N   S   C   W   S   K   D 1297 gcc gag tac ggc ctg tac agc atc tac cag ggc ggc atc ttc gag ctg aaa gag
433   A   E   Y   G   L   Y   S   I   Y   Q   G   G   I   F   E   L   K   E 1351 aac gac cgg atc ttc gtg agc gtg acc aac gag cac ctg atc gac atg gac cac
451   N   D   R   I   F   V   S   V   T   N   E   H   L   I   D   M   D   H 1405 gag gcc agc ttt ttc ggc gca ttc ctg gtc ggc gga ggg gga tcc ggc aac ggc
469   E   A   S   F   F   G   A   F   L   V   G   G   G   G   S   G   N   G 1459 aca tcc aat ggg acc agc gga acc tcc gaa gag act atc tct aca gtc cag gaa
487   T   S   N   G   T   S   G   T   S   E   E   T   I   S   T   V   Q   E 1513 aaa cag cag aat atc tcc cct ctc gtg cgg gag cgg gga cct cag cgg gtg gcc
505   K   Q   Q   N   I   S   P   L   V   R   E   R   G   P   Q   R   V   A 1567 gcc cat att aca ggc aca aga ggc cgg tcc aac acc ctg tcc tcc ccc aac tct
523   A   H   I   T   G   T   R   G   R   S   N   T   L   S   S   P   N   S 1621 aag aat gaa aag gcc ctc ggg aga aag atc aac tcc tgg gag tcc agc cgc tcc
541   K   N   E   K   A   L   G   R   K   I   N   S   W   E   S   S   R   S 1675 ggc cac tcc ttt ctg tcc aat ctg cac ctg aga aat ggg gag ctg gtc att cac
559   G   H   S   F   L   S   N   L   H   L   R   N   G   E   L   V   I   H 1729 gaa aag ggg ttt tac tat atc tac tct cag aca tac ttt agg ttt cag gaa gaa
577   E   K   G   F   Y   Y   I   Y   S   Q   T   Y   F   R   F   Q   E   E 1783 att aaa gaa aat aca aag aat gat aaa cag atg gtc cag tat atc tat aaa tac
595   I   K   E   N   T   K   N   D   K   Q   M   V   Q   Y   I   Y   K   Y 1837 act tcc tac cct gat cct att ctg ctg atg aaa agc gcc aga aac agc tgt tgg
613   T   S   Y   P   D   P   I   L   L   M   K   S   A   R   N   S   C   W 1891 agc aag gat gcc gaa tat ggg ctc tac tct atc tac cag ggg ggg att ttt gaa
631   S   K   D   A   E   Y   G   L   Y   S   I   Y   Q   G   G   I   F   E 1945 ctt aag gag aat gac aga atc ttt gtg tct gtg aca aat gag cat ctg att gat
649   L   K   E   N   D   R   I   F   V   S   V   T   N   E   H   L   I   D
```

Fig. 23B

```
1999  atg gat cac gaa gcc tca ttc ttt gga gcc ttt ctt gtg gga ggg ggc gga tct
 667   M   D   H   E   A   S   F   F   G   A   F   L   V   G   G   G   G   S 2053  ggt aat gga acc agc aac ggg acc gga tcc acc tct gag gaa aca ata tcc acc
 685   G   N   G   T   S   N   G   T   G   S   T   S   E   E   T   I   S   T 2107  gtc cag gag aag caa caa aac att tcc ccc ctc gtg cgc gaa cgg ggc cca cag
 703   V   Q   E   K   Q   Q   N   I   S   P   L   V   R   E   R   G   P   Q 2161  agg gtc gcc gct cac att aca ggg acc agg ggc cgc agc aat acc ctg tcc agc
 721   R   V   A   A   H   I   T   G   T   R   G   R   S   N   T   L   S   S 2215  ccg aac tcc aaa aat gag aaa gcg ctg ggg cgg aag att aat tcc tgg gaa agc
 739   P   N   S   K   N   E   K   A   L   G   R   K   I   N   S   W   E   S 2269  tcc aga agc ggg cac tcc ttc ctc agc aat ctg cat ctg cgc aac ggg gaa ctc
 757   S   R   S   G   H   S   F   L   S   N   L   H   L   R   N   G   E   L 2323  gtg att cat gag aag gga ttc tat tat atc tat tcc cag aca tac ttc cgc ttc
 775   V   I   H   E   K   G   F   Y   Y   I   Y   S   Q   T   Y   F   R   F 2377  caa gag gaa att aaa gag aac act aaa aac gat aaa caa atg gtt caa tac atc
 793   Q   E   E   I   K   E   N   T   K   N   D   K   Q   M   V   Q   Y   I 2431  tac aaa tat acc tct tac cca gat ccc atc ctc ctc atg aag agt gcc aga aac
 811   Y   K   Y   T   S   Y   P   D   P   I   L   L   M   K   S   A   R   N 2485  tcc tgc tgg tct aag gat gcg gaa tac gga ttg tac tcc atc tat caa ggg gga
 829   S   C   W   S   K   D   A   E   Y   G   L   Y   S   I   Y   Q   G   G 2539  atc ttt gag ttg aaa gaa aat gat cgc att ttc gtg tcc gtc acg aat gag cac
 847   I   F   E   L   K   E   N   D   R   I   F   V   S   V   T   N   E   H 2593  ctc ata gac atg gat cat gaa gcg agt ttc ttc ggg gct ttc ctc gtg ggt tga
 865   L   I   D   M   D   H   E   A   S   F   F   G   A   F   L   V   G   -
```

Fig. 23C

Leader: aa 1-19
ABD: 20-75
Linker: 76-85
VH: 86-204
Linker: 205-209
VL: 210-317
Linker: 318-330
TRAIL: 331-517
Linker: 518-525
TRAIL: 526-712
Linker: 713-720
TRAIL: 721-907

```
  1  atg gac tgg acc tgg cgc gtg ttt tgc ctg ctc gcc gtg gct cct ggg gcc cac
  1   M   D   W   T   W   R   V   F   C   L   L   A   V   A   P   G   A   H 55  agc cag cat gat gaa gcg gtg gat gcg aac agc ctg gcc gaa gcg aaa gtg ctg
 19   S   Q   H   D   E   A   V   D   A   N   S   L   A   E   A   K   V   L 109  gcc aac cgt gaa ctg gat aaa tat ggc gtg agc gat tac tat aaa aac ctg atc
 37   A   N   R   E   L   D   K   Y   G   V   S   D   Y   Y   K   N   L   I 163  aat aac gcg aaa acc gtg gaa ggc gtg aaa gcg ctg att gat gaa att ctg gcc
 55   N   N   A   K   T   V   E   G   V   K   A   L   I   D   E   I   L   A 217  gcg ctg ccg ggt ggt tca gga ggt ggt ggt tca gga ggt gag gtg cag ctg gtc
 73   A   L   P   G   G   S   G   G   G   G   S   G   G   E   V   Q   L   V 271  gag tct ggc ggc gga ctg gtg cag cct ggc ggc tcc ctg aga ctg tct tgc gct
 91   E   S   G   G   G   L   V   Q   P   G   G   S   L   R   L   S   C   A 325  gcc tcc ggc ttc tcc ctg acc aac tac ggc gtg cac tgg gtc cgg cag gct ccc
109   A   S   G   F   S   L   T   N   Y   G   V   H   W   V   R   Q   A   P 379  ggc aag gga ctg gaa tgg ctg ggc gtg att tgg tcc ggc ggc aac acc gac tac
127   G   K   G   L   E   W   L   G   V   I   W   S   G   G   N   T   D   Y 433  aac acc cct ttc acc tcc cgg ttc acc atc tcc cgg gac aac tcc aag aac acc
145   N   T   P   F   T   S   R   F   T   I   S   R   D   N   S   K   N   T 487  ctg tac ctg cag atg aac tcc ctg cgg gcc gag gac acc gcc gtg tac tac tgc
163   L   Y   L   Q   M   N   S   L   R   A   E   D   T   A   V   Y   Y   C 541  gcc agg gct ctg acc tac tac gac tac gag ttc gcc tac tgg ggc cag ggc acc
181   A   R   A   L   T   Y   Y   D   Y   E   F   A   Y   W   G   Q   G   T 595  aca gtg acc gtg tct agt ggc ggt ggc ggc tct gat att cag ctg acc cag tcc
199   T   V   T   V   S   S   G   G   G   G   S   D   I   Q   L   T   Q   S 649  ccc tcc ttc ctg tcc gcc tcc gtg ggc gac aga gtg acc atc acc tgc cgg gcc
217   P   S   F   L   S   A   S   V   G   D   R   V   T   I   T   C   R   A 703  tcc cag tcc atc ggc acc aac atc cac tgg tat cag cag aag cct ggc aag gcc
235   S   Q   S   I   G   T   N   I   H   W   Y   Q   Q   K   P   G   K   A 757  cct aag ctg ctg atc aag tac gcc tcc gag tct atc tcc ggc gtg cct tcc cgg
253   P   K   L   L   I   K   Y   A   S   E   S   I   S   G   V   P   S   R 811  ttc tcc ggc tcc ggc tct gga acc gag ttc acc ctg acc atc tcc agc ctg cag
271   F   S   G   S   G   S   G   T   E   F   T   L   T   I   S   S   L   Q 865  cct gag gac ttc gcc acc tac tac tgc cag cag aac aac aac tgg cct acc acc
289   P   E   D   F   A   T   Y   Y   C   Q   Q   N   N   N   W   P   T   T
```

Fig. 24A

```
 919  ttc ggc gct ggc acc aag ctg gaa atc aag aga ggt ggt tca ggc aac ggc acc
 307   F   G   A   G   T   K   L   E   I   K   R   G   G   S   G   N   G   T 973  agc aac ggg aca tcc ggc acc agc gag gaa acc att agc acc gtc cag gaa aag
 325   S   N   G   T   S   G   T   S   E   E   T   I   S   T   V   Q   E   K 1027  cag cag aac atc agc ccc ctg gtc cgg gag aga ggc ccc cag aga gtc gcc gcc
 343   Q   Q   N   I   S   P   L   V   R   E   R   G   P   Q   R   V   A   A 1081  cac atc acc ggc acc cgg ggc aga agc aac acc ctg agc agc ccc aac agc aag
 361   H   I   T   G   T   R   G   R   S   N   T   L   S   S   P   N   S   K 1135  aac gag aag gcc ctg ggc cgg aag atc aac agc tgg gag agc agc aga agc ggc
 379   N   E   K   A   L   G   R   K   I   N   S   W   E   S   S   R   S   G 1189  cac agc ttt ctg agc aac ctg cac ctg cgg aac ggc gag ctg gtc atc cac gag
 397   H   S   F   L   S   N   L   H   L   R   N   G   E   L   V   I   H   E 1243  aag ggc ttc tac tac atc tac agc cag acc tac ttc aga ttc caa gaa gag atc
 415   K   G   F   Y   Y   I   Y   S   Q   T   Y   F   R   F   Q   E   E   I 1297  aaa gag aac acc aag aac gac aag cag atg gtg cag tac atc tac aag tac acc
 433   K   E   N   T   K   N   D   K   Q   M   V   Q   Y   I   Y   K   Y   T 1351  agc tac ccc gac ccc atc ctg ctg atg aag tcc gcc cgg aac agc tgc tgg tcc
 451   S   Y   P   D   P   I   L   L   M   K   S   A   R   N   S   C   W   S 1405  aag gac gcc gag tac ggc ctg tac agc atc tac cag ggc ggc atc ttc gag ctg
 469   K   D   A   E   Y   G   L   Y   S   I   Y   Q   G   G   I   F   E   L 1459  aaa gag aac gac cgg atc ttc gtg agc gtg acc aac gag cac ctg atc gac atg
 487   K   E   N   D   R   I   F   V   S   V   T   N   E   H   L   I   D   M 1513  gac cac gag gcc agc ttt ttc ggc gca ttc ctg gtc ggc gga ggg gga tcc ggc
 505   D   H   E   A   S   F   F   G   A   F   L   V   G   G   G   G   S   G 1567  gga gga agc acc tcc gaa gag act atc tct aca gtc cag gaa aaa cag cag aat
 523   G   G   S   T   S   E   E   T   I   S   T   V   Q   E   K   Q   Q   N 1621  atc tcc cct ctc gtg cgg gag cgg gga cct cag cgg gtg gcc gcc cat att aca
 541   I   S   P   L   V   R   E   R   G   P   Q   R   V   A   A   H   I   T 1675  ggc aca aga ggc cgg tcc aac acc ctg tcc tcc ccc aac tct aag aat gaa aag
 559   G   T   R   G   R   S   N   T   L   S   S   P   N   S   K   N   E   K 1729  gcc ctc ggg aga aag atc aac tcc tgg gag tcc agc cgc tcc ggc cac tcc ttt
 577   A   L   G   R   K   I   N   S   W   E   S   S   R   S   G   H   S   F 1783  ctg tcc aat ctg cac ctg aga aat ggg gag ctg gtc att cac gaa aag ggg ttt
 595   L   S   N   L   H   L   R   N   G   E   L   V   I   H   E   K   G   F 1837  tac tat atc tac tct cag aca tac ttt agg ttt cag gaa gaa att aaa gaa aat
 613   Y   Y   I   Y   S   Q   T   Y   F   R   F   Q   E   E   I   K   E   N 1891  aca aag aat gat aaa cag atg gtc cag tat atc tat aaa tac act tcc tac cct
 631   T   K   N   D   K   Q   M   V   Q   Y   I   Y   K   Y   T   S   Y   P 1945  gat cct att ctg ctg atg aaa agc gcc aga aac agc tgt tgg agc aag gat gcc
 649   D   P   I   L   L   M   K   S   A   R   N   S   C   W   S   K   D   A 1999  gaa tat ggg ctc tac tct atc tac cag ggg ggg att ttt gaa ctt aag gag aat
 667   E   Y   G   L   Y   S   I   Y   Q   G   G   I   F   E   L   K   E   N
```

Fig. 24B

```
2053 gac aga atc ttt gtg tct gtg aca aat gag cat ctg att gat atg gat cac gaa
685   D   R   I   F   V   S   V   T   N   E   H   L   I   D   M   D   H   E 2107 gcc tca ttc ttt gga gcc ttt ctt gtg gga ggg ggc gga tct ggt ggc gga tcc
703   A   S   F   F   G   A   F   L   V   G   G   G   G   S   G   G   G   S 2161 acc tct gag gaa aca ata tcc acc gtc cag gag aag caa caa aac att tcc ccc
721   T   S   E   E   T   I   S   T   V   Q   E   K   Q   Q   N   I   S   P 2215 ctc gtg cgc gaa cgg ggc cca cag agg gtc gcc gct cac att aca ggg acc agg
739   L   V   R   E   R   G   P   Q   R   V   A   A   H   I   T   G   T   R 2269 ggc cgc agc aat acc ctg tcc agc ccg aac tcc aaa aat gag aaa gcg ctg ggg
757   G   R   S   N   T   L   S   S   P   N   S   K   N   E   K   A   L   G 2323 cgg aag att aat tcc tgg gaa agc tcc aga agc ggg cac tcc ttc ctc agc aat
775   R   K   I   N   S   W   E   S   S   R   S   G   H   S   F   L   S   N 2377 ctg cat ctg cgc aac ggg gaa ctc gtg att cat gag aag gga ttc tat tat atc
793   L   H   L   R   N   G   E   L   V   I   H   E   K   G   F   Y   Y   I 2431 tat tcc cag aca tac ttc cgc ttc caa gag gaa att aaa gag aac act aaa aac
811   Y   S   Q   T   Y   F   R   F   Q   E   E   I   K   E   N   T   K   N 2485 gat aaa caa atg gtt caa tac atc tac aaa tat acc tct tac cca gat ccc atc
829   D   K   Q   M   V   Q   Y   I   Y   K   Y   T   S   Y   P   D   P   I 2539 ctc ctc atg aag agt gcc aga aac tcc tgc tgg tct aag gat gcg gaa tac gga
847   L   L   M   K   S   A   R   N   S   C   W   S   K   D   A   E   Y   G 2593 ttg tac tcc atc tat caa ggg gga atc ttt gag ttg aaa gaa aat gat cgc att
865   L   Y   S   I   Y   Q   G   G   I   F   E   L   K   E   N   D   R   I 2647 ttc gtg tcc gtc acg aat gag cac ctc ata gac atg gat cat gaa gcg agt ttc
883   F   V   S   V   T   N   E   H   L   I   D   M   D   H   E   A   S   F 2701 ttc ggg gct ttc ctc gtg ggt tga
901   F   G   A   F   L   V   G   -
```

Fig. 24C

Leader: aa res. 1-19
FLAG tag with linkers: 20-33
VH: 34-152
Linker: 153-157
VL: 158-265
Linker: 266-268
ABD: 269-324
Linker: 325-341
TRAIL: 342-528
Linker: 529-536
TRAIL: 537-723
Linker: 724-731
TRAIL: 732-918

```
  1   atg gac tgg acc tgg cgc gtg ttt tgc ctg ctc gcc gtg gct cct ggg gcc cac
  1    M   D   W   T   W   R   V   F   C   L   L   A   V   A   P   G   A   H 55   agc ctc gag gcc agc gac tac aaa gac gat gac gat aaa gga gcc gag gtg cag
 19    S   L   E   A   S   D   Y   K   D   D   D   D   K   G   A   E   V   Q 109   ctg gtc gag tct ggc ggc gga ctg gtg cag cct ggc ggc tcc ctg aga ctg tct
 37    L   V   E   S   G   G   G   L   V   Q   P   G   G   S   L   R   L   S 163   tgc gct gcc tcc ggc ttc tcc ctg acc aac tac ggc gtg cac tgg gtc cgg cag
 55    C   A   A   S   G   F   S   L   T   N   Y   G   V   H   W   V   R   Q 217   gct ccc ggc aag gga ctg gaa tgg ctg ggc gtg att tgg tcc ggc ggc aac acc
 73    A   P   G   K   G   L   E   W   L   G   V   I   W   S   G   G   N   T 271   gac tac aac acc cct ttc acc tcc cgg ttc acc atc tcc cgg gac aac tcc aag
 91    D   Y   N   T   P   F   T   S   R   F   T   I   S   R   D   N   S   K 325   aac acc ctg tac ctg cag atg aac tcc ctg cgg gcc gag gac acc gcc gtg tac
109    N   T   L   Y   L   Q   M   N   S   L   R   A   E   D   T   A   V   Y 379   tac tgc gcc agg gct ctg acc tac tac gac tac gag ttc gcc tac tgg ggc cag
127    Y   C   A   R   A   L   T   Y   Y   D   Y   E   F   A   Y   W   G   Q 433   ggc acc aca gtg acc gtg tct agt ggc ggt ggc ggc tct gat att cag ctg acc
145    G   T   T   V   T   V   S   S   G   G   G   G   S   D   I   Q   L   T 487   cag tcc ccc tcc ttc ctg tcc gcc tcc gtg ggc gac aga gtg acc atc acc tgc
163    Q   S   P   S   F   L   S   A   S   V   G   D   R   V   T   I   T   C 541   cgg gcc tcc cag tcc atc ggc acc aac atc cac tgg tat cag cag aag cct ggc
181    R   A   S   Q   S   I   G   T   N   I   H   W   Y   Q   Q   K   P   G 595   aag gcc cct aag ctg ctg atc aag tac gcc tcc gag tct atc tcc ggc gtg cct
199    K   A   P   K   L   L   I   K   Y   A   S   E   S   I   S   G   V   P 649   tcc cgg ttc tcc ggc tcc ggc tct gga acc gag ttc acc ctg acc atc tcc agc
217    S   R   F   S   G   S   G   S   G   T   E   F   T   L   T   I   S   S 703   ctg cag cct gag gac ttc gcc acc tac tac tgc cag cag aac aac aac tgg cct
235    L   Q   P   E   D   F   A   T   Y   Y   C   Q   Q   N   N   N   W   P 757   acc acc ttc ggc gct ggc acc aag ctg gaa atc aag aga ggc ggc agc cag cat
253    T   T   F   G   A   G   T   K   L   E   I   K   R   G   G   S   Q   H
```

Fig. 25A

```
 811  gat gaa gcg gtg gat gcg aac agc ctg gcc gaa gcg aaa gtg ctg gcc aac cgt
 271   D   E   A   V   D   A   N   S   L   A   E   A   K   V   L   A   N   R 865  gaa ctg gat aaa tat ggc gtg agc gat tac tat aaa aac ctg atc aat aac gcg
 289   E   L   D   K   Y   G   V   S   D   Y   Y   K   N   L   I   N   N   A 919  aaa acc gtg gaa ggc gtg aaa gcg ctg att gat gaa att ctg gcc gcg ctg ccg
 307   K   T   V   E   G   V   K   A   L   I   D   E   I   L   A   A   L   P 973  gcg gcc gca ggc aac ggc acc agc aac ggg aca tcc gaa ttc acg cgt ggc acc
 325   A   A   A   G   N   G   T   S   N   G   T   S   E   F   T   R   G   T 1027  agc gag gaa acc att agc acc gtc cag gaa aag cag cag aac atc agc ccc ctg
 343   S   E   E   T   I   S   T   V   Q   E   K   Q   Q   N   I   S   P   L 1081  gtc cgg gag aga ggc ccc cag aga gtc gcc gcc cac atc acc ggc acc cgg ggc
 361   V   R   E   R   G   P   Q   R   V   A   A   H   I   T   G   T   R   G 1135  aga agc aac acc ctg agc agc ccc aac agc aag aac gag aag gcc ctg ggc cgg
 379   R   S   N   T   L   S   S   P   N   S   K   N   E   K   A   L   G   R 1189  aag atc aac agc tgg gag agc agc aga agc ggc cac agc ttt ctg agc aac ctg
 397   K   I   N   S   W   E   S   S   R   S   G   H   S   F   L   S   N   L 1243  cac ctg cgg aac ggc gag ctg gtc atc cac gag aag ggc ttc tac tac atc tac
 415   H   L   R   N   G   E   L   V   I   H   E   K   G   F   Y   Y   I   Y 1297  agc cag acc tac ttc aga ttc caa gaa gag atc aaa gag aac acc aag aac gac
 433   S   Q   T   Y   F   R   F   Q   E   E   I   K   E   N   T   K   N   D 1351  aag cag atg gtg cag tac atc tac aag tac acc agc tac ccc gac ccc atc ctg
 451   K   Q   M   V   Q   Y   I   Y   K   Y   T   S   Y   P   D   P   I   L 1405  ctg atg aag tcc gcc cgg aac agc tgc tgg tcc aag gac gcc gag tac ggc ctg
 469   L   M   K   S   A   R   N   S   C   W   S   K   D   A   E   Y   G   L 1459  tac agc atc tac cag ggc ggc atc ttc gag ctg aaa gag aac gac cgg atc ttc
 487   Y   S   I   Y   Q   G   G   I   F   E   L   K   E   N   D   R   I   F 1513  gtg agc gtg acc aac gag cac ctg atc gac atg gac cac gag gcc agc ttt ttc
 505   V   S   V   T   N   E   H   L   I   D   M   D   H   E   A   S   F   F 1567  ggc gca ttc ctg gtc ggc gga ggg gga tcc ggc gga gga agc acc tcc gaa gag
 523   G   A   F   L   V   G   G   G   G   S   G   G   G   S   T   S   E   E 1621  act atc tct aca gtc cag gaa aaa cag cag aat atc tcc cct ctc gtg cgg gag
 541   T   I   S   T   V   Q   E   K   Q   Q   N   I   S   P   L   V   R   E 1675  cgg gga cct cag cgg gtg gcc gcc cat att aca ggc aca aga ggc cgg tcc aac
 559   R   G   P   Q   R   V   A   A   H   I   T   G   T   R   G   R   S   N 1729  acc ctg tcc tcc ccc aac tct aag aat gaa aag gcc ctc ggg aga aag atc aac
 577   T   L   S   S   P   N   S   K   N   E   K   A   L   G   R   K   I   N
```

Fig. 25B

```
1783  tcc tgg gag tcc agc cgc tcc ggc cac tcc ttt ctg tcc aat ctg cac ctg aga
 595   S   W   E   S   S   R   S   G   H   S   F   L   S   N   L   H   L   R 1837  aat ggg gag ctg gtc att cac gaa aag ggg ttt tac tat atc tac tct cag aca
 613   N   G   E   L   V   I   H   E   K   G   F   Y   Y   I   Y   S   Q   T 1891  tac ttt agg ttt cag gaa gaa att aaa gaa aat aca aag aat gat aaa cag atg
 631   Y   F   R   F   Q   E   E   I   K   E   N   T   K   N   D   K   Q   M 1945  gtc cag tat atc tat aaa tac act tcc tac cct gat cct att ctg ctg atg aaa
 649   V   Q   Y   I   Y   K   Y   T   S   Y   P   D   P   I   L   L   M   K 1999  agc gcc aga aac agc tgt tgg agc aag gat gcc gaa tat ggg ctc tac tct atc
 667   S   A   R   N   S   C   W   S   K   D   A   E   Y   G   L   Y   S   I 2053  tac cag ggg ggg att ttt gaa ctt aag gag aat gac aga atc ttt gtg tct gtg
 685   Y   Q   G   G   I   F   E   L   K   E   N   D   R   I   F   V   S   V 2107  aca aat gag cat ctg att gat atg gat cac gaa gcc tca ttc ttt gga gcc ttt
 703   T   N   E   H   L   I   D   M   D   H   E   A   S   F   F   G   A   F 2161  ctt gtg gga ggg ggc gga tct ggt ggc gga tcc acc tct gag gaa aca ata tcc
 721   L   V   G   G   G   G   S   G   G   G   S   T   S   E   E   T   I   S 2215  acc gtc cag gag aag caa caa aac att tcc ccc ctc gtg cgc gaa cgg ggc cca
 739   T   V   Q   E   K   Q   Q   N   I   S   P   L   V   R   E   R   G   P 2269  cag agg gtc gcc gct cac att aca ggg acc agg ggc cgc agc aat acc ctg tcc
 757   Q   R   V   A   A   H   I   T   G   T   R   G   R   S   N   T   L   S 2323  agc ccg aac tcc aaa aat gag aaa gcg ctg ggg cgg aag att aat tcc tgg gaa
 775   S   P   N   S   K   N   E   K   A   L   G   R   K   I   N   S   W   E 2377  agc tcc aga agc ggg cac tcc ttc ctc agc aat ctg cat ctg cgc aac ggg gaa
 793   S   S   R   S   G   H   S   F   L   S   N   L   H   L   R   N   G   E 2431  ctc gtg att cat gag aag gga ttc tat tat atc tat tcc cag aca tac ttc cgc
 811   L   V   I   H   E   K   G   F   Y   Y   I   Y   S   Q   T   Y   F   R 2485  ttc caa gag gaa att aaa gag aac act aaa aac gat aaa caa atg gtt caa tac
 829   F   Q   E   E   I   K   E   N   T   K   N   D   K   Q   M   V   Q   Y 2539  atc tac aaa tat acc tct tac cca gat ccc atc ctc ctc atg aag agt gcc aga
 847   I   Y   K   Y   T   S   Y   P   D   P   I   L   L   M   K   S   A   R 2593  aac tcc tgc tgg tct aag gat gcg gaa tac gga ttg tac tcc atc tat caa ggg
 865   N   S   C   W   S   K   D   A   E   Y   G   L   Y   S   I   Y   Q   G 2647  gga atc ttt gag ttg aaa gaa aat gat cgc att ttc gtg tcc gtc acg aat gag
 883   G   I   F   E   L   K   E   N   D   R   I   F   V   S   V   T   N   E 2701  cac ctc ata gac atg gat cat gaa gcg agt ttc ttc ggg gct ttc ctc gtg ggt
 901   H   L   I   D   M   D   H   E   A   S   F   F   G   A   F   L   V   G 2755  tga
 919   -
```

Fig. 25C

Leader: aa res. 1-19
FLAG tag with linkers: 20-33
VH: 34-152
Linker: 153-157
VL: 158-265
Linker: 266-282
TRAIL: 283-469
Linker: 470-477
TRAIL: 478-664
Linker: 665-672
TRAIL: 673-859
Linker: 860-864
ABD: 865-920

```
  1  atg gac tgg acc tgg cgc gtg ttt tgc ctg ctc gcc gtg gct cct ggg gcc cac
  1   M   D   W   T   W   R   V   F   C   L   L   A   V   A   P   G   A   H 55  agc ctc gag gcc agc gac tac aaa gac gat gac gat aaa gga gcc gag gtg cag
 19   S   L   E   A   S   D   Y   K   D   D   D   D   K   G   A   E   V   Q 109  ctg gtc gag tct ggc ggc gga ctg gtg cag cct ggc ggc tcc ctg aga ctg tct
 37   L   V   E   S   G   G   G   L   V   Q   P   G   G   S   L   R   L   S 163  tgc gct gcc tcc ggc ttc tcc ctg acc aac tac ggc gtg cac tgg gtc cgg cag
 55   C   A   A   S   G   F   S   L   T   N   Y   G   V   H   W   V   R   Q 217  gct ccc ggc aag gga ctg gaa tgg ctg ggc gtg att tgg tcc ggc ggc aac acc
 73   A   P   G   K   G   L   E   W   L   G   V   I   W   S   G   G   N   T 271  gac tac aac acc cct ttc acc tcc cgg ttc acc atc tcc cgg gac aac tcc aag
 91   D   Y   N   T   P   F   T   S   R   F   T   I   S   R   D   N   S   K 325  aac acc ctg tac ctg cag atg aac tcc ctg cgg gcc gag gac acc gcc gtg tac
109   N   T   L   Y   L   Q   M   N   S   L   R   A   E   D   T   A   V   Y 379  tac tgc gcc agg gct ctg acc tac tac gac tac gag ttc gcc tac tgg ggc cag
127   Y   C   A   R   A   L   T   Y   Y   D   Y   E   F   A   Y   W   G   Q 433  ggc acc aca gtg acc gtg tct agt ggc ggt ggc ggc tct gat att cag ctg acc
145   G   T   T   V   T   V   S   S   G   G   G   G   S   D   I   Q   L   T 487  cag tcc ccc tcc ttc ctg tcc gcc tcc gtg ggc gac aga gtg acc atc acc tgc
163   Q   S   P   S   F   L   S   A   S   V   G   D   R   V   T   I   T   C 541  cgg gcc tcc cag tcc atc ggc acc aac atc cac tgg tat cag cag aag cct ggc
181   R   A   S   Q   S   I   G   T   N   I   H   W   Y   Q   Q   K   P   G 595  aag gcc cct aag ctg ctg atc aag tac gcc tcc gag tct atc tcc ggc gtg cct
199   K   A   P   K   L   L   I   K   Y   A   S   E   S   I   S   G   V   P 649  tcc cgg ttc tcc ggc tcc ggc tct gga acc gag ttc acc ctg acc atc tcc agc
217   S   R   F   S   G   S   G   S   G   T   E   F   T   L   T   I   S   S 703  ctg cag cct gag gac ttc gcc acc tac tac tgc cag cag aac aac aac tgg cct
235   L   Q   P   E   D   F   A   T   Y   Y   C   Q   Q   N   N   N   W   P
```

Fig. 26A

```
 757  acc acc ttc ggc gct ggc acc aag ctg gaa atc aag aga gcg gcc gca ggc aac
 253   T   T   F   G   A   G   T   K   L   E   I   K   R   A   A   A   G   N 811  ggc acc agc aac ggg aca tcc gaa ttc acg cgt ggc acc agc gag gaa acc att
 271   G   T   S   N   G   T   S   E   F   T   R   G   T   S   E   E   T   I 865  agc acc gtc cag gaa aag cag cag aac atc agc ccc ctg gtc cgg gag aga ggc
 289   S   T   V   Q   E   K   Q   Q   N   I   S   P   L   V   R   E   R   G 919  ccc cag aga gtc gcc gcc cac atc acc ggc acc cgg ggc aga agc aac acc ctg
 307   P   Q   R   V   A   A   H   I   T   G   T   R   G   R   S   N   T   L 973  agc agc ccc aac agc aag aac gag aag gcc ctg ggc cgg aag atc aac agc tgg
 325   S   S   P   N   S   K   N   E   K   A   L   G   R   K   I   N   S   W 1027  gag agc agc aga agc ggc cac agc ttt ctg agc aac ctg cac ctg cgg aac ggc
 343   E   S   S   R   S   G   H   S   F   L   S   N   L   H   L   R   N   G 1081  gag ctg gtc atc cac gag aag ggc ttc tac tac atc tac agc cag acc tac ttc
 361   E   L   V   I   H   E   K   G   F   Y   Y   I   Y   S   Q   T   Y   F 1135  aga ttc caa gaa gag atc aaa gag aac acc aag aac gac aag cag atg gtg cag
 379   R   F   Q   E   E   I   K   E   N   T   K   N   D   K   Q   M   V   Q 1189  tac atc tac aag tac acc agc tac ccc gac ccc atc ctg ctg atg aag tcc gcc
 397   Y   I   Y   K   Y   T   S   Y   P   D   P   I   L   L   M   K   S   A 1243  cgg aac agc tgc tgg tcc aag gac gcc gag tac ggc ctg tac agc atc tac cag
 415   R   N   S   C   W   S   K   D   A   E   Y   G   L   Y   S   I   Y   Q 1297  ggc ggc atc ttc gag ctg aaa gag aac gac cgg atc ttc gtg agc gtg acc aac
 433   G   G   I   F   E   L   K   E   N   D   R   I   F   V   S   V   T   N 1351  gag cac ctg atc gac atg gac cac gag gcc agc ttt ttc ggc gca ttc ctg gtc
 451   E   H   L   I   D   M   D   H   E   A   S   F   F   G   A   F   L   V 1405  ggc gga ggg gga tcc ggc gga gga agc acc tcc gaa gag act atc tct aca gtc
 469   G   G   G   G   S   G   G   G   S   T   S   E   E   T   I   S   T   V 1459  cag gaa aaa cag cag aat atc tcc cct ctc gtg cgg gag cgg gga cct cag cgg
 487   Q   E   K   Q   Q   N   I   S   P   L   V   R   E   R   G   P   Q   R 1513  gtg gcc gcc cat att aca ggc aca aga ggc cgg tcc aac acc ctg tcc tcc ccc
 505   V   A   A   H   I   T   G   T   R   G   R   S   N   T   L   S   S   P 1567  aac tct aag aat gaa aag gcc ctc ggg aga aag atc aac tcc tgg gag tcc agc
 523   N   S   K   N   E   K   A   L   G   R   K   I   N   S   W   E   S   S 1621  cgc tcc ggc cac tcc ttt ctg tcc aat ctg cac ctg aga aat ggg gag ctg gtc
 541   R   S   G   H   S   F   L   S   N   L   H   L   R   N   G   E   L   V 1675  att cac gaa aag ggg ttt tac tat atc tac tct cag aca tac ttt agg ttt cag
 559   I   H   E   K   G   F   Y   Y   I   Y   S   Q   T   Y   F   R   F   Q
```

Fig. 26B

```
1729 gaa gaa att aaa gaa aat aca aag aat gat aaa cag atg gtc cag tat atc tat
 577  E   E   I   K   E   N   T   K   N   D   K   Q   M   V   Q   Y   I   Y 1783 aaa tac act tcc tac cct gat cct att ctg ctg atg aaa agc gcc aga aac agc
 595  K   Y   T   S   Y   P   D   P   I   L   L   M   K   S   A   R   N   S 1837 tgt tgg agc aag gat gcc gaa tat ggg ctc tac tct atc tac cag ggg ggg att
 613  C   W   S   K   D   A   E   Y   G   L   Y   S   I   Y   Q   G   G   I 1891 ttt gaa ctt aag gag aat gac aga atc ttt gtg tct gtg aca aat gag cat ctg
 631  F   E   L   K   E   N   D   R   I   F   V   S   V   T   N   E   H   L 1945 att gat atg gat cac gaa gcc tca ttc ttt gga gcc ttt ctt gtg gga ggg ggc
 649  I   D   M   D   H   E   A   S   F   F   G   A   F   L   V   G   G   G 1999 gga tct ggt ggc gga tcc acc tct gag gaa aca ata tcc acc gtc cag gag aag
 667  G   S   G   G   G   S   T   S   E   E   T   I   S   T   V   Q   E   K 2053 caa caa aac att tcc ccc ctc gtg cgc gaa cgg ggc cca cag agg gtc gcc gct
 685  Q   Q   N   I   S   P   L   V   R   E   R   G   P   Q   R   V   A   A 2107 cac att aca ggg acc agg ggc cgc agc aat acc ctg tcc agc ccg aac tcc aaa
 703  H   I   T   G   T   R   G   R   S   N   T   L   S   S   P   N   S   K 2161 aat gag aaa gcg ctg ggg cgg aag att aat tcc tgg gaa agc tcc aga agc ggg
 721  N   E   K   A   L   G   R   K   I   N   S   W   E   S   S   R   S   G 2215 cac tcc ttc ctc agc aat ctg cat ctg cgc aac ggg gaa ctc gtg att cat gag
 739  H   S   F   L   S   N   L   H   L   R   N   G   E   L   V   I   H   E 2269 aag gga ttc tat tat atc tat tcc cag aca tac ttc cgc ttc caa gag gaa att
 757  K   G   F   Y   Y   I   Y   S   Q   T   Y   F   R   F   Q   E   E   I 2323 aaa gag aac act aaa aac gat aaa caa atg gtt caa tac atc tac aaa tat acc
 775  K   E   N   T   K   N   D   K   Q   M   V   Q   Y   I   Y   K   Y   T 2377 tct tac cca gat ccc atc ctc ctc atg aag agt gcc aga aac tcc tgc tgg tct
 793  S   Y   P   D   P   I   L   L   M   K   S   A   R   N   S   C   W   S 2431 aag gat gcg gaa tac gga ttg tac tcc atc tat caa ggg gga atc ttt gag ttg
 811  K   D   A   E   Y   G   L   Y   S   I   Y   Q   G   G   I   F   E   L 2485 aaa gaa aat gat cgc att ttc gtg tcc gtc acg aat gag cac ctc ata gac atg
 829  K   E   N   D   R   I   F   V   S   V   T   N   E   H   L   I   D   M 2539 gat cat gaa gcg agt ttc ttc ggg gct ttc ctc gtg ggt ggt ggt tca gga ggt
 847  D   H   E   A   S   F   F   G   A   F   L   V   G   G   G   S   G   G 2593 cag cat gat gaa gcg gtg gat gcg aac agc ctg gcc gaa gcg aaa gtg ctg gcc
 865  Q   H   D   E   A   V   D   A   N   S   L   A   E   A   K   V   L   A 2647 aac cgt gaa ctg gat aaa tat ggc gtg agc gat tac tat aaa aac ctg atc aat
 883  N   R   E   L   D   K   Y   G   V   S   D   Y   Y   K   N   L   I   N 2701 aac gcg aaa acc gtg gaa ggc gtg aaa gcg ctg att gat gaa att ctg gcc gcg
 901  N   A   K   T   V   E   G   V   K   A   L   I   D   E   I   L   A   A 2755 ctg ccg tga
 919  L   P   -
```

Fig. 26C

[V$_H$-V$_L$(FAP)]$_{hu36}$-scTrail (SEQ ID NO: 127)

Leader: aa res. 1-19
FLAG tag with linkers: 20-33
VH: 34-153
Linker: 154-158
VL: 159-270
Linker: 271-278
TRAIL: 279-465
Linker: 466-473
TRAIL: 474-660
Linker: 661-668
TRAIL: 669-855

```
  1   MDWTWRVFCL LAVAPGAHSL EASDYKDDDD KGAQVQLVES GGGLVKPGGS
 51   LRLSCKTSGY TFTENIIHWI RQAPGKGLEW IGWFHPGSGS IKYNEKFKDR
101   FTISADNAKN SLYLQMNSLR AEDTAVYYCA RHGGTGRGAM DYWGQGTLVT
151   VSSGGGGSEI VLTQSPATLS LSPGERATLS CRASKSVSTS AYSYMHWYQQ
201   KPGQAPRLLI YLASNLESGI PARFSGSGSG TDFTLTISSL EPEDFAVYYC
251   QHSRELPYTF GQGTKLEIKR AAAEFTRGTS EETISTVQEK QQNISPLVRE
301   RGPQRVAAHI TGTRGRSNTL SSPNSKNEKA LGRKINSWES SRSGHSFLSN
351   LHLRNGELVI HEKGFYYIYS QTYFRFQEEI KENTKNDKQM VQYIYKYTSY
401   PDPILLMKSA RNSCWSKDAE YGLYSIYQGG IFELKENDRI FVSVTNEHLI
451   DMDHEASFFG AFLVGGGGSG GGSTSEETIS TVQEKQQNIS PLVRERGPQR
501   VAAHITGTRG RSNTLSSPNS KNEKALGRKI NSWESSRSGH SFLSNLHLRN
551   GELVIHEKGF YYIYSQTYFR FQEEIKENTK NDKQMVQYIY KYTSYPDPIL
601   LMKSARNSCW SKDAEYGLYS IYQGGIFELK ENDRIFVSVT NEHLIDMDHE
651   ASFFGAFLVG GGGSGGGSTS EETISTVQEK QQNISPLVRE RGPQRVAAHI
701   TGTRGRSNTL SSPNSKNEKA LGRKINSWES SRSGHSFLSN LHLRNGELVI
751   HEKGFYYIYS QTYFRFQEEI KENTKNDKQM VQYIYKYTSY PDPILLMKSA
801   RNSCWSKDAE YGLYSIYQGG IFELKENDRI FVSVTNEHLI DMDHEASFFG
851   AFLVG
```

Fig. 27

V$_H$-V$_L$(FAP)]$_{C13}$-scTrail (SEQ ID NO: 128)

Leader: aa res. 1-19
FLAG tag with linkers: 20-33
VH: 34-152
Linker: 153-157
VL: 158-265
Linker: 266-273
TRAIL: 274-460
Linker: 461-468
TRAIL: 469-655
Linker: 656-663
TRAIL: 664-850

```
  1   MDWTWRVFCL LAVAPGAHSL EASDYKDDDD KGAEVQLVES GGTLVQPGGS
 51   LRLSCAASGF TFSSYAMSWI RQAPGKGLEW VSGISASGGY IDYADSVKGR
101   VTISRDNSKN MAYLQMSSLR AEDTALYYCA KGGNYQMLLD HWGQGTLVTV
151   SSGGGGSDIQ MTQSPSSLSA STGDRVTITC RASQDISSYL AWYQQAPGKA
201   PHLLMSGATT LQTGVPSRFS GSGSGTDFTL TITSLQSEDF ATYYCQQYYI
251   YPPTFGQGTR VEIKRAAAEF TRGTSEETIS TVQEKQQNIS PLVRERGPQR
301   VAAHITGTRG RSNTLSSPNS KNEKALGRKI NSWESSRSGH SFLSNLHLRN
351   GELVIHEKGF YYIYSQTYFR FQEEIKENTK NDKQMVQYIY KYTSYPDPIL
401   LMKSARNSCW SKDAEYGLYS IYQGGIFELK ENDRIFVSVT NEHLIDMDHE
451   ASFFGAFLVG GGGSGGGSTS EETISTVQEK QQNISPLVRE RGPQRVAAHI
501   TGTRGRSNTL SSPNSKNEKA LGRKINSWES SRSGHSFLSN LHLRNGELVI
551   HEKGFYYIYS QTYFRFQEEI KENTKNDKQM VQYIYKYTSY PDPILLMKSA
601   RNSCWSKDAE YGLYSIYQGG IFELKENDRI FVSVTNEHLI DMDHEASFFG
651   AFLVGGGGSG GGSTSEETIS TVQEKQQNIS PLVRERGPQR VAAHITGTRG
701   RSNTLSSPNS KNEKALGRKI NSWESSRSGH SFLSNLHLRN GELVIHEKGF
751   YYIYSQTYFR FQEEIKENTK NDKQMVQYIY KYTSYPDPIL LMKSARNSCW
801   SKDAEYGLYS IYQGGIFELK ENDRIFVSVT NEHLIDMDHE ASFFGAFLVG
```

Fig. 28

[V$_H$-V$_L$(FAP)]$_{C50}$-scTrail (SEQ ID NO: 129)

```
Leader: aa res. 1-19
FLAG tag with linkers: 20-33
VH: 34-159
Linker: 160-164
VL: 165-272
Linker: 273-280
TRAIL: 281-467
Linker: 468-475
TRAIL: 476-662
Linker: 663-670
TRAIL: 671-857
```

```
  1   MDWTWRVFCL LAVAPGAHSL EASDYKDDDD KGAEVQLVES GGGLVQPGGS
 51   LRLSCAASGF TFSNYWMSWV RQAPGKGLEW VANIKQDGSE KYYVDSVKGR
101   FTISRDNAKN SLYLQMNSLR AEDTAVYYCA RGSLCTDGSC PTIGPGPNWG
151   QGTLVTVSSG GGGSDIQMTQ SPSSLSASTG DRVTITCRAS QDISSYLAWY
201   QQAPGKAPHL LMSGATTLQT GVPSRFSGSG SGTDFTLTIT SLQSEDFATY
251   YCQQYYIYPP TFGQGTRVEI KRAAAEFTRG TSEETISTVQ EKQQNISPLV
301   RERGPQRVAA HITGTRGRSN TLSSPNSKNE KALGRKINSW ESSRSGHSFL
351   SNLHLRNGEL VIHEKGFYYI YSQTYFRFQE EIKENTKNDK QMVQYIYKYT
401   SYPDPILLMK SARNSCWSKD AEYGLYSIYQ GGIFELKEND RIFVSVTNEH
451   LIDMDHEASF FGAFLVGGGG SGGGSTSEET ISTVQEKQQN ISPLVRERGP
501   QRVAAHITGT RGRSNTLSSP NSKNEKALGR KINSWESSRS GHSFLSNLHL
551   RNGELVIHEK GFYYIYSQTY FRFQEEIKEN TKNDKQMVQY IYKYTSYPDP
601   ILLMKSARNS CWSKDAEYGL YSIYQGGIFE LKENDRIFVS VTNEHLIDMD
651   HEASFFGAFL VGGGGSGGGS TSEETISTVQ EKQQNISPLV RERGPQRVAA
701   HITGTRGRSN TLSSPNSKNE KALGRKINSW ESSRSGHSFL SNLHLRNGEL
751   VIHEKGFYYI YSQTYFRFQE EIKENTKNDK QMVQYIYKYT SYPDPILLMK
801   SARNSCWSKD AEYGLYSIYQ GGIFELKEND RIFVSVTNEH LIDMDHEASF
851   FGAFLVG
```

Fig. 29

RECOMBINANT TNF LIGAND FAMILY MEMBER POLYPEPTIDES WITH ANTIBODY BINDING DOMAIN AND USES THEREOF

This application is a continuation of U.S. application Ser. No. 14/009,186, filed Aug. 22, 2014, which is a U.S. National Stage Application of International Application No. PCT/EP2012/001426, filed Mar. 30, 2012, and claims the benefit of European Patent Application No. EP 11002745.5, filed Apr. 1, 2011, the disclosures of each of which are explicitly incorporated by reference herein in their entirety.

The present invention relates in general to the field of TNF ligand family members. In more detail the present invention relates to polypeptides comprising at least three components A, each of which comprises the sequence of a TNF homology domain (THD) of a TNF ligand family member, or a functional derivative thereof, and comprising at least one component B consisting of a $V_L$ region and a $V_H$ region linked directly to each other with a linker sequence L which has a length of ≤12 amino acid residues. Furthermore, the present invention also relates to nucleic acids encoding such polypeptides.

The members of the TNF ligand family are proinflammatory cytokines. Cytokines in general, and in particular members of the TNF ligand family, play a crucial role in the stimulation and coordination of the innate immune system as well as in the adaptive immune response (including both cellular and humoral immunity), induction of apoptosis, bone architecture, hair growth, teeth growth, development of perspiratory glands, lymph node development and many more (Aggarwal, B. B. (2003), Nat. Rev. Immunol. 3, 745-756). A dysregulation of the activity of members of the TNF ligand family can, however, lead to a multitude of pathologies. This includes for example septic shock, autoimmune diseases like rheumatoid arthritis, or neurodegenerative diseases. Tumor necrosis factor (TNF) is the name-giving and probably most important member of this large cytokine family.

Members of the TNF ligand family exert their biological function as homotrimers (Banner, D. W. et al, (1993), Cell 73, 431-445). Trimeric structures and likewise aggregations of higher order (e.g. oligomers or multimers of trimers) of such proteins may be encountered frequently in nature. Examples for this are the Cartilage Matrix Protein (CMP), which is a connective tissue protein (Beck et al. (1996), J. Mol. Biol. 256, 909-923), proteins of the family of collagens, like the C1q family to which C1q, collagen α1 (X), α2 (VII), the hibernation protein, ACRP30, the inner ear structure protein, cellebrin and multimerin belong (Kishore and Reid (1999), Immunopharmacol. 42, 15-21), and proteins of the collectin family such as lung surfactant protein A (SP-A) and mannose binding protein (MBP) (Epstein et al., (1996), Current Opinion in Immunology, Vol. 8, No. 1, 29-35).

Trimer formation occurs due to interactions between the individual monomers such as hydrophobic interactions, hydrogen bridges, covalent bonds (e.g. disulfide bonds), and/or Coulomb forces, but also occurs on basis of structural motifs, i.e. specific amino acid sequences which lead to formation of intermolecular supersecondary structures. In case of the members of the TNF ligand family, the three monomers associate in the homotrimeric structure via non-covalent hydrophobic bonds. In the active form they in turn activate members of the TNF receptor family which themselves do not possess any enzymatic activity. For example, TNF being a member of the TNF ligand family binds to the two membrane receptors TNFR1 and TNFR2 and mediates the oligomerization and the activation of inactive receptors. As a consequence of the receptor complex formation a signal cascade is initiated which brings about inter alia an association of cytoplasmatic adaptor proteins (Wajant, H. et al. (2003), Cell Death, Differ, 10, 45-65). The interaction of TNFR1 and TNFR2 with its ligand is characterized by binding of the receptors at the space between two of the three TNF monomers of the TNF homotrimer (Banner (1993), supra). This illustrates that TNF as well as all the other members of the TNF ligand family are only biologically active in the homotrimeric structure. Due to their function, members of the TNF ligand family and the respective membrane receptors, respectively, may be used for many kinds of treatments of diseases, such as infectious diseases, inflammatory diseases, metabolic diseases, diseases resulting from a dysregulation of apoptosis, neurodegenerative diseases and many more diseases. They play a particularly important role in the treatment of cancerous diseases because members of the TNF ligand family exhibit in general an antitumor activity. This applies in particular to TNF (Eggermont, A. M. and ten Hagen, T. L. (2003), Curr. Oncol. Rep. 5, 79-80), TRAIL (TNF related apoptosis using ligand), also termed Apo 2L (Weley et al. (1995), Immunity 6: 673-682; Petti et al. (1996), J. Biol. Chem. 271: 12687-12689) and FasL (CD95L). However, in vivo experiments showed strong systematic adverse reactions for TNF and agonists of the Fas receptor, and in vitro experiments indicate similarly toxic effects for certain TRAIL compounds (Jo et al. (2000) Nat Med 6: 564-567, Ichikawa et al. (2001) Nat Med 7: 954-960; Ogasawara et al. (1993) Nature 364: 806-809). For this reason, the clinical use of Fas activating ligands/agonists in a systemic application has so far been considered impossible due to safety concerns. However, due to the importance of TNF, TRAIL, FasL (CD95L) and other TNF ligand family members for this field, and due to the adverse reactions associated with their application in form of a clinical systemic administration, several alternative approaches were pursued in order to minimize the adverse reactions (Eggermont, A. M. and ten Hagen, T. L. (2003), Curr. Oncol. Rep. 5, 79-80).

WO 02/22680 describes for example fusion proteins which allow a targeted and tissue and/or cell-specific activity of cytokines by fusing the cytokine with an antigen-binding antibody. By this means it is achieved that the cytokine is not active on tissue or cells, respectively, which are not in contact with these fusion proteins, and that adverse reactions regarding these tissues and cells, respectively, are reduced.

In DE 102 47 755 an antibody-independent system is disclosed, which likewise allows for a targeted, tissue- and cell-specific action of the cytokines. The document discloses fusion proteins with a biologically active domain and a cell surface binding domain. Biological activity of the biologically active domain is mediated by binding of the cell surface binding domain to the respective cell surface. Besides of providing a reduction of adverse reactions for non-target tissue, this system may also be advantageously used for cell surface molecules on target cells for which no or only low specificity antibodies are available.

Apart from the above-mentioned adverse reactions it is additionally problematic that the active homotrimers of members of the TNF ligand family dissociate even at physiologically reasonable concentrations. This dissociation is reversible; however, the protein quickly loses its bioactivity because it is denaturing. It is assumed that this denaturing is due to the intermediate, unstable monomers (Smith, R. A. and Baglioni, C. (1987), J. Biol. Chem. 262, 6951-6954; Narhi, L. O. and Arakawa, T. (1987), Biochem. Biophys. Res. Commun 147, 740-746).

In a first attempt this problem has been addressed in the art for example in WO 01/25277. WO 01/25277 discloses single-chain TNFα polypeptides with 3 copies of a TNFα monomer. Due to the single chain nature, dissociation is prevented. A similar concept is disclosed in WO 2005/103077.

In addition it has been reported in the prior art that oligomeric molecules of TNF ligand family members exhibit increased activity but likewise increased toxicity (Koschny R et al. J Mol Med 2007; 85: 923-935; Gerspach J et al., Results Probl Cell Differ. 2009; 49:241-73. Review. Wyzgol et al JI 2010).

Thus, there is still in the art a need for novel and improved TNF ligand family derived compounds, which are preferably stable, exhibit few(er) or no adverse systemic reactions while in parallel maintaining biological specificity.

This object is solved by the present invention, in particular by means as set forth in the appended set of claims and as illustrated in the following.

The inventors of the present invention have surprisingly found that polypeptides of the present invention exhibit increased activity against tumors while they do at the same time surprisingly not exhibit increased toxicity towards non-tumor tissue.

Essentially, the polypeptides of the present invention are fusion proteins comprising on the one hand at least three TNF ligand family member monomers and comprising the variable domains of an antibody $V_L$ and $V_H$ region linked by a short linker as targeting moiety on the other hand. To increase specificity, to increase in vivo half-life and to modulate pharmacodynamic properties, the polypeptides according to the present invention may further comprise an albumin binding domain and/or other domains and/or other modifications.

Thus, in a first aspect the present invention relates to a polypeptide which comprises:
  a) at least three components A, each of which comprises the sequence of a TNF homology domain (THD) of a TNF ligand family member, or functional derivative thereof, and
  b) at least one component B consisting of a $V_L$ region and a $V_H$ region linked directly to each other with a linker sequence L which has a length of ≤12 amino acid residues.

The term "polypeptide" as used herein refers to a polymer composed of a sequence of amino acids. The term shall not be construed as limiting the length of the polypeptide unit. However, preferably, the polypeptide has a length of less than 1000 amino acids, more preferably less than 900 amino acids. The amino acids within the polymer of said polypeptide sequence are usually linked to each other via peptide bonds, but modifications of said peptide bond(s) or of side chain residues may be tolerable, provided the overall activity is not totally lost, e.g. the resulting chemical entity (e.g. components A) still trimerizes and activates its targets.

The TNF homology domain is the common structural feature shared by all TNF ligand family members Bodmer J L et al. (Trends Biochem Sci. 2002 January; 27(1):19-26.). It comprises the receptor binding sites and is thus critical for the biologic activity of the TNF ligand family members. A component A of the present invention may have as minimal motif the THD, e.g. of a given TNF ligand family member, but may for example also comprise longer sequence stretches of TNF ligand family members such as the sequence of the soluble form (shed or secreted, respectively) of said TNF ligand family member. The sequence may also comprise the entire extracellular domain of a TNF ligand family member, but preferably without the protease cleavage site naturally present in some of these TNF ligand family members, e.g. without a TACE/ADAM17 cleavage site in order to avoid cleavage of the fusion protein in the region comprising the three components A.

The THD domain may be for example selected from the TNF ligand family member group consisting of: FasL (CD95L), TRAIL, TNF, LT alpha, LT beta, CD30L, CD40L, OX40L, RANKL, TWEAK, LIGHT, CD27L, 4-1BBL, GITRL, APRIL, EDA 1, EDA 2, VEGI und BAFF. Particularly preferred are the human TNF ligand family members human FasL (CD95L), human TRAIL, human TNF, human LT alpha, human LT beta, human CD30L, human CD40L, human OX40L, human RANKL, human TWEAK, human LIGHT, human CD27L, human 4-1 BBL, human GITRL, human APRIL, human EDA 1, human EDA 2, human VEGI und human BAFF.

Further information, in particular about sequences of the TNF ligand family members, may be obtained for example from publicly accessible databases such as the GenBank: FasL (CD95L) (GenBank Accession No. NM_000639), TRAIL (TNF Related Apoptosis Inducing Ligand; GenBank Accession No. NM_003810), also Apo2L termed, TNF (Tumor Nekrose Faktor; GenBank Accession No. NM_000594), LT alpha (GenBank Accession No. NM_000595), Lymphotoxin beta (GenBank Accession No. NM_002341), CD30L (CD153; GenBank Accession No. NM_001244), CD40L (CD154; GenBank Accession No. NM_00074), OX40L (GenBank Accession No. NM_003326), RANKL (GenBank Accession No. NM_003701), TWEAK (GenBank Accession No. NM_003809), LIGHT (GenBank Accession No. NM_003807), CD27L (GenBank Accession No. NM_001252), 4-1 BBL (GenBank Accession No. NM_003811), GITRL (GenBank Accession No. NM_005092), APRIL (GenBank Accession No. NM_172089), EDA 1/2 (GenBank Accession No. NM_001399; NM_001005609), VEGI (GenBank Accession No. NM_005118) und BAFF (GenBank Accession No. NM_006573).

The sequences of the at least three components A of the polypeptides according to the invention may be selected independently of each other; e.g. the three components A may have the respective sequence of the same TNF ligand family member or may have the sequence of different TNF ligand family members or 2 of them may be identical while the other one differs in sequence (in terms of length and/or sequence). THD domains of different TNF ligand family members is in particular possible if the THD domain is selected from LT alpha or LT beta. Otherwise, it is particularly preferred if all three components A comprise the THD of the same TNF ligand family member. Certainly, similar considerations apply if the polypeptide according to the present invention comprises more than 3 components A. For example, the inventive polypeptide may comprise 4, 5, 6 or more components A. If the polypeptide according to the present invention comprises more than 3 components A then it is particularly preferred that the polypeptide comprises a multiple of three components A. By this means, two, three, four or more consecutively arranged trimers may be formed.

In a preferred embodiment a given component A may comprise or consist of one of the human sequences according to SEQ ID NOs.: 1-38 as indicated in Table 1 below, or functional fragments or functional derivatives thereof, which includes natural or artificial variations thereof or respective orthologs from other species. Preferred are orthologs from other mammalian species such as chimpanzee, mouse, swine, rat etc.

TABLE 1

| | | | |
|---|---|---|---|
| Possible Components A | | | |
| Name: | AA Position | SEQ ID NO: | Sequence |
| TRAIL | 120-281 | 1 | QRVAAHITGTRGRSNTLSSPNSKNEKALGRKINSWESSRSGHSFLSNLHLRNGELVIHEKGFYYIYSQTYFRFQEEIKENTKNDKQMVQYIYKYTSYPDPILLMKSARNSCWSKDAEYGLYSIYQGGIFELKENDRIFVSVTNEHLIDMDHEASFFGAFLVG |
| TRAIL | 118-281 | 2 | GPQRVAAHITGTRGRSNTLSSPNSKNEKALGRKINSWESSRSGHSFLSNLHLRNGELVIHEKGFYYIYSQTYFRFQEEIKENTKNDKQMVQYIYKYTSYPDPILLMKSARNSCWSKDAEYGLYSIYQGGIFELKENDRIFVSVTNEHLIDMDHEASFFGAFLVG |
| TRAIL | 116-281 | 3 | ERGPQRVAAHITGTRGRSNTLSSPNSKNEKALGRKINSWESSRSGHSFLSNLHLRNGELVIHEKGFYYIYSQTYFRFQEEIKENTKNDKQMVQYIYKYTSYPDPILLMKSARNSCWSKDAEYGLYSIYQGGIFELKENDRIFVSVTNEHLIDMDHEASFFGAFLVG |
| TRAIL | 114-281 | 4 | VRERGPQRVAAHITGTRGRSNTLSSPNSKNEKALGRKINSWESSRSGHSFLSNLHLRNGELVIHEKGFYYIYSQTYFRFQEEIKENTKNDKQMVQYIYKYTSYPDPILLMKSARNSCWSKDAEYGLYSIYQGGIFELKENDRIFVSVTNEHLIDMDHEASFFGAFLVG |
| TRAIL | 95-281 | 5 | TSEETISTVQEKQQNISPLVRERGPQRVAAHITGTRGRSNTLSSPNSKNEKALGRKINSWESSRSGHSFLSNLHLRNGELVIHEKGFYYIYSQTYFRFQEEIKENTKNDKQMVQYIYKYTSYPDPILLMKSARNSCWSKDAEYGLYSIYQGGIFELKENDRIFVSVTNEHLIDMDHEASFFGAFLVG |
| mouse TRAIL | 99-291 | 6 | TFQDTISTVPEKQLSTPPLPRGGRPQKVAAHITGITRRSNSALIPISKDGKTLGQKIESWESSRKGHSFLNHVLFRNGELVIEQEGLYYIYSQTYFRFQEAEDASKMVSKDKVRTKQLVQYIYKYTSYPDPIVLMKSARNSCWSRDAEYGLYSIYQGGLFELKKNDRIFVSVTNEHLMDLDQEASFFGAFLIN |
| FasL (CD95L) | 144-281 | 7 | RKVAHLTGKSNSRSMPLEWEDTYGIVLLSGVKYKKGGLVINETGLYFVYSKVYFRGQSCNNLPLSHKVYMRNSKYPQDLVMMEGKMMSYCTTGQMWARSSYLGAVFNLTSADHLYVNVSELSLVNFEESQTFFGLYKL |
| FasL (CD95L) | 142-281 | 8 | ELRKVAHLTGKSNSRSMPLEWEDTYGIVLLSGVKYKKGGLVINETGLYFVYSKVYFRGQSCNNLPLSHKVYMRNSKYPQDLVMMEGKMMSYCTTGQMWARSSYLGAVFNLTSADHLYVNVSELSLVNFEESQTFFGLYKL |
| FasL (CD95L) | 137-281 | 9 | PPEKKELRKVAHLTGKSNSRSMPLEWEDTYGIVLLSGVKYKKGGLVINETGLYFVYSKVYFRGQSCNNLPLSHKVYMRNSKYPQDLVMMEGKMMSYCTTGQMWARSSYLGAVFNLTSADHLYVNVSELSLVNFEESQTFFGLYKL |
| FasL (CD95L) | 130-281 | 10 | QIGHPSPPPEKKELRKVAHLTGKSNSRSMPLEWEDTYGIVLLSGVKYKKGGLVINETGLYFVYSKVYFRGQSCNNLPLSHKVYMRNSKYPQDLVMMEGKMMSYCTTGQMWARSSYLGAVFNLTSADHLYVNVSELSLVNFEESQTFFGLYKL |
| FasL (CD95L) | 120-281 | 11 | QMHTASSLEKQIGHPSPPPEKKELRKVAHLTGKSNSRSMPLEWEDTYGIVLLSGVKYKKGGLVINETGLYFVYSKVYFRGQSCNNLPLSHKVYMRNSKYPQDLVMMEGKMMSYCTTGQMWARSSYLGAVFNLTSADHLYVNVSELSLVNFEESQTFFGLYKL |

TABLE 1-continued

Possible Components A

| Name: | AA Position | SEQ ID NO: | Sequence |
|---|---|---|---|
| Mouse FasL (CD95L) | 137-279 | 12 | EKKEPRSVAHLTGNPHSRSIPLEWEDTYGTA LISGVKYKKGGLVINETGLYFVYSKVYFRGQS CNNQPLNHKVYMRNSKYPEDLVLMEEKRL NYCTTGQIWAHSSYLGAVFNLTSADHLYV NISQLSLINFEESKTFFGLYKL |
| TNF | 89-233 | 13 | VAHVVANPQAEGQLQWLNRRANALLANG VELRDNQLVVPSEGLYLIYSQVLFKGQGCPS THVLLTHTISRIAVSYQTKVNLLSAIKSPCQRE TPEGAEAKPWYEPIYLGGVFQLEKGDRLSAEI NRPDYLDFAESGQVYFGIIAL |
| TNF | 77-233 | 14 | VRSSSRTPSDKPVAHVVANPQAEGQLQWL NRRANALLANGVELRDNQLVVPSEGLYLIYS QVLFKGQGCPSTHVLLTHTISRIAVSYQTKV NLLSAIKSPCQRETPEGAEAKPWYEPIYLGGV FQLEKGDRLSAEINRPDYLDFAESGQVYFGII AL |
| LT alpha | 59-205 | 15 | SNLKPAAHLIGDPSKQNSLLWRANTDRAFL QDGFSLSNNSLLVPTSGIYFVYSQVVFSGKA YSPKATSSPLYLAHEVQLFSSQYPFHVPLLSS QKMVYPGLQEPWLHSMYHGAAFQLTQGD QLSTHTDGIPHLVLSPSTVFFGAFAL |
| LT beta | 82-244 | 16 | DLSPGLPAAHLIGAPLKGQGLGWETTKEQA FLTSGTQFSDAEGLALPQDGLYYLYCLVGYR GRAPPGGGDPQGRSVTLRSSLYRAGGAYG PGTPELLLEGAETVTPVLDPARRQGYGPLWY TSVGFGGLVQLRRGERVYVNISHPDMVDFA RGKTFFGAVMVG |
| LT beta | 86-244 | 17 | GLPAAHLIGAPLKGQGLGWETTKEQAFLTS GTQFSDAEGLALPQDGLYYLYCLVGYRGRA PPGGGDPQGRSVTLRSSLYRAGGAYGPGTP ELLLEGAETVTPVLDPARRQGYGPLWYTSV GFGGLVQLRRGERVYVNISHPDMVDFARG KTFFGAVMVG |
| CD30L | 97-234 | 18 | KSWAYLQVAKHLNKTKLSWNKDGILHGVR YQDGNLVIQFPGLYFIICQLQFLVQCPNNS VDLKLELLINKHIKKQALVTVCESGMQTKHV YQNLSQFLLDYLQVNTTISVNVDTFQYIDTS TFPLENVLSIFLYSNSD |
| CD30L | 102-234 | 19 | LQVAKHLNKTKLSWNKDGILHGVRYQDG NLVIQFPGLYFIICQLQFLVQCPNNSVDLKLE LLINKHIKKQALVTVCESGMQTKHVYQNLS QFLLDYLQVNTTISVNVDTFQYIDTSTFPLEN VLSIFLYSNSD |
| CD40L | 116-261 | 20 | GDQNPQIAAHVISEASSKTTSVLQWAEKGY YTMSNNLVTLENGKQLTVKRQGLYYIYAQV TFCSNREASSQAPFIASLCLKSPGRFERILLRA ANTHSSAKPCGQQSIHLGGVFELQPGASVF VNVTDPSQVSHGTGFTSFGLLKL |
| CD40L | 113-261 | 21 | MQKGDQNPQIAAHVISEASSKTTSVLQWAE KGYYTMSNNLVTLENGKQLTVKRQGLYYIY AQVTFCSNREASSQAPFIASLCLKSPGRFERIL LRAANTHSSAKPCGQQSIHLGGVFELQPGA SVFVNVTDPSQVSHGTGFTSFGLLKL |
| OX40L | 52-183 | 22 | VSHRYPRIQSIKVQFTEYKKEKGFILTSQKEDE IMKVQNNSVIINCDGFYLISLKGYFSQEVNIS LHYQKDEEPLFQLKKVRSVNSLMVASLTYKD KVYLNVTTDNTSLDDPHVNGGELILIHQNP GEFCVL |
| OX40L | 55-183 | 23 | RYPRIQSIKVQFTEYKKEKGFILTSQKEDEIMK VQNNSVIINCDGFYLISLKGYFSQEVNISLHY QKDEEPLFQLKKVRSVNSLMVASLTYKDKVY LNVTTDNTSLDDPHVNGGELILIHQNPGEF CVL |

TABLE 1-continued

Possible Components A

| Name: | AA Position | SEQ ID NO: | Sequence |
|---|---|---|---|
| RANKL | 161-317 | 24 | EAQPFAHLTINATDIPSGSHKVSLSSWYHDR GWAKISNMTFSNGKLIVNQDGFYYLYANIC FRHHETSGDLATEYLQLMVYVTKTSIKIPSSH TLMKGGSTKYWSGNSEFHFYSINVGGFFKL RSGEEISIEVSNPSLLDPDQDATYFGAFKVRD ID |
| RANKL | 140-317 | 25 | IRAEKAMVDGSWLDLAKRSKLEAQPFAHLTI NATDIPSGSHKVSLSSWYHDRGWAKISNMT FSNGKLIVNQDGFYYLYANICFRHHETSGDL ATEYLQLMVYVTKTSIKIPSSHTLMKGGSTKY WSGNSEFHFYSINVGGFFKLRSGEEISIEVSNP SLLDPDQDATYFGAFKVRDID |
| TWEAK | 94-249 | 26 | SAPKGRKTRARRAIAAHYEVHPRPGQDGA QAGVDGTVSGWEEARINSSSPLRYNRQIGE FIVTRAGLYYLYCQVHFDEGKAVYLKLDLLV DGVLALRCLEEFSATAASSLGPQLRLCQVSG LLALRPGSSLRIRTLPWAHLKAAPFLTYFGLF QVH |
| TWEAK | 105-249 | 27 | RAIAAHYEVHPRPGQDGAQAGVDGTVSG WEEARINSSSPLRYNRQIGEFIVTRAGLYYLY CQVHFDEGKAVYLKLDLLVDGVLALRCLEEF SATAASSLGPQLRLCQVSGLLALRPGSSLRIR TLPWAHLKAAPFLTYFGLFQVH |
| LIGHT | 83-240 | 28 | LIQERRSHEVNPAAHLTGANSSLTGSGGPLL WETQLGLAFLRGLSYHDGALVVTKAGYYYI YSKVQLGGVGCPLGLASTITHGLYKRTPRYP EELELLVSQQSPCGRATSSSRVWWDSSFLGG VVHLEAGEKVVVRVLDERLVRLRDGTRSYF GAFMV |
| CD27L | 51-193 | 29 | ESLGWDVAELQLNHTGPQQDPRLYWQGG PALGRSFLHGPELDKGQLRIHRDGIYMVHI QVTLAICSSTTASRHHPTTLAVGICSPASRSIS LLRLSFHQGCTIASQRLTPLARGDTLCTNLT GTLLPSRNTDETFFGVQWVRP |
| CD27L | 56-193 | 30 | DVAELQLNHTGPQQDPRLYWQGGPALGR SFLHGPELDKGQLRIHRDGIYMVHIQVTLAI CSSTTASRHHPTTLAVGICSPASRSISLLRLSF HQGCTIASQRLTPLARGDTLCTNLTGTLLPS RNTDETFFGVQWVRP |
| 4-1 BBL | 85-254 | 31 | LDLRQGMFAQLVAQNVLLIDGPLSWYSDP GLAGVSLTGGLSYKEDTKELVVAKAGVYYVF FQLELRRVVAGEGSGSVSLALHLQPLRSAAG AAALALTVDLPPASSEARNSAFGFQGRLLHL SAGQRLGVHLHTEARARHAWQLTQGATV LGLFRVTPEIPAGLPSPRSE |
| GITRL | 50-177 | 32 | QLETAKEPCMAKFGPLPSKWQMASSEPPCV NKVSDWKLEILQNGLYLIYGQVAPNANYN DVAPFEVRLYKNKDMIQTLTNKSKIQNVGG TYELHVGDTIDLIFNSEHQVLKNNTYWGIILL ANPQFIS |
| APRIL | 112-250 | 33 | KKQHSVLHLVPINATSKDDSDVTEVMWQP ALRRGRGLQAQGYGVRIQDAGVYLLYSQV LFQDVTFTMGQVVSREGQGRQETLFRCIRS MPSHPDRAYNSCYSAGVFHLHQGDILSVIIP RARAKLNLSPHGTFLGFVKL |
| EDA-1 | 245-391 | 34 | ENQPAVVHLQGQGSAIQVKNDLSGGVLN DWSRITMNPKVFKLHPRSGELEVLVDGTYFI YSQVEVYYINFTDFASYEVVVDEKPFLQCTRS IETGKTNYNTCYTAGVCLLKARQKIAVKMV HADISINMSKHTTFFGAIRLGEAPAS |
| EDA-2 | 245-389 | 35 | ENQPAVVHLQGQGSAIQVKNDLSGGVLN DWSRITMNPKVFKLHPRSGELEVLVDGTYFI YSQVYYINFTDFASYEVVVDEKPFLQCTRSIE |

TABLE 1-continued

Possible Components A

| Name: | AA Position | SEQ ID NO: | Sequence |
|---|---|---|---|
| | | | TGKTNYNTCYTAGVCLLKARQKIAVKMVH ADISINMSKHTTFFGAIRLGEAPAS |
| VEGI | 72-251 | 36 | LKGQEFAPSHQQVYAPLRADGDKPRAHLT VVRQTPTQHFKNQFPALHWEHELGLAFTK NRMNYTNKFLLIPESGDYFIYSQVTFRGMTS ECSEIRQAGRPNKPDSITVVITKVTDSYPEPT QLLMGTKSVCEVGSNWFQPIYLGAMFSLQE GDKLMVNVSDISLVDYTKEDKTFFGAFLL |
| VEGI | 93-251 | 37 | DKPRAHLTVVRQTPTQHFKNQFPALHWEH ELGLAFTKNRMNYTNKFLLIPESGDYFIYSQV TFRGMTSECSEIRQAGRPNKPDSITVVITKVT DSYPEPTQLLMGTKSVCEVGSNWFQPIYLG AMFSLQEGDKLMVNVSDISLVDYTKEDKTFF GAFLL |
| BAFF | 134-285 | 38 | AVQGPEETVTQDCLQLIADSETPTIQKGSYT FVPWLLSFKRGSALEEKENKILVKETGYFFIYG QVLYTDKTYAMGHLIQRKKVHVFGDELSLV TLFRCIQNMPETLPNNSCYSAGIAKLEEGDEL QLAIPRENAQISLDGDVTFFGALKLL |

The column "Amino acid position" indicates the amino acid residues in the full length native protein, i.e. the sequence given in the sequence column corresponds to the respective amino acid residues in the full length sequence. For example, SEQ ID NO: 1 corresponds to amino acid residues 120-281 of full length human TRAIL.

Information about natural variations of SEQ ID NOs: 1-38 and respective orthologs from other species may be easily obtained from publicly accessible databases comprising information about proteins of the TNF ligand family members or respective nucleic acid sequences. Examples for such databases are UniProt; SwissProt, TrEMBL, Protein Information Resource (PIR); Genbank, EMBL-Bank; DNA data bank of Japan (DDBJ) etc. Orthologs of other species may in particular be likewise identified via e.g. BLAST searches on basis of the respective SEQ ID NOs: 1-38.

Preferred substitutions in human TRAIL in this regard affect at least one of the following amino acids of human TRAIL: R130, G160, Y189, R191, Q193, E195, N199, K201, Y213, T214, S215, H264, 1266, D267, D269. Preferred amino acid substitutions of human TRAIL are at least one of the following substitutions: R130E, G160M, Y189A, Y189Q, R191K, Q193S, Q193R, E195R, N199V, N199R, K201R, Y213W, T214R, S215D, H264R, 1266L, D267Q, D269H, D269R, or D269K. Double or multiple substitutions are also possible, e.g. Y213W/S215D; E195R/D269H, T214R/D269H; Q193S/N199V/K201R/Y213W/S215D. Functional mutants of TRAIL are for example described in R. F. Kelley et al. (J. Biol. Chem.; 280 (2005) 2205-2212) M. MacFarlane et al. (Cancer Res 65 (2005) 11265-11270), A. M. van der Sloot et al. (Proc. Natl. Acad. Sci. USA 103 (2006) 8634-8639), V. Tur et al. (J. Biol. Chem. 283 (2008) 20560-20568), and Gasparian et al. (Apoptosis 14 (2009) 778-787). Functional mutants of TRAIL are in particular TRAIL (96-281), TRAIL (96-281)-Y189N/R191K/Q193R/H264R/I266L/D267Q, TRAIL (96-281)-Y189A/Q193S/N199V/K201/Y213W/S215D, TRAIL (96-281)-Q193S/N199V/K201R/Y213W/S215N, TRAIL (96-281)-Y189Q/R191K/Q193R/H264R/I266L/D267Q, TRAIL (114-281), TRAIL (114-281)-D269H/E195R, TRAIL (114-281)-D269H, TRAIL (114-281)-D218H, TRAIL (114-281)-D218Y, TRAIL (114-281)-Y189A/Q193S/N199V/K201/Y213W/S215D, TRAIL (114-281)-Y189N/R191K/Q193R/H264R/I266LD267Q, TRAIL (114-281)-Y189N/R191K/Q193R/H264R/I266L/D267Q/D269H, and TRAIL (114-281)-Y189N/R191K/Q193R/H264R/I266L/D269H.

As mentioned above, a component A as used herein refers to a polypeptide comprising the sequence of a TNF homology domain (THD); or a functional derivative thereof. Since the polypeptides of the present invention comprise three of said components A, trimer formation and thus the formation of the active conformation is possible. A polypeptide according to the present invention furthermore exhibits due to the presence of the at least 3 components A binding activity for the binding partners of TNF ligand family members, such as membrane-bound receptors. Functional derivatives of the TNF ligand family member sequence may exhibit (slightly) different activities and biological functions, e.g. regarding specificity or selectivity, but their overall biological function is maintained. In particular, the receptor binding activity should be maintained.

In the prior art, a multitude of methods is disclosed which allow the assessment of the biological activity of a protein, polypeptide or other molecule, respectively. Examples are protein analytical methods such as Immunoblot, ELISA, Radioimmunoassay, Immune precipitation, Surface Plasmon Resonance (Biacore), Quartz Crystal Microbalance (QCM); cell and tissue analytical methods such as immunocytochemistry, immunohistochemistry, fluorescence microscopy, FACS; cell function assays: such as cytokine-release assays, proliferation and cell cycle assays ($^3$H-thymidine incorporation, CFSE staining), cytotoxicity assays, apoptosis assays, NFkB bandshift (EMSA) and reporter gene (Luciferase) assays, kinase assays (e.g. in Antibodies: a laboratory manual. Harlow & Lane, Cold Spring Harbor Laboratory Press; 1 edition (Dec. 1, 1988) Current Protocols in Immunology, Wiley and Sons, 1992); Cell Biology, A Laboratory Handbook 3rd ed., J Celis et al, eds. Elsevier, 2006). By this means a person skilled in the art will readily be able to assess whether a functional fragment or functional derivative of the soluble TNF ligand family member sequence retains the overall properties of the soluble TNF ligand family member (e.g. induction of apoptosis/cell death or activation of NFkB).

The term "derivative", e.g. a functional derivative of the THD sequence or of one of the sequences according to SEQ ID NOs.: 1-38, is intended to refer also to sequences which exhibit a functional and structural similarity to the respective reference sequence. In particular the respective derivative will preferably exhibit a sequence identity of at least 50%, more preferably at least 60%, more preferably at least 70%, more preferably at least 80%, more preferably at least 85%, more preferably at least 90%, more preferably at least 92%, more preferably at least 94%, more preferably at least 95%, more preferably at least 96%, more preferably at least 97%, more preferably at least 98%, and most preferably at least 99% sequence identity with the respective reference sequence. A person skilled in the art will understand that such levels of sequence identity are preferably less than 100%. The derivative sequence and the reference sequence may differ from each other in terms of one or more insertions, deletions and/or substitutions.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

Methods for comparing the identity of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197) and finds the best single region of similarity between two sequences.

Functional derivatives in component A may in particular exhibit selective receptor binding properties, or may be optimized regarding bioactivity or other properties such as stability. In particular such derivatives may exhibit altered sequences at protease cleavage sites.

Derivatives as used herein in particular include those amino acid sequences which exhibit (for example in the context of a given level of sequence identity) in view of the respective reference sequence conservative substitutions. Conservative amino acid substitutions are preferably considered to occur within a group of amino acid residues which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, lie) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art.

Insertions, deletions and substitutions are in particular at such sequence positions possible where they do not induce a change in the three-dimensional structure or where they do not affect the binding region. A change in three-dimensional structure by means of insertions or deletions may for example be verified with CD spectral analysis (circular dichroism) (Urry 1985, Absorption, Circular Dichroism and ORD of Polypeptides, in: Modern Physical Methods in Biochemistry, Neuberger et al. (Eds.), Elsevier, Amsterdam, NL).

Suitable methods for producing derivatives of polypeptide sequences according to the present invention or components thereof, which exhibit in view of the reference sequence a substitution, are for example disclosed in U.S. Pat. Nos. 4,737,462, 4,588,585, 4,959,314, 5,116,943, 4,879,111 and 5,017,691. The production of derivatives as used herein is described in general in Maniatis et al. (2001), Molecular Cloning: A Laboratory Manual, Cold Spring Harbor Laboratory Press. For this approach individual codons may simply be skipped, added or exchanged. Derivatives of polypeptide sequences mentioned herein may in particular be such polypeptide sequences which are stabilized vis-à-vis the respective reference sequence and which are less prone to physiological degradation. An example for such modification is the stabilization of the protein backbone by substitution of the amid-like bonds by using e.g. g-amino acids.

Derivatives of sequences according to the invention may in particular be produced by introducing changes into the nucleic acid sequence which encode the respective polypeptide reference sequence. Such changes may be insertions, deletions and/or substitutions of one or more nucleotides, preferably without induction of a frame shift. In the art, a multitude of methods is known for introducing such changes to nucleic acid sequences. A most common technique is the oligonucleotide-directed site-specific mutagenesis (see Comack B., Current Protocols in Molecular Biology, 8.01-8.5.9, Ausubel F. et al., 1991). Briefly, an oligonucleotide is synthesized which exhibits the sequence of a specific mutation. This oligonucleotide is then hybridized with the template (reference sequence). Preferably, this technique is used for a single-stranded template. After annealing of the modified oligonucleotide and the template, a DNA-dependent DNA polymerase is added in order to synthesize the second strand of the oligonucleotide which is complementary to the templated DNA strand. As a result, a heteroduplex molecule is formed, which comprises a mismatch, which is due to the above-mentioned mutation in the oligonucleotide. The oligonucleotide sequence is then introduced in a suitable plasmid which is in turn introduced into a suitable host cell. In the host cell the oligonucleotide is then replicated. By this means a nucleic acid sequence is obtained with specific changes (mutations) which may be used for the production of derivatives according to the present invention.

In a preferred embodiment of the present invention all and/or at least three components A of the polypeptide according to the present invention have the sequence of SEQ ID NO: 1 and/or SEQ ID NO: 5.

Preferably, the at least three components A of the polypeptides according to the present invention are linked to each other by at least two intervening peptide linkers P. In other words, two given components A within the polypeptide according to the present invention are preferably linked to each other directly via a peptide linker (e.g. A-P-A-P-A). Peptide linkers P are preferably flexible amino acid stretches and/or do not affect the intrinsic trimerization properties of the components A within the polypeptide according to the present invention. Preferably, such peptide linkers P are less than 50, even more preferably less than 45, even more preferably less than 40, even more preferably less than 35, even more preferably less than 30, even more preferably less than 25, even more preferably less than 20, even more preferably less than 15, even more preferably less than 10 amino acids long. Alternatively or in addition, the peptide linkers P have preferably an amino acid length of 1 amino acid or more, 2 amino acids or more, 3 amino acids or more, 4 amino acids or more, 5 amino acids or more, 6 amino acids or more, 7 amino acids or more, and/or 8 amino acids or more. A peptide linker linking two components A of a polypeptide of the present invention may thus have for example an amino acid length in the range of 2 to 50 amino acids, 2 to 30 amino acids, 3 to 25 amino acids, 4 to 16 amino acids, 4 to 12 amino acids or any other combination of amino acids lengths disclosed above for peptide linkers. Particularly preferred are peptide linker lengths of 1 to 8 amino acids, e.g. 4 or 8 amino acids.

In terms of amino acid sequence, the peptide linkers P linking the components A within the polypeptide of the present invention are preferably glycine (G) rich peptide linkers, i.e. are amino acid sequences with a high glycine content of more than 50%; e.g. from at least 60 to 80%, for example of about 75%. Other amino acids which may be present in the peptide linker are for example serine residues or less preferably alanine residues or glutamine residues. The peptide linker P may be composed of repetitive units. For example the linker may comprise several units of GG (SEQ ID NO: 40); GGS (SEQ ID NO: 55); GSG (SEQ ID NO: 54), or SGG (SEQ ID NO: 53) and combinations thereof. The peptide linker may also be of type which may easily be modified, e.g. glycosylated. An example for such sequence are SEQ ID NOs: 83-91. Particularly preferred examples for a peptide linker P linking two components A of the present invention are selected from the group of sequences as depicted in Table 2 below:

TABLE 2

Possible Peptide linkers

| Name: | Length | SEQ ID NO: | Sequence |
|---|---|---|---|
| $(G)_1$ | 1 | 39 | G |
| $(G)_2$ | 2 | 40 | GG |
| $(G)_3$ | 3 | 41 | GGG |
| $(G)_4$ | 4 | 42 | GGGG |
| $(G)_5$ | 5 | 43 | GGGGG |
| $(G)_6$ | 6 | 44 | GGGGGG |
| $(G)_7$ | 7 | 45 | GGGGGGG |
| $(G)_8$ | 8 | 46 | GGGGGGGG |
| GGGS | 4 | 47 | GGGS |
| $(GGGS)_2$ | 8 | 48 | GGGSGGGS |
| $(GGGS)_3$ | 12 | 49 | GGGSGGGSGGGS |
| GGGGS | 5 | 50 | GGGGS |
| $(GGGGS)_2$ | 10 | 51 | GGGGSGGGGS |
| $(GGGGS)_3$ | 15 | 52 | GGGGSGGGGSGGGGS |
| $(SGG)_1$ | 3 | 53 | SGG |
| $(GSG)_1$ | 3 | 54 | GSG |
| $(GGS)_1$ | 3 | 55 | GGS |
| $(SGGG)_1$ | 4 | 56 | SGGG |
| $(GSGG)_1$ | 4 | 57 | GSGG |
| $(GGSG)_1$ | 4 | 58 | GGSG |
| $(SGGGG)_1$ | 5 | 59 | SGGGG |
| $(GSGGG)_1$ | 5 | 60 | GSGGG |
| $(GGSGG)_1$ | 5 | 61 | GGSGG |
| $(GGGSG)_1$ | 5 | 62 | GGGSG |
| $(SGG)_2$ | 6 | 63 | SGGSGG |
| $(GSG)_2$ | 6 | 64 | GSGGSG |
| $(GGS)_2$ | 6 | 65 | GGSGGS |
| $(SGGG)_2$ | 8 | 66 | SGGGSGGG |
| $(GSGG)_2$ | 8 | 67 | GSGGGSGG |
| $(GGSG)_2$ | 8 | 68 | GGSGGGSG |
| $(SGGGG)_2$ | 10 | 69 | SGGGGSGGGG |
| $(GSGGG)_2$ | 10 | 70 | GSGGGGSGGG |
| $(GGSGG)_2$ | 10 | 71 | GGSGGGGSGG |
| $(GGGSG)_2$ | 10 | 72 | GGGSGGGGSG |
| $(SGG)_3$ | 9 | 73 | SGGSGGSGG |

TABLE 2-continued

Possible Peptide linkers

| Name: | Length | SEQ ID NO: | Sequence |
|---|---|---|---|
| (GSG)3 | 9 | 74 | GSGGSGGSG |
| (GGS)3 | 9 | 75 | GGSGGSGGS |
| (SGGG)3 | 12 | 76 | SGGGSGGGSGGG |
| (GSGG)3 | 12 | 77 | GSGGGSGGGSGG |
| (GGSG)3 | 12 | 78 | GGSGGGSGGGSG |
| (SGGGG)3 | 15 | 79 | SGGGGSGGGGSGGGG |
| (GSGGG)3 | 15 | 80 | GSGGGGSGGGGSGGG |
| (GGSGG)3 | 15 | 81 | GGSGGGGSGGGGSGG |
| (GGGSG)3 | 15 | 82 | GGGSGGGGSGGGGSG |
| N-Glyco | 9 | 83 | GNGTSNGTS |
| N-Glyco (1) | 9 | 84 | GNGTSNGTG |
| N-Glyco (2) | 9 | 85 | GNGTSNGTSG |
| N-Glyco (3) | 9 | 86 | GNGTSNGTGS |
| N-Glyco (4) | 13 | 87 | GNGTSNGTSNGTS |
| N-Glyco (5) | 13 | 88 | GGGSGNGTSNGTGS |
| N-Glyco (6) | 13 | 89 | GNGTSNGTGSGGGS |
| N-Glyco (7) | 13 | 90 | GGGSGNGTSNGTSG |
| N-Glyco (8) | 13 | 91 | GNGTSNGTSGGGGS |

A person skilled in the art will understand that the above mentioned linker peptides may also be combined and a multitude of other flexible linker sequences may be utilized in similar manner as long as they do preferably not interfere with the trimeric assembly of component A. SEQ ID NO: 48, 88 and 90 are particularly preferred as peptide linker P linking two components A of the polypeptide according to the present invention. Preferably the peptide linkers P linking the components A within the polypeptide of the present invention do not comprise any cysteine residues in order to avoid formation of intramolecular disulfide bridges which could negatively impact the trimer formation of the components A.

The at least two peptide linkers P linking the least three components A of the polypeptides according to the present invention may be in principle selected independently of each other; e.g. the at least two peptide linkers P may have the same sequence or may have different sequences (in terms of length and/or sequence). However, it is particularly preferred if the peptide linkers P linking the at least three components A are identical. Certainly, similar considerations apply if the polypeptide according to the present invention comprises more than 3 components A and more than two peptide linkers P linking said components A. The peptide linkers P are linked to the components A via a covalent bond to the C-terminus of a first component A and a covalent bond to the N-terminus of the subsequent component A. Preferably, the linkages are peptide bonds.

Specific examples of polypeptides according to the present invention comprise as components A SEQ ID NO: 5 and preferably SEQ ID NOs: 48, 88 and/or 90 as peptide linkers P.

As mentioned above, the polypeptides according to the present invention comprise alongside the at least three components A at least one component B consisting of a $V_L$ region and a $V_H$ region linked directly to each other with a linker sequence L which has a length of ≤12 amino acids.

The terms "$V_L$" and "$V_H$" refer to the $V_L$ and $V_H$ regions of an antibody, i.e. the N-terminal variable region of the light chain of an immunoglobulin and the N-terminal variable region of the heavy chain of an immunoglobulin, respectively. Both terms are well understood in the art and are structurally well defined. The individual $V_L$ and $V_H$ regions are each composed of 3 hypervariable regions (CDR1, CDR2, CDR3; CDR: complementarity determining region) and 4 framework regions (FR1, FR2, FR3, FR4). Identifying the respective subregions within a given sequence is routine in the art and may for example be accomplished by IgBlast of the NCBI, v-base of the MRC, v-base2 hosted by EUGENE, on-line programs provided by the group of Andrew Martin and/or the ExPASy Proteomics Server. Kabat nomenclature may also be useful (Martin, A. C. R. PROTEINS: Structure, Function and Genetics, 25 (1996), 130-133). The variable regions of the heavy and the light chain form together the binding region of an antibody. In immunoglobulins, the $V_L$ and $V_H$ regions are on different polypeptide chains. In the polypeptides of the present invention the $V_L$ and $V_H$ regions are on the same chain. Interaction of a $V_L$ domain with a $V_H$ domain (intra- or intermolecularly) allows the polypeptide of the present invention to bind to the respective target antigen.

Preferably, the $V_L$ and the $V_H$ region of the polypeptide according to the present invention are $V_L$ and $V_H$ regions of an antibody binding (preferably) specifically to a cell surface molecule (cell surface antigen), in particular to a cell surface molecule selected from the group consisting of: a cytokine receptor, a growth factor receptor, an integrin, a cell adhesion molecule and/or a cell type- or tissue-specific cell surface antigen, cell surface expressed tumor-associated antigens (TAA), carbohydrates. A tumor-associated antigen may for example be expressed on tumor cells per se, on malignant cells, on stroma cells, on tumor endothelium and other tumor localized cell types.

In a preferred embodiment the $V_L$ and the $V_H$ region of the polypeptide according to the present invention are $V_L$ and $V_H$ regions of an antibody binding to a target antigen selected from the group consisting of: the erbB family of tyrosine kinase receptors (EGFR, HER2, HER3, HER4), VEGFRs, hetermeric integrin $a_x \beta_x$ receptor family, fibroblast activation protein (FAP), galectin, EpCAM, CEA, CD44 and tumor specific variants thereof (CD44v) and other tumor selective cell surface markers, CD2, CD5, CD7, CD19, CD20, CD21, CD22, CD24, CD25, CD30, CD33, CD38, CD40, CD52, CD56, CD71, CD72, CD73, CD105, CD117, CD123, c-Met, PDGFR, IGF1-R, HMW-MAA, TAG-72, GD2, GD3, GM2, folate receptor, Le$^y$, MUC-1, MUC-2, PSMA, PSCA, uPAR, Claudin 18.2, etc. Particularly preferred targets are the members of the erbB family of tyrosine kinase receptors and tumor stroma selective targets such as FAP.

As proof of concept, EGFR is used as target antigen in the appended examples.

Respective $V_H$ and $V_L$ sequences may easily be obtained by a person skilled in the art. Polypeptide and nucleic acid sequences for many antibodies are readily available in the art (see for example Expasy sequence database, PubMed etc.). Alternatively, a person skilled in the art may determine the sequence of available antibodies of the desired specificity or may even produce a new antibody against the desired target antigen by immunizing an animal suitable for antibody production with the antigen, isolating antigen specific B-cell clones and sequencing the respective $V_L$ and $V_H$ genes. Antibodies (and subsequently antibody sequences) may also be obtained from recombinant antibody libraries, e.g. immune, naive, semi-synthetic or fully synthetic antibody libraries. Isolation from such libraries can be achieved by different means, e.g. by phage display, ribosome display, yeast display, bacterial display, high-throughput screening, etc. By means of genetic engineering said sequences may then be included in a nucleic acid sequence encoding a polypeptide of the present invention.

A person skilled in the art will understand that the $V_H$ and $V_L$ regions in the polypeptide according to the present invention may be artificial, i.e. need not be derived from a de facto naturally occurring antibody. Rather this terminology is intended to reflect that said regions exhibit the general architecture of $V_L$ and $V_H$ regions. The $V_L$ and $V_H$ regions of the polypeptides according to the present invention may for example be humanized sequences, e.g. while the CDRs are of mouse origin, the framework regions are of human origin. The $V_L$ and $V_H$ regions may be for example deimmunized and/or fully human.

A particularly preferred $V_L$ region is SEQ ID NO: 92 if the target antigen is EGFR (see for example in SEQ ID NOs: 102 and 107).

A particularly preferred $V_H$ region is SEQ ID NO: 93 if the target antigen is EGFR (see for example in SEQ ID NOs: 102 and 107).

Particularly preferred $V_L$ regions if the target antigen is FAP are the amino acid sequences according to SEQ ID NOs: 130-132 (see for example in SEQ ID NOs: 127-129).

Particularly preferred $V_H$ regions if the target antigen is FAP are the amino acid sequences according to SEQ ID NOs: 133-135 (see for example in SEQ ID NOs: 127-129).

The TRAIL fusion proteins according to SEQ ID NOs: 127-129 are examples of tumorstroma targeted TRAIL fusion proteins recognizing the selective tumorstroma marker fibroblast activation protein (FAP). Thus, TRAIL proapoptotic activity is directed to the tumor environment and through juxtatropic presentation of the TRAIL module within the fusion protein, apoptosis is signaled in trans to the tumor cell. Highly specific apoptotic activity of the TRAIL module ensures efficient antitumoral therapeutic action towards a wide variety of carcinomas, as FAP overexpression is a prominent and common feature of a variety of epithelial cancers, including breast, colon, pancreas and lung, with a variable stroma content comprising 10 to 90% of total tumor mass (Garin Chesa et al, 1990, PNAS 87:7235-7239).

The fusion proteins according to SEQ ID NOs: 127-129 are FAP specific and exhibit high binding affinity typically in the nanomolar range (e.g. 10-30 nM). The components B of the fusion proteins according to SEQ ID NOs: 127-129 are 1) a humanized variant, generated by CDR grafting, and being species crossreactive between mouse and human (SEQ ID NOs: 130, 133, 136 and 127), thus allowing preclinical studies in murine tumor models; 2) two fully human components B, isolated by guided selection from a naïve human Ig library (SEQ ID NOs: 131, 134, 137 and 128, and SEQ ID NOs: 132, 135, 138 and 129) and binding to different epitopes at the extracellular domain of human FAP, one characterized by competition with the murine mab F19 (SEQ ID NOs: 131, 134, 137 and 128), the other one not competing with F19 for FAP binding (SEQ ID NOs: 132, 135, 138 and 129).

The $V_L$ region and the $V_H$ region may be arranged in any suitable manner in the polypeptide according to the present invention. Preferably, the region comprising the $V_L$ region and the $V_H$ region is arranged N-terminally of the region comprising the three components A.

As mentioned above, the $V_L$ region and a $V_H$ region of component B of the polypeptides according to the present invention are linked directly to each other with a linker sequence L which has a length of ≤12 amino acids. Linker sequence L is preferably a flexible amino acid stretch. Preferably, such linker sequence L is less than 11, even more preferably less than 10, even more preferably less than 9, even more preferably less than 8, even more preferably less than 7, even more preferably less than 6 amino acids long. In addition, the linker sequence L may have preferably an amino acid length of 0 amino acids or more, 1 amino acid or more, 2 amino acids or more, 3 amino acids or more, 4 amino acids or more, 5 amino acids or more, 6 amino acids or more, 7 amino acids or more, and/or 8 amino acids or more. A linker sequence L linking the $V_L$ and $V_H$ region of a component B of a polypeptide of the present invention may thus have for example an amino acid length in the range of 0 to 12 amino acids, 1 to 12 amino acids, 2 to 10 amino acids, 3 to 10 amino acids, 3 to 9 amino acids, 3 to 6 amino acids, 4 to 8 amino acids, 4 to 7 amino acids, 4 to 12 amino acids or any other combination of amino acids lengths disclosed above for linker sequence L. Particularly preferred are linker sequence L lengths of 0 to 5 amino acids, in particular 5 amino acids.

In terms of amino acid sequence, the linker sequence L linking the $V_L$ and $V_H$ region of a component B of a polypeptide of the present invention is preferably a glycine (G) rich peptide linker, i.e. has an amino acid sequences with a high glycine content of more than 50%; e.g. from at least 60 to 90%, for example of about 80%. Other amino acids which may be present in the linker sequence L are for example serine residues or less preferably alanine residues or glutamine residues. The linker sequence L may be composed of repetitive units. For example the linker may comprise two, three or four units of GG (SEQ ID NO: 40); GGS (SEQ ID NO: 55); GSG (SEQ ID NO: 54), or SGG (SEQ ID NO: 53) and combinations thereof. Particularly preferred examples for a linker sequence L linking the $V_L$ and $V_H$ region of a component B of a polypeptide of the present invention are selected from the group of sequences as depicted in Table 2 above (except for those sequences exceeding the length restriction of linker sequence L. Thus, if a linker sequence L is present, the linker sequence L may for example be selected from linker sequences of SEQ ID NOs. 39-51, and 53-78.

SEQ ID NO: 50 is particularly preferred as linker sequence L linking the $V_L$ and $V_H$ region of a component B of a polypeptide of the present invention. Preferably the linker sequence L does not comprise any cysteine residues in order to avoid formation of intramolecular disulfide bridges, which could for example negatively impact the correct formation of the $V_H$ or $V_1$ secondary structure of the polypeptide according to the present invention.

Linker sequence L may certainly be selected independently for each component B present in the polypeptide according to the present invention and independently of any peptide linker P selected for linking the components A. Linker sequence L links the $V_L$ region and the $V_H$ region via a covalent bond. Preferably the linkages are peptide bonds.

Component B may have (from N- to C-Terminus) the sequence:

V$_L$ region-linker sequence L-V$_H$ region or may have the sequence

V$_H$ region-linker sequence L-V$_L$ region.

The arrangement V$_H$ region-linker sequence L-V$_L$ region is particularly preferred.

In a particularly preferred embodiment, component B has the sequence of SEQ ID NO: 94 which is composed of SEQ ID NOs: 93, 50 and 92 (see for example in SEQ ID NOs: 102 and 107).

In this context the present invention also relates to a polypeptide comprising the sequence of SEQ ID NO: 92, SEQ ID NO: 93, SEQ ID NO: 92 and SEQ ID NO: 93, and/or SEQ ID NO: 94.

In further particularly preferred embodiments, component B has the sequence of any of SEQ ID NOs: 136-138 which are composed of SEQ ID NOs: 133, 50 and 130 (see for example in SEQ ID NO: 127), SEQ ID NOs: 134, 50 and 131 (see for example in SEQ ID NO: 128), and SEQ ID NOs: 135, 50 and 132 (see for example in SEQ ID NO: 129), respectively.

In this context the present invention also relates to a polypeptide comprising the sequence according to SEQ ID NO: 130, SEQ ID NO: 133, SEQ ID NO: 130 and SEQ ID NO: 133, and/or SEQ ID NO: 136, to a polypeptide comprising the sequence according to SEQ ID NO: 131, SEQ ID NO: 134, SEQ ID NO: 131 and SEQ ID NO: 134, and/or SEQ ID NO: 137, and to a polypeptide comprising the sequence according to SEQ ID NO: 132, SEQ ID NO: 135, SEQ ID NO: 132 and SEQ ID NO: 135, and/or SEQ ID NO: 138.

It will be understood by a person skilled in the art that a component B of a polypeptide according to the present invention does not comprise any antibody constant regions such as in Fab fragments.

Polypeptides according to the present invention comprise at least three components A and at least one component B. Preferably, the region comprising the at least three components A is linked to component B via a peptide linker X. Peptide linker X can in principle be any sequence as long as it does neither interfere with formation of the THD trimer nor with the association of a V$_H$ domain with a V$_L$ domain. In particular, there is no absolute length restriction with regard to linker X and no requirement for flexibility. However, preferably X is less than 50, even more preferably less than 45, even more preferably less than 40, even more preferably less than 35, even more preferably less than 30, even more preferably less than 25, even more preferably less than 20, even more preferably ≤15 amino acids long. Thus, linker X can be for example a linker as defined above for peptide linkers P or linking sequence L. In a particularly preferred embodiment linker X may for example comprise the sequence GNGTSNGTS (SEQ ID NO:83), which allows for glycosylation of a polypeptide of the present invention and thus improves stability of the overall polypeptide. The glycosylation residues are then the Asn residues. Specific examples for sequences of linker X may for example be AAAEFTRG (SEQ ID NO: 95), AAAGNGTSNGTSEFTRG (SEQ ID NO: 105), and GGSGNGTSNGTSG (SEQ ID NO: 106). The latter two allow again for glycosylation of the polypeptide according to the present invention.

The structure of the polypeptide according to the present invention may for example comprise (from N- to C-Terminus; B: component B; X: peptide linker X; A: a component A; P: peptide linker P):

B-X-A-P-A-P-A, or may be

A-P-A-P-A-X-B.

Specific examples of polypeptides according to the present invention comprise as components A SEQ ID NO: 5 and as component B SEQ ID NO: 94, preferably with SEQ ID NOs: 48, 88 and/or 90 as peptide linkers P. SEQ ID NO: 102 and SEQ ID NO: 107 (SEQ ID NO: 107 corresponds to amino acids 34-850 of SEQ ID NO: 102, i.e. does not include the leader sequence and the FLAG tag) are preferred examples of the present invention. Further preferred examples of the polypeptides according to the present invention, are sequences according to SEQ ID NOs: 125 and 126 comprising an albumin binding domain (ABD), and sequences according to SEQ ID NOs: 127-129 comprising a FAP-specific component B.

In a further aspect, the present invention relates to a polypeptide which comprises the sequence of SEQ ID NO: 96.

In a further aspect the present invention relates to a polypeptide which comprises:
  a) at least three components A, each of which comprises the sequence of a TNF homology domain (THD) of a TNF ligand family member, or functional derivative thereof, and
  b) a sequence comprising a glycosylation motif.

Glycosylation motifs comprise for instance nitrogen atoms in asparagine or arginine side-chains. Examples for glycosylation motifs are disclosed for instance above in SEQ ID NOs: 83-91. Specific examples of such polypeptides are polypeptides comprising the sequence of SEQ ID NO: 97, or SEQ ID NO: 98.

Besides, the polypeptides according to the present invention should preferably not comprise any endopeptidase recognition and/or cleavage sites, at least not within the structures B-X-A-P-A-P-A or A-P-A-P-A-X-B, respectively (presence of endopeptidase cleavage sites N- or C-terminal thereof will not affect the overall function of the polypeptide according to the present invention and their presence is thus not critical). In other words, the polypeptide according to the present invention should preferably not comprise any endopeptidase recognition and/or cleavage sites within the region comprising the at least three components A and the at least one component B and the linker in between. Presence of endopeptidease cleavage sites will significantly reduce the half-life of a polypeptide according to the present invention and may severely impact the efficacy of the polypeptide according to the present invention, because interaction of important domains is abolished. For example, separation of one component A from the polypeptide according to the present invention via endopeptidase cleavage will prevent trimer formation. Likewise, if component B is separated from the components A, any targeting effect is lost. This may be prevented by removing/altering respective endopeptidase recognition sites, by removing the endopeptidase cleavage sites and or by doing both. In this context, it is particularly preferred, if the components A in the polypeptide according to the present invention do not comprise a TACE cleavage site. TACE (TNF-alpha-converting enzyme, also termed ADAM17) is a member of the ADAM protease family and represents the enzyme physiologically processing for example the initially membrane bound TNF and others. TACE cleaves the membrane bound form whereby TNF is released (shed). Thus, a TNF based component A preferably lacks the Ala76-Val77 cleavage site of TNF. Lacking the cleavage site implies that the cleavage site may be deleted or is altered e.g. by means of substitution or insertion. Alternatively, or preferably in addition, the protease binding site within the stalk region of a TNF ligand, e.g. amino acid 77-88 of TNF-(Val-Arg-Ser-Ser-Ser-Arg-Thr-Pro-Ser-Glu-Lys-Pro), may be altered (or preferably deleted) to avoid recognition of the polypeptide of the present invention by TACE.

Polypeptides according to the present invention may comprise further polypeptide sequences and domains, which are however entirely optional.

One such optional element which may or may not be present in a polypeptide according to the present invention is the presence of one or more albumin binding domains (ABDs) within a polypeptide according to the present invention. The polypeptides according to the present invention may further comprise such an albumin binding domain in particular with the purpose to prolong the plasma half-life of the polypeptide of the present invention and thereby maintain therapeutically effective plasma concentrations. Serum albumin possesses an extraordinary long plasma half-life in humans. The plasma half-life of human serum albumin is in the range of 19 days. Apart from IgG no other soluble serum protein is known to exhibit such long half-life. The albumin binding domain (ABD) may be any molecule with affinity for albumin such as certain peptides, antibody fragments, alternative scaffolds, and small chemicals (for review see Kontermann BioDrugs 2009, 23:93-109, incorporated herein by reference). Particularly preferred examples of albumin binding domains in a polypeptide according to the present invention are selected for example from the group consisting of: albumin binding antibodies and albumin binding antibody derivatives, such as albumin binding Fab fragments, albumin binding scFv antibodies, and protein G of *Streptococcus* strain G148. Most preferred is the ABD of protein G of *Streptococcus* strain G148 comprising the sequence QHDEAVDANSLAEAKVLANRE LDKYGVS-DYYKNLINNAKTVEGVKALIDEILAALP (SEQ ID NO: 99) and non-immunogenic variants or derivatives thereof (e.g. as described in Johnsson et al. Protein Eng. Des. Sel. 21 (2008) pp 515-527 and Hopp et al. Protein Eng. Des. Sel. 23 (2010) pp 827-834, both incorporated herein by reference). Alternatively, the polypeptide according to the present invention may simply be a fusion protein with albumin moiety itself, or a fragment or derivative thereof. An example of such polypeptide is SEQ ID NO: 103.

In a particularly preferred embodiment, the polypeptide according to the present invention comprises an albumin binding domain as described above, for example an albumin binding domain according to SEQ ID NO: 99 or a derivative thereof which is capable of binding albumin, such as a sequence having at least 60% identity, preferably at least 70% identity, more preferably at least 80%, even more preferably at least 90% identity to SEQ ID NO: 99 over the entire length of SEQ ID NO: 99, or a fragment of SEQ ID NO: 99 or of a derivative thereof capable of binding albumin, such as a fragment consisting of a continuous stretch of amino acids representing at least 40%, preferably at least 50%, preferably at least 60%, more preferably at least 70%, even more preferably at least 80% of the full length sequence of SEQ ID NO: 99 or of a derivative thereof.

Preferably, the position of the ABD within the polypeptide according to the present invention is selected such that it does not significantly interfere with the bioactivity of the polypeptide according to the present invention, e.g. of inducing apoptosis in target cells, such as cancer cells. It is particularly preferred that the optional ABD is located between components A and component B of the polypeptide according to the present invention. For example, in a particularly preferred embodiment, component B is located N-terminally to components A and the optional ABD is located between components A and component B, e.g. forming a fusion protein having the structure N-K-[component B]-X-ABD-P-[components A]-X-C, wherein K is an optional $V_H$ leader sequence, X and P are optional linkers as described herein which may or may not comprise a glycosylation site, and N and C represent the N-terminal and the C-terminal end of the fusion protein, respectively. An example for such a polypeptide according to the present invention is given in SEQ ID NO: 125 (FIG. 25).

In another particularly preferred embodiment, the optional albumin binding domain is located downstream of components A of the polypeptide according to the present invention. For example, in a particularly preferred embodiment, component B is located N-terminally to components A and the optional ABD is located C-terminally to components A. Thus, in a particularly preferred embodiment, the polypeptide according to the present invention exhibits the structure N-K-[component B]-X-[components A]-P-ABD-X-C, wherein K is an optional $V_H$ leader sequence, X and P are optional linkers as described herein which may or may not comprise a glycosylation site, and N and C represent the N-terminal and the C-terminal end of the fusion protein, respectively. Preferably, ABD is located at the C-terminal end of the polypeptide according to the present invention. An example of such a polypeptide according to the present invention is given in SEQ ID NO: 126 (FIG. 26).

Another optional element which may or may not be present in a polypeptide according to the present invention is a tag allowing for example the detection and or purification of a polypeptide according to the invention. Examples for such tags are for example a His-tag, a FLAG-tag (DYKDDDDK; SEQ ID NO: 100), a HA-tag, a STREP-tag, a myc-tag, GST. Preferably, such tag is positioned outside the region comprising the at least three components A and the at least one component B. If so, it is possible to position a protease cleavage site (such as a thrombin cleavage site) adjacent to the tag, e.g. directly C-terminally of the tag. This will allow to remove the tag for example after purification.

Another optional but preferred element which may or may not be present in a polypeptide according to the present invention is a leader or signal peptide sequence such as the $V_H$ leader sequence MDWTWRVFCLLAVAPGAHS (SEQ ID NO: 101) or Igκ (METDTLLLWVLLLWVPGSTG; SEQ ID NO: 108). Such sequences may affect processing and targeting of the polypeptide according to the present invention after translation if produced in matching cell systems. For example, the $V_H$ leader sequence (if used for example in a mammalian) directs a polypeptide according to the present invention into the secretory pathway and thus allows for easier purification of the secreted product from culture supernatants. As with the detection and purification tags mentioned above, such leader or signal peptide sequence is positioned at the very N-Terminus of the polypeptide according to the present invention, thus allowing a cotranslational translocation into the ER and physiological processing in suitable mammalian expression systems such as CHO cells. In this regard a person skilled in the art will understand that if herein a polypeptide sequence is given with a leader sequence herein, then said polypeptide will for example after expression in a mammalian expression no longer comprise said leader sequence. Certainly, any such polypeptide without leader sequence falls within the scope of the present invention. In particular, polypeptides comprising the sequence of SEQ ID NOs: 96, 97, 98, 102, and/or 103 without the leader sequence of SEQ ID NO: 101 are embodiments of the present invention. Likewise, polypeptides comprising the sequence of SEQ ID NOs: 96, 97, 98, 102, and/or 103 without the leader sequence of SEQ ID NO: 101 and without the FLAG tag sequence of SEQ ID NO: 100 are embodiments of the present invention.

Likewise a polypeptide according to the present invention may optionally exhibit modifications. For instance, the polypeptide according to the present invention may be altered with regard to its hydrodynamic volume. The hydrodynamic volume of a protein can be increased by attaching highly flexible, hydrophilic molecules such as polyethylene glycol and/or carbohydrates. PEGylation, i.e. the chemical coupling of polyethylene glycol (PEG) is frequently used in the art. PEG is composed of ethylene oxide units connected in a linear or branched configuration and of varying length. For example, one or several PEG chains of 5 to 40 kDa may be conjugated to a polypeptide according to the present invention. However, PEGylation should preferably not be achieved in random manner because such approach may negatively impact the trimerization or targeting properties of the polypeptides according to the present invention. Preferably, the PEGylation sites are not within the region comprising the at least three components A and the at least one component B. PEG moieties may for example be attached to the polypeptide according to the present invention via cysteine residues. These cysteine residues are preferably positioned outside the region comprising the at least three components A and the at least one component B. Several other techniques are also known in the art. PEG mimetics may certainly also be used to modify the polypeptides according to the present invention.

A further possible modification of the polypeptides according to the present invention is—as already indicated above—glycosylation. Glycosylation can positively influence the half-life and stability of a polypeptide according to the present invention. N- as well as O-glycosylation may be contemplated. The inventors of the present invention have for example shown that glycosylation is possible by introducing a linker X which has the sequence GNGTSNGTS (SEQ ID NO: 83). Glycosylation sites at other sequence positions of the polypeptide according to the present invention are certainly also possible. Preferably, such glycosylation sites do not (significantly) impact the targeting and the respective functional activity of the THD of the TNF ligand family member within the polypeptide according to the present invention. Examples for such polypeptides are the polypeptides with the sequence of SEQ ID NO: 97, 98 and 103.

Other possible modifications of the polypeptides according to the present invention include for example HESylation (modification with hydroxyethyl starch) and modification with polysialic acid (PSA).

In general, the production of polypeptides is well-known in the art and a person skilled in the art can easily arrive at a polypeptide according of the present invention by means of routine methods (see for example Maniatis, et al. (2001), Molecular Cloning: A Laboratory Manual, Cold Spring Harbor Laboratory Press). In general, the production of polypeptides and proteins, respectively, is achieved by creating a DNA sequence encoding the same, followed by subsequent transformation of a suitable host with the respective DNA sequence and expression of the modified DNA sequence. Alternatively, the polypeptides according to the present invention may be chemically synthesized.

The present invention relates also to polypeptide complexes of the polypeptides according to the present invention, e.g. homodimeric and/or homotrimeric complexes of polypeptides according to the present invention. Thus, the polypeptide according to the present invention is preferably capable of forming multimers, such as dimers, trimers, tetramers etc., preferably dimers. Preferably, component B is capable of forming multimers, such as dimers, trimers, tetramers etc. Thus, in a particular preferred embodiment, component B is selected such that multimerization, such as dimerization, of the polypeptide according to the present invention is possible. In a particularly preferred embodiment, the polypeptide according to the present invention exhibits a multimeric form, such as a dimeric, trimeric, tetrameric etc. form, most preferably a dimeric form. Thus, preferably the polypeptide according to the present invention is multimeric, such as dimeric, trimeric or tetrameric, preferably dimeric. Accordingly, in a particular preferred embodiment the polypeptide complex according to the present invention is dimeric. A dimeric polypeptide according to the present invention comprises at least 6 components A.

In a further aspect the present invention also relates to a nucleic acid encoding a polypeptide according to the present invention. The nucleic acid may be DNA or RNA or a hybrid thereof. Preferably, the nucleic acid also comprises sequences allowing for the expression of the polypeptide according to the present invention in a suitable expression system. The nucleic acid can be codon optimized for the respective expression system.

In a further aspect the present invention also relates to a vector comprising a nucleic acid according to the present invention. Preferably, the vector provides for transcription and expression of the polypeptide according to the present invention in a suitable host cell system.

In a further aspect the present invention also relates to a (host) cell comprising a nucleic acid according to the present invention, a vector according to the present invention, a polypeptide according to the present invention, or a polypeptide complex according to the present invention. If the host cell is a human host cell, it is an isolated host cell outside the human body.

In a further aspect the present invention relates to a non-human organism comprising a nucleic acid according to the present invention, a vector according to the present invention, a polypeptide according to the present invention, a polypeptide complex according to the present invention or a host cell according to the present invention.

In a further aspect the present invention relates to nucleic acid according to the present invention, a vector according to the present invention, a polypeptide according to the present invention, a polypeptide complex according to the present invention and/or a host cell according to the present invention in a method for treatment of the human or animal body by surgery or therapy and diagnostic methods practised on the human or animal body. Preferably, the method of treatment relates to the treatment of cancer, autoimmune or degenerative diseases.

In this context the present invention also relates to a pharmaceutical composition comprising a nucleic acid according to the present invention, a vector according to the present invention, a polypeptide according to the present invention, a polypeptide complex according to the present invention and/or a host cell according to the present invention and optionally a pharmaceutically acceptable carrier, adjuvant, and/or vehicle. A particularly preferred pharmaceutical composition comprises a polypeptide comprising the sequence of SEQ ID NO: 102, 103, 107, 125, 126, 127, 128 and/or 129.

The pharmaceutical composition typically comprises a safe and effective amount of the compounds according to the invention (polypeptides, nucleic acids, vectors) as defined above. As used here, "safe and effective amount" means an amount of the compounds as defined above, that is sufficient to significantly induce a positive modification of a condition to be treated, for example of cancer and/or a tumor. At the same time, however, a "safe and effective amount" is preferably small enough to avoid serious side-effects, that is to say to permit a sensible relationship between advantage and risk. The determination of these limits typically lies within the scope of sensible medical judgment. A "safe and effective amount" of the compounds according to the invention as defined above will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The medicament according to the invention can be used according to the invention for human and also for veterinary medical purposes, as a pharmaceutical composition.

The pharmaceutical composition of the present invention typically contains a pharmaceutically acceptable carrier. The expression "pharmaceutically acceptable carrier" as used herein preferably includes the liquid or non-liquid basis of the inventive medicament. If the inventive medicament is provided in liquid form, the carrier will typically be pyrogen-free water; isotonic saline or buffered (aqueous) solutions, e.g. phosphate, citrate etc. buffered solutions. Particularly for injection of the inventive medicament, a buffer, preferably an aqueous buffer, may be used, containing a sodium salt. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well, which are suitable for administration to a person. The term "compatible" as used here means that the constituents of the inventive medicament are capable of being mixed with the compound according to the invention as defined above in such a manner that no interaction occurs which would substantially reduce the pharmaceutical effectiveness of the inventive medicament under usual use conditions. Pharmaceutically acceptable carriers must, of course, have sufficiently high purity and sufficiently low toxicity to make them suitable for administration to a person to be treated. Some examples of compounds which can be used as pharmaceutically acceptable carriers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined in principle by the manner in which the inventive medicaments are administered. The inventive medicaments can be administered, for example, systemically. Routes for administration include, for example, transdermale, inhalation, oral, parenteral, including subcutaneous or intravenous injections, topical and/or intranasal routes. The suitable amount of the inventive medicament to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive medicament is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

All references cited herein are incorporated herein in their entirety.

In the following a brief description of the appended figures will be given. The figures are intended to illustrate the present invention in more detail. However, they are not intended to limit the subject matter of the invention to any extent.

FIG. 1: Schematic illustration of exemplary polypeptides according to the present invention:

A) K=$V_H$ leader (e.g. SEQ ID NO: 101);
F=tag (i.e. FLAG tag; see for instance SEQ ID NO: 100);
L=linker sequence L, e.g. 15 aa long (e.g. (GGGGS)$_3$; SEQ ID NO: 52);
X=peptide linker X (see for instance SEQ ID NO: 95);
P=peptide linker P (e.g. SEQ ID NO: 48);
A=component A (e.g. TRAIL aa residues 95-281, SEQ ID NO: 5).
An example for such polypeptide is SEQ ID NO: 96 (FIG. 20).

B) K=$V_H$ leader (e.g. SEQ ID NO: 101);
F=tag (i.e. FLAG tag; see for instance SEQ ID NO: 100);
L=linker sequence L, ≤12 aa long (e.g. (GGGGS); SEQ ID NO:50);
X=peptide linker X (see for instance SEQ ID NO: 95);
P=peptide linker P (e.g. SEQ ID NO: 48);
A=component A (e.g. TRAIL aa residues 95-281; SEQ ID NO: 5).
An example for such polypeptide is SEQ ID NO: 102 (FIG. 21).

C) K=$V_H$ leader (e.g. SEQ ID NO: 101);
F=tag (i.e. FLAG tag; see for instance SEQ ID NO: 100);
L=linker sequence L, e.g. 15 aa long (e.g. (GGGGS)$_3$; SEQ ID NO: 52);
X=peptide linker X including glycosylation site (see for instance SEQ ID NO: 105);
P=peptide linker P (e.g. SEQ ID NO: 48);

A=component A (e.g. TRAIL aa residues 95-281; SEQ ID NO: 5).

An example for such polypeptide is SEQ ID NO: 97 (FIG. 22).

D) K=V$_H$ leader (e.g. SEQ ID NO: 101);
F=tag (i.e. FLAG tag; see for instance SEQ ID NO: 100);
L=linker sequence L, e.g. 15 aa long (e.g. (GGGGS)$_3$; SEQ ID NO: 52);
X=peptide linker X including glycosylation site (see for instance SEQ ID NO: 105);
P=peptide linker P including glycosylation site (e.g. P$_1$: (SEQ ID NO: 90); P$_2$: SEQ ID NO: 88);
A=component A (e.g. TRAIL aa residues 95-281; SEQ ID NO: 5).

An example for such polypeptide is SEQ ID NO: 98 (FIG. 23).

E) K=V$_H$ leader (e.g. SEQ ID NO: 101);
ABD=Albumin binding domain (see for instance SEQ ID NO: 99);
Q=Linker sequence (e.g. GGSGGGSGG; SEQ ID NO: 71);
L=linker sequence L, ≤12 aa long (e.g. (GGGGS); SEQ ID NO: 50);
X=peptide linker X including glycosylation site (see for instance SEQ ID NO: 106);
P=peptide linker P with (e.g. SEQ ID NO: 88) or without glycosylation site (e.g. SEQ ID NO 48: GGGSGGGS);
A=component A (e.g. TRAIL aa residues 95-281, SEQ ID NO: 5).

An example for such polypeptide is SEQ ID NO: 103 (FIG. 24).

F) K=V$_H$ leader (e.g. SEQ ID NO: 101);
F=tag (i.e. FLAG tag; see for instance SEQ ID NO: 100);
L=linker sequence L, ≤12 aa long (e.g. (GGGGS); SEQ ID NO: 50);
Q=Linker sequence (e.g. GGS; SEQ ID NO: 55);
ABD=Albumin binding domain (see for instance SEQ ID NO: 99);
X=peptide linker X including glycosylation site (see for instance SEQ ID NO: 105);
P=peptide linker P (e.g. GGGSGGGS; SEQ ID NO: 48);
A=component A (e.g. TRAIL aa residues 95-281, SEQ ID NO: 5).

An example for such polypeptide is SEQ ID NO: 125 (FIG. 25).

G) K=V$_H$ leader (e.g. SEQ ID NO: 101);
F=tag (i.e. FLAG tag; see for instance SEQ ID NO: 100);
L=linker sequence L, ≤12 aa long (e.g. (GGGGS); SEQ ID NO: 50);
X=peptide linker X including glycosylation site (see for instance SEQ ID NO: 105);
P$_1$=peptide linker P$_1$ (e.g. GGGSGGGS; SEQ ID NO: 48);
P$_2$=peptide linker P$_2$ (e.g. GGSGG; SEQ ID NO: 61);
A=component A (e.g. TRAIL aa residues 95-281, SEQ ID NO: 5);
ABD=Albumin binding domain (see for instance SEQ ID NO: 99).

An example for such polypeptide is SEQ ID NO: 126 (FIG. 26).

FIG. 2: Purified polypeptides of SEQ ID NO: 104 (lane 1), SEQ ID NO: 96 (lane 2), SEQ ID NO: 102 (lane 3) and of glycosylated SEQ ID NO: 97 (lane 4) were analyzed by SDS-PAGE (reducing conditions) followed by silver staining (upper, left, 1 µg protein per lane) or Western blotting (lower, 250 ng protein per lane) using monoclonal anti-TRAIL or anti-FLAG antibodies in combination with alkaline phosphatase-conjugated secondary antibody. The glycosylated polypeptide of SEQ ID NO: 97 was treated with N-glycosidase and analysed by SDS-PAGE and Coomassie staining (upper, right). SEQ ID NO: 104 is a single chain TRAIL polypeptide with three copies of TRAIL 95-281 (SEQ ID NO: 5) linked by two glycine linkers and comprising an N-terminal Flag-tag. However, the polypeptide does not comprise any region B as specified herein.

Figure 3:
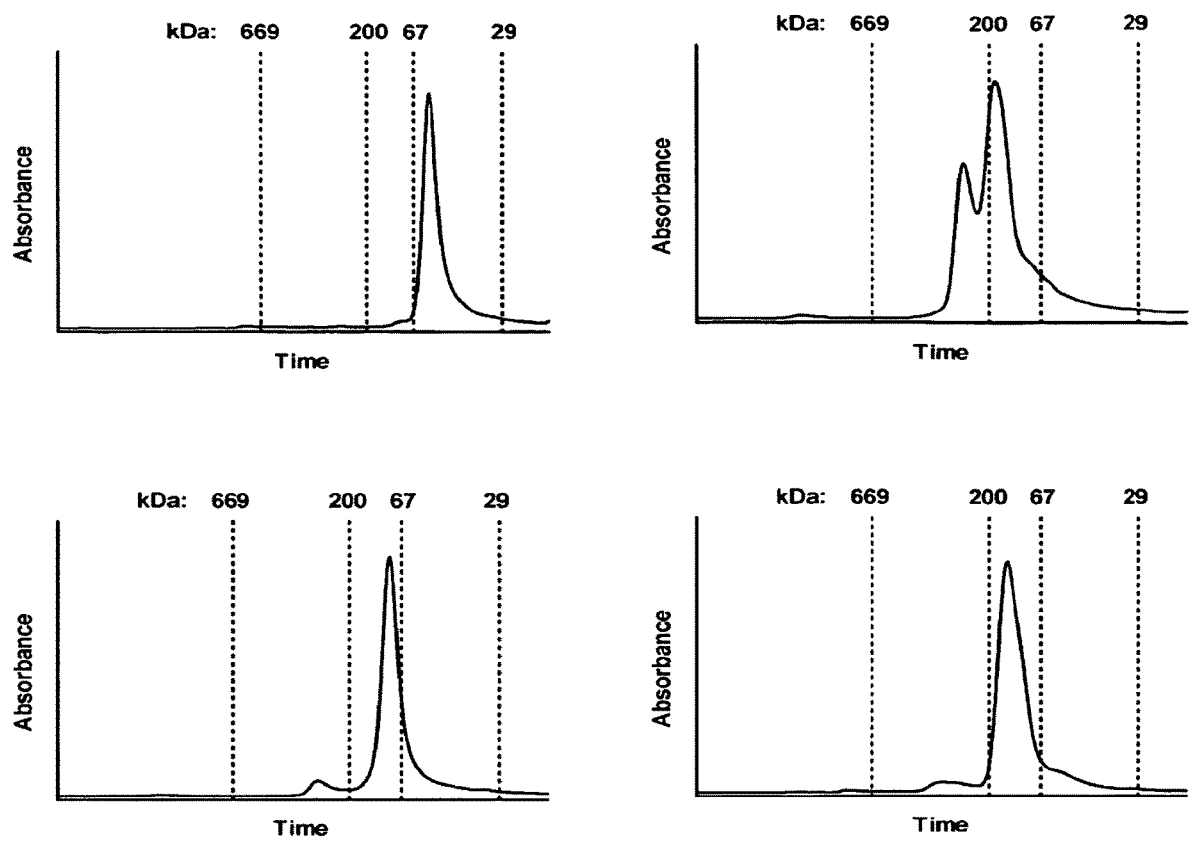

FIG. 3 Purified polypeptides of SEQ ID NO: 104 (upper left), SEQ ID NO: 96 (lower left), SEQ ID NO: 102 (upper right) and of glycosylated SEQ ID NO: 97 (lower right) were separated by size exclusion chromatography on a BioSuite 250 column. The retention times of the molecular weight standards thyroglobulin (669 kDa), β-amylase (200 kDa), bovine serum albumin (67 kDa) and carbonic anhydrase (29 kDa) are indicated by dotted lines.

Figure 4:
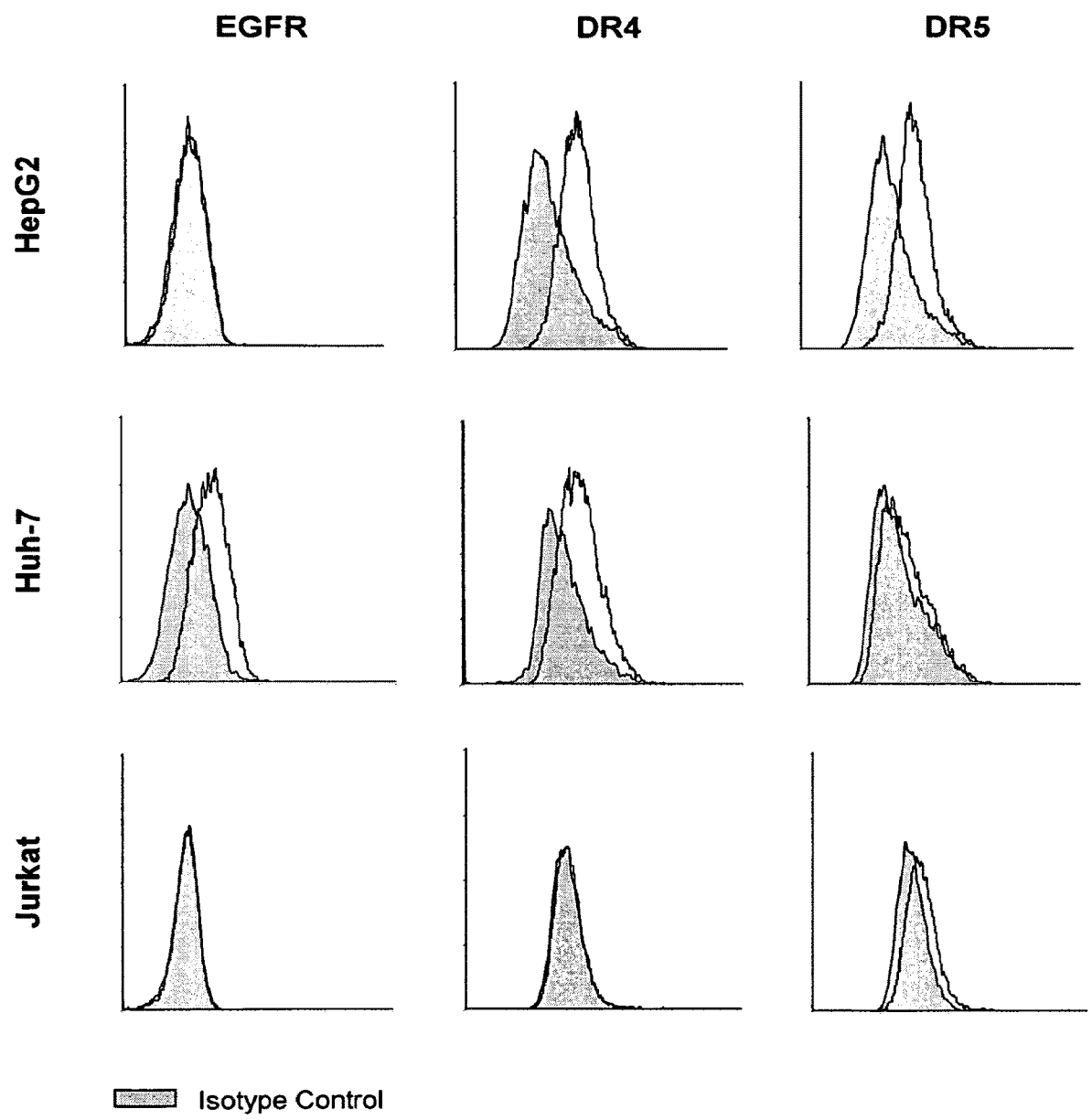

FIG. 4 Flow cytometric analysis of expression of EGF receptor and proapoptotic TRAIL receptors DR4 and DR5 in Jurkat, Huh-7 and HepG2 cell lines.

FIG. 5 Flow cytometric analysis: (A) Blocking of the binding of Cetuximab to target-negative (HepG2) and target-positive cells (Huh-7) by an excess of SEQ ID NO: 102; (B) Binding of SEQ ID NO: 102 and SEQ ID NO: 96 to HepG2 and Huh-7 cells. "scFv" represents an anti-EGFR specific antibody fragment used for competition.

FIG. 6 Target-independent induction of cell death: (A) EGFR low/negative HepG2 cells were sensitized with 500 ng/ml Bortezomib and treated with serial dilutions of SEQ ID NO: 102 (open squares), KillerTRAIL™ (inverted filled triangle), SEQ ID NO: 96 (open circles) and SEQ ID NO:104. Cell viability was determined using crystal violet staining. Results from four independent experiments are shown (mean±S.E.M.). (B) Jurkat cells (1×10$^5$/well) were used for a similar experiment as described in (A). Jurkat cells were not sensitized. Results from three independent experiments are shown (mean±S.E.M.). Viability of Jurkat cells was determined using the MTT assay.

FIG. 7. EGFR-directed induction of cell death in EGFR+ Huh-7 hepatocellular carcinoma cells sensitized with 250 ng/ml Bortezomib and treated in duplicates with serial dilutions of SEQ ID NO: 102 (open squares), SEQ ID NO: 96 (open circles), SEQ ID NO: 97 (open diamond), and SEQ ID NO: 104 as control (left side of panel). For quantification of the targeting effect, cells were additionally preincubated with an excess of EGFR-specific antibody Cetuximab (70 nM) before adding the test polypeptides (graphs of SEQ ID NO: 102 (middle panel) and SEQ ID NO: 96 (right panel). For easy comparison, dose response curves of the respective reagents in absence of cetuximab from the left panel were plotted again in these two panels. Results from four independent experiments are shown (mean±S.E.M.).

Figure 8:
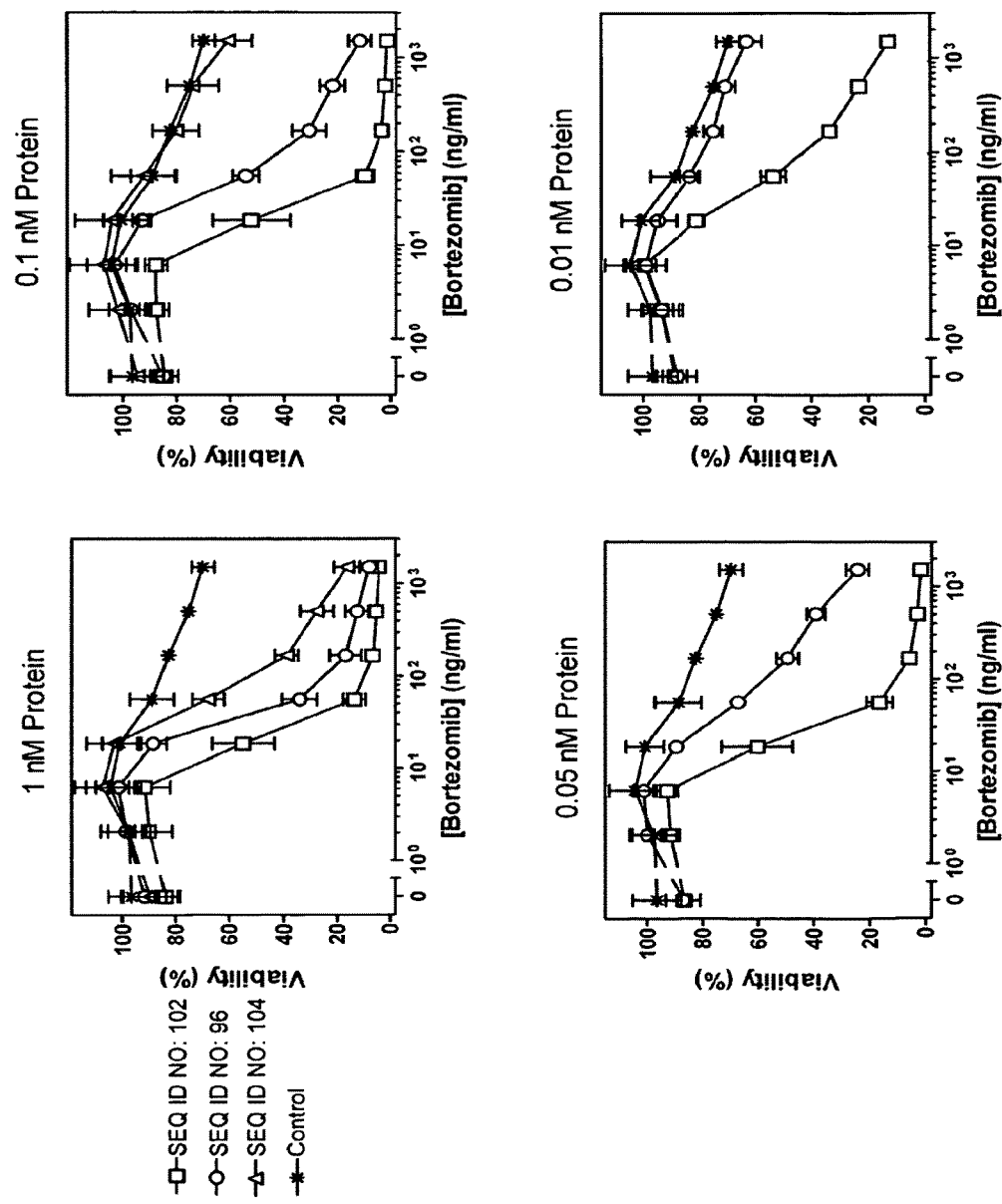

FIG. 8: EGFR-directed induction of cell death in Huh-7 hepatocellular carcinoma cells as in FIG. 7 with the exception that constant concentrations of the test proteins were used for preincubation (30 min), followed by addition of serial dilutions of Bortezomib. Control: Bortezomib alone. Results from three independent experiments are shown (mean±S.E.M.).

FIG. 9: EGFR specific TRAIL fusion proteins lack hepatotoxic activity. Groups of 3 CD1 mice were treated intraperitonally with indicated fusion proteins or control reagents: negative control: PBS; positive control: aggregated FasL (CD95L) fusion protein. (A) Plasma samples were prepared after 4 h and 24 h and the activity of alanine aminotransferase (ALT) was assayed using an enzymatic assay (Bioo Scientific, Austin, Tex.). Dashed line indicates upper normal level of ALT (physiologic range in adult human: 35-50 U/L). (B) Mice were sacrificed after 24 h except for positive control (animals treated with an aggregated FasL (CD95L) fusion protein show phenotypic signs of severe systemic toxicity after 2-4 hrs and die after ~5 hrs, samples were taken after 4 hrs) and liver biopsies were taken for determination of caspase-3 activity using a specific AMC-coupled peptide substrate (Enzo Lifesciences, Lörrach, Germany).

Figure 10:
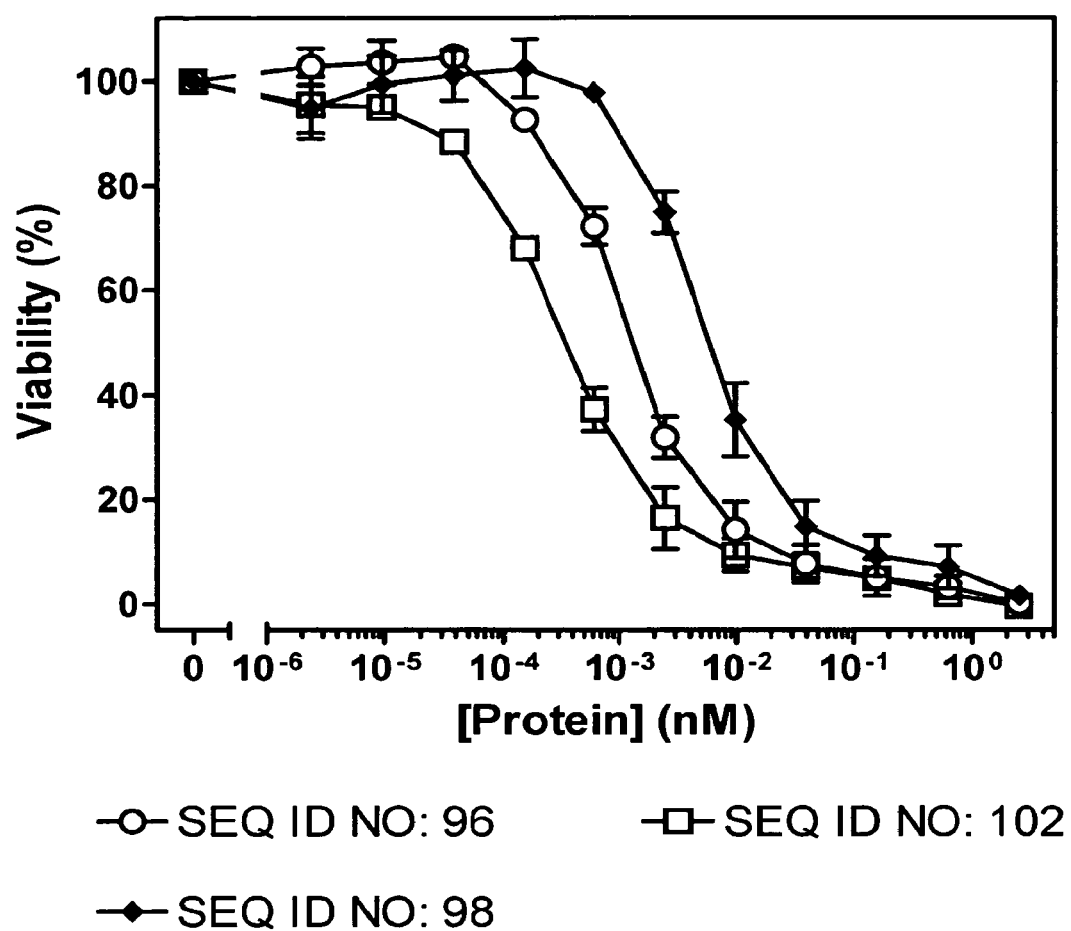

FIG. 10: EGFR-directed induction of cell death by single-chain TRAIL fusions on NCI-H460 cells. NCI-H460 non-small lung cancer cells ($3 \times 10^4$/well) were seeded in 96-well plates and cultivated for 24 h. Then, cells were sensitized with 2.5 µg/ml cycloheximide and treated in duplicates with serial dilutions of the indicated fusion proteins. After 16 h, cell viability was determined using crystal violet staining. Results from two independent experiments are shown (mean±S.E.M.). $EC_{50}$ values were $1.2 \pm 0.08 \times 10^{-12}$ M for SEQ ID NO: 96, $3.4 \pm 0.28 \times 10^{-13}$ M for SEQ ID NO: 102 and $5.8 \pm 1.5 \times 10^{-12}$ M for SEQ ID NO: 98.

FIG. 11: Biochemical characterization of N-glycosylated polypeptide according to the present invention (SEQ ID NO: 98). (A) SEQ ID NO: 98 was treated with N-glycosidase and analysed by SDS-PAGE and Coomassie staining. (B) SEQ ID NO: 98 and SEQ ID NO: 96 were separated by size exclusion chromatography on a BioSuite 450 column (Waters). The retention times of the molecular weight standards apoferritin (443 kDa), β-amylase (200 kDa), bovine serum albumin (67 kDa) and carbonic anhydrase (29 kDa) were indicated by dotted lines.

Figure 12:
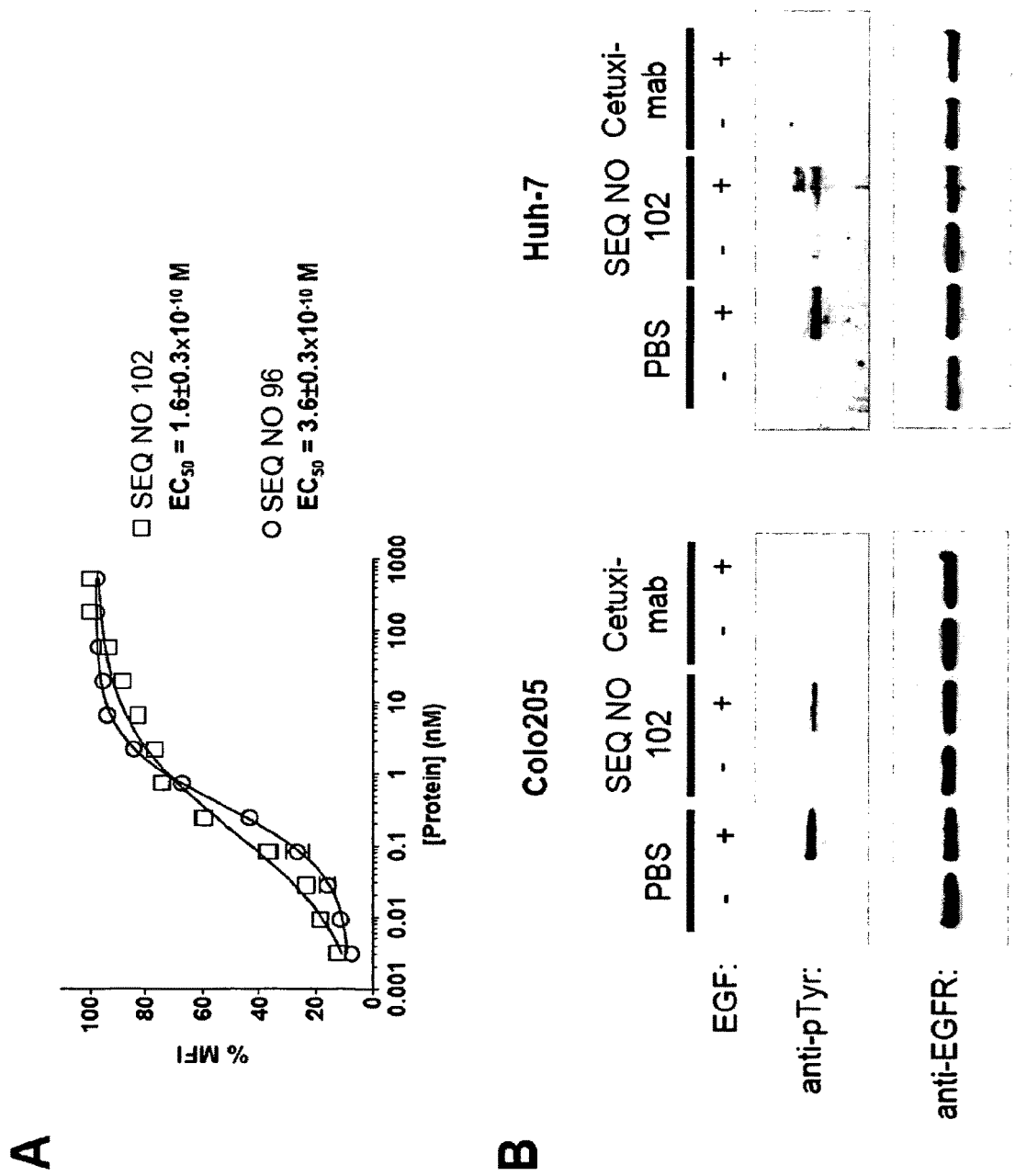

FIG. 12: Receptor interaction of EGFR-specific TRAIL fusion proteins. (A) Dose response relationship of TRAIL fusion protein binding to EGFR+ NCI-H460 cells by indirect immunofluorescence flow cytometry to reveal concentration of half maximum binding ($EC_{50}$) (mean SEM, n=4). (B) Colo205 and Huh-7 cells were serum-starved overnight and then incubated with 2 nM of SEQ ID NO: 102, Cetuximab, and PBS for control, respectively. After 10 min, 50 ng/ml EGF were added and cells were incubated for additional 20 min followed by cell lysis. EGF receptors were immuno-precipitated using a specific mouse monoclonal antibody and subjected to SDS-PAGE followed by immunoblotting with phosphotyrosine antibody (anti-pTyr). Total amounts of EGFR were determined by reprobing the membrane with EGFR-specific rabbit polyclonal antibody (anti-EGFR).

FIG. 13: Caspase dependence of cell death and impact of the component B of SEQ ID NO: 102. (A) Colo205 cells (left) and Huh-7 cells (right) were sensitized with 25 ng/ml and 250 ng/ml bortezomib, respectively, and treated with different concentrations of SEQ ID NO: 102 with or without the presence of pan-caspase inhibitor zVADfmk or caspase-3 inhibitor zDEVDfmk (both inhibitors: 20 µM for Colo205 and 10 µM for Huh-7). After 16 h, cell viability was determined using MTT staining (Colo205) or crystal violet staining (Huh-7) and data were normalized using bortezomib-treated cells as control (mean SEM, n=3). (B) $1 \times 10^4$ Colo205 cells per well were grown in 96-well plates using medium with 0.1% FCS. Upon stimulation with 50 ng/ml EGF and sensitization with 10 ng/ml bortezomib, cells were incubated with equimolar concentrations of SEQ ID NO: 102 (open squares), SEQ ID NO: 102+anti-TRAIL mAb 2E5 (filled squares) or Cetuximab (circles) for four days and cell number was assayed by the MTT method using bortezomib/EGF-treated cells as control for normalization (mean SEM, n=2). (C) $1 \times 10^4$ Huh-7 cells per well were grown in 96-well plates and treated with 20 ng/ml bortezomib or with a combination of bortezomib and 10 µM zVADfmk. Then, cells were incubated with equimolar concentrations of SEQ ID NO: 102 (open squares), SEQ ID NO: 102+zVADfmk (filled squares), Cetuximab (open circles) or Cetuximab+zVADfmk (filled circles) for three days and cell viability was assayed by the MTT method using bortezomib-treated cells and bortezomib/zVADfmk-treated cells, respectively, as control for normalization (mean SEM, n=3).

Figure 14:
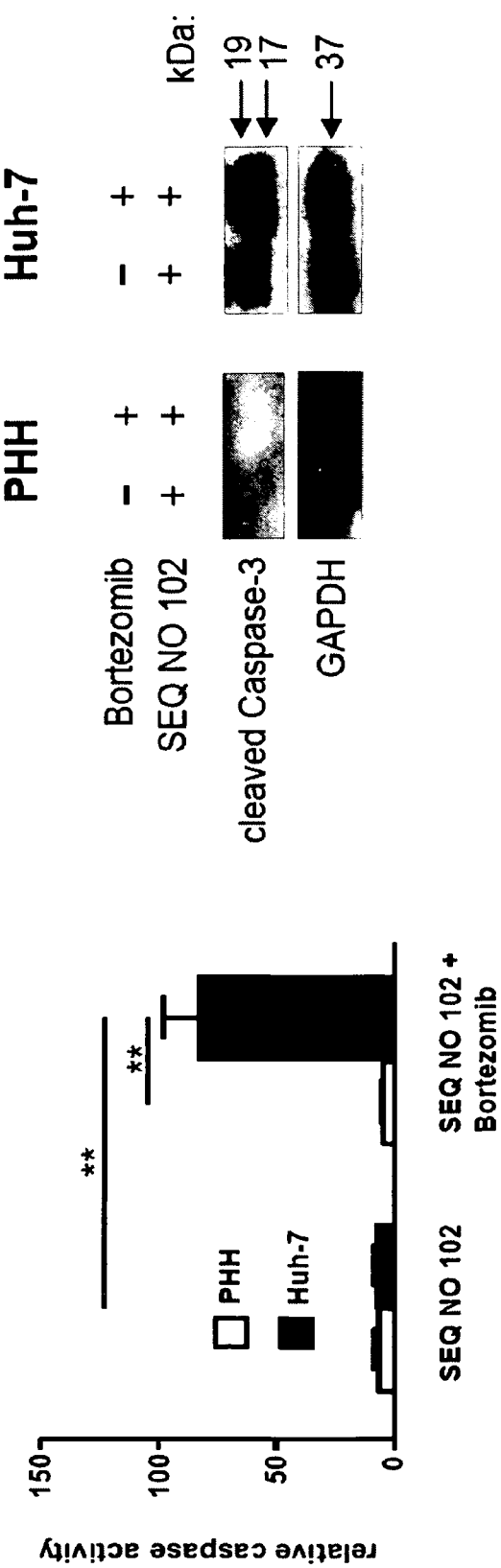

FIG. 14: In vitro tolerance of TRAIL fusion proteins to primary tissues. (A) Relative caspase activity (fold increase compared to untreated) in primary human hepatocytes (PHH, mean SEM, n=5) or Huh-7 hepatocarcinoma cells (mean SEM, n=7) after incubation with 1.1 nM SEQ ID NO: 102 in presence or without 500 ng/ml bortezomib. Asterisks indicate statistical significance. (B) Cleavage of caspase-3 in PHH (left) and Huh-7 cells (right) after incubation with 500 ng/ml bortezomib, 1.1 nM SEQ ID NO: 102 or both was analyzed by immunoblotting.

FIG. 15: Antitumor activity of TRAIL fusion proteins in a Colo205 xenograft tumor model. (A) Tumor volume as a function of time after i.p. application of PBS (open diamonds), bortezomib (filled triangles), SEQ ID NO: 104 (lacking component B)+bortezomib (open triangles), SEQ ID NO: 97 (L>12 amino acids)+bortezomib (circles), SEQ ID NO: 102 (L<12 amino acids)+bortezomib (filled diamonds) or SEQ ID NO: 102 only (squares). Arrows, protein application; asterisks, bortezomib application; symbols, mean of tumor volumes 95% confidence interval (CI), n=12 tumors/treatment group. (B) Individual tumor volumes at day 14. Bars, mean of tumor volumes 95% CI.

Figure 16:
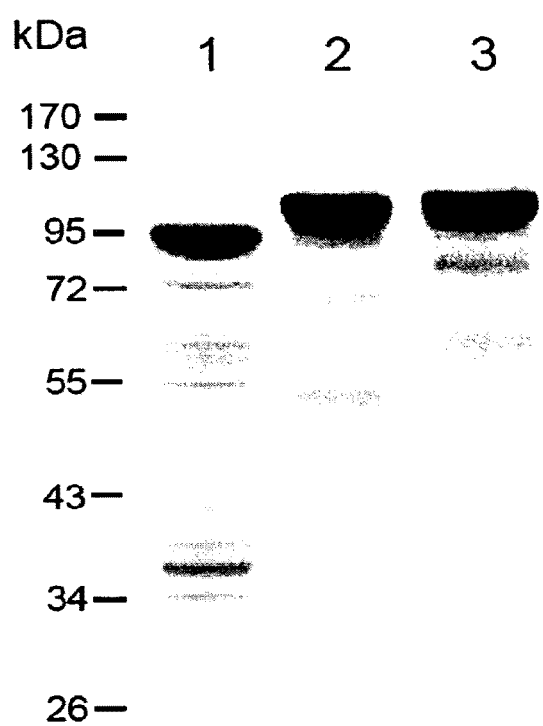

FIG. 16: Coomassie-stained SDS-PAGE of affinity-purified SEQ ID NO: 102 (lane 1), SEQ ID NO: 125 (lane 2) and SEQ ID NO: 126 (lane 3). 5 µg of the proteins were loaded under reducing conditions.

FIG. 17: Albumin binding of SEQ ID NO: 125 and SEQ ID NO: 126. Both proteins were incubated for 1 h at RT with equimolar concentrations of human serum albumin (HSA) or mouse serum albumin (MSA) and subsequently separated by size exclusion chromatography. Thyroglobulin (669 kDa), apoferritin (443 kDa), -amylase (200 kDa), bovine serum albumin (67 kDa), carbonic anhydrase (29 kDa) and FLAG peptide (1 kDa) were used as standard proteins/peptides.

Figure 18:
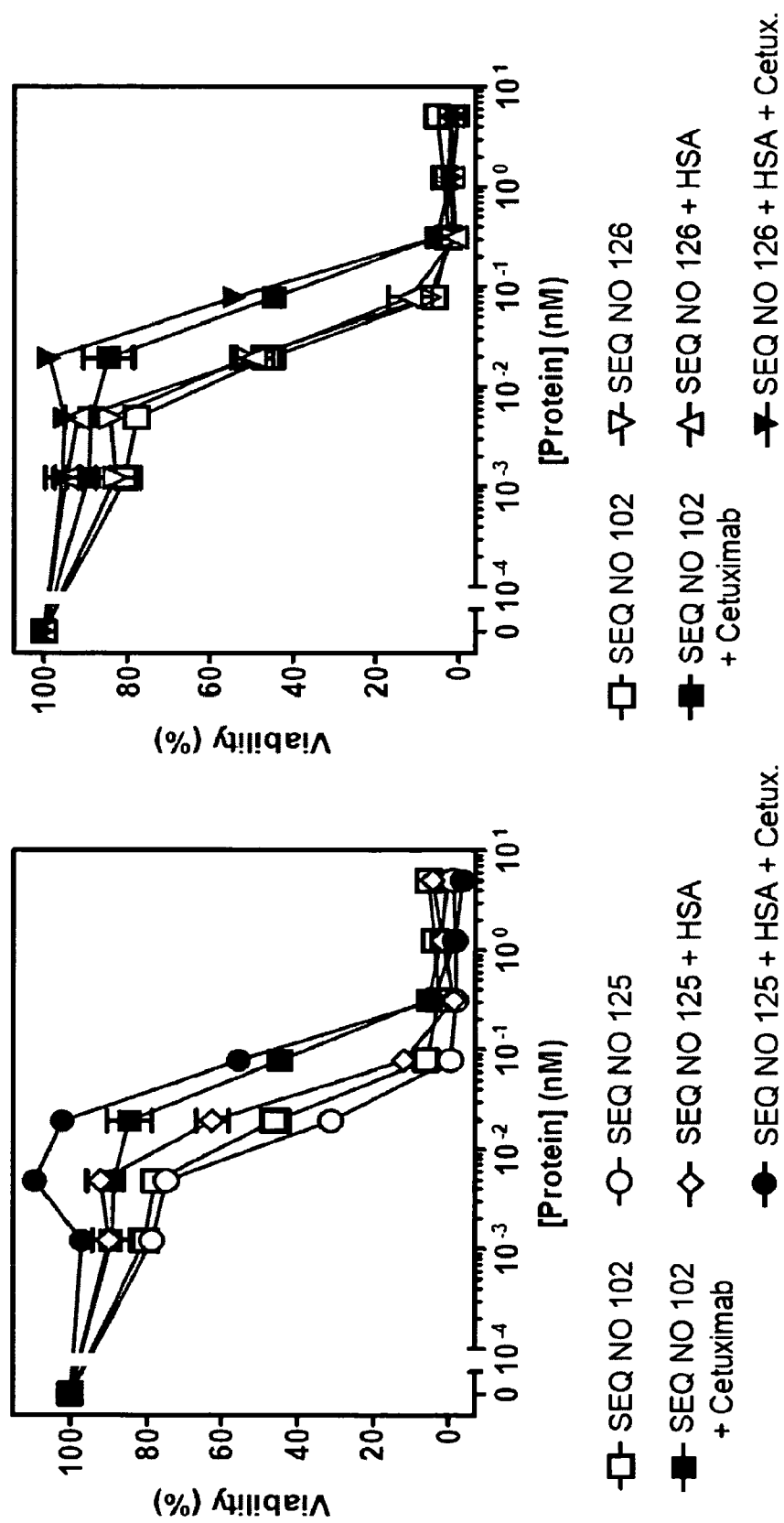

FIG. 18: Bioactivity of SEQ ID NO: 125 and SEQ ID NO: 126 in vitro. Huh-7 hepatocarcinoma cells were sensitized with bortezomib (250 ng/ml) and treated with serial dilutions of SEQ ID NO: 102, SEQ ID NO: 125 (left panel) and SEQ ID NO: 126 (right panel) in triplicates. After 16 h, cell viability was determined using crystal violet staining. For quantification of the targeting effect, cells were preincubated with an excess of Cetuximab (70 nM) before adding SEQ ID NO: 102, SEQ ID NO: 125 and SEQ ID NO: 126. SEQ ID NO: 125 and SEQ ID NO: 126 were additionally incubated in presence of 100 µg/ml HSA. The values for SEQ ID NO: 102 were plotted in both panels for comparison.

FIG. 19: Pharmacokinetics of SEQ ID NO: 102 (A) and SEQ ID NO: 125 (B). 25 µg of protein were injected i.v. in CD1 mice and serum samples were taken at the depicted time points followed by detection of scTRAIL molecules via ELISA.

FIG. 20A-20C: SEQUENCE OF SEQ ID NO: 96.
FIG. 21A-21C: SEQUENCE OF SEQ ID NO: 102.
FIG. 22A-22C: SEQUENCE OF SEQ ID NO: 97.
FIG. 23A-23C: SEQUENCE OF SEQ ID NO: 98.
FIG. 24A-24C: SEQUENCE OF SEQ ID NO: 103.
FIG. 25A-25C: SEQUENCE OF SEQ ID NO: 125.
FIG. 26A-26C: SEQUENCE OF SEQ ID NO: 126.
FIG. 27: Sequence of SEQ ID NO: 127.
FIG. 28: Sequence of SEQ ID NO: 128.
FIG. 29: Sequence of SEQ ID NO: 129.

EXAMPLES

In the following, general examples illustrating various embodiments and aspects of the invention are presented. However, the present invention shall not be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Biochemical Analysis

1. Polypeptide Production
1.1 Principle

Three human TRAIL domains encompassing aa residues 95-281 (TRAIL) (SEQ ID NO: 5) were fused with (GGGS)$_2$ peptide linkers P (SEQ ID NO: 48) yielding so called single-chain TRAIL (scTRAIL) (SEQ ID NO: 104). EGFR-specific antibody fragments consisting of V$_H$ (SEQ ID NO: 93) and V$_L$ (SEQ ID NO: 92) were fused N-terminally to scTRAIL (SEQ ID NO: 104). (GGGGS)$_3$ (SEQ ID NO: 52) or GGGGS (SEQ ID NO: 50) peptide linkers between V$_H$ (SEQ ID NO: 93) and V$_L$ (SEQ ID NO: 92) were chosen to obtain a polypeptide according to the present invention (SEQ ID NOs: 96 and 102). A V$_H$ leader (K) (SEQ ID NO: 101) and a FLAG tag (F) (SEQ ID NO: 100) were placed in front of the antibody region. For a glycosylated polypeptide according to the present invention, a linker with two N-glycosylation sites (GNGTSNGTS) (SEQ ID NO: 83) was placed between V$_L$ (SEQ ID NO: 92) and scTRAIL (SEQ ID NO: 104).

1.2 Plasmids and Cell Lines

An pIRESpuro-scTRAIL expression construct for human scTRAIL (SEQ ID NO: 104) was obtained by EcoRI/NotI cloning of a synthesized sequence coding for three TRAIL components (aa residues 95-281) connected by sequences encoding (GGGS)$_2$ linker motifs into a construct described previously (Schneider et al, 2010, Cell Death. Disease. 2010). For the generation of the EGFR-specific V$_H$-V$_L$-scTRAIL expression construct, a synthesized coding sequence of humanized V$_H$ and V$_L$ sequences (huC225) was amplified using the oligonucleotides CGAGGTGCAGCTG-GTCGAG (SEQ ID NO: 109) and TGCGGCCGCTCTCT-TGATTTC (SEQ ID NO: 110). Next, this template was annealed with the oligonucleotide ATATATCTCGAGGC-CAGCGACTACAAAGACGATGACGATAAAGGAGC-CGAGGTGCAGCTGG TCGAG (SEQ ID NO: 111) to insert an XhoI site and a FLAG tag coding sequence. After strand elongation, the whole sequence was amplified by the oligonucleotides ATATATCTCGAGGCCAGCGAC (SEQ ID NO: 112) and ATATGAATTCTGCGGCCG CTCTCTT-GATTTC (SEQ ID NO: 113). The PCR product was then cloned via XhoI/EcoRI into pCR3 (Invitrogen), carrying an V$_H$ leader. The scTRAIL coding sequence of this construct was then inserted via EcoRI/XbaI sites. The EGFR-specific construct for SEQ ID NO: 102 was derived from pCR3-VH-VL-scTRAIL by shortening linker L from (GGGGS)$_3$ to GGGGS. Therefore, two PCR products were generated using the oligonucleotide (1)
(SEQ ID NO: 114)
CCCACAGCCTCGAGGCCAG and (2)
(SEQ ID NO: 115)
GAGCCGCCACCGCCACTAG vas well as (3)
(SEQ ID NO: 116)
CTAGTGGCGGTGGCGGCTCTGATATTCAGCTGA CCCAGTCC
and (4)
(SEQ ID NO: 117)
TGAATTCTGCGGCCGCTCTC.

After annealing of the products at the underlined regions and strand elongation, the whole sequence was amplified by the oligonucleotides (1) and (4) followed by XhoI/NotI cloning into pCR3-V$_H$-V$_L$-scTRAIL. A glycosylated variant of SEQ ID NO: 96 was generated by two PCR amplifications of the huC225 VH-VL coding sequence in pCR3-VH-VL-sc-TRAIL using the oligonucleotides (1) CCCACAGCCTC-GAGGCCAG (SEQ ID NO: 118) and CCCGTTGCTGGT-GCCGTTGCCTGCG GCCGCTCTCTTG (SEQ ID NO: 119), respectively (1) and ATATGAATTCGGATGTC-CCGTT GCTGGTGCCGTTG (SEQ ID NO: 120), followed by XhoI/EcoRI cloning in pCR3-VH-VL-scTRAIL. The construct for expression of SEQ ID NO: 98 was generated by two sequential PCR amplifications of the TRAIL coding sequence using the oligonucleotides GCACATC-CAATGGGACCAGCGGAACCTCCGAAGAGAC-TATCTC (SEQ ID NO: 121) and CCCGTTGCTGGTTC-CATTACCAGATCCGCCCCCTCC (SEQ ID NO: 122), respectively ATATATGGATCCGGCAACGGCACATC-CAATGGGACCAG (SEQ ID NO: 123) and ATATATG-GATCCGGTCCCGTTGCTGGTTCCATTAC (SEQ ID NO: 124), followed by BamHI cloning into the expression construct for SEQ ID NO: 97.

HEK293, HepG2, NCI-H460, Colo205 and Jurkat, cells were obtained from the American Type Culture Collection (Manassas, Va.). Cells were cultured in RPMI 1640 medium (Invitrogen, Karlsruhe, Germany) supplemented with 5% fetal calf serum (FCS, HyClone), respectively 10% FCS for HepG2. Huh-7D12 liver carcinoma cells were obtained from Heike Bantel, Hannover Medical School, Hannover, Germany and were cultured in DMEM (Invitrogen, Karlsruhe, Germany) supplemented with 10% FCS.

1.3 Production and Purification of Recombinant Proteins

The TRAIL fusion proteins of SEQ ID NOs: 96, 97, 98, 102, 125, and 126 were produced in HEK293 cells after stable transfection with the corresponding expression plasmids using Lipofectamine 2000 (Invitrogen) and generation of a pool of stably expressing clones. For protein production, stable clones were expanded and grown in RPMI 1640, 5% FCS, to 90% confluency and subsequently cultured in serum-free Optimem (Invitrogen) supplemented with 50 μM ZnCl$_2$, replacing media two times every 3 days. The supernatants were pooled and recombinant proteins were purified first by IMAC using Ni-NTA-Agarose (Qiagen, Hilden, Germany). After elution with 100 mM imidazol and dialysis against PBS, the proteins were further purified by affinity chromatography using anti-FLAG mAb M2 agarose (Sigma-Aldrich, Steinheim, Germany). The bound proteins were eluted with 100 μg/ml FLAG peptide (peptides&elephants, Potsdam, Germany) and dialysed against PBS. scTRAIL and SEQ ID NOs: 97 and 98 were purified in a single M2 agarose affinity chromatography step. After concentration of purified proteins using Vivaspin centrifugal concentrators with 50 or 10 kDa MWCO (Sartorius Stedim, Aubagne, France), the protein concentration was measured with a spectrophotometer (NanoDrop products, Wilmington, Del.) and aliquots were stored at −80° C.

1.4 SDS-PAGE and Western Blot Analysis

Purified polypeptides of SEQ ID NO: 96, SEQ ID NO: 102, SEQ ID NO: 104, 125, 126 and of glycosylated SEQ ID NO: 97 were analyzed by SDS-PAGE (reducing conditions) followed by silver staining (1 µg protein per lane), Coomassie staining or Western blotting (250 ng protein per lane) using monoclonal anti-TRAIL (MAB687, R&D Systems, Wiesbaden, Germany) or anti-FLAG antibodies (M2, Sigma-Aldrich) in combination with alkaline phosphatase-conjugated secondary antibody (Sigma-Aldrich). The glycosylated polypeptide of SEQ ID NO: 97 was treated with N-glycosidase and analysed by SDS-PAGE and Coomassie staining. For deglycosylation, protein (5 µg) was denatured in the presence of SDS and DTT prior to addition of Nonidet P-40 and 500 units of PNGaseF (New England Biolabs, Frankfurt a. M., Germany) according to the supplier's instructions. After 1 h incubation at 37° C., samples were subjected to SDS-PAGE. For Western blotting, an anti-TRAIL antibody MAB687 (R&D Systems, Wiesbaden, Germany) and anti-FLAG M2 mAb (Sigma-Aldrich) were used, followed by an anti-mouse alkaline phosphatase-coupled secondary antibody (Sigma-Aldrich) for detection.

The results of the SDS PAGE/Western Blot analysis verified the increase in molecular mass of SEQ ID NOs: 96, 97 and 102 vs. SEQ ID NO: 104. The increase of molecular mass of SEQ ID NOs: 125 and 126 vs. SEQ ID NO: 102 has been verified by SDS page and Coomassie staining. SEQ ID NO: 97 showed reduced migration in SDS PAGE, which is conform with effective glycosylation of the protein. This was confirmed by PNGaseF treatment of the fusion protein, which removes carbohydrate side chains in glycoproteins, resulting in a shift of the specific band towards the mass of the non-glycosylated form. Furthermore, the assays confirmed the presence of TRAIL as well as of the FLAG-tag in all 4 polypeptides.

1.5 Size Exclusion Chromatography and Albumin Binding Assay

Purified polypeptides of SEQ ID NO: 96, SEQ ID NO: 102, SEQ ID NO: 104 and of glycosylated SEQ ID NO: 97 were separated by size exclusion chromatography on a BioSuite 250 HR SEC (300×7.8) column (Waters, Millipore Corp., Milford, Mass.) equilibrated in PBS and eluted at a flow rate of 0.5 ml/min.

Albumin binding to the polypeptides of SEQ ID NOs: 125 and 126 has been verified by incubating the polypeptides with human serum albumin or mouse serum albumin and determining protein-protein interaction by size exclusion chromatography as described above.

1.6 Immunoprecipitation and Protein Analysis

For immunoprecipitations, cells were lysed on ice in RIPA buffer (50 mM Tris, pH 7.5, 150 mM NaCl, 10 mM sodium fluoride, 20 mM glycerophosphate, 1 mM EDTA, 1% NP40, 1 mM sodium orthovanadate, 0.5 mM phenylmethylsulfonyl fluoride, 0.1% SDS, 0.25% sodium deoxycholate) with Complete protease inhibitor (Roche Diagnostics, Mannheim, Germany) and lysates were clarified by centrifugation (16 000 g, 10 min, 4° C.). 1.5 mg lysate protein was incubated with 1.5 µg mouse anti-EGFR Ab-13 mAb (Neomarkers, Fremont, Calif., USA) under gentle shaking at 4° C. overnight. Immune complexes were captured with protein G sepharose (KPL, Gaithersburg, Md., USA) and washed three times with RIPA buffer. Proteins were analyzed by SDS-PAGE and Western blotting using mouse anti-phosphotyrosine P-Tyr-100 mAb (Cell Signaling Technology, Danvers, Mass., USA) and rabbit anti-EGFR 1005 antibody (Santa Cruz Biotechnology, Santa Cruz, Calif., USA) followed by HRP-conjugated secondary antibodies. ECL (Pierce Biotechnology, Rockford, Ill., USA) was used for visualization.

Caspases were detected by immunoblotting using a rabbit polyclonal antibody against cleaved caspase-3 (Cell Signaling Technology). GAPDH as internal control was detected with a rabbit polyclonal antibody (Cell Signaling Technology). HRP-conjugated secondary antibodies (Zymed Laboratories, San Fransisco, Calif., USA) and ECL were used for visualization.

Example 2: Flow Cytometry, Cell Death Assay, ALT and Caspase Activities 2.1 Flow Cytometry $5 \times 10^5$ cells were suspended in PBA buffer (PBS, 0.025% BSA, 0.02% sodium azide) and incubated for 1 h at 4° C. with the indicated scTRAIL fusion proteins (2 µg/ml). After washing the cells three times with PBA buffer, bound fusion proteins were detected by anti-human TRAIL mAb MAB687 (2.5 µg/ml, R&D Systems) and fluorescein isothiocyanate-labelled rabbit anti-mouse IgG Ab (1:200, Sigma-Aldrich), followed by three washing steps with PBA each. For blocking of scTRAIL fusion protein binding to EGFRs (see FIG. 5B), a divalent variant of huC225 (huC225Cys, 50 µg/ml, kindly provided by Celonic GmbH, Jülich, Germany) was added 30 min before addition of SEQ ID NO: 96 and SEQ ID NO: 102, respectively. Expression of TRAIL receptors was detected by anti-TRAIL R1 mAb MAB347 and anti-TRAIL R2 mAb MAB6311 (4 µg/ml each, R&D Systems) in conjunction with anti-mouse IgG-FITC. EGFR expression was detected by a phycoerythrin-labelled anti-human EGFR mAb sc-101 (4 µg/ml, Santa Cruz Biotech., Santa Cruz, Calif.) (see FIG. 4). For binding inhibition, purified SEQ ID NO: 102 (50 µg/ml) was added 30 min prior addition of Alexa Fluor 488-coupled mAb Cetuximab (1 µg/ml) (see FIG. 5A).

The assays determined the expression levels of EGF receptor and proapoptotic TRAIL receptors DR4 and DR5 in Huh-7 and Hep2G hepatocellular carcinoma cell lines and the T cell leukemia line Jurkat, revealing Huh7 as EGFR+, DR4+, DR5 low; HepG2 as EGFR low/negative, DR4+, DR5+; and Jurkat as EGFR negative, DR4 negative, DR5 low (see FIG. 4). Furthermore, blocking of the binding of anti EGFR mab Cetuximab to EGFR+ cells (Huh-7) by an excess of EGFR receptor specific TRAIL protein (SEQ ID NO: 102) revealed functional expression of the EGFR specific $V_H$-$V_L$ domain within the fusion protein of SEQ ID NO: 102 (FIG. 5A, right panel); as expected, the marginal Cetuximab staining of EGFR low/negative HepG2 cells could not be further reduced by an excess of the fusion protein of SEQ ID NO: 102, and likely reflect nonspecific background staining of the reagent. Likewise, binding of the EGFR targeting fusion proteins SEQ ID NO: 102 and SEQ ID NO: 96 to EGFR+ Huh-7 cells was partially blockable by an excess of an anti-EGFR specific antibody fragment, whereby the remaining signal could be attributed to specific binding of the fusion proteins via the TRAIL domain to their cognate TRAIL receptors. In this experimental setting, binding of fusion proteins was clearly discernable for DR4+

DR5+HepG2 cells, too, with little blocking of the signal by addition of an anti-EGFR specific antibody fragment due to low expression of EGFRs at or below the detection level in these cells.

2.2 Cell Death Assays

Huh-7 ($3\times10^4$), HepG2 ($3\times10^4$), Colo205 ($5\times10^4$ per well) or Jurkat cells ($1\times10^5$) were grown in 100 µl culture medium in 96-well plates for 24 h, followed by treatment with the indicated concentrations of SEQ ID NOs: 96, 102, 125, 126 and 104 or 'KillerTRAIL' (Axxora Deutschland GmbH, Lörrach, Germany) in triplicates (see FIGS. 6-8 and 18). As a positive control, cells were killed with 0.25% Triton X-100. Cell death assays with Huh-7 and HepG2 cells were performed in the absence (FIG. 6, Jurkat cells) or presence of Bortezomib (FIG. 7, Huh-7: 250 ng/ml, FIG. 6, HepG2: 500 ng/ml, FIG. 18, Huh-7: 250 ng/ml), Selleck Chemicals, Houston, Tex.). Bortezomib was added 30 min prior incubation with the proapoptotic ligands to sensitize cells for the induction of cell death (FIGS. 6, 7). Alternatively, cells were preincubated for 30 min with the indicated concentrations of TRAIL fusion proteins followed by addition of serial dilutions of Bortezomib (FIG. 8). TRAIL only treated cells are shown in each panel for the applied TRAIL concentration (Bortezomib 0 ng/ml) (FIG. 8). After 16 h incubation, cell viability was determined either by crystal violet staining (Huh-7, HepG2) or the MTT method (Jurkat) (Wuest et al., 2002). In the latter case a lysis buffer consisting of 15% SDS in DMF/$H_2O$ (1:1), pH 4.5 (with 80% acetic acid) was used. To demonstrate target antigen-dependent induction of cell death, cells were preincubated for 30 min with competing Cetuximab mAb (10 µg/ml, Merck, Darmstadt, Germany) (FIG. 18) or alternatively EGFR specific huC225Cys (10 µg/ml) (FIG. 7).

2.3 Alanine Aminotransaminase (ALT) and Caspase Activities

Groups of three CD1 mice (Janvier, Le Genest-St-Isle, France) were treated i.p. with 1 nmol of fusion proteins according to SEQ ID NO: 102 and SEQ ID NO: 97, 0.1 nmol FasL fusion protein (positive control) and PBS (negative control), respectively. Blood samples were taken from the tail after 4 h and 24 h and incubated on ice. Clotted blood was centrifuged (10 000 g, 10 min, 4° C.) and serum samples were stored at −80° C. Activity of alanine aminotransaminase was determined by an enzymatic assay (BIOO Scientific, Austin, Tex., USA). To determine caspase-3 activity in the liver tissue, mice were sacrificed after 24 h (positive control after 5 h) and liver biopsies were taken. Homogenates were prepared in lysis buffer (200 mM NaCl, 20 mM Tris, 1% NP-40, pH 7.4). 10 µg of protein were analyzed by conversion of the fluorogenic substrate Ac-DMQD-AMC (Enzo Life Sciences). Caspase activity in PHH and Huh-7 cells was determined as published by Seidel et al. (Hepatology 2005, 42:113-120).

Example 3: Xenograft Mouse Tumor Model 8-week-old female NMRI nu/nu mice (Janvier) were injected s.c. with $3\times10^6$ Colo205 cells in 100 µl PBS at left and right dorsal sides. Treatment started 6 days after tumor cell inoculation when tumors reached about 100 $mm^3$. Mice received 8 daily i.p. injections of 0.45 nmol of the affinity-purified TRAIL fusion proteins according to SEQ ID NOs: 104, 97, and 102, respectively. On day 1, 3, 5 and 7 of treatment, mice received additionally 5 µg bortezomib in 100 µl PBS i.p. three hours before protein injection. The control groups received 100 µl PBS or 5 µg bortezomib at the same time intervals. Tumor growth was monitored as described in Schneider et al. (Cell Death Dis. 2010; 1: e68) and Kim et al. (Bioconjug. Chem. 2011; 22: 1631-1637). The Tukey's test was applied for statistics.

Description of Results Disclosed in Examples 1, 2 and 3

The main aim of the shown examples was the improvement of the proapoptotic activity of scTRAIL fusion proteins under retention of their tumor selectivity, i.e. non-reactivity towards normal, non-malignant tissue. In principle, the same rules apply for other proapoptotic members of the TNF family, as well as all other non-apoptotic, tissue and immune-regulatory TNF ligands that are inactive as soluble ligands or require membrane targeting to restrict their activity to the relevant tissue or cell types. The examples are also not restricted to the specific target antigen used exemplarily (EGFR), but apply, in principle, to all other tissue or cell selective targets, including, for tumor therapeutic purposes, tumor stroma markers such as fibroblast activation protein.

Construction and Preparation of scTRAIL Fusion Proteins

For generation of functionally improved scFv-TRAIL fusion proteins, first, the genetic code of scTRAIL was adapted for higher protein yields in mammalian expression systems. Among the various linker motifs suitable to connect 3 Trail molecules (components A) the $(GGGS)1-4$ motifs were tested, with the shorter linkers $(GGGS)_1$ (SEQ ID NO: 47) and $(GGGS)_2$ (SEQ ID NO: 48) being superior to longer linkers with respect to protein stability, tendency to aggregate and display identical or better apoptosis inducing activity.

The inventors used EGFR targeting as a model system. Like other members of the erbB family of receptor tyrosine kinases, the EGFR (erbB1) is an established tumor marker, which is overexpressed in several carcinomas, including lung and liver cancer (Olayioye et al, 2000). For generation of the EGFR specific fusion protein of SEQ ID NO: 96, the construct was N-terminally fused with component B, a humanized and codon-optimized antibody fragment derived from the anti-EGFR mAb Cetuximab (C225) (Naramura et al, 1993) (SEQ ID NO: 94). A FLAG tag (F) was placed N-terminal of component B for purification and detection purposes (FIG. 1A). TRAIL bioactivity depends on the oligomerization state, in particular relevant for TRAILR2 (DR5), which is poorly activated by soluble, trimeric forms of TRAIL (Wajant et al, 2001). For SEQ ID NO: 102 the linker L between $V_H$ and $V_L$ was shortened from $(GGGGS)_3$ (SEQ ID NO: 52) to GGGGS (SEQ ID NO: 50). In an independent approach to improve basal protein stability and protection from proteolytic processing during expression culture conditions, two variants of SEQ ID NO: 96 were designed, in which i) the linker X connecting component A and B comprised two N-glycosylation sites, yielding a monomeric glycosylated form (SEQ ID NO:97) and ii) in addition, the two glycin linkers (P) connecting the three TRAIL components were replaced by linkers (P1, P2) each comprising two N-glycosylation sites, too (FIG. 1) (SEQ ID NO: 98).

Following expression in stably transfected HEK293 cells, the purification of SEQ ID NO: 96 and SEQ ID NO: 102 was accomplished both by IMAC due to intrinsic histidine residues of TRAIL and by M2 mAb affinity chromatography. For example, yields of >3 mg highly pure protein per liter cell culture supernatant were achievable for both fusion proteins. SDS-PAGE and Western blot analysis of the purified proteins revealed single protein bands with an approx. molecular mass of 70 kDa and 100 kDa for scTRAIL (SEQ ID NO: 104) and EGFR specific $V_H$-$V_L$-scTRAIL fusion proteins SEQ ID NOs: 96 and 102, respectively, matching the expected calculated molecular masses of the single stranded monomers of 68, 93 and 94 kDa (FIG. 2). The apparent molecular mass of SEQ ID NO: 97 was increased compared to SEQ ID NO: 96, in accordance with effective glycosylation of the introduced linker. N-glycosidase treatment of SEQ ID NO: 97 resulted in a protein with a molecular mass essentially identical to that of its non-glycosylated derivative. The introduction of N-glycosylation sites in SEQ ID NO: 96 improved protein stability and protection from degradation during the production process, evident from strong reduction of degradation products present in culture supernatants (not shown). This allows a single-step purification of glycosylated variants such as SEQ ID NO: 97 with M2 agarose to gain a purification grade comparable to that of non-glycosylated fusion proteins after a two-step purification and thus overall higher yields of purified, bioactive protein.

The gel filtration analysis of fusion proteins (SEQ ID NO: 104) and SEQ ID NO: 96 (both, with and without glycosylation) indicated that the majority of protein (>94%) exists as a monomer (FIG. 3), whereas retention times decrease from scTRAIL (SEQ ID NO: 104) to SEQ ID NO: 97, according to the increase in molecular size. Concerning scTRAIL (SEQ ID NO: 104), the molecular mass deduced from SEC was slightly lower compared to that calculated from SDS-PAGE (FIG. 2), which is a characteristic of this molecule and not a hint for degradation (Schneider et al, 2010). Interestingly, SEC of SEQ ID NO: 102 revealed the presence of two peaks. The major peak near 200 kDa could be attributed to a dimer, whereas the minor peak could represent trimeric and/or tetrameric forms of the fusion protein.

TRAIL fusion proteins comprising an albumin binding domain (ABD) either between component A and component B (SEQ ID NO: 125) or at the C-terminus of the fusion protein (SEQ ID NO: 126) have been purified from HEK293 cells as described above. The increase in molecular weight, which is essentially the result of the introduction of the ABD, can be seen on the Coomassie stained SDS-PAGE gel depicted in FIG. 16.

Size exclusion chromatographie experiments showed that the TRAIL fusion proteins comprising an albumin binding domain are indeed capable of binding both, humen and mouse serum albumin (FIG. 17).

EGFR-Specific Binding of scTRAIL Fusion Proteins

The specific antigen binding of various scTRAIL fusion proteins to EGFR-positive cells was analysed by flow cytometry of two HCC cell lines. Whereas EGFRs in HepG2 cells were barely detectable and thus considered target antigen low/negative, EGFR expression was clearly revealed in Huh-7 cells (FIG. 4), although EGFR levels in this HCC line appear moderate compared with EGFR over-expressing A431 cells (data not shown). Consistent with this, the binding of labelled Cetuximab to the EGFR-positive Huh-7 cells can be blocked by preincubation with 0.5 μM of SEQ ID NO: 102 (FIG. 5). Incubation of HepG2 and Huh-7 cells with SEQ ID NO: 96 or SEQ ID NO: 102 resulted in binding of the proteins to both cell lines, but competition of fusion protein binding by preincubation of cells with the anti-EGFR huC225 (2 μM) was only possible on Huh-7 cells (FIG. 2C). The intermediate fluorescence signal observed upon competition of fusion protein binding to Huh-7 cells likely reflects binding of the TRAIL domain (component A of the fusion protein) to TRAIL receptors. This is consistent with the weaker and non-blockable binding of SEQ ID NO: 96 and SEQ ID NO: 102 on EGFR low/neg. HepG2 cells. Binding competition of both fusion proteins to EGFR-positive cells is an indicator for the structural integrity and functionality of the targeting domain (component B).

Quantitative binding studies of TRAIL fusion proteins to EGFR+, DR4+5+ NCI-H460 cells revealed significantly different (P=0.003) EC50 values for TRAIL fusion protein according to SEQ ID NO: 97 ($3.6\pm0.3\times10^{-10}$ M) and TRAIL fusion protein according to SEQ ID NO: 102 ($1.6\pm0.3\times10^{-10}$ M), implicating an avidity effect of the specific molecular composition of the divalent TRAIL fusion protein according to SEQ ID NO: 102 and therefore potentially superior targeting compared to TRAIL fusion protein according to SEQ ID NO: 97 (FIG. 12A). Furthermore, it has been investigated whether the TRAIL fusion protein according to SEQ ID NO: 102 exhibits the functional activity of blocking EGF-induced EGFR autophosphorylation. Cetuximab served as a positive control in this experiment. Functional blocking of EGF-stimulated receptor activation by the divalent TRAIL fusion protein according to SEQ ID NO: 102 could be demonstrated for both Colo205 (FIG. 12B, left panel) and Huh7 (FIG. 12B, right panel) cells.

Target-Independent Induction of Cell Death by scTRAIL Fusion Proteins

To investigate the basic bioactivity of scTRAIL fusion proteins without the influence of targeting domains, we first analysed cell death induction on the target-negative cell lines HepG2 (hepatoma) and Jurkat (T cell leukemia) and compared it with a non targeting scTRAIL molecule. On all cell lines analysed, SEQ ID NO: 102 exerted an approximately tenfold increased bioactivity compared to SEQ ID NO: 96 or its glycosylated form (SEQ ID NO: 97). As a reference, the bioactivity of a commercially available highly active TRAIL preparation, so-called 'KillerTRAIL'(Enzo Lifesciences), was found to be comparable with the activity of SEQ ID NO: 96. Due to the low or even deficient target antigen expression of HepG2 cells, the apoptosis inducing activity of SEQ ID NO: 102 and SEQ ID NO: 96 was not influenced by the presence of an at least 7-fold excess (70 nM) of Cetuximab (not shown). The bioactivity of SEQ ID NO: 96 on target negative cells did not differ from the one of SEQ ID NO: 104 (scTRAIL). On EGFR-negative, DR4-$DR5^{weak}$ Jurkat cells, which are known to be sensitive for apoptosis induced by TRAIL complexes but not by soluble TRAIL, we found a higher apoptosis-inducing activity of SEQ ID NO: 102 compared to KillerTRAIL and no reactivity towards the SEQ ID NOs: 96 and 104 (FIG. 6).

EGFR-Directed Enhancement of Cell Death by scTRAIL Fusion Proteins

The EGFR-positive liver carcinoma cell line Huh-7 was chosen to demonstrate the enhancement in bioactivity achievable due to the receptor targeting capacity of SEQ ID NO: 96 and SEQ ID NO: 102. Compared to scTRAIL (SEQ ID NO: 104), SEQ ID NO: 96 showed tenfold better apoptosis-inducing activity on Huh-7 cells (FIG. 7). The competition of this bioactivity with an excess of Cetuximab (70 nM) revealed a right shift of EC50 of SEQ ID NO: 96 in the same order of magnitude, pointing to the functionality of EGFR targeting responsible for the improvement of scTRAIL bioactivity. Glycosylated SEQ ID NO: 97 exerted identical bioactivity compared to its non-glycosylated variant, indicating that glycosylation at this site did not impact bioactivity. SEQ ID NO: 102 showed a tenfold enhanced bioactivity in relation to SEQ ID NO: 96. The competition of activity of SEQ ID NO: 102 with the same molar excess of Cetuximab also resulted in a comparable shift in the dose response curve, confirming that targeting further improves the already increased bioactivity of this fusion protein.

Furthermore, dimeric TRAIL fusion proteins comprising an albumin binding domain (ABD) (SEQ ID NOs: 125 and 126) exhibited bioactivity comparable to the dimeric TRAIL fusion protein lacking an ABD (SEQ ID NO: 102) indicating that the introduction of an ABD as performed for TRAIL fusion proteins according to SEQ ID NOs: 125 and 126 does not significantly influence the bioactivity of EGFR-directed enhancement of cell death (FIG. 18).

In another experimental setup, Huh-7 cells were pre-treated with a fixed dose of the various TRAIL fusion proteins followed by titration of the apoptosis sensitizer Bortezomib (FIG. 8). At a protein concentration of 1 nM and above, the tested SEQ ID NOs: 102, 96 and 104 were nearly equally efficient in induction of complete apoptosis in these cells when sensitized with Bortezomib. In contrast, at protein concentrations of 0.1 nM and below, a strong synergistic effect of Bortezomib sensitization and the EGFR targeting ability of the constructs became visible. At a protein concentration of 0.05 nM, only SEQ ID NOs: 96 and 102 were able to synergize with Bortezomib, whereby SEQ ID NO: 102 showed higher bioactivity compared to SEQ ID NO: 96 at this concentration. Superior activity of SEQ ID NO: 102 was even more apparent at 0.01 nM of fusion proteins (FIG. 8).

A nearly complete block of cell death by either pan-caspase (zVADfmk) or caspase-3 selective (zDEVDfmk) inhibitors (FIG. 13A) and failure of necrostatin-1 to prevent or reduce cell death (data not shown) indicated that Huh-7 and Colo205 undergo predominantly apoptotic cell death upon treatment with TRAIL fusion proteins. Cetuximab blocked EGF-induced autophosphorylation of EGF receptors (FIG. 12B). Further, cetuximab by itself, though blocking EGF-induced autophosphorylation of EGFR in Colo205 and in Huh7 cells (FIG. 12B), did not substantially affect growth of these two cancer cell lines in a 4-day culture (FIG. 13B, C). Likewise, when SEQ ID NO: 102-induced apoptosis was prevented, either by presence of neutralizing anti-TRAIL antibodies in SEQ ID NO: 102 treated Colo205 cell cultures (FIG. 13B) or by treating Huh-7 cell cultures with pan-caspase inhibitors (FIG. 13C), only a marginal growth inhibition was noted during the 4 day observation period. Together, for the cells and the in vitro conditions studied here, the data indicate that i) SEQ ID NO: 102-induced cell death requires TRAIL signaling and ii) blocking EGFR function by the SEQ ID NO: 102 does not contribute to rapid apoptosis induction.

Binding Affinity of SEQ ID NO: 96 and SEQ ID NO: 102 to Cells

The specific molecular composition of SEQ ID NO: 102 implies avidity effects and thus potential superior targeting functions as compared to SEQ ID NO: 96. Therefore, we determined dissociation constants of both fusion proteins on EGFR-positive, DR4+5+ NCI-H460 cells under equilibrium binding conditions at 4° C. by indirect immunofluorescence flow cytometry with an anti-TRAIL antibody. The $K_D$ of the interaction between the scTRAIL fusion proteins and NCI-H460 cells at 4° C. was determined by Lineweaver-Burk kinetic analysis (Lineweaver and Burk, 1934; Benedict et al, 1997) and was found to be 4-fold lower for the fusion protein of SEQ ID NO: 102 ($6.5 \pm 0.9 \times 10^{-8}$ M for SEQ ID NO: 96 and $1.7 \pm 1.2 \times 10^{-8}$ M for SEQ ID NO: 102, respectively). In principle, the measured $K_D$ values reflect cell surface interactions of both functional domains in the fusion protein, the EGFR targeting domain (Component B) and the TRAIL domain, (components A), with their respective receptors. However, because SEQ ID NO: 102 binding to TRAILR+, EGFR negative cells such as Jurkat resulted in only very weak signals in this assay (data not shown), we reason that the signals revealed for NCI-H460 are largely due to binding of the fusion protein via its $V_H$-$V_L$ domain to EGFRs. In fact, under the assay conditions (4° C.) applied, dynamic clustering of TRAILR that could account for stable receptor ligand interactions and thus apparent enhanced affinity is prevented. Therefore, we attribute this increased affinity largely to an avidity effect of the bivalent targeting domain (component B) of this particular fusion protein (SEQ ID NO: 102).

Lack of Systemic Toxicity of SEQ ID NO: 102 and Pharmacokinetics

To assess whether the strongly increased bioactivity of SEQ ID NO: 102 in vitro diminishes the advantageous tumor selectivity of TRAIL, we studied systemic tolerance and effects of in vivo application on the reportedly most sensitive organ concerning untolerable TRAIL side effects, the liver. Groups of 3 CD1 mice were treated intraperitonally with indicated reagents (FIG. 9): neg. control: PBS; pos. control: aggregated FasL fusion protein; SEQ ID NO: 102 and SEQ ID NO: 96 (A) Plasma samples were prepared after 4 h and 24 h and the activity of alanine aminotransferase (ALT) was assayed using an enzymatic assay. Dashed line indicates upper normal level of ALT (35-50 U/L). (B) Mice were sacrificed after 24 h except for pos. control (animals treated with an aggregated FasL fusion protein show phenotypic signs of severe systemic toxicity after 2-4 hrs and die after ~5 hrs, samples were taken after 4 hrs) and liver biopsies were taken for determination of caspase-3 activity using a specific AMC-coupled peptide substrate. The data clearly show that the SEQ ID NO: 102, despite its strongly increased apoptotic activity in vitro on target positive tumor cell lines (compared to non-targeted scTRAIL and the most active commercially available TRAIL) remains systemically well tolerated at doses up to 3 mg/kg in mouse models. Moreover, biochemical parameters of organ (liver) specific pathology confirm the phenotypic tolerance to this TRAIL fusion proteins, with only a transient marginal increase in ALT values to the upper normal limit 4 hrs after application. Lack of caspase activation and baseline ALT after 24 hrs, when bioactive fusion protein is still detectable in the blood ($T\alpha_{1/2}$=2h, $T\beta_{1/2}$ 3h; plasma conc at t=24h: 100 ng/ml with an applied iv dose of 100 µg/animal; proof that SEQ ID NO: 102 maintain tumor selectivity and can be safely applied in vivo.

Furthermore, a comparison of Huh-7 hepatoma cells and primary human hepatocytes (PHH) for caspase-3 activation by SEQ ID NO: 102 in presence of bortezomib showed a strong, bortezomib-dependent caspase-3 activation in the tumor cells, whereas normal liver cells were neither affected by the scTRAIL fusion protein alone nor in combination with bortezomib (FIG. 14A). These results were confirmed by immunoblot analysis of cleaved caspase-3 in Huh-7 and PHH, with no detectable caspase activation in combination treated PHH, whereas robust caspase processing was detectable in sensitive Huh7 carcinoma cells (FIG. 14B).

Antitumoral Activity of SEQ ID NO: 102 in a Xenograft Tumor Model

Given the in vitro data, showing superior bioactivity of the divalent TRAIL fusion protein according to SEQ ID NO: 102 compared with the monovalent TRAIL fusion protein according to SEQ ID NO: 97 or scTRAIL according to SEQ ID NO: 104 in particular at low protein concentrations, eight doses of 0.45 nmol protein were injected i.p. in a daily regimen in combination with bortezomib cotreatment every second day. The systemic treatment started after establishment of solid, vascularized tumors and tumor growth was monitored for 22 days. Bortezomib treatment by itself did not interfere with progressive tumor growth, whereas scTRAIL according to SEQ ID NO: 104 and the monovalent TRAIL fusion protein according to SEQ ID NO: 97 both delayed tumor growth, but at the low dosage applied, did not induce regression of tumors. In contrast, upon treatment with the divalent TRAIL fusion protein according to SEQ ID NO: 102, a strong reduction of tumor size and prolonged survival in all animals, with macroscopically undetectable tumors in 11/12 (+bortezomib) and 9/12 (w/o bortezomib) cases was recorded (FIG. 15). Interestingly, under the treatment conditions applied there was only a slight, but statistically not significant benefit of cotreatment with bortezomib, although at termination of treatment the combination group presented with slower regrowth of tumors (FIG. 15A).

Introduction of an Albumin Binding Domain Increases the In Vivo Half-Life of TRAIL Fusion Proteins The pharmacokinetics, in particular, the in vivo half-lives for the dimeric TRAIL fusion protein according to SEQ ID NO: 102 lacking an albumin binding domain (ABD) and the dimeric fusion protein comprising an ABD between component A and component B of the TRAIL fusion protein (SEQ ID NO: 125) have been compared. To this end, 25 µg of fusion proteins were injected i.v. in CD1 mice and serum samples were analyzed at certain time points after injection by ELISA assay (FIG. 19). It has been demonstrated that the in vivo serum half-life increases from about 3 hours for the construct without ABD (SEQ ID NO: 102) to about 20 hours for the construct comprising an ABD (SEQ ID NO: 125) (FIG. 19). As indicated above, the constructs comprising an ABD exert a similar bioactivity compared to the constructs lacking an ABD (Figure. 18) indicating that the ABD does not negatively influence bioactivity, but exerts advantageous properties regarding pharmacokinetic properties, such as in vivo serum half-life. Thus, the TRAIL fusion proteins, preferably dimeric TRAIL fusion proteins, as described above comprising an ABD, such as the dimeric TRAIL fusion proteins according to SEQ ID NO: 125 and 126, are particularly preferred embodiments of the polypeptide according to the present invention.

The inventors of the present invention have thus provided evidence for an improved concept in targeted cancer therapy. It may be that polypeptides according to the present invention form oligomers while polypeptides such as SEQ ID NO: 96 remain strictly monomeric. If so, it is surprising that the potential oligomeric structure of the polypeptides according to the present invention does not result in an increased systemic toxicity. The presence of higher-order aggregates in preparations of recombinant TRAIL constructs (e.g. His-TRAIL, crosslinked FLAG-TRAIL) has been reported previously to be responsible for an increased toxicity towards some non-malignant tissue cells (reviewed by Koschny et al, 2007). Thus, the inventors provide new formats of highly active and tumor selective TRAIL molecules with improved in vivo stability and pharmacokinetic properties, thus reaching an unprecedented potential as tumor therapeutic.

The invention claimed is:

1. A polypeptide comprising:
   a) at least three components A, each of which comprises the sequence of a TNF homology domain (THD) of 4-1BBL having at least 90% sequence identity to SEQ ID NO: 31, and
   b) at least one component B consisting of a $V_L$ region and a $V_H$ region linked directly to each other with a linker sequence L which has a length of ≤12 amino acids, wherein the $V_L$ and $V_H$ regions are of an antibody that binds to a cell surface molecule selected from the group consisting of: a cytokine receptor, a growth factor receptor, an integrin, a cell adhesion molecule and/or a cell type- or tissue-specific cell surface antigen, cell surface expressed tumor-associated antigens (TAA), and carbohydrates.

2. The polypeptide according to claim 1, wherein the at least three components A are identical.

3. The polypeptide according to claim 1, wherein component A comprises a sequence having at least 95% sequence identity to SEQ ID NOs: 31.

4. The polypeptide according claim 1, wherein the at least 3 components A are directly linked to each other via at least two intervening peptide linkers (peptide linker P).

5. The polypeptide according to claim 4, wherein the at least two peptide linkers P are selected from the group consisting of SEQ ID NOs: 39-90, and 91.

6. The polypeptide according to claim 5, wherein the at least two peptide linkers P are selected from SEQ ID NOs: 48, 88, and 90.

7. The polypeptide according to claim 1, wherein the $V_L$ region is selected from the group consisting of SEQ ID NOs: 92 and 130-132, and wherein the $V_H$ region is selected from the group consisting of SEQ ID NOs: 93 and 133-135.

8. The polypeptide according to claim 7, wherein the $V_L$ region is SEQ ID NO: 92 and the $V_H$ region is SEQ ID NO: 93.

9. The polypeptide according to claim 1, wherein the $V_L$ and $V_H$ region of a component B are linked with a linker sequence L selected from the group consisting of SEQ ID NOs: 39-51 and 53-78.

10. The polypeptide according to claim 9, wherein the linker sequence L is SEQ ID NO: 50.

11. The polypeptide according to claim 1, wherein component B has the sequence of SEQ ID NO: 94, 136, 137 or 138.

12. The polypeptide according to claim 1, wherein the polypeptide comprises a glycosylation motif and/or is glycosylated and/or comprises an albumin binding domain (ABD).

13. The polypeptide according to claim 1, wherein the polypeptide comprises an albumin binding domain (ABD) located between component A and component B or downstream of component A.

14. The polypeptide according to claim 13, wherein the polypeptide comprises an albumin binding domain (ABD) located at the C-terminal end of the polypeptide.

15. A nucleic acid encoding for the polypeptides according to claim 1.

16. The polypeptide complex comprising the polypeptide according to claim 1.

17. The polypeptide complex according to claim 16, which is a dimeric and/or trimeric complex.

18. A pharmaceutical composition comprising at least one polypeptide according to claim 1, optionally further comprising at least one pharmaceutically acceptable carrier, adjuvant, and/or vehicle.

* * * * *

SEQUENCE LISTING

```
<160> NUMBER OF SEQ ID NOS: 138

<210> SEQ ID NO 1
<211> LENGTH: 162
<212> TYPE: PRT
<213> ORGANISM: Homo sapiens

<400> SEQUENCE: 1

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly
```

<210> SEQ ID NO 2
<211> LENGTH: 164
<212> TYPE: PRT
<213> ORGANISM: Homo sapiens

<400> SEQUENCE: 2

Gly Pro Gln Arg Val Ala Ala His Ile Thr Gly Thr Arg Gly Arg Ser
1               5                   10                  15

Asn Thr Leu Ser Ser Pro Asn Ser Lys Asn Glu Lys Ala Leu Gly Arg
            20                  25                  30

Lys Ile Asn Ser Trp Glu Ser Ser Arg Ser Gly His Ser Phe Leu Ser
        35                  40                  45

Asn Leu His Leu Arg Asn Gly Glu Leu Val Ile His Glu Lys Gly Phe
    50                  55                  60

Tyr Tyr Ile Tyr Ser Gln Thr Tyr Phe Arg Phe Gln Glu Glu Ile Lys
65                  70                  75                  80

Glu Asn Thr Lys Asn Asp Lys Gln Met Val Gln Tyr Ile Tyr Lys Tyr
                85                  90                  95

Thr Ser Tyr Pro Asp Pro Ile Leu Leu Met Lys Ser Ala Arg Asn Ser
            100                 105                 110

Cys Trp Ser Lys Asp Ala Glu Tyr Gly Leu Tyr Ser Ile Tyr Gln Gly
        115                 120                 125

Gly Ile Phe Glu Leu Lys Glu Asn Asp Arg Ile Phe Val Ser Val Thr
    130                 135                 140

Asn Glu His Leu Ile Asp Met Asp His Glu Ala Ser Phe Phe Gly Ala
145                 150                 155                 160

Phe Leu Val Gly

<210> SEQ ID NO 3
<211> LENGTH: 166
<212> TYPE: PRT
<213> ORGANISM: Homo sapiens

<400> SEQUENCE: 3

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
            20                  25                  30

Gly Arg Lys Ile Asn Ser Trp Glu Ser Ser Arg Ser Gly His Ser Phe
        35                  40                  45

Leu Ser Asn Leu His Leu Arg Asn Gly Glu Leu Val Ile His Glu Lys
    50                  55                  60

Gly Phe Tyr Tyr Ile Tyr Ser Gln Thr Tyr Phe Arg Phe Gln Glu Glu
65                  70                  75                  80

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
        115                 120                 125

Gln Gly Gly Ile Phe Glu Leu Lys Glu Asn Asp Arg Ile Phe Val Ser
    130                 135                 140

Val Thr Asn Glu His Leu Ile Asp Met Asp His Glu Ala Ser Phe Phe
145                 150                 155                 160

Gly Ala Phe Leu Val Gly

<210> SEQ ID NO 4
<211> LENGTH: 168
<212> TYPE: PRT
<213> ORGANISM: Homo sapiens

<400> SEQUENCE: 4

Val Arg Glu Arg Gly Pro Gln Arg Val Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 5
<211> LENGTH: 187
<212> TYPE: PRT
<213> ORGANISM: Homo sapiens

<400> SEQUENCE: 5

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp

```
145                 150                 155                 160
Arg Ile Phe Val Ser Val Thr Asn Glu His Leu Ile Asp Met Asp His
                165                 170                 175
Glu Ala Ser Phe Phe Gly Ala Phe Leu Val Gly
            180                 185
```

<210> SEQ ID NO 6
<211> LENGTH: 193
<212> TYPE: PRT
<213> ORGANISM: Mus musculus

<400> SEQUENCE: 6

```
Thr Phe Gln Asp Thr Ile Ser Thr Val Pro Glu Lys Gln Leu Ser Thr
1               5                   10                  15
Pro Pro Leu Pro Arg Gly Gly Arg Pro Gln Lys Val Ala Ala His Ile
                20                  25                  30
Thr Gly Ile Thr Arg Arg Ser Asn Ser Ala Leu Ile Pro Ile Ser Lys
            35                  40                  45
Asp Gly Lys Thr Leu Gly Gln Lys Ile Glu Ser Trp Glu Ser Ser Arg
    50                  55                  60
Lys Gly His Ser Phe Leu Asn His Val Leu Phe Arg Asn Gly Glu Leu
65                  70                  75                  80
Val Ile Glu Gln Glu Gly Leu Tyr Tyr Ile Tyr Ser Gln Thr Tyr Phe
                85                  90                  95
Arg Phe Gln Glu Ala Glu Asp Ala Ser Lys Met Val Ser Lys Asp Lys
                100                 105                 110
Val Arg Thr Lys Gln Leu Val Gln Tyr Ile Tyr Lys Tyr Thr Ser Tyr
            115                 120                 125
Pro Asp Pro Ile Val Leu Met Lys Ser Ala Arg Asn Ser Cys Trp Ser
    130                 135                 140
Arg Asp Ala Glu Tyr Gly Leu Tyr Ser Ile Tyr Gln Gly Gly Leu Phe
145                 150                 155                 160
Glu Leu Lys Lys Asn Asp Arg Ile Phe Val Ser Val Thr Asn Glu His
                165                 170                 175
Leu Met Asp Leu Asp Gln Glu Ala Ser Phe Phe Gly Ala Phe Leu Ile
            180                 185                 190
Asn
```

<210> SEQ ID NO 7
<211> LENGTH: 138
<212> TYPE: PRT
<213> ORGANISM: Homo sapiens

<400> SEQUENCE: 7

```
Arg Lys Val Ala His Leu Thr Gly Lys Ser Asn Ser Arg Ser Met Pro
1               5                   10                  15
Leu Glu Trp Glu Asp Thr Tyr Gly Ile Val Leu Leu Ser Gly Val Lys
                20                  25                  30
Tyr Lys Lys Gly Gly Leu Val Ile Asn Glu Thr Gly Leu Tyr Phe Val
            35                  40                  45
Tyr Ser Lys Val Tyr Phe Arg Gly Gln Ser Cys Asn Asn Leu Pro Leu
    50                  55                  60
Ser His Lys Val Tyr Met Arg Asn Ser Lys Tyr Pro Gln Asp Leu Val
65                  70                  75                  80
Met Met Glu Gly Lys Met Met Ser Tyr Cys Thr Thr Gly Gln Met Trp
                85                  90                  95
```

Ala Arg Ser Ser Tyr Leu Gly Ala Val Phe Asn Leu Thr Ser Ala Asp
            100                 105                 110

His Leu Tyr Val Asn Val Ser Glu Leu Ser Leu Val Asn Phe Glu Glu
        115                 120                 125

Ser Gln Thr Phe Phe Gly Leu Tyr Lys Leu
        130                 135

<210> SEQ ID NO 8
<211> LENGTH: 140
<212> TYPE: PRT
<213> ORGANISM: Homo sapiens

<400> SEQUENCE: 8

Glu Leu Arg Lys Val Ala His Leu Thr Gly Lys Ser Asn Ser Arg Ser
1               5                   10                  15

Met Pro Leu Glu Trp Glu Asp Thr Tyr Gly Ile Val Leu Leu Ser Gly
            20                  25                  30

Val Lys Tyr Lys Lys Gly Gly Leu Val Ile Asn Glu Thr Gly Leu Tyr
        35                  40                  45

Phe Val Tyr Ser Lys Val Tyr Phe Arg Gly Gln Ser Cys Asn Asn Leu
    50                  55                  60

Pro Leu Ser His Lys Val Tyr Met Arg Asn Ser Lys Tyr Pro Gln Asp
65                  70                  75                  80

Leu Val Met Met Glu Gly Lys Met Met Ser Tyr Cys Thr Thr Gly Gln
                85                  90                  95

Met Trp Ala Arg Ser Ser Tyr Leu Gly Ala Val Phe Asn Leu Thr Ser
            100                 105                 110

Ala Asp His Leu Tyr Val Asn Val Ser Glu Leu Ser Leu Val Asn Phe
        115                 120                 125

Glu Glu Ser Gln Thr Phe Phe Gly Leu Tyr Lys Leu
    130                 135                 140

<210> SEQ ID NO 9
<211> LENGTH: 145
<212> TYPE: PRT
<213> ORGANISM: Homo sapiens

<400> SEQUENCE: 9

Pro Pro Glu Lys Lys Glu Leu Arg Lys Val Ala His Leu Thr Gly Lys
1               5                   10                  15

Ser Asn Ser Arg Ser Met Pro Leu Glu Trp Glu Asp Thr Tyr Gly Ile
            20                  25                  30

Val Leu Leu Ser Gly Val Lys Tyr Lys Lys Gly Gly Leu Val Ile Asn
        35                  40                  45

Glu Thr Gly Leu Tyr Phe Val Tyr Ser Lys Val Tyr Phe Arg Gly Gln
    50                  55                  60

Ser Cys Asn Asn Leu Pro Leu Ser His Lys Val Tyr Met Arg Asn Ser
65                  70                  75                  80

Lys Tyr Pro Gln Asp Leu Val Met Met Glu Gly Lys Met Met Ser Tyr
                85                  90                  95

Cys Thr Thr Gly Gln Met Trp Ala Arg Ser Ser Tyr Leu Gly Ala Val
            100                 105                 110

Phe Asn Leu Thr Ser Ala Asp His Leu Tyr Val Asn Val Ser Glu Leu
        115                 120                 125

Ser Leu Val Asn Phe Glu Glu Ser Gln Thr Phe Phe Gly Leu Tyr Lys
    130                 135                 140

Leu
145

<210> SEQ ID NO 10
<211> LENGTH: 152
<212> TYPE: PRT
<213> ORGANISM: Homo sapiens

<400> SEQUENCE: 10

Gln Ile Gly His Pro Ser Pro Pro Glu Lys Lys Glu Leu Arg Lys
1               5                   10                  15

Val Ala His Leu Thr Gly Lys Ser Asn Ser Arg Ser Met Pro Leu Glu
            20                  25                  30

Trp Glu Asp Thr Tyr Gly Ile Val Leu Leu Ser Gly Val Lys Tyr Lys
        35                  40                  45

Lys Gly Gly Leu Val Ile Asn Glu Thr Gly Leu Tyr Phe Val Tyr Ser
    50                  55                  60

Lys Val Tyr Phe Arg Gly Gln Ser Cys Asn Asn Leu Pro Leu Ser His
65                  70                  75                  80

Lys Val Tyr Met Arg Asn Ser Lys Tyr Pro Gln Asp Leu Val Met Met
                85                  90                  95

Glu Gly Lys Met Met Ser Tyr Cys Thr Thr Gly Gln Met Trp Ala Arg
            100                 105                 110

Ser Ser Tyr Leu Gly Ala Val Phe Asn Leu Thr Ser Ala Asp His Leu
        115                 120                 125

Tyr Val Asn Val Ser Glu Leu Ser Leu Val Asn Phe Glu Glu Ser Gln
    130                 135                 140

Thr Phe Phe Gly Leu Tyr Lys Leu
145                 150

<210> SEQ ID NO 11
<211> LENGTH: 162
<212> TYPE: PRT
<213> ORGANISM: Homo sapiens

<400> SEQUENCE: 11

Gln Met His Thr Ala Ser Ser Leu Glu Lys Gln Ile Gly His Pro Ser
1               5                   10                  15

Pro Pro Pro Glu Lys Lys Glu Leu Arg Lys Val Ala His Leu Thr Gly
            20                  25                  30

Lys Ser Asn Ser Arg Ser Met Pro Leu Glu Trp Glu Asp Thr Tyr Gly
        35                  40                  45

Ile Val Leu Leu Ser Gly Val Lys Tyr Lys Lys Gly Gly Leu Val Ile
    50                  55                  60

Asn Glu Thr Gly Leu Tyr Phe Val Tyr Ser Lys Val Tyr Phe Arg Gly
65                  70                  75                  80

Gln Ser Cys Asn Asn Leu Pro Leu Ser His Lys Val Tyr Met Arg Asn
                85                  90                  95

Ser Lys Tyr Pro Gln Asp Leu Val Met Met Glu Gly Lys Met Met Ser
            100                 105                 110

Tyr Cys Thr Thr Gly Gln Met Trp Ala Arg Ser Ser Tyr Leu Gly Ala
        115                 120                 125

Val Phe Asn Leu Thr Ser Ala Asp His Leu Tyr Val Asn Val Ser Glu
    130                 135                 140

Leu Ser Leu Val Asn Phe Glu Glu Ser Gln Thr Phe Phe Gly Leu Tyr
145                 150                 155                 160

Lys Leu

<210> SEQ ID NO 12
<211> LENGTH: 143
<212> TYPE: PRT
<213> ORGANISM: Mus musculus

<400> SEQUENCE: 12

Glu Lys Lys Glu Pro Arg Ser Val Ala His Leu Thr Gly Asn Pro His
1               5                   10                  15

Ser Arg Ser Ile Pro Leu Glu Trp Glu Asp Thr Tyr Gly Thr Ala Leu
            20                  25                  30

Ile Ser Gly Val Lys Tyr Lys Lys Gly Leu Val Ile Asn Glu Thr
        35                  40                  45

Gly Leu Tyr Phe Val Tyr Ser Lys Val Tyr Phe Arg Gly Gln Ser Cys
    50                  55                  60

Asn Asn Gln Pro Leu Asn His Lys Val Tyr Met Arg Asn Ser Lys Tyr
65                  70                  75                  80

Pro Glu Asp Leu Val Leu Met Glu Gly Lys Arg Leu Asn Tyr Cys Thr
                85                  90                  95

Thr Gly Gln Ile Trp Ala His Ser Ser Tyr Leu Gly Ala Val Phe Asn
            100                 105                 110

Leu Thr Ser Ala Asp His Leu Tyr Val Asn Ile Ser Gln Leu Ser Leu
        115                 120                 125

Ile Asn Phe Glu Glu Ser Lys Thr Phe Phe Gly Leu Tyr Lys Leu
    130                 135                 140

<210> SEQ ID NO 13
<211> LENGTH: 145
<212> TYPE: PRT
<213> ORGANISM: Homo sapiens

<400> SEQUENCE: 13

Val Ala His Val Val Ala Asn Pro Gln Ala Glu Gly Gln Leu Gln Trp
1               5                   10                  15

Leu Asn Arg Arg Ala Asn Ala Leu Leu Ala Asn Gly Val Glu Leu Arg
            20                  25                  30

Asp Asn Gln Leu Val Val Pro Ser Glu Gly Leu Tyr Leu Ile Tyr Ser
        35                  40                  45

Gln Val Leu Phe Lys Gly Gln Gly Cys Pro Ser Thr His Val Leu Leu
    50                  55                  60

Thr His Thr Ile Ser Arg Ile Ala Val Ser Tyr Gln Thr Lys Val Asn
65                  70                  75                  80

Leu Leu Ser Ala Ile Lys Ser Pro Cys Gln Arg Glu Thr Pro Glu Gly
                85                  90                  95

Ala Glu Ala Lys Pro Trp Tyr Glu Pro Ile Tyr Leu Gly Gly Val Phe
            100                 105                 110

Gln Leu Glu Lys Gly Asp Arg Leu Ser Ala Glu Ile Asn Arg Pro Asp
        115                 120                 125

Tyr Leu Asp Phe Ala Glu Ser Gly Gln Val Tyr Phe Gly Ile Ile Ala
    130                 135                 140

Leu
145

<210> SEQ ID NO 14
<211> LENGTH: 157

```
<212> TYPE: PRT
<213> ORGANISM: Homo sapiens

<400> SEQUENCE: 14

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 15
<211> LENGTH: 147
<212> TYPE: PRT
<213> ORGANISM: homo sapiens

<400> SEQUENCE: 15

Ser Asn Leu Lys Pro Ala Ala His Leu Ile Gly Asp Pro Ser Lys Gln
1               5                   10                  15

Asn Ser Leu Leu Trp Arg Ala Asn Thr Asp Arg Ala Phe Leu Gln Asp
                20                  25                  30

Gly Phe Ser Leu Ser Asn Asn Ser Leu Leu Val Pro Thr Ser Gly Ile
            35                  40                  45

Tyr Phe Val Tyr Ser Gln Val Val Phe Ser Gly Lys Ala Tyr Ser Pro
    50                  55                  60

Lys Ala Thr Ser Ser Pro Leu Tyr Leu Ala His Glu Val Gln Leu Phe
65                  70                  75                  80

Ser Ser Gln Tyr Pro Phe His Val Pro Leu Leu Ser Ser Gln Lys Met
                85                  90                  95

Val Tyr Pro Gly Leu Gln Glu Pro Trp Leu His Ser Met Tyr His Gly
            100                 105                 110

Ala Ala Phe Gln Leu Thr Gln Gly Asp Gln Leu Ser Thr His Thr Asp
        115                 120                 125

Gly Ile Pro His Leu Val Leu Ser Pro Ser Thr Val Phe Phe Gly Ala
130                 135                 140

Phe Ala Leu
145

<210> SEQ ID NO 16
<211> LENGTH: 163
<212> TYPE: PRT
<213> ORGANISM: Homo sapiens
```

<400> SEQUENCE: 16

Asp Leu Ser Pro Gly Leu Pro Ala Ala His Leu Ile Gly Ala Pro Leu
1               5                   10                  15

Lys Gly Gln Gly Leu Gly Trp Glu Thr Thr Lys Glu Gln Ala Phe Leu
            20                  25                  30

Thr Ser Gly Thr Gln Phe Ser Asp Ala Glu Gly Leu Ala Leu Pro Gln
        35                  40                  45

Asp Gly Leu Tyr Tyr Leu Tyr Cys Leu Val Gly Tyr Arg Gly Arg Ala
    50                  55                  60

Pro Pro Gly Gly Gly Asp Pro Gln Gly Arg Ser Val Thr Leu Arg Ser
65                  70                  75                  80

Ser Leu Tyr Arg Ala Gly Gly Ala Tyr Gly Pro Gly Thr Pro Glu Leu
                85                  90                  95

Leu Leu Glu Gly Ala Glu Thr Val Thr Pro Val Leu Asp Pro Ala Arg
            100                 105                 110

Arg Gln Gly Tyr Gly Pro Leu Trp Tyr Thr Ser Val Gly Phe Gly Gly
        115                 120                 125

Leu Val Gln Leu Arg Arg Gly Glu Arg Val Tyr Val Asn Ile Ser His
    130                 135                 140

Pro Asp Met Val Asp Phe Ala Arg Gly Lys Thr Phe Phe Gly Ala Val
145                 150                 155                 160

Met Val Gly

<210> SEQ ID NO 17
<211> LENGTH: 159
<212> TYPE: PRT
<213> ORGANISM: Homo sapiens

<400> SEQUENCE: 17

Gly Leu Pro Ala Ala His Leu Ile Gly Ala Pro Leu Lys Gly Gln Gly
1               5                   10                  15

Leu Gly Trp Glu Thr Thr Lys Glu Gln Ala Phe Leu Thr Ser Gly Thr
            20                  25                  30

Gln Phe Ser Asp Ala Glu Gly Leu Ala Leu Pro Gln Asp Gly Leu Tyr
        35                  40                  45

Tyr Leu Tyr Cys Leu Val Gly Tyr Arg Gly Arg Ala Pro Pro Gly Gly
    50                  55                  60

Gly Asp Pro Gln Gly Arg Ser Val Thr Leu Arg Ser Ser Leu Tyr Arg
65                  70                  75                  80

Ala Gly Gly Ala Tyr Gly Pro Gly Thr Pro Glu Leu Leu Leu Glu Gly
                85                  90                  95

Ala Glu Thr Val Thr Pro Val Leu Asp Pro Ala Arg Arg Gln Gly Tyr
            100                 105                 110

Gly Pro Leu Trp Tyr Thr Ser Val Gly Phe Gly Gly Leu Val Gln Leu
        115                 120                 125

Arg Arg Gly Glu Arg Val Tyr Val Asn Ile Ser His Pro Asp Met Val
    130                 135                 140

Asp Phe Ala Arg Gly Lys Thr Phe Phe Gly Ala Val Met Val Gly
145                 150                 155

<210> SEQ ID NO 18
<211> LENGTH: 138
<212> TYPE: PRT
<213> ORGANISM: Homo sapiens

<400> SEQUENCE: 18

-continued

```
Lys Ser Trp Ala Tyr Leu Gln Val Ala Lys His Leu Asn Lys Thr Lys
1               5                   10                  15

Leu Ser Trp Asn Lys Asp Gly Ile Leu His Gly Val Arg Tyr Gln Asp
            20                  25                  30

Gly Asn Leu Val Ile Gln Phe Pro Gly Leu Tyr Phe Ile Ile Cys Gln
            35                  40                  45

Leu Gln Phe Leu Val Gln Cys Pro Asn Asn Ser Val Asp Leu Lys Leu
        50                  55                  60

Glu Leu Leu Ile Asn Lys His Ile Lys Lys Gln Ala Leu Val Thr Val
65                  70                  75                  80

Cys Glu Ser Gly Met Gln Thr Lys His Val Tyr Gln Asn Leu Ser Gln
                85                  90                  95

Phe Leu Leu Asp Tyr Leu Gln Val Asn Thr Thr Ile Ser Val Asn Val
            100                 105                 110

Asp Thr Phe Gln Tyr Ile Asp Thr Ser Thr Phe Pro Leu Glu Asn Val
            115                 120                 125

Leu Ser Ile Phe Leu Tyr Ser Asn Ser Asp
        130                 135

<210> SEQ ID NO 19
<211> LENGTH: 133
<212> TYPE: PRT
<213> ORGANISM: Homo sapiens

<400> SEQUENCE: 19

Leu Gln Val Ala Lys His Leu Asn Lys Thr Lys Leu Ser Trp Asn Lys
1               5                   10                  15

Asp Gly Ile Leu His Gly Val Arg Tyr Gln Asp Gly Asn Leu Val Ile
            20                  25                  30

Gln Phe Pro Gly Leu Tyr Phe Ile Ile Cys Gln Leu Gln Phe Leu Val
            35                  40                  45

Gln Cys Pro Asn Asn Ser Val Asp Leu Lys Leu Glu Leu Leu Ile Asn
        50                  55                  60

Lys His Ile Lys Lys Gln Ala Leu Val Thr Val Cys Glu Ser Gly Met
65                  70                  75                  80

Gln Thr Lys His Val Tyr Gln Asn Leu Ser Gln Phe Leu Leu Asp Tyr
                85                  90                  95

Leu Gln Val Asn Thr Thr Ile Ser Val Asn Val Asp Thr Phe Gln Tyr
            100                 105                 110

Ile Asp Thr Ser Thr Phe Pro Leu Glu Asn Val Leu Ser Ile Phe Leu
            115                 120                 125

Tyr Ser Asn Ser Asp
    130

<210> SEQ ID NO 20
<211> LENGTH: 146
<212> TYPE: PRT
<213> ORGANISM: Homo sapiens

<400> SEQUENCE: 20

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
            35                  40                  45
```

```
Lys Arg Gln Gly Leu Tyr Tyr Ile Tyr Ala Gln Val Thr Phe Cys Ser
 50                  55                  60

Asn Arg Glu Ala Ser Ser Gln Ala Pro Phe Ile Ala Ser Leu Cys Leu
 65                  70                  75                  80

Lys Ser Pro Gly Arg Phe Glu Arg Ile Leu Arg Ala Ala Asn Thr
             85                  90                  95

His Ser Ser Ala Lys Pro Cys Gly Gln Gln Ser Ile His Leu Gly Gly
             100                 105                 110

Val Phe Glu Leu Gln Pro Gly Ala Ser Val Phe Val Asn Val Thr Asp
         115                 120                 125

Pro Ser Gln Val Ser His Gly Thr Gly Phe Thr Ser Phe Gly Leu Leu
         130                 135                 140

Lys Leu
145

<210> SEQ ID NO 21
<211> LENGTH: 149
<212> TYPE: PRT
<213> ORGANISM: Homo sapiens

<400> SEQUENCE: 21

Met Gln Lys Gly Asp Gln Asn Pro Gln Ile Ala Ala His Val Ile Ser
 1               5                   10                  15

Glu Ala Ser Ser Lys Thr Thr Ser Val Leu Gln Trp Ala Glu Lys Gly
                 20                  25                  30

Tyr Tyr Thr Met Ser Asn Asn Leu Val Thr Leu Glu Asn Gly Lys Gln
             35                  40                  45

Leu Thr Val Lys Arg Gln Gly Leu Tyr Tyr Ile Tyr Ala Gln Val Thr
 50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
             85                  90                  95

Ala Asn Thr His Ser Ser Ala Lys Pro Cys Gly Gln Gln Ser Ile His
             100                 105                 110

Leu Gly Gly Val Phe Glu Leu Gln Pro Gly Ala Ser Val Phe Val Asn
         115                 120                 125

Val Thr Asp Pro Ser Gln Val Ser His Gly Thr Gly Phe Thr Ser Phe
         130                 135                 140

Gly Leu Leu Lys Leu
145

<210> SEQ ID NO 22
<211> LENGTH: 132
<212> TYPE: PRT
<213> ORGANISM: Homo sapiens

<400> SEQUENCE: 22

Val Ser His Arg Tyr Pro Arg Ile Gln Ser Ile Lys Val Gln Phe Thr
 1               5                   10                  15

Glu Tyr Lys Lys Glu Lys Gly Phe Ile Leu Thr Ser Gln Lys Glu Asp
                 20                  25                  30

Glu Ile Met Lys Val Gln Asn Asn Ser Val Ile Ile Asn Cys Asp Gly
             35                  40                  45

Phe Tyr Leu Ile Ser Leu Lys Gly Tyr Phe Ser Gln Glu Val Asn Ile
 50                  55                  60
```

Ser Leu His Tyr Gln Lys Asp Glu Pro Leu Phe Gln Leu Lys Lys
 65                  70                  75                  80

Val Arg Ser Val Asn Ser Leu Met Val Ala Ser Leu Thr Tyr Lys Asp
                 85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130

<210> SEQ ID NO 23
<211> LENGTH: 129
<212> TYPE: PRT
<213> ORGANISM: Homo sapiens

<400> SEQUENCE: 23

Arg Tyr Pro Arg Ile Gln Ser Ile Lys Val Gln Phe Thr Glu Tyr Lys
 1               5                  10                  15

Lys Glu Lys Gly Phe Ile Leu Thr Ser Gln Lys Glu Asp Glu Ile Met
                20                  25                  30

Lys Val Gln Asn Asn Ser Val Ile Ile Asn Cys Asp Gly Phe Tyr Leu
            35                  40                  45

Ile Ser Leu Lys Gly Tyr Phe Ser Gln Glu Val Asn Ile Ser Leu His
        50                  55                  60

Tyr Gln Lys Asp Glu Glu Pro Leu Phe Gln Leu Lys Lys Val Arg Ser
 65                  70                  75                  80

Val Asn Ser Leu Met Val Ala Ser Leu Thr Tyr Lys Asp Lys Val Tyr
                 85                  90                  95

Leu Asn Val Thr Thr Asp Asn Thr Ser Leu Asp Asp Phe His Val Asn
            100                 105                 110

Gly Gly Glu Leu Ile Leu Ile His Gln Asn Pro Gly Glu Phe Cys Val
        115                 120                 125

Leu

<210> SEQ ID NO 24
<211> LENGTH: 157
<212> TYPE: PRT
<213> ORGANISM: Homo sapiens

<400> SEQUENCE: 24

Glu Ala Gln Pro Phe Ala His Leu Thr Ile Asn Ala Thr Asp Ile Pro
 1               5                  10                  15

Ser Gly Ser His Lys Val Ser Leu Ser Ser Trp Tyr His Asp Arg Gly
                20                  25                  30

Trp Ala Lys Ile Ser Asn Met Thr Phe Ser Asn Gly Lys Leu Ile Val
            35                  40                  45

Asn Gln Asp Gly Phe Tyr Tyr Leu Tyr Ala Asn Ile Cys Phe Arg His
        50                  55                  60

His Glu Thr Ser Gly Asp Leu Ala Thr Glu Tyr Leu Gln Leu Met Val
 65                  70                  75                  80

Tyr Val Thr Lys Thr Ser Ile Lys Ile Pro Ser Ser His Thr Leu Met
                 85                  90                  95

Lys Gly Gly Ser Thr Lys Tyr Trp Ser Gly Asn Ser Glu Phe His Phe
            100                 105                 110

Tyr Ser Ile Asn Val Gly Gly Phe Lys Leu Arg Ser Gly Glu Glu
            115                 120                 125

Ile Ser Ile Glu Val Ser Asn Pro Ser Leu Leu Asp Pro Asp Gln Asp
        130                 135                 140

Ala Thr Tyr Phe Gly Ala Phe Lys Val Arg Asp Ile Asp
145                 150                 155

<210> SEQ ID NO 25
<211> LENGTH: 178
<212> TYPE: PRT
<213> ORGANISM: Homo sapiens

<400> SEQUENCE: 25

Ile Arg Ala Glu Lys Ala Met Val Asp Gly Ser Trp Leu Asp Leu Ala
1               5                   10                  15

Lys Arg Ser Lys Leu Glu Ala Gln Pro Phe Ala His Leu Thr Ile Asn
            20                  25                  30

Ala Thr Asp Ile Pro Ser Gly Ser His Lys Val Ser Leu Ser Ser Trp
        35                  40                  45

Tyr His Asp Arg Gly Trp Ala Lys Ile Ser Asn Met Thr Phe Ser Asn
    50                  55                  60

Gly Lys Leu Ile Val Asn Gln Asp Gly Phe Tyr Tyr Leu Tyr Ala Asn
65                  70                  75                  80

Ile Cys Phe Arg His His Glu Thr Ser Gly Asp Leu Ala Thr Glu Tyr
                85                  90                  95

Leu Gln Leu Met Val Tyr Val Thr Lys Thr Ser Ile Lys Ile Pro Ser
            100                 105                 110

Ser His Thr Leu Met Lys Gly Gly Ser Thr Lys Tyr Trp Ser Gly Asn
        115                 120                 125

Ser Glu Phe His Phe Tyr Ser Ile Asn Val Gly Gly Phe Phe Lys Leu
    130                 135                 140

Arg Ser Gly Glu Glu Ile Ser Ile Glu Val Ser Asn Pro Ser Leu Leu
145                 150                 155                 160

Asp Pro Asp Gln Asp Ala Thr Tyr Phe Gly Ala Phe Lys Val Arg Asp
                165                 170                 175

Ile Asp

<210> SEQ ID NO 26
<211> LENGTH: 156
<212> TYPE: PRT
<213> ORGANISM: Homo sapiens

<400> SEQUENCE: 26

Ser Ala Pro Lys Gly Arg Lys Thr Arg Ala Arg Arg Ala Ile Ala Ala
1               5                   10                  15

His Tyr Glu Val His Pro Arg Pro Gly Gln Asp Gly Ala Gln Ala Gly
            20                  25                  30

Val Asp Gly Thr Val Ser Gly Trp Glu Glu Ala Arg Ile Asn Ser Ser
        35                  40                  45

Ser Pro Leu Arg Tyr Asn Arg Gln Ile Gly Glu Phe Ile Val Thr Arg
    50                  55                  60

Ala Gly Leu Tyr Tyr Leu Tyr Cys Gln Val His Phe Asp Glu Gly Lys
65                  70                  75                  80

Ala Val Tyr Leu Lys Leu Asp Leu Leu Val Asp Gly Val Leu Ala Leu
                85                  90                  95

Arg Cys Leu Glu Glu Phe Ser Ala Thr Ala Ala Ser Ser Leu Gly Pro

```
                    100                 105                 110
Gln Leu Arg Leu Cys Gln Val Ser Gly Leu Leu Ala Leu Arg Pro Gly
            115                 120                 125

Ser Ser Leu Arg Ile Arg Thr Leu Pro Trp Ala His Leu Lys Ala Ala
130                 135                 140

Pro Phe Leu Thr Tyr Phe Gly Leu Phe Gln Val His
145                 150                 155

<210> SEQ ID NO 27
<211> LENGTH: 145
<212> TYPE: PRT
<213> ORGANISM: Homo sapiens

<400> SEQUENCE: 27

Arg Ala Ile Ala Ala His Tyr Glu Val His Pro Arg Pro Gly Gln Asp
1               5                   10                  15

Gly Ala Gln Ala Gly Val Asp Gly Thr Val Ser Gly Trp Glu Glu Ala
            20                  25                  30

Arg Ile Asn Ser Ser Pro Leu Arg Tyr Asn Arg Gln Ile Gly Glu
        35                  40                  45

Phe Ile Val Thr Arg Ala Gly Leu Tyr Tyr Leu Tyr Cys Gln Val His
    50                  55                  60

Phe Asp Glu Gly Lys Ala Val Tyr Leu Lys Leu Asp Leu Leu Val Asp
65                  70                  75                  80

Gly Val Leu Ala Leu Arg Cys Leu Glu Glu Phe Ser Ala Thr Ala Ala
                85                  90                  95

Ser Ser Leu Gly Pro Gln Leu Arg Leu Cys Gln Val Ser Gly Leu Leu
            100                 105                 110

Ala Leu Arg Pro Gly Ser Ser Leu Arg Ile Arg Thr Leu Pro Trp Ala
        115                 120                 125

His Leu Lys Ala Ala Pro Phe Leu Thr Tyr Phe Gly Leu Phe Gln Val
    130                 135                 140

His
145

<210> SEQ ID NO 28
<211> LENGTH: 158
<212> TYPE: PRT
<213> ORGANISM: Homo sapiens

<400> SEQUENCE: 28

Leu Ile Gln Glu Arg Arg Ser His Glu Val Asn Pro Ala Ala His Leu
1               5                   10                  15

Thr Gly Ala Asn Ser Ser Leu Thr Gly Ser Gly Gly Pro Leu Leu Trp
            20                  25                  30

Glu Thr Gln Leu Gly Leu Ala Phe Leu Arg Gly Leu Ser Tyr His Asp
        35                  40                  45

Gly Ala Leu Val Val Thr Lys Ala Gly Tyr Tyr Ile Tyr Ser Lys
    50                  55                  60

Val Gln Leu Gly Gly Val Gly Cys Pro Leu Gly Leu Ala Ser Thr Ile
65                  70                  75                  80

Thr His Gly Leu Tyr Lys Arg Thr Pro Arg Tyr Pro Glu Glu Leu Glu
                85                  90                  95

Leu Leu Val Ser Gln Gln Ser Pro Cys Gly Arg Ala Thr Ser Ser Ser
            100                 105                 110

Arg Val Trp Trp Asp Ser Ser Phe Leu Gly Gly Val Val His Leu Glu
```

```
                115                 120                 125
Ala Gly Glu Lys Val Val Arg Val Leu Asp Glu Arg Leu Val Arg
    130                 135                 140

Leu Arg Asp Gly Thr Arg Ser Tyr Phe Gly Ala Phe Met Val
145                 150                 155
```

<210> SEQ ID NO 29
<211> LENGTH: 143
<212> TYPE: PRT
<213> ORGANISM: Homo sapiens

<400> SEQUENCE: 29

```
Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro
    130                 135                 140
```

<210> SEQ ID NO 30
<211> LENGTH: 138
<212> TYPE: PRT
<213> ORGANISM: Homo sapiens

<400> SEQUENCE: 30

```
Asp Val Ala Glu Leu Gln Leu Asn His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Arg Asp Gly Ile
        35                  40                  45

Tyr Met Val His Ile Gln Val Thr Leu Ala Ile Cys Ser Ser Thr Thr
    50                  55                  60

Ala Ser Arg His His Pro Thr Thr Leu Ala Val Gly Ile Cys Ser Pro
65                  70                  75                  80

Ala Ser Arg Ser Ile Ser Leu Leu Arg Leu Ser Phe His Gln Gly Cys
                85                  90                  95

Thr Ile Ala Ser Gln Arg Leu Thr Pro Leu Ala Arg Gly Asp Thr Leu
            100                 105                 110

Cys Thr Asn Leu Thr Gly Thr Leu Leu Pro Ser Arg Asn Thr Asp Glu
        115                 120                 125

Thr Phe Phe Gly Val Gln Trp Val Arg Pro
    130                 135
```

```
<210> SEQ ID NO 31
<211> LENGTH: 170
<212> TYPE: PRT
<213> ORGANISM: Homo sapiens

<400> SEQUENCE: 31

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Leu Ala
            85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
            115                 120                 125

Gly Val His Leu His Thr Glu Ala Arg Ala Arg His Ala Trp Gln Leu
            130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 32
<211> LENGTH: 128
<212> TYPE: PRT
<213> ORGANISM: Homo sapiens

<400> SEQUENCE: 32

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
            85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125

<210> SEQ ID NO 33
<211> LENGTH: 139
<212> TYPE: PRT
<213> ORGANISM: Homo sapiens

<400> SEQUENCE: 33
```

```
Lys Lys Gln His Ser Val Leu His Leu Val Pro Ile Asn Ala Thr Ser
1               5                   10                  15

Lys Asp Asp Ser Asp Val Thr Glu Val Met Trp Gln Pro Ala Leu Arg
            20                  25                  30

Arg Gly Arg Gly Leu Gln Ala Gln Gly Tyr Gly Val Arg Ile Gln Asp
        35                  40                  45

Ala Gly Val Tyr Leu Leu Tyr Ser Gln Val Leu Phe Gln Asp Val Thr
    50                  55                  60

Phe Thr Met Gly Gln Val Val Ser Arg Glu Gly Gln Gly Arg Gln Glu
65              70                  75                  80

Thr Leu Phe Arg Cys Ile Arg Ser Met Pro Ser His Pro Asp Arg Ala
            85                  90                  95

Tyr Asn Ser Cys Tyr Ser Ala Gly Val Phe His Leu His Gln Gly Asp
        100                 105                 110

Ile Leu Ser Val Ile Ile Pro Arg Ala Arg Ala Lys Leu Asn Leu Ser
        115                 120                 125

Pro His Gly Thr Phe Leu Gly Phe Val Lys Leu
    130                 135
```

<210> SEQ ID NO 34
<211> LENGTH: 147
<212> TYPE: PRT
<213> ORGANISM: Homo sapiens

<400> SEQUENCE: 34

```
Glu Asn Gln Pro Ala Val Val His Leu Gln Gly Gln Gly Ser Ala Ile
1               5                   10                  15

Gln Val Lys Asn Asp Leu Ser Gly Gly Val Leu Asn Asp Trp Ser Arg
            20                  25                  30

Ile Thr Met Asn Pro Lys Val Phe Lys Leu His Pro Arg Ser Gly Glu
        35                  40                  45

Leu Glu Val Leu Val Asp Gly Thr Tyr Phe Ile Tyr Ser Gln Val Glu
    50                  55                  60

Val Tyr Tyr Ile Asn Phe Thr Asp Phe Ala Ser Tyr Glu Val Val Val
65              70                  75                  80

Asp Glu Lys Pro Phe Leu Gln Cys Thr Arg Ser Ile Glu Thr Gly Lys
            85                  90                  95

Thr Asn Tyr Asn Thr Cys Tyr Thr Ala Gly Val Cys Leu Leu Lys Ala
        100                 105                 110

Arg Gln Lys Ile Ala Val Lys Met Val His Ala Asp Ile Ser Ile Asn
        115                 120                 125

Met Ser Lys His Thr Thr Phe Phe Gly Ala Ile Arg Leu Gly Glu Ala
    130                 135                 140

Pro Ala Ser
145
```

<210> SEQ ID NO 35
<211> LENGTH: 145
<212> TYPE: PRT
<213> ORGANISM: Homo sapiens

<400> SEQUENCE: 35

```
Glu Asn Gln Pro Ala Val Val His Leu Gln Gly Gln Gly Ser Ala Ile
1               5                   10                  15

Gln Val Lys Asn Asp Leu Ser Gly Gly Val Leu Asn Asp Trp Ser Arg
            20                  25                  30
```

Ile Thr Met Asn Pro Lys Val Phe Lys Leu His Pro Arg Ser Gly Glu
            35                  40                  45

Leu Glu Val Leu Val Asp Gly Thr Tyr Phe Ile Tyr Ser Gln Val Tyr
 50                  55                  60

Tyr Ile Asn Phe Thr Asp Phe Ala Ser Tyr Glu Val Val Val Asp Glu
 65                  70                  75                  80

Lys Pro Phe Leu Gln Cys Thr Arg Ser Ile Glu Thr Gly Lys Thr Asn
                 85                  90                  95

Tyr Asn Thr Cys Tyr Thr Ala Gly Val Cys Leu Leu Lys Ala Arg Gln
                100                 105                 110

Lys Ile Ala Val Lys Met Val His Ala Asp Ile Ser Ile Asn Met Ser
            115                 120                 125

Lys His Thr Thr Phe Phe Gly Ala Ile Arg Leu Gly Glu Ala Pro Ala
        130                 135                 140

Ser
145

<210> SEQ ID NO 36
<211> LENGTH: 180
<212> TYPE: PRT
<213> ORGANISM: Homo sapiens

<400> SEQUENCE: 36

Leu Lys Gly Gln Glu Phe Ala Pro Ser His Gln Val Tyr Ala Pro
 1               5                  10                  15

Leu Arg Ala Asp Gly Asp Lys Pro Arg Ala His Leu Thr Val Val Arg
             20                  25                  30

Gln Thr Pro Thr Gln His Phe Lys Asn Gln Phe Pro Ala Leu His Trp
         35                  40                  45

Glu His Glu Leu Gly Leu Ala Phe Thr Lys Asn Arg Met Asn Tyr Thr
 50                  55                  60

Asn Lys Phe Leu Leu Ile Pro Glu Ser Gly Asp Tyr Phe Ile Tyr Ser
 65                  70                  75                  80

Gln Val Thr Phe Arg Gly Met Thr Ser Glu Cys Ser Glu Ile Arg Gln
                 85                  90                  95

Ala Gly Arg Pro Asn Lys Pro Asp Ser Ile Thr Val Val Ile Thr Lys
                100                 105                 110

Val Thr Asp Ser Tyr Pro Glu Pro Thr Gln Leu Leu Met Gly Thr Lys
            115                 120                 125

Ser Val Cys Glu Val Gly Ser Asn Trp Phe Gln Pro Ile Tyr Leu Gly
        130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
        180

<210> SEQ ID NO 37
<211> LENGTH: 159
<212> TYPE: PRT
<213> ORGANISM: Homo sapiens

<400> SEQUENCE: 37

Asp Lys Pro Arg Ala His Leu Thr Val Val Arg Gln Thr Pro Thr Gln
 1               5                  10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
 50                  55                  60

Gly Met Thr Ser Glu Cys Ser Glu Ile Arg Gln Ala Gly Arg Pro Asn
 65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
130                 135                 140

Asp Tyr Thr Lys Glu Asp Lys Thr Phe Phe Gly Ala Phe Leu Leu
145                 150                 155

<210> SEQ ID NO 38
<211> LENGTH: 152
<212> TYPE: PRT
<213> ORGANISM: Homo sapiens

<400> SEQUENCE: 38

Ala Val Gln Gly Pro Glu Glu Thr Val Thr Gln Asp Cys Leu Gln Leu
 1               5                  10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
 50                  55                  60

Gln Val Leu Tyr Thr Asp Lys Thr Tyr Ala Met Gly His Leu Ile Gln
 65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
130                 135                 140

Phe Phe Gly Ala Leu Lys Leu Leu
145                 150

<210> SEQ ID NO 39
<211> LENGTH: 1
<212> TYPE: PRT
<213> ORGANISM: Artificial Sequence
<220> FEATURE:
<223> OTHER INFORMATION: Linker

<400> SEQUENCE: 39

Gly
1

```
<210> SEQ ID NO 40
<211> LENGTH: 2
<212> TYPE: PRT
<213> ORGANISM: Artificial Sequence
<220> FEATURE:
<223> OTHER INFORMATION: Linker

<400> SEQUENCE: 40

Gly Gly
1

<210> SEQ ID NO 41
<211> LENGTH: 3
<212> TYPE: PRT
<213> ORGANISM: Artificial Sequence
<220> FEATURE:
<223> OTHER INFORMATION: Linker

<400> SEQUENCE: 41

Gly Gly Gly
1

<210> SEQ ID NO 42
<211> LENGTH: 4
<212> TYPE: PRT
<213> ORGANISM: Artificial Sequence
<220> FEATURE:
<223> OTHER INFORMATION: Linker

<400> SEQUENCE: 42

Gly Gly Gly Gly
1

<210> SEQ ID NO 43
<211> LENGTH: 5
<212> TYPE: PRT
<213> ORGANISM: Artificial Sequence
<220> FEATURE:
<223> OTHER INFORMATION: Linker

<400> SEQUENCE: 43

Gly Gly Gly Gly Gly
1               5

<210> SEQ ID NO 44
<211> LENGTH: 6
<212> TYPE: PRT
<213> ORGANISM: Artificial Sequence
<220> FEATURE:
<223> OTHER INFORMATION: Linker

<400> SEQUENCE: 44

Gly Gly Gly Gly Gly Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Linker

<400> SEQUENCE: 45

Gly Gly Gly Gly Gly Gly Gly
1               5
```

```
<210> SEQ ID NO 46
<211> LENGTH: 8
<212> TYPE: PRT
<213> ORGANISM: Artificial Sequence
<220> FEATURE:
<223> OTHER INFORMATION: Linker

<400> SEQUENCE: 46

Gly Gly Gly Gly Gly Gly Gly Gly
1               5

<210> SEQ ID NO 47
<211> LENGTH: 4
<212> TYPE: PRT
<213> ORGANISM: Artificial Sequence
<220> FEATURE:
<223> OTHER INFORMATION: LInker

<400> SEQUENCE: 47

Gly Gly Gly Ser
1

<210> SEQ ID NO 48
<211> LENGTH: 8
<212> TYPE: PRT
<213> ORGANISM: Artificial Sequence
<220> FEATURE:
<223> OTHER INFORMATION: Linker

<400> SEQUENCE: 48

Gly Gly Gly Ser Gly Gly Gly Ser
1               5

<210> SEQ ID NO 49
<211> LENGTH: 12
<212> TYPE: PRT
<213> ORGANISM: Artificial Sequence
<220> FEATURE:
<223> OTHER INFORMATION: Linker

<400> SEQUENCE: 49

Gly Gly Gly Ser Gly Gly Gly Ser Gly Gly Gly Ser
1               5                   10

<210> SEQ ID NO 50
<211> LENGTH: 5
<212> TYPE: PRT
<213> ORGANISM: Artificial Sequence
<220> FEATURE:
<223> OTHER INFORMATION: Linker

<400> SEQUENCE: 50

Gly Gly Gly Gly Ser
1               5

<210> SEQ ID NO 51
<211> LENGTH: 10
<212> TYPE: PRT
<213> ORGANISM: Artificial Sequence
<220> FEATURE:
<223> OTHER INFORMATION: Linker

<400> SEQUENCE: 51

Gly Gly Gly Gly Ser Gly Gly Gly Gly Ser
1               5                   10

<210> SEQ ID NO 52
```

```
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 3
<212> TYPE: PRT
<213> ORGANISM: Artificial Sequence
<220> FEATURE:
<223> OTHER INFORMATION: Linker

<400> SEQUENCE: 53

Ser Gly Gly
1

<210> SEQ ID NO 54
<211> LENGTH: 3
<212> TYPE: PRT
<213> ORGANISM: Artificial Sequence
<220> FEATURE:
<223> OTHER INFORMATION: Linker

<400> SEQUENCE: 54

Gly Ser Gly
1

<210> SEQ ID NO 55
<211> LENGTH: 3
<212> TYPE: PRT
<213> ORGANISM: Artificial Sequence
<220> FEATURE:
<223> OTHER INFORMATION: Linker

<400> SEQUENCE: 55

Gly Gly Ser
1

<210> SEQ ID NO 56
<211> LENGTH: 4
<212> TYPE: PRT
<213> ORGANISM: Artificial Sequence
<220> FEATURE:
<223> OTHER INFORMATION: Linker

<400> SEQUENCE: 56

Ser Gly Gly Gly
1

<210> SEQ ID NO 57
<211> LENGTH: 4
<212> TYPE: PRT
<213> ORGANISM: Artificial Sequence
<220> FEATURE:
<223> OTHER INFORMATION: Linker

<400> SEQUENCE: 57

Gly Ser Gly Gly
1

<210> SEQ ID NO 58
<211> LENGTH: 4
```

```
<212> TYPE: PRT
<213> ORGANISM: Artificial Sequence
<220> FEATURE:
<223> OTHER INFORMATION: Linker

<400> SEQUENCE: 58

Gly Gly Ser Gly
1

<210> SEQ ID NO 59
<211> LENGTH: 5
<212> TYPE: PRT
<213> ORGANISM: Artificial Sequence
<220> FEATURE:
<223> OTHER INFORMATION: Linker

<400> SEQUENCE: 59

Ser Gly Gly Gly Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Linker

<400> SEQUENCE: 60

Gly Ser Gly Gly Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Linker

<400> SEQUENCE: 61

Gly Gly Ser Gly Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Linker

<400> SEQUENCE: 62

Gly Gly Gly Ser Gly
1               5

<210> SEQ ID NO 63
<211> LENGTH: 6
<212> TYPE: PRT
<213> ORGANISM: Artificial Sequence
<220> FEATURE:
<223> OTHER INFORMATION: Linker

<400> SEQUENCE: 63

Ser Gly Gly Ser Gly Gly
1               5

<210> SEQ ID NO 64
<211> LENGTH: 6
<212> TYPE: PRT
```

```
<213> ORGANISM: Artificial Sequence
<220> FEATURE:
<223> OTHER INFORMATION: Linker

<400> SEQUENCE: 64

Gly Ser Gly Gly Ser Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Linker

<400> SEQUENCE: 65

Gly Gly Ser Gly Gly Ser
1               5

<210> SEQ ID NO 66
<211> LENGTH: 8
<212> TYPE: PRT
<213> ORGANISM: Artificial Sequence
<220> FEATURE:
<223> OTHER INFORMATION: Linker

<400> SEQUENCE: 66

Ser Gly Gly Gly Ser Gly Gly Gly
1               5

<210> SEQ ID NO 67
<211> LENGTH: 8
<212> TYPE: PRT
<213> ORGANISM: Artificial Sequence
<220> FEATURE:
<223> OTHER INFORMATION: Linker

<400> SEQUENCE: 67

Gly Ser Gly Gly Gly Ser Gly Gly
1               5

<210> SEQ ID NO 68
<211> LENGTH: 8
<212> TYPE: PRT
<213> ORGANISM: Artificial Sequence
<220> FEATURE:
<223> OTHER INFORMATION: Linker

<400> SEQUENCE: 68

Gly Gly Ser Gly Gly Gly Ser Gly
1               5

<210> SEQ ID NO 69
<211> LENGTH: 10
<212> TYPE: PRT
<213> ORGANISM: Artificial Sequence
<220> FEATURE:
<223> OTHER INFORMATION: Linker

<400> SEQUENCE: 69

Ser Gly Gly Gly Gly Ser Gly Gly Gly Gly
1               5                   10

<210> SEQ ID NO 70
<211> LENGTH: 10
<212> TYPE: PRT
<213> ORGANISM: Artificial Sequence
```

```
<220> FEATURE:
<223> OTHER INFORMATION: Linker

<400> SEQUENCE: 70

Gly Ser Gly Gly Gly Gly Ser Gly Gly Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Linker

<400> SEQUENCE: 71

Gly Gly Ser Gly Gly Gly Gly Ser Gly Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Linker

<400> SEQUENCE: 72

Gly Gly Gly Ser Gly Gly Gly Gly Ser Gly
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Linker

<400> SEQUENCE: 73

Ser Gly Gly Ser Gly Gly Ser Gly Gly
1               5

<210> SEQ ID NO 74
<211> LENGTH: 9
<212> TYPE: PRT
<213> ORGANISM: Artificial Sequence
<220> FEATURE:
<223> OTHER INFORMATION: Linker

<400> SEQUENCE: 74

Gly Ser Gly Gly Ser Gly Gly Ser Gly
1               5

<210> SEQ ID NO 75
<211> LENGTH: 9
<212> TYPE: PRT
<213> ORGANISM: Artificial Sequence
<220> FEATURE:
<223> OTHER INFORMATION: Linker

<400> SEQUENCE: 75

Gly Gly Ser Gly Gly Ser Gly Gly Ser
1               5

<210> SEQ ID NO 76
<211> LENGTH: 12
<212> TYPE: PRT
<213> ORGANISM: Artificial Sequence
<220> FEATURE:
```

```
<223> OTHER INFORMATION: Linker

<400> SEQUENCE: 76

Ser Gly Gly Gly Ser Gly Gly Gly Ser Gly Gly Gly
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Linker

<400> SEQUENCE: 77

Gly Ser Gly Gly Gly Ser Gly Gly Gly Ser Gly Gly
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Linker

<400> SEQUENCE: 78

Gly Gly Ser Gly Gly Gly Ser Gly Gly Gly Ser Gly
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Linker

<400> SEQUENCE: 79

Ser Gly Gly Gly Gly Ser Gly Gly Gly Ser Gly Gly Gly Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Linker

<400> SEQUENCE: 80

Gly Ser Gly Gly Gly Gly Ser Gly Gly Gly Ser Gly Gly Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Linker

<400> SEQUENCE: 81

Gly Gly Ser Gly Gly Gly Gly Ser Gly Gly Gly Ser Gly Gly
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Linker
```

<400> SEQUENCE: 82

Gly Gly Gly Ser Gly Gly Gly Gly Ser Gly Gly Gly Gly Ser Gly
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: Linker

<400> SEQUENCE: 83

Gly Asn Gly Thr Ser Asn Gly Thr Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Linker

<400> SEQUENCE: 84

Gly Asn Gly Thr Ser Asn Gly Thr Gly
1               5

<210> SEQ ID NO 85
<211> LENGTH: 10
<212> TYPE: PRT
<213> ORGANISM: Artificial Sequence
<220> FEATURE:
<223> OTHER INFORMATION: Linker

<400> SEQUENCE: 85

Gly Asn Gly Thr Ser Asn Gly Thr Ser Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Linker

<400> SEQUENCE: 86

Gly Asn Gly Thr Ser Asn Gly Thr Gly Ser
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Linker

<400> SEQUENCE: 87

Gly Asn Gly Thr Ser Asn Gly Thr Ser Asn Gly Thr Ser
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Linker

```
<400> SEQUENCE: 88

Gly Gly Gly Ser Gly Asn Gly Thr Ser Asn Gly Thr Gly Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Linker

<400> SEQUENCE: 89

Gly Asn Gly Thr Ser Asn Gly Thr Gly Ser Gly Gly Gly Ser
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Linker

<400> SEQUENCE: 90

Gly Gly Gly Ser Gly Asn Gly Thr Ser Asn Gly Thr Ser Gly
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Linker

<400> SEQUENCE: 91

Gly Asn Gly Thr Ser Asn Gly Thr Ser Gly Gly Gly Gly Ser
1               5                   10

<210> SEQ ID NO 92
<211> LENGTH: 108
<212> TYPE: PRT
<213> ORGANISM: Artificial Sequence
<220> FEATURE:
<223> OTHER INFORMATION: VL sequence EGFR

<400> SEQUENCE: 92

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Leu Glu Ile Lys Arg
            100                 105

<210> SEQ ID NO 93
<211> LENGTH: 119
<212> TYPE: PRT
```

<213> ORGANISM: Artificial Sequence
<220> FEATURE:
<223> OTHER INFORMATION: VH sequence EGFR

<400> SEQUENCE: 93

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser
            115
```

<210> SEQ ID NO 94
<211> LENGTH: 232
<212> TYPE: PRT
<213> ORGANISM: Artificial Sequence
<220> FEATURE:
<223> OTHER INFORMATION: VH-VL sequence anti EGFR

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Ser Asp Ile Gln Leu
            115                 120                 125

Thr Gln Ser Pro Ser Phe Leu Ser Ala Ser Val Gly Asp Arg Val Thr
    130                 135                 140

Ile Thr Cys Arg Ala Ser Gln Ser Ile Gly Thr Asn Ile His Trp Tyr
145                 150                 155                 160

Gln Gln Lys Pro Gly Lys Ala Pro Lys Leu Leu Ile Lys Tyr Ala Ser
                165                 170                 175

Glu Ser Ile Ser Gly Val Pro Ser Arg Phe Ser Gly Ser Gly Ser Gly
            180                 185                 190

Thr Glu Phe Thr Leu Thr Ile Ser Ser Leu Gln Pro Glu Asp Phe Ala
            195                 200                 205
```

Thr Tyr Tyr Cys Gln Gln Asn Asn Asn Trp Pro Thr Thr Phe Gly Ala
            210                 215                 220

Gly Thr Lys Leu Glu Ile Lys Arg
225                 230

<210> SEQ ID NO 95
<211> LENGTH: 8
<212> TYPE: PRT
<213> ORGANISM: Artificial Sequence
<220> FEATURE:
<223> OTHER INFORMATION: Linker

<400> SEQUENCE: 95

Ala Ala Ala Glu Phe Thr Arg Gly
1               5

<210> SEQ ID NO 96
<211> LENGTH: 860
<212> TYPE: PRT
<213> ORGANISM: Artificial Sequence
<220> FEATURE:
<223> OTHER INFORMATION: VH-VL(EGFR)-scTRAIL fusion protein

<400> SEQUENCE: 96

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

Gly Thr Thr Val Thr Val Ser Ser Gly Gly Gly Gly Ser Gly Gly Gly
145                 150                 155                 160

Gly Ser Gly Gly Gly Gly Ser Asp Ile Gln Leu Thr Gln Ser Pro Ser
                165                 170                 175

Phe Leu Ser Ala Ser Val Gly Asp Arg Val Thr Ile Thr Cys Arg Ala
            180                 185                 190

Ser Gln Ser Ile Gly Thr Asn Ile His Trp Tyr Gln Gln Lys Pro Gly
        195                 200                 205

Lys Ala Pro Lys Leu Leu Ile Lys Tyr Ala Ser Glu Ser Ile Ser Gly
    210                 215                 220

Val Pro Ser Arg Phe Ser Gly Ser Gly Ser Gly Thr Glu Phe Thr Leu
225                 230                 235                 240

Thr Ile Ser Ser Leu Gln Pro Glu Asp Phe Ala Thr Tyr Tyr Cys Gln
            245                 250                 255

Gln Asn Asn Asn Trp Pro Thr Thr Phe Gly Ala Gly Thr Lys Leu Glu
        260                 265                 270

```
Ile Lys Arg Ala Ala Ala Glu Phe Thr Arg Gly Thr Ser Glu Glu Thr
            275                 280                 285
Ile Ser Thr Val Gln Glu Lys Gln Gln Asn Ile Ser Pro Leu Val Arg
        290                 295                 300
Glu Arg Gly Pro Gln Arg Val Ala Ala His Ile Thr Gly Thr Arg Gly
305                 310                 315                 320
Arg Ser Asn Thr Leu Ser Ser Pro Asn Ser Lys Asn Glu Lys Ala Leu
                325                 330                 335
Gly Arg Lys Ile Asn Ser Trp Glu Ser Ser Arg Ser Gly His Ser Phe
            340                 345                 350
Leu Ser Asn Leu His Leu Arg Asn Gly Glu Leu Val Ile His Glu Lys
        355                 360                 365
Gly Phe Tyr Tyr Ile Tyr Ser Gln Thr Tyr Phe Arg Phe Gln Glu Glu
    370                 375                 380
Ile Lys Glu Asn Thr Lys Asn Asp Lys Gln Met Val Gln Tyr Ile Tyr
385                 390                 395                 400
Lys Tyr Thr Ser Tyr Pro Asp Pro Ile Leu Leu Met Lys Ser Ala Arg
                405                 410                 415
Asn Ser Cys Trp Ser Lys Asp Ala Glu Tyr Gly Leu Tyr Ser Ile Tyr
            420                 425                 430
Gln Gly Gly Ile Phe Glu Leu Lys Glu Asn Asp Arg Ile Phe Val Ser
        435                 440                 445
Val Thr Asn Glu His Leu Ile Asp Met Asp His Glu Ala Ser Phe Phe
    450                 455                 460
Gly Ala Phe Leu Val Gly Gly Gly Ser Gly Gly Gly Ser Thr Ser
465                 470                 475                 480
Glu Glu Thr Ile Ser Thr Val Gln Glu Lys Gln Gln Asn Ile Ser Pro
                485                 490                 495
Leu Val Arg Glu Arg Gly Pro Gln Arg Val Ala Ala His Ile Thr Gly
            500                 505                 510
Thr Arg Gly Arg Ser Asn Thr Leu Ser Ser Pro Asn Ser Lys Asn Glu
        515                 520                 525
Lys Ala Leu Gly Arg Lys Ile Asn Ser Trp Glu Ser Ser Arg Ser Gly
    530                 535                 540
His Ser Phe Leu Ser Asn Leu His Leu Arg Asn Gly Glu Leu Val Ile
545                 550                 555                 560
His Glu Lys Gly Phe Tyr Tyr Ile Tyr Ser Gln Thr Tyr Phe Arg Phe
                565                 570                 575
Gln Glu Glu Ile Lys Glu Asn Thr Lys Asn Asp Lys Gln Met Val Gln
            580                 585                 590
Tyr Ile Tyr Lys Tyr Thr Ser Tyr Pro Asp Pro Ile Leu Leu Met Lys
        595                 600                 605
Ser Ala Arg Asn Ser Cys Trp Ser Lys Asp Ala Glu Tyr Gly Leu Tyr
    610                 615                 620
Ser Ile Tyr Gln Gly Gly Ile Phe Glu Leu Lys Glu Asn Asp Arg Ile
625                 630                 635                 640
Phe Val Ser Val Thr Asn Glu His Leu Ile Asp Met Asp His Glu Ala
                645                 650                 655
Ser Phe Phe Gly Ala Phe Leu Val Gly Gly Gly Ser Gly Gly Gly Gly
            660                 665                 670
Ser Thr Ser Glu Glu Thr Ile Ser Thr Val Gln Glu Lys Gln Gln Asn
        675                 680                 685
```

```
Ile Ser Pro Leu Val Arg Glu Arg Gly Pro Gln Arg Val Ala Ala His
    690             695                 700
Ile Thr Gly Thr Arg Gly Arg Ser Asn Thr Leu Ser Ser Pro Asn Ser
705             710                 715                 720
Lys Asn Glu Lys Ala Leu Gly Arg Lys Ile Asn Ser Trp Glu Ser Ser
                725                 730                 735
Arg Ser Gly His Ser Phe Leu Ser Asn Leu His Leu Arg Asn Gly Glu
                740                 745                 750
Leu Val Ile His Glu Lys Gly Phe Tyr Tyr Ile Tyr Ser Gln Thr Tyr
                755                 760                 765
Phe Arg Phe Gln Glu Glu Ile Lys Glu Asn Thr Lys Asn Asp Lys Gln
770                 775                 780
Met Val Gln Tyr Ile Tyr Lys Tyr Thr Ser Tyr Pro Asp Pro Ile Leu
785                 790                 795                 800
Leu Met Lys Ser Ala Arg Asn Ser Cys Trp Ser Lys Asp Ala Glu Tyr
                805                 810                 815
Gly Leu Tyr Ser Ile Tyr Gln Gly Gly Ile Phe Glu Leu Lys Glu Asn
                820                 825                 830
Asp Arg Ile Phe Val Ser Val Thr Asn Glu His Leu Ile Asp Met Asp
                835                 840                 845
His Glu Ala Ser Phe Phe Gly Ala Phe Leu Val Gly
                850                 855                 860

<210> SEQ ID NO 97
<211> LENGTH: 869
<212> TYPE: PRT
<213> ORGANISM: Artificial Sequence
<220> FEATURE:
<223> OTHER INFORMATION: VH-VL(EGFR)-scTRAIL fusion protein with
      glycosylation motif

<400> SEQUENCE: 97

Met Asp Trp Thr Trp Arg Val Phe Cys Leu Leu Ala Val Ala Pro Gly
1               5                   10                  15
Ala His Ser Leu Glu Ala Ser Asp Tyr Lys Asp Asp Asp Asp Lys Gly
                20                  25                  30
Ala Glu Val Gln Leu Val Glu Ser Gly Gly Gly Leu Val Gln Pro Gly
                35                  40                  45
Gly Ser Leu Arg Leu Ser Cys Ala Ala Ser Gly Phe Ser Leu Thr Asn
        50                  55                  60
Tyr Gly Val His Trp Val Arg Gln Ala Pro Gly Lys Gly Leu Glu Trp
65              70                  75                  80
Leu Gly Val Ile Trp Ser Gly Gly Asn Thr Asp Tyr Asn Thr Pro Phe
                85                  90                  95
Thr Ser Arg Phe Thr Ile Ser Arg Asp Asn Ser Lys Asn Thr Leu Tyr
                100                 105                 110
Leu Gln Met Asn Ser Leu Arg Ala Glu Asp Thr Ala Val Tyr Tyr Cys
                115                 120                 125
Ala Arg Ala Leu Thr Tyr Tyr Asp Tyr Glu Phe Ala Tyr Trp Gly Gln
                130                 135                 140
Gly Thr Val Thr Val Ser Ser Gly Gly Gly Gly Ser Gly Gly Gly Gly
145                 150                 155                 160
Gly Ser Gly Gly Gly Gly Ser Asp Ile Gln Leu Thr Gln Ser Pro Ser
                165                 170                 175
Phe Leu Ser Ala Ser Val Gly Asp Arg Val Thr Ile Thr Cys Arg Ala
                180                 185                 190
```

```
Ser Gln Ser Ile Gly Thr Asn Ile His Trp Tyr Gln Gln Lys Pro Gly
    195                 200                 205

Lys Ala Pro Lys Leu Leu Ile Lys Tyr Ala Ser Glu Ser Ile Ser Gly
210                 215                 220

Val Pro Ser Arg Phe Ser Gly Ser Gly Ser Gly Thr Glu Phe Thr Leu
225                 230                 235                 240

Thr Ile Ser Ser Leu Gln Pro Glu Asp Phe Ala Thr Tyr Tyr Cys Gln
                245                 250                 255

Gln Asn Asn Asn Trp Pro Thr Thr Phe Gly Ala Gly Thr Lys Leu Glu
                260                 265                 270

Ile Lys Arg Ala Ala Gly Asn Gly Thr Ser Asn Gly Thr Ser Glu
                275                 280                 285

Phe Thr Arg Gly Thr Ser Glu Glu Thr Ile Ser Thr Val Gln Glu Lys
            290                 295                 300

Gln Gln Asn Ile Ser Pro Leu Val Arg Glu Arg Gly Pro Gln Arg Val
305                 310                 315                 320

Ala Ala His Ile Thr Gly Thr Arg Gly Arg Ser Asn Thr Leu Ser Ser
                325                 330                 335

Pro Asn Ser Lys Asn Glu Lys Ala Leu Gly Arg Lys Ile Asn Ser Trp
                340                 345                 350

Glu Ser Ser Arg Ser Gly His Ser Phe Leu Ser Asn Leu His Leu Arg
            355                 360                 365

Asn Gly Glu Leu Val Ile His Glu Lys Gly Phe Tyr Tyr Ile Tyr Ser
370                 375                 380

Gln Thr Tyr Phe Arg Phe Gln Glu Glu Ile Lys Glu Asn Thr Lys Asn
385                 390                 395                 400

Asp Lys Gln Met Val Gln Tyr Ile Tyr Lys Tyr Thr Ser Tyr Pro Asp
                405                 410                 415

Pro Ile Leu Leu Met Lys Ser Ala Arg Asn Ser Cys Trp Ser Lys Asp
                420                 425                 430

Ala Glu Tyr Gly Leu Tyr Ser Ile Tyr Gln Gly Gly Ile Phe Glu Leu
            435                 440                 445

Lys Glu Asn Asp Arg Ile Phe Val Ser Val Thr Asn Glu His Leu Ile
            450                 455                 460

Asp Met Asp His Glu Ala Ser Phe Phe Gly Ala Phe Leu Val Gly Gly
465                 470                 475                 480

Gly Gly Ser Gly Gly Gly Ser Thr Ser Glu Glu Thr Ile Ser Thr Val
                485                 490                 495

Gln Glu Lys Gln Gln Asn Ile Ser Pro Leu Val Arg Glu Arg Gly Pro
            500                 505                 510

Gln Arg Val Ala Ala His Ile Thr Gly Thr Arg Gly Arg Ser Asn Thr
            515                 520                 525

Leu Ser Ser Pro Asn Ser Lys Asn Glu Lys Ala Leu Gly Arg Lys Ile
530                 535                 540

Asn Ser Trp Glu Ser Ser Arg Ser Gly His Ser Phe Leu Ser Asn Leu
545                 550                 555                 560

His Leu Arg Asn Gly Glu Leu Val Ile His Glu Lys Gly Phe Tyr Tyr
                565                 570                 575

Ile Tyr Ser Gln Thr Tyr Phe Arg Phe Gln Glu Glu Ile Lys Glu Asn
            580                 585                 590

Thr Lys Asn Asp Lys Gln Met Val Gln Tyr Ile Tyr Lys Tyr Thr Ser
            595                 600                 605
```

```
Tyr Pro Asp Pro Ile Leu Leu Met Lys Ser Ala Arg Asn Ser Cys Trp
    610                 615                 620

Ser Lys Asp Ala Glu Tyr Gly Leu Tyr Ser Ile Tyr Gln Gly Gly Ile
625                 630                 635                 640

Phe Glu Leu Lys Glu Asn Asp Arg Ile Phe Val Ser Val Thr Asn Glu
                645                 650                 655

His Leu Ile Asp Met Asp His Glu Ala Ser Phe Phe Gly Ala Phe Leu
            660                 665                 670

Val Gly Gly Gly Ser Gly Gly Ser Thr Ser Glu Glu Thr Ile
            675                 680                 685

Ser Thr Val Gln Glu Lys Gln Gln Asn Ile Ser Pro Leu Val Arg Glu
690                 695                 700

Arg Gly Pro Gln Arg Val Ala Ala His Ile Thr Gly Thr Arg Gly Arg
705                 710                 715                 720

Ser Asn Thr Leu Ser Ser Pro Asn Ser Lys Asn Glu Lys Ala Leu Gly
            725                 730                 735

Arg Lys Ile Asn Ser Trp Glu Ser Arg Ser Gly His Ser Phe Leu
            740                 745                 750

Ser Asn Leu His Leu Arg Asn Gly Glu Leu Val Ile His Glu Lys Gly
            755                 760                 765

Phe Tyr Tyr Ile Tyr Ser Gln Thr Tyr Phe Arg Phe Gln Glu Glu Ile
770                 775                 780

Lys Glu Asn Thr Lys Asn Asp Lys Gln Met Val Gln Tyr Ile Tyr Lys
785                 790                 795                 800

Tyr Thr Ser Tyr Pro Asp Pro Ile Leu Leu Met Lys Ser Ala Arg Asn
                805                 810                 815

Ser Cys Trp Ser Lys Asp Ala Glu Tyr Gly Leu Tyr Ser Ile Tyr Gln
            820                 825                 830

Gly Gly Ile Phe Glu Leu Lys Glu Asn Asp Arg Ile Phe Val Ser Val
            835                 840                 845

Thr Asn Glu His Leu Ile Asp Met Asp His Glu Ala Ser Phe Phe Gly
    850                 855                 860

Ala Phe Leu Val Gly
865

<210> SEQ ID NO 98
<211> LENGTH: 881
<212> TYPE: PRT
<213> ORGANISM: Artificial Sequence
<220> FEATURE:
<223> OTHER INFORMATION: VH-VL(EGFR)-scTRAIL fusion protein with
      glycosylation motif

<400> SEQUENCE: 98

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
            35                  40                  45

Gly Ser Leu Arg Leu Ser Cys Ala Ala Ser Gly Phe Ser Leu Thr Asn
        50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95
```

-continued

```
Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
            115                 120                 125

Ala Arg Ala Leu Thr Tyr Tyr Asp Tyr Glu Phe Ala Tyr Trp Gly Gln
            130                 135                 140

Gly Thr Thr Val Thr Val Ser Ser Gly Gly Gly Ser Gly Gly Gly
145                 150                 155                 160

Gly Ser Gly Gly Gly Ser Asp Ile Gln Leu Thr Gln Ser Pro Ser
            165                 170                 175

Phe Leu Ser Ala Ser Val Gly Asp Arg Val Thr Ile Thr Cys Arg Ala
            180                 185                 190

Ser Gln Ser Ile Gly Thr Asn Ile His Trp Tyr Gln Gln Lys Pro Gly
            195                 200                 205

Lys Ala Pro Lys Leu Leu Ile Lys Tyr Ala Ser Glu Ser Ile Ser Gly
            210                 215                 220

Val Pro Ser Arg Phe Ser Gly Ser Gly Ser Gly Thr Glu Phe Thr Leu
225                 230                 235                 240

Thr Ile Ser Ser Leu Gln Pro Glu Asp Phe Ala Thr Tyr Tyr Cys Gln
            245                 250                 255

Gln Asn Asn Asn Trp Pro Thr Thr Phe Gly Ala Gly Thr Lys Leu Glu
            260                 265                 270

Ile Lys Arg Ala Ala Ala Gly Asn Gly Thr Ser Asn Gly Thr Ser Glu
            275                 280                 285

Phe Thr Arg Gly Thr Ser Glu Glu Thr Ile Ser Thr Val Gln Glu Lys
            290                 295                 300

Gln Gln Asn Ile Ser Pro Leu Val Arg Glu Arg Gly Pro Gln Arg Val
305                 310                 315                 320

Ala Ala His Ile Thr Gly Thr Arg Gly Arg Ser Asn Thr Leu Ser Ser
            325                 330                 335

Pro Asn Ser Lys Asn Glu Lys Ala Leu Gly Arg Lys Ile Asn Ser Trp
            340                 345                 350

Glu Ser Ser Arg Ser Gly His Ser Phe Leu Ser Asn Leu His Leu Arg
            355                 360                 365

Asn Gly Glu Leu Val Ile His Glu Lys Gly Phe Tyr Tyr Ile Tyr Ser
            370                 375                 380

Gln Thr Tyr Phe Arg Phe Gln Glu Glu Ile Lys Glu Asn Thr Lys Asn
385                 390                 395                 400

Asp Lys Gln Met Val Gln Tyr Ile Tyr Lys Tyr Thr Ser Tyr Pro Asp
            405                 410                 415

Pro Ile Leu Leu Met Lys Ser Ala Arg Asn Ser Cys Trp Ser Lys Asp
            420                 425                 430

Ala Glu Tyr Gly Leu Tyr Ser Ile Tyr Gln Gly Gly Ile Phe Glu Leu
            435                 440                 445

Lys Glu Asn Asp Arg Ile Phe Val Ser Val Thr Asn Glu His Leu Ile
            450                 455                 460

Asp Met Asp His Glu Ala Ser Phe Phe Gly Ala Phe Leu Val Gly Gly
465                 470                 475                 480

Gly Gly Ser Gly Asn Gly Thr Ser Asn Gly Thr Ser Gly Thr Ser Glu
            485                 490                 495

Glu Thr Ile Ser Thr Val Gln Glu Lys Gln Gln Asn Ile Ser Pro Leu
            500                 505                 510
```

Val Arg Glu Arg Gly Pro Gln Arg Val Ala Ala His Ile Thr Gly Thr
    515                 520                 525

Arg Gly Arg Ser Asn Thr Leu Ser Ser Pro Asn Ser Lys Asn Glu Lys
530                 535                 540

Ala Leu Gly Arg Lys Ile Asn Ser Trp Glu Ser Ser Arg Ser Gly His
545                 550                 555                 560

Ser Phe Leu Ser Asn Leu His Leu Arg Asn Gly Glu Leu Val Ile His
                565                 570                 575

Glu Lys Gly Phe Tyr Tyr Ile Tyr Ser Gln Thr Tyr Phe Arg Phe Gln
            580                 585                 590

Glu Glu Ile Lys Glu Asn Thr Lys Asn Asp Lys Gln Met Val Gln Tyr
        595                 600                 605

Ile Tyr Lys Tyr Thr Ser Tyr Pro Asp Pro Ile Leu Leu Met Lys Ser
    610                 615                 620

Ala Arg Asn Ser Cys Trp Ser Lys Asp Ala Glu Tyr Gly Leu Tyr Ser
625                 630                 635                 640

Ile Tyr Gln Gly Gly Ile Phe Glu Leu Lys Glu Asn Asp Arg Ile Phe
                645                 650                 655

Val Ser Val Thr Asn Glu His Leu Ile Asp Met Asp His Glu Ala Ser
            660                 665                 670

Phe Phe Gly Ala Phe Leu Val Gly Gly Gly Ser Gly Asn Gly Thr
        675                 680                 685

Ser Asn Gly Thr Gly Ser Thr Ser Glu Glu Thr Ile Ser Thr Val Gln
    690                 695                 700

Glu Lys Gln Gln Asn Ile Ser Pro Leu Val Arg Glu Arg Gly Pro Gln
705                 710                 715                 720

Arg Val Ala Ala His Ile Thr Gly Thr Arg Gly Arg Ser Asn Thr Leu
                725                 730                 735

Ser Ser Pro Asn Ser Lys Asn Glu Lys Ala Leu Gly Arg Lys Ile Asn
            740                 745                 750

Ser Trp Glu Ser Ser Arg Ser Gly His Ser Phe Leu Ser Asn Leu His
        755                 760                 765

Leu Arg Asn Gly Glu Leu Val Ile His Glu Lys Gly Phe Tyr Tyr Ile
    770                 775                 780

Tyr Ser Gln Thr Tyr Phe Arg Phe Gln Glu Glu Ile Lys Glu Asn Thr
785                 790                 795                 800

Lys Asn Asp Lys Gln Met Val Gln Tyr Ile Tyr Lys Tyr Thr Ser Tyr
                805                 810                 815

Pro Asp Pro Ile Leu Leu Met Lys Ser Ala Arg Asn Ser Cys Trp Ser
            820                 825                 830

Lys Asp Ala Glu Tyr Gly Leu Tyr Ser Ile Tyr Gln Gly Gly Ile Phe
        835                 840                 845

Glu Leu Lys Glu Asn Asp Arg Ile Phe Val Ser Val Thr Asn Glu His
    850                 855                 860

Leu Ile Asp Met Asp His Glu Ala Ser Phe Phe Gly Ala Phe Leu Val
865                 870                 875                 880

Gly

<210> SEQ ID NO 99
<211> LENGTH: 56
<212> TYPE: PRT
<213> ORGANISM: Streptococcus sp. G148

<400> SEQUENCE: 99

```
Gln His Asp Glu Ala Val Asp Ala Asn Ser Leu Ala Glu Ala Lys Val
1               5                   10                  15

Leu Ala Asn Arg Glu Leu Asp Lys Tyr Gly Val Ser Tyr Tyr Lys
            20                  25                  30

Asn Leu Ile Asn Asn Ala Lys Thr Val Glu Gly Val Lys Ala Leu Ile
            35                  40                  45

Asp Glu Ile Leu Ala Ala Leu Pro
        50              55

<210> SEQ ID NO 100
<211> LENGTH: 8
<212> TYPE: PRT
<213> ORGANISM: Artificial Sequence
<220> FEATURE:
<223> OTHER INFORMATION: FLAG-TAG

<400> SEQUENCE: 100

Asp Tyr Lys Asp Asp Asp Asp Lys
1               5

<210> SEQ ID NO 101
<211> LENGTH: 19
<212> TYPE: PRT
<213> ORGANISM: Homo sapiens

<400> SEQUENCE: 101

Met Asp Trp Thr Trp Arg Val Phe Cys Leu Leu Ala Val Ala Pro Gly
1               5                   10                  15

Ala His Ser

<210> SEQ ID NO 102
<211> LENGTH: 850
<212> TYPE: PRT
<213> ORGANISM: Artificial Sequence
<220> FEATURE:
<223> OTHER INFORMATION: VH-VL(EGFR)-scTRAIL fusion protein

<400> SEQUENCE: 102

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
            20                  25                  30

Ala Glu Val Gln Leu Val Glu Ser Gly Gly Leu Val Gln Pro Gly
        35                  40                  45

Gly Ser Leu Arg Leu Ser Cys Ala Ala Ser Gly Phe Ser Leu Thr Asn
        50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

Gly Thr Thr Val Thr Val Ser Ser Gly Gly Gly Gly Ser Asp Ile Gln
145                 150                 155                 160

Leu Thr Gln Ser Pro Ser Phe Leu Ser Ala Ser Val Gly Asp Arg Val
```

-continued

```
                165                 170                 175
Thr Ile Thr Cys Arg Ala Ser Gln Ser Ile Gly Thr Asn Ile His Trp
                180                 185                 190
Tyr Gln Gln Lys Pro Gly Lys Ala Pro Lys Leu Leu Ile Lys Tyr Ala
                195                 200                 205
Ser Glu Ser Ile Ser Gly Val Pro Ser Arg Phe Ser Gly Ser Gly Ser
                210                 215                 220
Gly Thr Glu Phe Thr Leu Thr Ile Ser Ser Leu Gln Pro Glu Asp Phe
225                 230                 235                 240
Ala Thr Tyr Tyr Cys Gln Gln Asn Asn Trp Pro Thr Thr Phe Gly
                245                 250                 255
Ala Gly Thr Lys Leu Glu Ile Lys Arg Ala Ala Ala Glu Phe Thr Arg
                260                 265                 270
Gly Thr Ser Glu Glu Thr Ile Ser Thr Val Gln Glu Lys Gln Gln Asn
                275                 280                 285
Ile Ser Pro Leu Val Arg Glu Arg Gly Pro Gln Arg Val Ala Ala His
                290                 295                 300
Ile Thr Gly Thr Arg Gly Arg Ser Asn Thr Leu Ser Ser Pro Asn Ser
305                 310                 315                 320
Lys Asn Glu Lys Ala Leu Gly Arg Lys Ile Asn Ser Trp Glu Ser Ser
                325                 330                 335
Arg Ser Gly His Ser Phe Leu Ser Asn Leu His Leu Arg Asn Gly Glu
                340                 345                 350
Leu Val Ile His Glu Lys Gly Phe Tyr Tyr Ile Tyr Ser Gln Thr Tyr
                355                 360                 365
Phe Arg Phe Gln Glu Glu Ile Lys Glu Asn Thr Lys Asn Asp Lys Gln
                370                 375                 380
Met Val Gln Tyr Ile Tyr Lys Tyr Thr Ser Tyr Pro Asp Pro Ile Leu
385                 390                 395                 400
Leu Met Lys Ser Ala Arg Asn Ser Cys Trp Ser Lys Asp Ala Glu Tyr
                405                 410                 415
Gly Leu Tyr Ser Ile Tyr Gln Gly Gly Ile Phe Glu Leu Lys Glu Asn
                420                 425                 430
Asp Arg Ile Phe Val Ser Val Thr Asn Glu His Leu Ile Asp Met Asp
                435                 440                 445
His Glu Ala Ser Phe Phe Gly Ala Phe Leu Val Gly Gly Gly Ser
                450                 455                 460
Gly Gly Gly Ser Thr Ser Glu Glu Thr Ile Ser Thr Val Gln Glu Lys
465                 470                 475                 480
Gln Gln Asn Ile Ser Pro Leu Val Arg Glu Arg Gly Pro Gln Arg Val
                485                 490                 495
Ala Ala His Ile Thr Gly Thr Arg Gly Arg Ser Asn Thr Leu Ser Ser
                500                 505                 510
Pro Asn Ser Lys Asn Glu Lys Ala Leu Gly Arg Lys Ile Asn Ser Trp
                515                 520                 525
Glu Ser Ser Arg Ser Gly His Ser Phe Leu Ser Asn Leu His Leu Arg
                530                 535                 540
Asn Gly Glu Leu Val Ile His Glu Lys Gly Phe Tyr Tyr Ile Tyr Ser
545                 550                 555                 560
Gln Thr Tyr Phe Arg Phe Gln Glu Glu Ile Lys Glu Asn Thr Lys Asn
                565                 570                 575
Asp Lys Gln Met Val Gln Tyr Ile Tyr Lys Tyr Thr Ser Tyr Pro Asp
                580                 585                 590
```

```
Pro Ile Leu Leu Met Lys Ser Ala Arg Asn Ser Cys Trp Ser Lys Asp
        595                 600                 605

Ala Glu Tyr Gly Leu Tyr Ser Ile Tyr Gln Gly Gly Ile Phe Glu Leu
        610                 615                 620

Lys Glu Asn Asp Arg Ile Phe Val Ser Val Thr Asn Glu His Leu Ile
625                 630                 635                 640

Asp Met Asp His Glu Ala Ser Phe Phe Gly Ala Phe Leu Val Gly Gly
                645                 650                 655

Gly Gly Ser Gly Gly Ser Thr Ser Glu Glu Thr Ile Ser Thr Val
        660                 665                 670

Gln Glu Lys Gln Gln Asn Ile Ser Pro Leu Val Arg Glu Arg Gly Pro
        675                 680                 685

Gln Arg Val Ala Ala His Ile Thr Gly Thr Arg Gly Arg Ser Asn Thr
        690                 695                 700

Leu Ser Ser Pro Asn Ser Lys Asn Glu Lys Ala Leu Gly Arg Lys Ile
705                 710                 715                 720

Asn Ser Trp Glu Ser Ser Arg Ser Gly His Ser Phe Leu Ser Asn Leu
                725                 730                 735

His Leu Arg Asn Gly Glu Leu Val Ile His Glu Lys Gly Phe Tyr Tyr
        740                 745                 750

Ile Tyr Ser Gln Thr Tyr Phe Arg Phe Gln Glu Glu Ile Lys Glu Asn
        755                 760                 765

Thr Lys Asn Asp Lys Gln Met Val Gln Tyr Ile Tyr Lys Tyr Thr Ser
770                 775                 780

Tyr Pro Asp Pro Ile Leu Leu Met Lys Ser Ala Arg Asn Ser Cys Trp
785                 790                 795                 800

Ser Lys Asp Ala Glu Tyr Gly Leu Tyr Ser Ile Tyr Gln Gly Gly Ile
                805                 810                 815

Phe Glu Leu Lys Glu Asn Asp Arg Ile Phe Val Ser Val Thr Asn Glu
                820                 825                 830

His Leu Ile Asp Met Asp His Glu Ala Ser Phe Phe Gly Ala Phe Leu
        835                 840                 845

Val Gly
    850

<210> SEQ ID NO 103
<211> LENGTH: 907
<212> TYPE: PRT
<213> ORGANISM: Artificial Sequence
<220> FEATURE:
<223> OTHER INFORMATION: VH-VL(EGFR)-scTRAIL fusion protein with ABD

<400> SEQUENCE: 103

Met Asp Trp Thr Trp Arg Val Phe Cys Leu Leu Ala Val Ala Pro Gly
1               5                   10                  15

Ala His Ser Gln His Asp Glu Ala Val Asp Ala Asn Ser Leu Ala Glu
                20                  25                  30

Ala Lys Val Leu Ala Asn Arg Glu Leu Asp Lys Tyr Gly Val Ser Asp
            35                  40                  45

Tyr Tyr Lys Asn Leu Ile Asn Asn Ala Lys Thr Val Glu Gly Val Lys
        50                  55                  60

Ala Leu Ile Asp Glu Ile Leu Ala Ala Leu Pro Gly Gly Ser Gly Gly
65                  70                  75                  80

Gly Gly Ser Gly Gly Glu Val Gln Leu Val Glu Ser Gly Gly Gly Leu
                85                  90                  95
```

-continued

```
Val Gln Pro Gly Gly Ser Leu Arg Leu Ser Cys Ala Ala Ser Gly Phe
            100                 105                 110

Ser Leu Thr Asn Tyr Gly Val His Trp Val Arg Gln Ala Pro Gly Lys
            115                 120                 125

Gly Leu Glu Trp Leu Gly Val Ile Trp Ser Gly Gly Asn Thr Asp Tyr
            130                 135                 140

Asn Thr Pro Phe Thr Ser Arg Phe Thr Ile Ser Arg Asp Asn Ser Lys
145                 150                 155                 160

Asn Thr Leu Tyr Leu Gln Met Asn Ser Leu Arg Ala Glu Asp Thr Ala
                165                 170                 175

Val Tyr Tyr Cys Ala Arg Ala Leu Thr Tyr Tyr Asp Tyr Glu Phe Ala
            180                 185                 190

Tyr Trp Gly Gln Gly Thr Thr Val Thr Val Ser Ser Gly Gly Gly Gly
            195                 200                 205

Ser Asp Ile Gln Leu Thr Gln Ser Pro Ser Phe Leu Ser Ala Ser Val
            210                 215                 220

Gly Asp Arg Val Thr Ile Thr Cys Arg Ala Ser Gln Ser Ile Gly Thr
225                 230                 235                 240

Asn Ile His Trp Tyr Gln Gln Lys Pro Gly Lys Ala Pro Lys Leu Leu
                245                 250                 255

Ile Lys Tyr Ala Ser Glu Ser Ile Ser Gly Val Pro Ser Arg Phe Ser
            260                 265                 270

Gly Ser Gly Ser Gly Thr Glu Phe Thr Leu Thr Ile Ser Ser Leu Gln
            275                 280                 285

Pro Glu Asp Phe Ala Thr Tyr Tyr Cys Gln Gln Asn Asn Asn Trp Pro
            290                 295                 300

Thr Thr Phe Gly Ala Gly Thr Lys Leu Glu Ile Lys Arg Gly Gly Ser
305                 310                 315                 320

Gly Asn Gly Thr Ser Asn Gly Thr Ser Gly Thr Ser Glu Glu Thr Ile
                325                 330                 335

Ser Thr Val Gln Glu Lys Gln Gln Asn Ile Ser Pro Leu Val Arg Glu
            340                 345                 350

Arg Gly Pro Gln Arg Val Ala Ala His Ile Thr Gly Thr Arg Gly Arg
            355                 360                 365

Ser Asn Thr Leu Ser Ser Pro Asn Ser Lys Asn Glu Lys Ala Leu Gly
            370                 375                 380

Arg Lys Ile Asn Ser Trp Glu Ser Ser Arg Ser Gly His Ser Phe Leu
385                 390                 395                 400

Ser Asn Leu His Leu Arg Asn Gly Glu Leu Val Ile His Glu Lys Gly
                405                 410                 415

Phe Tyr Tyr Ile Tyr Ser Gln Thr Tyr Phe Arg Phe Gln Glu Glu Ile
            420                 425                 430

Lys Glu Asn Thr Lys Asn Asp Lys Gln Met Val Gln Tyr Ile Tyr Lys
            435                 440                 445

Tyr Thr Ser Tyr Pro Asp Pro Ile Leu Leu Met Lys Ser Ala Arg Asn
            450                 455                 460

Ser Cys Trp Ser Lys Asp Ala Glu Tyr Gly Leu Tyr Ser Ile Tyr Gln
465                 470                 475                 480

Gly Gly Ile Phe Glu Leu Lys Glu Asn Asp Arg Ile Phe Val Ser Val
                485                 490                 495

Thr Asn Glu His Leu Ile Asp Met Asp His Glu Ala Ser Phe Phe Gly
            500                 505                 510
```

Ala Phe Leu Val Gly Gly Gly Ser Gly Gly Ser Thr Ser Glu
515                 520                 525

Glu Thr Ile Ser Thr Val Gln Glu Lys Gln Gln Asn Ile Ser Pro Leu
530                 535                 540

Val Arg Glu Arg Gly Pro Gln Arg Val Ala Ala His Ile Thr Gly Thr
545                 550                 555                 560

Arg Gly Arg Ser Asn Thr Leu Ser Ser Pro Asn Ser Lys Asn Glu Lys
                565                 570                 575

Ala Leu Gly Arg Lys Ile Asn Ser Trp Glu Ser Ser Arg Ser Gly His
            580                 585                 590

Ser Phe Leu Ser Asn Leu His Leu Arg Asn Gly Glu Leu Val Ile His
        595                 600                 605

Glu Lys Gly Phe Tyr Tyr Ile Tyr Ser Gln Thr Tyr Phe Arg Phe Gln
610                 615                 620

Glu Glu Ile Lys Glu Asn Thr Lys Asn Asp Lys Gln Met Val Gln Tyr
625                 630                 635                 640

Ile Tyr Lys Tyr Thr Ser Tyr Pro Asp Pro Ile Leu Leu Met Lys Ser
                645                 650                 655

Ala Arg Asn Ser Cys Trp Ser Lys Asp Ala Glu Tyr Gly Leu Tyr Ser
            660                 665                 670

Ile Tyr Gln Gly Gly Ile Phe Glu Leu Lys Glu Asn Asp Arg Ile Phe
        675                 680                 685

Val Ser Val Thr Asn Glu His Leu Ile Asp Met Asp His Glu Ala Ser
690                 695                 700

Phe Phe Gly Ala Phe Leu Val Gly Gly Gly Ser Gly Gly Gly Ser
705                 710                 715                 720

Thr Ser Glu Glu Thr Ile Ser Thr Val Gln Glu Lys Gln Gln Asn Ile
                725                 730                 735

Ser Pro Leu Val Arg Glu Arg Gly Pro Gln Arg Val Ala Ala His Ile
            740                 745                 750

Thr Gly Thr Arg Gly Arg Ser Asn Thr Leu Ser Ser Pro Asn Ser Lys
        755                 760                 765

Asn Glu Lys Ala Leu Gly Arg Lys Ile Asn Ser Trp Glu Ser Ser Arg
770                 775                 780

Ser Gly His Ser Phe Leu Ser Asn Leu His Leu Arg Asn Gly Glu Leu
785                 790                 795                 800

Val Ile His Glu Lys Gly Phe Tyr Tyr Ile Tyr Ser Gln Thr Tyr Phe
                805                 810                 815

Arg Phe Gln Glu Glu Ile Lys Glu Asn Thr Lys Asn Asp Lys Gln Met
            820                 825                 830

Val Gln Tyr Ile Tyr Lys Tyr Thr Ser Tyr Pro Asp Pro Ile Leu Leu
        835                 840                 845

Met Lys Ser Ala Arg Asn Ser Cys Trp Ser Lys Asp Ala Glu Tyr Gly
850                 855                 860

Leu Tyr Ser Ile Tyr Gln Gly Gly Ile Phe Glu Leu Lys Glu Asn Asp
865                 870                 875                 880

Arg Ile Phe Val Ser Val Thr Asn Glu His Leu Ile Asp Met Asp His
                885                 890                 895

Glu Ala Ser Phe Phe Gly Ala Phe Leu Val Gly
            900                 905

<210> SEQ ID NO 104
<211> LENGTH: 577
<212> TYPE: PRT

<213> ORGANISM: Artificial Sequence
<220> FEATURE:
<223> OTHER INFORMATION: scTRAIL fusion protein

<400> SEQUENCE: 104

```
Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly Gly Gly Gly Ser Gly
            180                 185                 190

Gly Gly Ser Thr Ser Glu Glu Thr Ile Ser Thr Val Gln Glu Lys Gln
        195                 200                 205

Gln Asn Ile Ser Pro Leu Val Arg Glu Arg Gly Pro Gln Arg Val Ala
    210                 215                 220

Ala His Ile Thr Gly Thr Arg Gly Arg Ser Asn Thr Leu Ser Ser Pro
225                 230                 235                 240

Asn Ser Lys Asn Glu Lys Ala Leu Gly Arg Lys Ile Asn Ser Trp Glu
                245                 250                 255

Ser Ser Arg Ser Gly His Ser Phe Leu Ser Asn Leu His Leu Arg Asn
            260                 265                 270

Gly Glu Leu Val Ile His Glu Lys Gly Phe Tyr Tyr Ile Tyr Ser Gln
        275                 280                 285

Thr Tyr Phe Arg Phe Gln Glu Glu Ile Lys Glu Asn Thr Lys Asn Asp
    290                 295                 300

Lys Gln Met Val Gln Tyr Ile Tyr Lys Tyr Thr Ser Tyr Pro Asp Pro
305                 310                 315                 320

Ile Leu Leu Met Lys Ser Ala Arg Asn Ser Cys Trp Ser Lys Asp Ala
                325                 330                 335

Glu Tyr Gly Leu Tyr Ser Ile Tyr Gln Gly Gly Ile Phe Glu Leu Lys
            340                 345                 350

Glu Asn Asp Arg Ile Phe Val Ser Val Thr Asn Glu His Leu Ile Asp
        355                 360                 365

Met Asp His Glu Ala Ser Phe Phe Gly Ala Phe Leu Val Gly Gly Gly
    370                 375                 380

Gly Ser Gly Gly Gly Ser Thr Ser Glu Glu Thr Ile Ser Thr Val Gln
```

```
            385                 390                 395                 400
Glu Lys Gln Gln Asn Ile Ser Pro Leu Val Arg Glu Arg Gly Pro Gln
                405                 410                 415

Arg Val Ala Ala His Ile Thr Gly Thr Arg Gly Arg Ser Asn Thr Leu
            420                 425                 430

Ser Ser Pro Asn Ser Lys Asn Glu Lys Ala Leu Gly Arg Lys Ile Asn
            435                 440                 445

Ser Trp Glu Ser Ser Arg Ser Gly His Ser Phe Leu Ser Asn Leu His
            450                 455                 460

Leu Arg Asn Gly Glu Leu Val Ile His Glu Lys Gly Phe Tyr Tyr Ile
465                 470                 475                 480

Tyr Ser Gln Thr Tyr Phe Arg Phe Gln Glu Glu Ile Lys Glu Asn Thr
                485                 490                 495

Lys Asn Asp Lys Gln Met Val Gln Tyr Ile Tyr Lys Tyr Thr Ser Tyr
            500                 505                 510

Pro Asp Pro Ile Leu Leu Met Lys Ser Ala Arg Asn Ser Cys Trp Ser
            515                 520                 525

Lys Asp Ala Glu Tyr Gly Leu Tyr Ser Ile Tyr Gln Gly Gly Ile Phe
            530                 535                 540

Glu Leu Lys Glu Asn Asp Arg Ile Phe Val Ser Val Thr Asn Glu His
545                 550                 555                 560

Leu Ile Asp Met Asp His Glu Ala Ser Phe Phe Gly Ala Phe Leu Val
                565                 570                 575

Gly
```

<210> SEQ ID NO 105
<211> LENGTH: 17
<212> TYPE: PRT
<213> ORGANISM: Artificial Sequence
<220> FEATURE:
<223> OTHER INFORMATION: Linker

<400> SEQUENCE: 105

```
Ala Ala Ala Gly Asn Gly Thr Ser Asn Gly Thr Ser Glu Phe Thr Arg
1               5                   10                  15

Gly
```

<210> SEQ ID NO 106
<211> LENGTH: 13
<212> TYPE: PRT
<213> ORGANISM: Artificial Sequence
<220> FEATURE:
<223> OTHER INFORMATION: Linker

<400> SEQUENCE: 106

```
Gly Gly Ser Gly Asn Gly Thr Ser Asn Gly Thr Ser Gly
1               5                   10
```

<210> SEQ ID NO 107
<211> LENGTH: 817
<212> TYPE: PRT
<213> ORGANISM: Artificial Sequence
<220> FEATURE:
<223> OTHER INFORMATION: VH-VL(EGFR)-scTRAIL fusion protein

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
```

```
            20                  25                  30
Gly Val His Trp Val Arg Gln Ala Pro Gly Lys Gly Leu Glu Trp Leu
                35                  40                  45
Gly Val Ile Trp Ser Gly Gly Asn Thr Asp Tyr Asn Thr Pro Phe Thr
         50                  55                  60
Ser Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Thr Val Thr Val Ser Ser Gly Gly Gly Ser Asp Ile Gln Leu
            115                 120                 125
Thr Gln Ser Pro Ser Phe Leu Ser Ala Ser Val Gly Asp Arg Val Thr
            130                 135                 140
Ile Thr Cys Arg Ala Ser Gln Ser Ile Gly Thr Asn Ile His Trp Tyr
145                 150                 155                 160
Gln Gln Lys Pro Gly Lys Ala Pro Lys Leu Leu Ile Lys Tyr Ala Ser
                165                 170                 175
Glu Ser Ile Ser Gly Val Pro Ser Arg Phe Ser Gly Ser Gly Ser Gly
                180                 185                 190
Thr Glu Phe Thr Leu Thr Ile Ser Ser Leu Gln Pro Glu Asp Phe Ala
            195                 200                 205
Thr Tyr Tyr Cys Gln Gln Asn Asn Asn Trp Pro Thr Thr Phe Gly Ala
            210                 215                 220
Gly Thr Lys Leu Glu Ile Lys Arg Ala Ala Ala Glu Phe Thr Arg Gly
225                 230                 235                 240
Thr Ser Glu Glu Thr Ile Ser Thr Val Gln Glu Lys Gln Gln Asn Ile
                245                 250                 255
Ser Pro Leu Val Arg Glu Arg Gly Pro Gln Arg Val Ala Ala His Ile
            260                 265                 270
Thr Gly Thr Arg Gly Arg Ser Asn Thr Leu Ser Ser Pro Asn Ser Lys
            275                 280                 285
Asn Glu Lys Ala Leu Gly Arg Lys Ile Asn Ser Trp Glu Ser Ser Arg
            290                 295                 300
Ser Gly His Ser Phe Leu Ser Asn Leu His Leu Arg Asn Gly Glu Leu
305                 310                 315                 320
Val Ile His Glu Lys Gly Phe Tyr Tyr Ile Tyr Ser Gln Thr Tyr Phe
                325                 330                 335
Arg Phe Gln Glu Glu Ile Lys Glu Asn Thr Lys Asn Asp Lys Gln Met
                340                 345                 350
Val Gln Tyr Ile Tyr Lys Tyr Thr Ser Tyr Pro Asp Pro Ile Leu Leu
            355                 360                 365
Met Lys Ser Ala Arg Asn Ser Cys Trp Ser Lys Asp Ala Glu Tyr Gly
            370                 375                 380
Leu Tyr Ser Ile Tyr Gln Gly Gly Ile Phe Glu Leu Lys Glu Asn Asp
385                 390                 395                 400
Arg Ile Phe Val Ser Val Thr Asn Glu His Leu Ile Asp Met Asp His
                405                 410                 415
Glu Ala Ser Phe Phe Gly Ala Phe Leu Val Gly Gly Gly Ser Gly
            420                 425                 430
Gly Gly Ser Thr Ser Glu Glu Thr Ile Ser Thr Val Gln Glu Lys Gln
            435                 440                 445
```

-continued

Gln Asn Ile Ser Pro Leu Val Arg Glu Arg Gly Pro Gln Arg Val Ala
    450                 455                 460

Ala His Ile Thr Gly Thr Arg Gly Arg Ser Asn Thr Leu Ser Ser Pro
465                 470                 475                 480

Asn Ser Lys Asn Glu Lys Ala Leu Gly Arg Lys Ile Asn Ser Trp Glu
            485                 490                 495

Ser Ser Arg Ser Gly His Ser Phe Leu Ser Asn Leu His Leu Arg Asn
                500                 505                 510

Gly Glu Leu Val Ile His Glu Lys Gly Phe Tyr Tyr Ile Tyr Ser Gln
            515                 520                 525

Thr Tyr Phe Arg Phe Gln Glu Glu Ile Lys Glu Asn Thr Lys Asn Asp
    530                 535                 540

Lys Gln Met Val Gln Tyr Ile Tyr Lys Tyr Thr Ser Tyr Pro Asp Pro
545                 550                 555                 560

Ile Leu Leu Met Lys Ser Ala Arg Asn Ser Cys Trp Ser Lys Asp Ala
                565                 570                 575

Glu Tyr Gly Leu Tyr Ser Ile Tyr Gln Gly Gly Ile Phe Glu Leu Lys
                580                 585                 590

Glu Asn Asp Arg Ile Phe Val Ser Val Thr Asn Glu His Leu Ile Asp
    595                 600                 605

Met Asp His Glu Ala Ser Phe Phe Gly Ala Phe Leu Val Gly Gly Gly
    610                 615                 620

Gly Ser Gly Gly Gly Ser Thr Ser Glu Glu Thr Ile Ser Thr Val Gln
625                 630                 635                 640

Glu Lys Gln Gln Asn Ile Ser Pro Leu Val Arg Glu Arg Gly Pro Gln
                645                 650                 655

Arg Val Ala Ala His Ile Thr Gly Thr Arg Gly Arg Ser Asn Thr Leu
                660                 665                 670

Ser Ser Pro Asn Ser Lys Asn Glu Lys Ala Leu Gly Arg Lys Ile Asn
    675                 680                 685

Ser Trp Glu Ser Ser Arg Ser Gly His Ser Phe Leu Ser Asn Leu His
    690                 695                 700

Leu Arg Asn Gly Glu Leu Val Ile His Glu Lys Gly Phe Tyr Tyr Ile
705                 710                 715                 720

Tyr Ser Gln Thr Tyr Phe Arg Phe Gln Glu Glu Ile Lys Glu Asn Thr
                725                 730                 735

Lys Asn Asp Lys Gln Met Val Gln Tyr Ile Tyr Lys Tyr Thr Ser Tyr
            740                 745                 750

Pro Asp Pro Ile Leu Leu Met Lys Ser Ala Arg Asn Ser Cys Trp Ser
    755                 760                 765

Lys Asp Ala Glu Tyr Gly Leu Tyr Ser Ile Tyr Gln Gly Gly Ile Phe
770                 775                 780

Glu Leu Lys Glu Asn Asp Arg Ile Phe Val Ser Val Thr Asn Glu His
785                 790                 795                 800

Leu Ile Asp Met Asp His Glu Ala Ser Phe Phe Gly Ala Phe Leu Val
            805                 810                 815

Gly

<210> SEQ ID NO 108
<211> LENGTH: 20
<212> TYPE: PRT
<213> ORGANISM: Homo sapiens

<400> SEQUENCE: 108

```
Met Glu Thr Asp Thr Leu Leu Leu Trp Val Leu Leu Leu Trp Val Pro
1               5                   10                  15

Gly Ser Thr Gly
            20
```

<210> SEQ ID NO 109
<211> LENGTH: 19
<212> TYPE: DNA
<213> ORGANISM: Artificial Sequence
<220> FEATURE:
<223> OTHER INFORMATION: Primer

<400> SEQUENCE: 109
cgaggtgcag ctggtcgag                                             19

<210> SEQ ID NO 110
<211> LENGTH: 21
<212> TYPE: DNA
<213> ORGANISM: Artificial Sequence
<220> FEATURE:
<223> OTHER INFORMATION: Primer

<400> SEQUENCE: 110
tgcggccgct ctcttgattt c                                          21

<210> SEQ ID NO 111
<211> LENGTH: 66
<212> TYPE: DNA
<213> ORGANISM: Artificial Sequence
<220> FEATURE:
<223> OTHER INFORMATION: Primer

<400> SEQUENCE: 111
atatatctcg aggccagcga ctacaaagac gatgacgata aaggagccga ggtgcagctg   60
gtcgag                                                             66

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
atatatctcg aggccagcga c                                          21

<210> SEQ ID NO 113
<211> LENGTH: 31
<212> TYPE: DNA
<213> ORGANISM: Artificial Sequence
<220> FEATURE:
<223> OTHER INFORMATION: Primer

<400> SEQUENCE: 113
atatgaattc tgcggccgct ctcttgattt c                               31

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
cccacagcct cgaggccag                                                19

<210> SEQ ID NO 115
<211> LENGTH: 19
<212> TYPE: DNA
<213> ORGANISM: Artificial Sequence
<220> FEATURE:
<223> OTHER INFORMATION: Primer

<400> SEQUENCE: 115
gagccgccac cgccactag                                                19

<210> SEQ ID NO 116
<211> LENGTH: 41
<212> TYPE: DNA
<213> ORGANISM: Artificial Sequence
<220> FEATURE:
<223> OTHER INFORMATION: Primer

<400> SEQUENCE: 116
ctagtggcgg tggcggctct gatattcagc tgacccagtc c                       41

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
tgaattctgc ggccgctctc                                               20

<210> SEQ ID NO 118
<211> LENGTH: 19
<212> TYPE: DNA
<213> ORGANISM: Artificial Sequence
<220> FEATURE:
<223> OTHER INFORMATION: Primer

<400> SEQUENCE: 118
cccacagcct cgaggccag                                                19

<210> SEQ ID NO 119
<211> LENGTH: 37
<212> TYPE: DNA
<213> ORGANISM: Artificial Sequence
<220> FEATURE:
<223> OTHER INFORMATION: Primer

<400> SEQUENCE: 119
cccgttgctg gtgccgttgc ctgcggccgc tctcttg                            37

<210> SEQ ID NO 120
<211> LENGTH: 35
<212> TYPE: DNA
<213> ORGANISM: Artificial Sequence
<220> FEATURE:
<223> OTHER INFORMATION: Primer

<400> SEQUENCE: 120
atatgaattc ggatgtcccg ttgctggtgc cgttg                              35

<210> SEQ ID NO 121
<211> LENGTH: 43
<212> TYPE: DNA
<213> ORGANISM: Artificial Sequence

```
<220> FEATURE:
<223> OTHER INFORMATION: Primer

<400> SEQUENCE: 121
gcacatccaa tgggaccagc ggaacctccg aagagactat ctc          43

<210> SEQ ID NO 122
<211> LENGTH: 36
<212> TYPE: DNA
<213> ORGANISM: Artificial Sequence
<220> FEATURE:
<223> OTHER INFORMATION: Primer

<400> SEQUENCE: 122
cccgttgctg gttccattac cagatccgcc ccctcc                  36

<210> SEQ ID NO 123
<211> LENGTH: 38
<212> TYPE: DNA
<213> ORGANISM: Artificial Sequence
<220> FEATURE:
<223> OTHER INFORMATION: Primer

<400> SEQUENCE: 123
atatatggat ccggcaacgg cacatccaat gggaccag                38

<210> SEQ ID NO 124
<211> LENGTH: 35
<212> TYPE: DNA
<213> ORGANISM: Artificial Sequence
<220> FEATURE:
<223> OTHER INFORMATION: Primer

<400> SEQUENCE: 124
atatatggat ccggtcccgt tgctggttcc attac                   35

<210> SEQ ID NO 125
<211> LENGTH: 918
<212> TYPE: PRT
<213> ORGANISM: Artificial Sequence
<220> FEATURE:
<223> OTHER INFORMATION: VH-VL(EGFR)-ABD-Glyco-scTrail

<400> SEQUENCE: 125
```

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

```
Gly Thr Thr Val Thr Val Ser Ser Gly Gly Gly Ser Asp Ile Gln
145                 150                 155                 160

Leu Thr Gln Ser Pro Ser Phe Leu Ser Ala Ser Val Gly Asp Arg Val
            165                 170                 175

Thr Ile Thr Cys Arg Ala Ser Gln Ser Ile Gly Thr Asn Ile His Trp
        180                 185                 190

Tyr Gln Gln Lys Pro Gly Lys Ala Pro Lys Leu Leu Ile Lys Tyr Ala
    195                 200                 205

Ser Glu Ser Ile Ser Gly Val Pro Ser Arg Phe Ser Gly Ser Gly Ser
210                 215                 220

Gly Thr Glu Phe Thr Leu Thr Ile Ser Ser Leu Gln Pro Glu Asp Phe
225                 230                 235                 240

Ala Thr Tyr Tyr Cys Gln Gln Asn Asn Asn Trp Pro Thr Thr Phe Gly
            245                 250                 255

Ala Gly Thr Lys Leu Glu Ile Lys Arg Gly Gly Ser Gln His Asp Glu
        260                 265                 270

Ala Val Asp Ala Asn Ser Leu Ala Glu Ala Lys Val Leu Ala Asn Arg
    275                 280                 285

Glu Leu Asp Lys Tyr Gly Val Ser Asp Tyr Tyr Lys Asn Leu Ile Asn
290                 295                 300

Asn Ala Lys Thr Val Glu Gly Val Lys Ala Leu Ile Asp Glu Ile Leu
305                 310                 315                 320

Ala Ala Leu Pro Ala Ala Gly Asn Gly Thr Ser Asn Gly Thr Ser
            325                 330                 335

Glu Phe Thr Arg Gly Thr Ser Glu Glu Thr Ile Ser Thr Val Gln Glu
        340                 345                 350

Lys Gln Gln Asn Ile Ser Pro Leu Val Arg Glu Arg Gly Pro Gln Arg
    355                 360                 365

Val Ala Ala His Ile Thr Gly Thr Arg Gly Arg Ser Asn Thr Leu Ser
370                 375                 380

Ser Pro Asn Ser Lys Asn Glu Lys Ala Leu Gly Arg Lys Ile Asn Ser
385                 390                 395                 400

Trp Glu Ser Ser Arg Ser Gly His Ser Phe Leu Ser Asn Leu His Leu
            405                 410                 415

Arg Asn Gly Glu Leu Val Ile His Glu Lys Gly Phe Tyr Tyr Ile Tyr
        420                 425                 430

Ser Gln Thr Tyr Phe Arg Phe Gln Glu Glu Ile Lys Glu Asn Thr Lys
    435                 440                 445

Asn Asp Lys Gln Met Val Gln Tyr Ile Tyr Lys Tyr Thr Ser Tyr Pro
450                 455                 460

Asp Pro Ile Leu Leu Met Lys Ser Ala Arg Asn Ser Cys Trp Ser Lys
465                 470                 475                 480

Asp Ala Glu Tyr Gly Leu Tyr Ser Ile Tyr Gln Gly Gly Ile Phe Glu
            485                 490                 495

Leu Lys Glu Asn Asp Arg Ile Phe Val Ser Val Thr Asn Glu His Leu
        500                 505                 510

Ile Asp Met Asp His Glu Ala Ser Phe Phe Gly Ala Phe Leu Val Gly
    515                 520                 525

Gly Gly Gly Ser Gly Gly Ser Thr Ser Glu Glu Thr Ile Ser Thr
530                 535                 540

Val Gln Glu Lys Gln Gln Asn Ile Ser Pro Leu Val Arg Glu Arg Gly
545                 550                 555                 560
```

```
Pro Gln Arg Val Ala His Ile Thr Gly Thr Gly Arg Ser Asn
            565                 570                 575

Thr Leu Ser Ser Pro Asn Ser Lys Asn Glu Lys Ala Leu Gly Arg Lys
        580                 585                 590

Ile Asn Ser Trp Glu Ser Ser Arg Ser Gly His Ser Phe Leu Ser Asn
        595                 600                 605

Leu His Leu Arg Asn Gly Glu Leu Val Ile His Glu Lys Gly Phe Tyr
    610                 615                 620

Tyr Ile Tyr Ser Gln Thr Tyr Phe Arg Phe Gln Glu Glu Ile Lys Glu
625                 630                 635                 640

Asn Thr Lys Asn Asp Lys Gln Met Val Gln Tyr Ile Tyr Lys Tyr Thr
                645                 650                 655

Ser Tyr Pro Asp Pro Ile Leu Leu Met Lys Ser Ala Arg Asn Ser Cys
            660                 665                 670

Trp Ser Lys Asp Ala Glu Tyr Gly Leu Tyr Ser Ile Tyr Gln Gly Gly
        675                 680                 685

Ile Phe Glu Leu Lys Glu Asn Asp Arg Ile Phe Val Ser Val Thr Asn
    690                 695                 700

Glu His Leu Ile Asp Met Asp His Glu Ala Ser Phe Phe Gly Ala Phe
705                 710                 715                 720

Leu Val Gly Gly Gly Ser Gly Gly Gly Ser Thr Ser Glu Thr
                725                 730                 735

Ile Ser Thr Val Gln Glu Lys Gln Gln Asn Ile Ser Pro Leu Val Arg
            740                 745                 750

Glu Arg Gly Pro Gln Arg Val Ala Ala His Ile Thr Gly Thr Arg Gly
        755                 760                 765

Arg Ser Asn Thr Leu Ser Ser Pro Asn Ser Lys Asn Glu Lys Ala Leu
    770                 775                 780

Gly Arg Lys Ile Asn Ser Trp Glu Ser Ser Arg Ser Gly His Ser Phe
785                 790                 795                 800

Leu Ser Asn Leu His Leu Arg Asn Gly Glu Leu Val Ile His Glu Lys
                805                 810                 815

Gly Phe Tyr Tyr Ile Tyr Ser Gln Thr Tyr Phe Arg Phe Gln Glu Glu
            820                 825                 830

Ile Lys Glu Asn Thr Lys Asn Asp Lys Gln Met Val Gln Tyr Ile Tyr
        835                 840                 845

Lys Tyr Thr Ser Tyr Pro Asp Pro Ile Leu Leu Met Lys Ser Ala Arg
    850                 855                 860

Asn Ser Cys Trp Ser Lys Asp Ala Glu Tyr Gly Leu Tyr Ser Ile Tyr
865                 870                 875                 880

Gln Gly Gly Ile Phe Glu Leu Lys Glu Asn Asp Arg Ile Phe Val Ser
                885                 890                 895

Val Thr Asn Glu His Leu Ile Asp Met Asp His Glu Ala Ser Phe Phe
            900                 905                 910

Gly Ala Phe Leu Val Gly
            915

<210> SEQ ID NO 126
<211> LENGTH: 920
<212> TYPE: PRT
<213> ORGANISM: Artificial Sequence
<220> FEATURE:
<223> OTHER INFORMATION: VH-VL(EGFR)-Glyco-scTrail-ABD

<400> SEQUENCE: 126
```

-continued

```
Met Asp Trp Thr Trp Arg Val Phe Cys Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Leu Val Gln Pro Gly
            35                  40                  45

Gly Ser Leu Arg Leu Ser Cys Ala Ala Ser Gly Phe Ser Leu Thr Asn
            50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
            115                 120                 125

Ala Arg Ala Leu Thr Tyr Tyr Asp Tyr Glu Phe Ala Tyr Trp Gly Gln
            130                 135                 140

Gly Thr Thr Val Thr Val Ser Ser Gly Gly Gly Gly Ser Asp Ile Gln
145                 150                 155                 160

Leu Thr Gln Ser Pro Ser Phe Leu Ser Ala Ser Val Gly Asp Arg Val
                165                 170                 175

Thr Ile Thr Cys Arg Ala Ser Gln Ser Ile Gly Thr Asn Ile His Trp
            180                 185                 190

Tyr Gln Gln Lys Pro Gly Lys Ala Pro Lys Leu Leu Ile Lys Tyr Ala
            195                 200                 205

Ser Glu Ser Ile Ser Gly Val Pro Ser Arg Phe Ser Gly Ser Gly Ser
            210                 215                 220

Gly Thr Glu Phe Thr Leu Thr Ile Ser Ser Leu Gln Pro Glu Asp Phe
225                 230                 235                 240

Ala Thr Tyr Tyr Cys Gln Gln Asn Asn Asn Trp Pro Thr Thr Phe Gly
                245                 250                 255

Ala Gly Thr Lys Leu Glu Ile Lys Arg Ala Ala Ala Gly Asn Gly Thr
            260                 265                 270

Ser Asn Gly Thr Ser Glu Phe Thr Arg Gly Thr Ser Glu Glu Thr Ile
            275                 280                 285

Ser Thr Val Gln Glu Lys Gln Gln Asn Ile Ser Pro Leu Val Arg Glu
            290                 295                 300

Arg Gly Pro Gln Arg Val Ala Ala His Ile Thr Gly Thr Arg Gly Arg
305                 310                 315                 320

Ser Asn Thr Leu Ser Ser Pro Asn Ser Lys Asn Glu Lys Ala Leu Gly
            325                 330                 335

Arg Lys Ile Asn Ser Trp Glu Ser Ser Arg Ser Gly His Ser Phe Leu
            340                 345                 350

Ser Asn Leu His Leu Arg Asn Gly Glu Leu Val Ile His Glu Lys Gly
            355                 360                 365

Phe Tyr Tyr Ile Tyr Ser Gln Thr Tyr Phe Arg Phe Gln Glu Glu Ile
            370                 375                 380

Lys Glu Asn Thr Lys Asn Asp Lys Gln Met Val Gln Tyr Ile Tyr Lys
385                 390                 395                 400

Tyr Thr Ser Tyr Pro Asp Pro Ile Leu Leu Met Lys Ser Ala Arg Asn
            405                 410                 415

Ser Cys Trp Ser Lys Asp Ala Glu Tyr Gly Leu Tyr Ser Ile Tyr Gln
```

```
              420                 425                 430
Gly Gly Ile Phe Glu Leu Lys Glu Asn Asp Arg Ile Phe Val Ser Val
            435                 440                 445

Thr Asn Glu His Leu Ile Asp Met Asp His Glu Ala Ser Phe Phe Gly
    450                 455                 460

Ala Phe Leu Val Gly Gly Gly Ser Gly Gly Ser Thr Ser Glu
465                 470                 475                 480

Glu Thr Ile Ser Thr Val Gln Glu Lys Gln Gln Asn Ile Ser Pro Leu
                485                 490                 495

Val Arg Glu Arg Gly Pro Gln Arg Val Ala His Ile Thr Gly Thr
                500                 505                 510

Arg Gly Arg Ser Asn Thr Leu Ser Ser Pro Asn Ser Lys Asn Glu Lys
            515                 520                 525

Ala Leu Gly Arg Lys Ile Asn Ser Trp Glu Ser Ser Arg Ser Gly His
        530                 535                 540

Ser Phe Leu Ser Asn Leu His Leu Arg Asn Gly Glu Leu Val Ile His
545                 550                 555                 560

Glu Lys Gly Phe Tyr Tyr Ile Tyr Ser Gln Thr Tyr Phe Arg Phe Gln
                565                 570                 575

Glu Glu Ile Lys Glu Asn Thr Lys Asn Asp Lys Gln Met Val Gln Tyr
            580                 585                 590

Ile Tyr Lys Tyr Thr Ser Tyr Pro Asp Pro Ile Leu Leu Met Lys Ser
        595                 600                 605

Ala Arg Asn Ser Cys Trp Ser Lys Asp Ala Glu Tyr Gly Leu Tyr Ser
    610                 615                 620

Ile Tyr Gln Gly Gly Ile Phe Glu Leu Lys Glu Asn Asp Arg Ile Phe
625                 630                 635                 640

Val Ser Val Thr Asn Glu His Leu Ile Asp Met Asp His Glu Ala Ser
                645                 650                 655

Phe Phe Gly Ala Phe Leu Val Gly Gly Gly Ser Gly Gly Ser
            660                 665                 670

Thr Ser Glu Glu Thr Ile Ser Thr Val Gln Glu Lys Gln Gln Asn Ile
        675                 680                 685

Ser Pro Leu Val Arg Glu Arg Gly Pro Gln Arg Val Ala His Ile
    690                 695                 700

Thr Gly Thr Arg Gly Arg Ser Asn Thr Leu Ser Ser Pro Asn Ser Lys
705                 710                 715                 720

Asn Glu Lys Ala Leu Gly Arg Lys Ile Asn Ser Trp Glu Ser Ser Arg
                725                 730                 735

Ser Gly His Ser Phe Leu Ser Asn Leu His Leu Arg Asn Gly Glu Leu
            740                 745                 750

Val Ile His Glu Lys Gly Phe Tyr Tyr Ile Tyr Ser Gln Thr Tyr Phe
        755                 760                 765

Arg Phe Gln Glu Glu Ile Lys Glu Asn Thr Lys Asn Asp Lys Gln Met
    770                 775                 780

Val Gln Tyr Ile Tyr Lys Tyr Thr Ser Tyr Pro Asp Pro Ile Leu Leu
785                 790                 795                 800

Met Lys Ser Ala Arg Asn Ser Cys Trp Ser Lys Asp Ala Glu Tyr Gly
                805                 810                 815

Leu Tyr Ser Ile Tyr Gln Gly Gly Ile Phe Glu Leu Lys Glu Asn Asp
            820                 825                 830

Arg Ile Phe Val Ser Val Thr Asn Glu His Leu Ile Asp Met Asp His
        835                 840                 845
```

-continued

Glu Ala Ser Phe Phe Gly Ala Phe Leu Val Gly Gly Ser Gly Gly
    850                 855                 860

Gln His Asp Glu Ala Val Asp Ala Asn Ser Leu Ala Glu Ala Lys Val
865                 870                 875                 880

Leu Ala Asn Arg Glu Leu Asp Lys Tyr Gly Val Ser Asp Tyr Tyr Lys
                885                 890                 895

Asn Leu Ile Asn Asn Ala Lys Thr Val Glu Gly Val Lys Ala Leu Ile
            900                 905                 910

Asp Glu Ile Leu Ala Ala Leu Pro
            915                 920

<210> SEQ ID NO 127
<211> LENGTH: 855
<212> TYPE: PRT
<213> ORGANISM: Artificial Sequence
<220> FEATURE:
<223> OTHER INFORMATION: [VH-VL(FAP)hu36]-scTrail

<400> SEQUENCE: 127

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Gln Val Gln Leu Val Glu Ser Gly Gly Gly Leu Val Lys Pro Gly
        35                  40                  45

Gly Ser Leu Arg Leu Ser Cys Lys Thr Ser Gly Tyr Thr Phe Thr Glu
    50                  55                  60

Asn Ile Ile His Trp Ile Arg Gln Ala Pro Gly Lys Gly Leu Glu Trp
65                  70                  75                  80

Ile Gly Trp Phe His Pro Gly Ser Gly Ser Ile Lys Tyr Asn Glu Lys
                85                  90                  95

Phe Lys Asp Arg Phe Thr Ile Ser Ala Asp Asn Ala Lys Asn Ser Leu
            100                 105                 110

Tyr Leu Gln Met Asn Ser Leu Arg Ala Glu Asp Thr Ala Val Tyr Tyr
        115                 120                 125

Cys Ala Arg His Gly Gly Thr Gly Arg Gly Ala Met Asp Tyr Trp Gly
    130                 135                 140

Gln Gly Thr Leu Val Thr Val Ser Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Lys Ser Val Ser Thr Ser Ala Tyr
            180                 185                 190

Ser Tyr Met His Trp Tyr Gln Gln Lys Pro Gly Gln Ala Pro Arg Leu
        195                 200                 205

Leu Ile Tyr Leu Ala Ser Asn Leu Glu Ser Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln His Ser Arg Glu Leu
                245                 250                 255

Pro Tyr Thr Phe Gly Gln Gly Thr Lys Leu Glu Ile Lys Arg Ala Ala
            260                 265                 270

Ala Glu Phe Thr Arg Gly Thr Ser Glu Glu Thr Ile Ser Thr Val Gln
        275                 280                 285

```
Glu Lys Gln Gln Asn Ile Ser Pro Leu Val Arg Glu Arg Gly Pro Gln
    290                 295                 300
Arg Val Ala Ala His Ile Thr Gly Thr Arg Gly Arg Ser Asn Thr Leu
305                 310                 315                 320
Ser Ser Pro Asn Ser Lys Asn Glu Lys Ala Leu Gly Arg Lys Ile Asn
                325                 330                 335
Ser Trp Glu Ser Ser Arg Ser Gly His Ser Phe Leu Ser Asn Leu His
            340                 345                 350
Leu Arg Asn Gly Glu Leu Val Ile His Glu Lys Gly Phe Tyr Tyr Ile
                355                 360                 365
Tyr Ser Gln Thr Tyr Phe Arg Phe Gln Glu Glu Ile Lys Glu Asn Thr
370                 375                 380
Lys Asn Asp Lys Gln Met Val Gln Tyr Ile Tyr Lys Tyr Thr Ser Tyr
385                 390                 395                 400
Pro Asp Pro Ile Leu Leu Met Lys Ser Ala Arg Asn Ser Cys Trp Ser
                405                 410                 415
Lys Asp Ala Glu Tyr Gly Leu Tyr Ser Ile Tyr Gln Gly Gly Ile Phe
                420                 425                 430
Glu Leu Lys Glu Asn Asp Arg Ile Phe Val Ser Val Thr Asn Glu His
                435                 440                 445
Leu Ile Asp Met Asp His Glu Ala Ser Phe Phe Gly Ala Phe Leu Val
450                 455                 460
Gly Gly Gly Gly Ser Gly Gly Ser Thr Ser Glu Thr Ile Ser
465                 470                 475                 480
Thr Val Gln Glu Lys Gln Gln Asn Ile Ser Pro Leu Val Arg Glu Arg
                485                 490                 495
Gly Pro Gln Arg Val Ala Ala His Ile Thr Gly Thr Arg Gly Arg Ser
            500                 505                 510
Asn Thr Leu Ser Ser Pro Asn Ser Lys Asn Glu Lys Ala Leu Gly Arg
                515                 520                 525
Lys Ile Asn Ser Trp Glu Ser Ser Arg Ser Gly His Ser Phe Leu Ser
            530                 535                 540
Asn Leu His Leu Arg Asn Gly Glu Leu Val Ile His Glu Lys Gly Phe
545                 550                 555                 560
Tyr Tyr Ile Tyr Ser Gln Thr Tyr Phe Arg Phe Gln Glu Glu Ile Lys
                565                 570                 575
Glu Asn Thr Lys Asn Asp Lys Gln Met Val Gln Tyr Ile Tyr Lys Tyr
                580                 585                 590
Thr Ser Tyr Pro Asp Pro Ile Leu Leu Met Lys Ser Ala Arg Asn Ser
            595                 600                 605
Cys Trp Ser Lys Asp Ala Glu Tyr Gly Leu Tyr Ser Ile Tyr Gln Gly
610                 615                 620
Gly Ile Phe Glu Leu Lys Glu Asn Asp Arg Ile Phe Val Ser Val Thr
625                 630                 635                 640
Asn Glu His Leu Ile Asp Met Asp His Glu Ala Ser Phe Phe Gly Ala
                645                 650                 655
Phe Leu Val Gly Gly Gly Gly Ser Gly Gly Gly Ser Thr Ser Glu Glu
            660                 665                 670
Thr Ile Ser Thr Val Gln Glu Lys Gln Gln Asn Ile Ser Pro Leu Val
            675                 680                 685
Arg Glu Arg Gly Pro Gln Arg Val Ala Ala His Ile Thr Gly Thr Arg
690                 695                 700
```

Gly Arg Ser Asn Thr Leu Ser Ser Pro Asn Ser Lys Asn Glu Lys Ala
705                 710                 715                 720

Leu Gly Arg Lys Ile Asn Ser Trp Glu Ser Ser Arg Ser Gly His Ser
            725                 730                 735

Phe Leu Ser Asn Leu His Leu Arg Asn Gly Glu Leu Val Ile His Glu
            740                 745                 750

Lys Gly Phe Tyr Tyr Ile Tyr Ser Gln Thr Tyr Phe Arg Phe Gln Glu
            755                 760                 765

Glu Ile Lys Glu Asn Thr Lys Asn Asp Lys Gln Met Val Gln Tyr Ile
            770                 775                 780

Tyr Lys Tyr Thr Ser Tyr Pro Asp Pro Ile Leu Leu Met Lys Ser Ala
785                 790                 795                 800

Arg Asn Ser Cys Trp Ser Lys Asp Ala Glu Tyr Gly Leu Tyr Ser Ile
            805                 810                 815

Tyr Gln Gly Gly Ile Phe Glu Leu Lys Glu Asn Asp Arg Ile Phe Val
            820                 825                 830

Ser Val Thr Asn Glu His Leu Ile Asp Met Asp His Glu Ala Ser Phe
            835                 840                 845

Phe Gly Ala Phe Leu Val Gly
    850                 855

<210> SEQ ID NO 128
<211> LENGTH: 850
<212> TYPE: PRT
<213> ORGANISM: Artificial Sequence
<220> FEATURE:
<223> OTHER INFORMATION: [VH-VL(FAP)C13]-scTrail

<400> SEQUENCE: 128

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
            20                  25                  30

Ala Glu Val Gln Leu Val Glu Ser Gly Gly Thr Leu Val Gln Pro Gly
            35                  40                  45

Gly Ser Leu Arg Leu Ser Cys Ala Ala Ser Gly Phe Thr Phe Ser Ser
    50                  55                  60

Tyr Ala Met Ser Trp Ile Arg Gln Ala Pro Gly Lys Gly Leu Glu Trp
65                  70                  75                  80

Val Ser Gly Ile Ser Ala Ser Gly Gly Tyr Ile Asp Tyr Ala Asp Ser
            85                  90                  95

Val Lys Gly Arg Val Thr Ile Ser Arg Asp Asn Ser Lys Asn Met Ala
            100                 105                 110

Tyr Leu Gln Met Ser Ser Leu Arg Ala Glu Asp Thr Ala Leu Tyr Tyr
            115                 120                 125

Cys Ala Lys Gly Gly Asn Tyr Gln Met Leu Leu Asp His Trp Gly Gln
    130                 135                 140

Gly Thr Leu Val Thr Val Ser Ser Gly Gly Gly Gly Ser Asp Ile Gln
145                 150                 155                 160

Met Thr Gln Ser Pro Ser Ser Leu Ser Ala Ser Thr Gly Asp Arg Val
            165                 170                 175

Thr Ile Thr Cys Arg Ala Ser Gln Asp Ile Ser Ser Tyr Leu Ala Trp
            180                 185                 190

Tyr Gln Gln Ala Pro Gly Lys Ala Pro His Leu Leu Met Ser Gly Ala
            195                 200                 205

```
Thr Thr Leu Gln Thr Gly Val Pro Ser Arg Phe Ser Gly Ser Gly Ser
    210                 215                 220
Gly Thr Asp Phe Thr Leu Thr Ile Thr Ser Leu Gln Ser Glu Asp Phe
225                 230                 235                 240
Ala Thr Tyr Tyr Cys Gln Gln Tyr Tyr Ile Tyr Pro Pro Thr Phe Gly
                245                 250                 255
Gln Gly Thr Arg Val Glu Ile Lys Arg Ala Ala Ala Glu Phe Thr Arg
                260                 265                 270
Gly Thr Ser Glu Glu Thr Ile Ser Thr Val Gln Glu Lys Gln Gln Asn
                275                 280                 285
Ile Ser Pro Leu Val Arg Glu Arg Gly Pro Gln Arg Val Ala Ala His
    290                 295                 300
Ile Thr Gly Thr Arg Gly Arg Ser Asn Thr Leu Ser Ser Pro Asn Ser
305                 310                 315                 320
Lys Asn Glu Lys Ala Leu Gly Arg Lys Ile Asn Ser Trp Glu Ser Ser
                325                 330                 335
Arg Ser Gly His Ser Phe Leu Ser Asn Leu His Leu Arg Asn Gly Glu
                340                 345                 350
Leu Val Ile His Glu Lys Gly Phe Tyr Tyr Ile Tyr Ser Gln Thr Tyr
                355                 360                 365
Phe Arg Phe Gln Glu Glu Ile Lys Glu Asn Thr Lys Asn Asp Lys Gln
    370                 375                 380
Met Val Gln Tyr Ile Tyr Lys Tyr Thr Ser Tyr Pro Asp Pro Ile Leu
385                 390                 395                 400
Leu Met Lys Ser Ala Arg Asn Ser Cys Trp Ser Lys Asp Ala Glu Tyr
                405                 410                 415
Gly Leu Tyr Ser Ile Tyr Gln Gly Gly Ile Phe Glu Leu Lys Glu Asn
                420                 425                 430
Asp Arg Ile Phe Val Ser Val Thr Asn Glu His Leu Ile Asp Met Asp
    435                 440                 445
His Glu Ala Ser Phe Phe Gly Ala Phe Leu Val Gly Gly Gly Gly Ser
    450                 455                 460
Gly Gly Gly Ser Thr Ser Glu Glu Thr Ile Ser Thr Val Gln Glu Lys
465                 470                 475                 480
Gln Gln Asn Ile Ser Pro Leu Val Arg Glu Arg Gly Pro Gln Arg Val
                485                 490                 495
Ala Ala His Ile Thr Gly Thr Arg Gly Arg Ser Asn Thr Leu Ser Ser
                500                 505                 510
Pro Asn Ser Lys Asn Glu Lys Ala Leu Gly Arg Lys Ile Asn Ser Trp
    515                 520                 525
Glu Ser Ser Arg Ser Gly His Ser Phe Leu Ser Asn Leu His Leu Arg
    530                 535                 540
Asn Gly Glu Leu Val Ile His Glu Lys Gly Phe Tyr Tyr Ile Tyr Ser
545                 550                 555                 560
Gln Thr Tyr Phe Arg Phe Gln Glu Glu Ile Lys Glu Asn Thr Lys Asn
                565                 570                 575
Asp Lys Gln Met Val Gln Tyr Ile Tyr Lys Tyr Thr Ser Tyr Pro Asp
                580                 585                 590
Pro Ile Leu Leu Met Lys Ser Ala Arg Asn Ser Cys Trp Ser Lys Asp
    595                 600                 605
Ala Glu Tyr Gly Leu Tyr Ser Ile Tyr Gln Gly Gly Ile Phe Glu Leu
    610                 615                 620
Lys Glu Asn Asp Arg Ile Phe Val Ser Val Thr Asn Glu His Leu Ile
```

```
            625                 630                 635                 640
Asp Met Asp His Glu Ala Ser Phe Phe Gly Ala Phe Leu Val Gly Gly
                    645                 650                 655

Gly Gly Ser Gly Gly Gly Ser Thr Ser Glu Glu Thr Ile Ser Thr Val
            660                 665                 670

Gln Glu Lys Gln Gln Asn Ile Ser Pro Leu Val Arg Glu Arg Gly Pro
            675                 680                 685

Gln Arg Val Ala Ala His Ile Thr Gly Thr Arg Gly Arg Ser Asn Thr
            690                 695                 700

Leu Ser Ser Pro Asn Ser Lys Asn Glu Lys Ala Leu Gly Arg Lys Ile
705                 710                 715                 720

Asn Ser Trp Glu Ser Ser Arg Ser Gly His Ser Phe Leu Ser Asn Leu
                    725                 730                 735

His Leu Arg Asn Gly Glu Leu Val Ile His Glu Lys Gly Phe Tyr Tyr
                    740                 745                 750

Ile Tyr Ser Gln Thr Tyr Phe Arg Phe Gln Glu Glu Ile Lys Glu Asn
            755                 760                 765

Thr Lys Asn Asp Lys Gln Met Val Gln Tyr Ile Tyr Lys Tyr Thr Ser
770                 775                 780

Tyr Pro Asp Pro Ile Leu Leu Met Lys Ser Ala Arg Asn Ser Cys Trp
785                 790                 795                 800

Ser Lys Asp Ala Glu Tyr Gly Leu Tyr Ser Ile Tyr Gln Gly Gly Ile
                    805                 810                 815

Phe Glu Leu Lys Glu Asn Asp Arg Ile Phe Val Ser Val Thr Asn Glu
            820                 825                 830

His Leu Ile Asp Met Asp His Glu Ala Ser Phe Phe Gly Ala Phe Leu
            835                 840                 845

Val Gly
    850

<210> SEQ ID NO 129
<211> LENGTH: 857
<212> TYPE: PRT
<213> ORGANISM: Artificial Sequence
<220> FEATURE:
<223> OTHER INFORMATION: [VH-VL(FAP)C50]-scTrail

<400> SEQUENCE: 129

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
            35                  40                  45

Gly Ser Leu Arg Leu Ser Cys Ala Ala Ser Gly Phe Thr Phe Ser Asn
    50                  55                  60

Tyr Trp Met Ser Trp Val Arg Gln Ala Pro Gly Lys Gly Leu Glu Trp
65              70                  75                  80

Val Ala Asn Ile Lys Gln Asp Gly Ser Glu Lys Tyr Tyr Val Asp Ser
                85                  90                  95

Val Lys Gly Arg Phe Thr Ile Ser Arg Asp Asn Ala Lys Asn Ser Leu
            100                 105                 110

Tyr Leu Gln Met Asn Ser Leu Arg Ala Glu Asp Thr Ala Val Tyr Tyr
            115                 120                 125

Cys Ala Arg Gly Ser Leu Cys Thr Asp Gly Ser Cys Pro Thr Ile Gly
```

```
            130                 135                 140
Pro Gly Pro Asn Trp Gly Gln Gly Thr Leu Val Thr Val Ser Ser Gly
145                 150                 155                 160

Gly Gly Gly Ser Asp Ile Gln Met Thr Gln Ser Pro Ser Ser Leu Ser
                165                 170                 175

Ala Ser Thr Gly Asp Arg Val Thr Ile Thr Cys Arg Ala Ser Gln Asp
                180                 185                 190

Ile Ser Ser Tyr Leu Ala Trp Tyr Gln Gln Ala Pro Gly Lys Ala Pro
                195                 200                 205

His Leu Leu Met Ser Gly Ala Thr Thr Leu Gln Thr Gly Val Pro Ser
                210                 215                 220

Arg Phe Ser Gly Ser Gly Ser Gly Thr Asp Phe Thr Leu Thr Ile Thr
225                 230                 235                 240

Ser Leu Gln Ser Glu Asp Phe Ala Thr Tyr Tyr Cys Gln Gln Tyr Tyr
                245                 250                 255

Ile Tyr Pro Pro Thr Phe Gly Gln Gly Thr Arg Val Glu Ile Lys Arg
                260                 265                 270

Ala Ala Ala Glu Phe Thr Arg Gly Thr Ser Glu Glu Thr Ile Ser Thr
                275                 280                 285

Val Gln Glu Lys Gln Gln Asn Ile Ser Pro Leu Val Arg Glu Arg Gly
                290                 295                 300

Pro Gln Arg Val Ala Ala His Ile Thr Gly Thr Arg Gly Arg Ser Asn
305                 310                 315                 320

Thr Leu Ser Ser Pro Asn Ser Lys Asn Glu Lys Ala Leu Gly Arg Lys
                325                 330                 335

Ile Asn Ser Trp Glu Ser Ser Arg Ser Gly His Ser Phe Leu Ser Asn
                340                 345                 350

Leu His Leu Arg Asn Gly Glu Leu Val Ile His Glu Lys Gly Phe Tyr
                355                 360                 365

Tyr Ile Tyr Ser Gln Thr Tyr Phe Arg Phe Gln Glu Glu Ile Lys Glu
                370                 375                 380

Asn Thr Lys Asn Asp Lys Gln Met Val Gln Tyr Ile Tyr Lys Tyr Thr
385                 390                 395                 400

Ser Tyr Pro Asp Pro Ile Leu Leu Met Lys Ser Ala Arg Asn Ser Cys
                405                 410                 415

Trp Ser Lys Asp Ala Glu Tyr Gly Leu Tyr Ser Ile Tyr Gln Gly Gly
                420                 425                 430

Ile Phe Glu Leu Lys Glu Asn Asp Arg Ile Phe Val Ser Val Thr Asn
                435                 440                 445

Glu His Leu Ile Asp Met Asp His Glu Ala Ser Phe Phe Gly Ala Phe
                450                 455                 460

Leu Val Gly Gly Gly Ser Gly Gly Gly Ser Thr Ser Glu Glu Thr
465                 470                 475                 480

Ile Ser Thr Val Gln Glu Lys Gln Gln Asn Ile Ser Pro Leu Val Arg
                485                 490                 495

Glu Arg Gly Pro Gln Arg Val Ala Ala His Ile Thr Gly Thr Arg Gly
                500                 505                 510

Arg Ser Asn Thr Leu Ser Ser Pro Asn Ser Lys Asn Glu Lys Ala Leu
                515                 520                 525

Gly Arg Lys Ile Asn Ser Trp Glu Ser Ser Arg Ser Gly His Ser Phe
                530                 535                 540

Leu Ser Asn Leu His Leu Arg Asn Gly Glu Leu Val Ile His Glu Lys
545                 550                 555                 560
```

-continued

```
Gly Phe Tyr Tyr Ile Tyr Ser Gln Thr Tyr Phe Arg Phe Gln Glu Glu
                565                 570                 575

Ile Lys Glu Asn Thr Lys Asn Asp Lys Gln Met Val Gln Tyr Ile Tyr
            580                 585                 590

Lys Tyr Thr Ser Tyr Pro Asp Pro Ile Leu Leu Met Lys Ser Ala Arg
        595                 600                 605

Asn Ser Cys Trp Ser Lys Asp Ala Glu Tyr Gly Leu Tyr Ser Ile Tyr
    610                 615                 620

Gln Gly Gly Ile Phe Glu Leu Lys Glu Asn Asp Arg Ile Phe Val Ser
625                 630                 635                 640

Val Thr Asn Glu His Leu Ile Asp Met Asp His Glu Ala Ser Phe Phe
                645                 650                 655

Gly Ala Phe Leu Val Gly Gly Gly Ser Gly Gly Gly Ser Thr Ser
            660                 665                 670

Glu Glu Thr Ile Ser Thr Val Gln Glu Lys Gln Gln Asn Ile Ser Pro
        675                 680                 685

Leu Val Arg Glu Arg Gly Pro Gln Arg Val Ala Ala His Ile Thr Gly
    690                 695                 700

Thr Arg Gly Arg Ser Asn Thr Leu Ser Ser Pro Asn Ser Lys Asn Glu
705                 710                 715                 720

Lys Ala Leu Gly Arg Lys Ile Asn Ser Trp Glu Ser Ser Arg Ser Gly
                725                 730                 735

His Ser Phe Leu Ser Asn Leu His Leu Arg Asn Gly Glu Leu Val Ile
            740                 745                 750

His Glu Lys Gly Phe Tyr Tyr Ile Tyr Ser Gln Thr Tyr Phe Arg Phe
        755                 760                 765

Gln Glu Glu Ile Lys Glu Asn Thr Lys Asn Asp Lys Gln Met Val Gln
    770                 775                 780

Tyr Ile Tyr Lys Tyr Thr Ser Tyr Pro Asp Pro Ile Leu Leu Met Lys
785                 790                 795                 800

Ser Ala Arg Asn Ser Cys Trp Ser Lys Asp Ala Glu Tyr Gly Leu Tyr
                805                 810                 815

Ser Ile Tyr Gln Gly Gly Ile Phe Glu Leu Lys Glu Asn Asp Arg Ile
            820                 825                 830

Phe Val Ser Val Thr Asn Glu His Leu Ile Asp Met Asp His Glu Ala
        835                 840                 845

Ser Phe Phe Gly Ala Phe Leu Val Gly
    850                 855

<210> SEQ ID NO 130
<211> LENGTH: 112
<212> TYPE: PRT
<213> ORGANISM: Artificial Sequence
<220> FEATURE:
<223> OTHER INFORMATION: VL(FAP)hu36

<400> SEQUENCE: 130

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Ala Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Ala
    50                  55                  60
```

```
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Tyr Thr Phe Gly Gln Gly Thr Lys Leu Glu Ile Lys Arg
            100                 105                 110
```

<210> SEQ ID NO 131
<211> LENGTH: 108
<212> TYPE: PRT
<213> ORGANISM: Artificial Sequence
<220> FEATURE:
<223> OTHER INFORMATION: VL(FAP)C13

<400> SEQUENCE: 131

```
Asp Ile Gln Met Thr Gln Ser Pro Ser Ser Leu Ser Ala Ser Thr Gly
 1               5                  10                  15

Asp Arg Val Thr Ile Thr Cys Arg Ala Ser Gln Asp Ile Ser Ser Tyr
                 20                  25                  30

Leu Ala Trp Tyr Gln Gln Ala Pro Gly Lys Ala Pro His Leu Leu Met
             35                  40                  45

Ser Gly Ala Thr Thr Leu Gln Thr Gly Val Pro Ser Arg Phe Ser Gly
     50                  55                  60

Ser Gly Ser Gly Thr Asp Phe Thr Leu Thr Ile Thr Ser Leu Gln Ser
 65                  70                  75                  80

Glu Asp Phe Ala Thr Tyr Tyr Cys Gln Gln Tyr Tyr Ile Tyr Pro Pro
                 85                  90                  95

Thr Phe Gly Gln Gly Thr Arg Val Glu Ile Lys Arg
            100                 105
```

<210> SEQ ID NO 132
<211> LENGTH: 108
<212> TYPE: PRT
<213> ORGANISM: Artificial Sequence
<220> FEATURE:
<223> OTHER INFORMATION: VL(FAP)C50

<400> SEQUENCE: 132

```
Asp Ile Gln Met Thr Gln Ser Pro Ser Ser Leu Ser Ala Ser Thr Gly
 1               5                  10                  15

Asp Arg Val Thr Ile Thr Cys Arg Ala Ser Gln Asp Ile Ser Ser Tyr
                 20                  25                  30

Leu Ala Trp Tyr Gln Gln Ala Pro Gly Lys Ala Pro His Leu Leu Met
             35                  40                  45

Ser Gly Ala Thr Thr Leu Gln Thr Gly Val Pro Ser Arg Phe Ser Gly
     50                  55                  60

Ser Gly Ser Gly Thr Asp Phe Thr Leu Thr Ile Thr Ser Leu Gln Ser
 65                  70                  75                  80

Glu Asp Phe Ala Thr Tyr Tyr Cys Gln Gln Tyr Tyr Ile Tyr Pro Pro
                 85                  90                  95

Thr Phe Gly Gln Gly Thr Arg Val Glu Ile Lys Arg
            100                 105
```

<210> SEQ ID NO 133
<211> LENGTH: 120
<212> TYPE: PRT
<213> ORGANISM: Artificial Sequence
<220> FEATURE:
<223> OTHER INFORMATION: VH(FAP)hu36

<400> SEQUENCE: 133

```
Gln Val Gln Leu Val Glu Ser Gly Gly Gly Leu Val Lys Pro Gly Gly
1               5                   10                  15

Ser Leu Arg Leu Ser Cys Lys Thr Ser Gly Tyr Thr Phe Thr Glu Asn
            20                  25                  30

Ile Ile His Trp Ile Arg Gln Ala Pro Gly Lys Gly Leu Glu Trp Ile
        35                  40                  45

Gly Trp Phe His Pro Gly Ser Gly Ser Ile Lys Tyr Asn Glu Lys Phe
    50                  55                  60

Lys Asp Arg Phe Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Gly Thr Gly Arg Gly Ala Met Asp Tyr Trp Gly Gln
            100                 105                 110

Gly Thr Leu Val Thr Val Ser Ser
        115                 120
```

<210> SEQ ID NO 134
<211> LENGTH: 119
<212> TYPE: PRT
<213> ORGANISM: Artificial Sequence
<220> FEATURE:
<223> OTHER INFORMATION: VH(FAP)C13

<400> SEQUENCE: 134

```
Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Gly Ile Ser Ala Ser Gly Gly Tyr Ile Asp Tyr Ala Asp Ser Val
    50                  55                  60

Lys Gly Arg Val Thr Ile Ser Arg Asp Asn Ser Lys Asn Met Ala Tyr
65                  70                  75                  80

Leu Gln Met Ser Ser Leu Arg Ala Glu Asp Thr Ala Leu Tyr Tyr Cys
                85                  90                  95

Ala Lys Gly Gly Asn Tyr Gln Met Leu Leu Asp His Trp Gly Gln Gly
            100                 105                 110

Thr Leu Val Thr Val Ser Ser
        115
```

<210> SEQ ID NO 135
<211> LENGTH: 126
<212> TYPE: PRT
<213> ORGANISM: Artificial Sequence
<220> FEATURE:
<223> OTHER INFORMATION: VH(FAP)C50

<400> SEQUENCE: 135

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45
```

```
Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Leu Cys Thr Asp Gly Ser Cys Pro Thr Ile Gly Pro
            100                 105                 110

Gly Pro Asn Trp Gly Gln Gly Thr Leu Val Thr Val Ser Ser
            115                 120                 125

<210> SEQ ID NO 136
<211> LENGTH: 237
<212> TYPE: PRT
<213> ORGANISM: Artificial Sequence
<220> FEATURE:
<223> OTHER INFORMATION: VH-VL(FAP)hu36

<400> SEQUENCE: 136

Gln Val Gln Leu Val Glu Ser Gly Gly Gly Leu Val Lys Pro Gly Gly
 1               5                  10                  15

Ser Leu Arg Leu Ser Cys Lys Thr Ser Gly Tyr Thr Phe Thr Glu Asn
                20                  25                  30

Ile Ile His Trp Ile Arg Gln Ala Pro Gly Lys Gly Leu Glu Trp Ile
             35                  40                  45

Gly Trp Phe His Pro Gly Ser Gly Ser Ile Lys Tyr Asn Glu Lys Phe
     50                  55                  60

Lys Asp Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Gly Thr Gly Arg Gly Ala Met Asp Tyr Trp Gly Gln
            100                 105                 110

Gly Thr Leu Val Thr Val Ser Ser Gly Gly Gly Gly Ser Glu Ile Val
            115                 120                 125

Leu Thr Gln Ser Pro Ala Thr Leu Ser Leu Ser Pro Gly Glu Arg Ala
            130                 135                 140

Thr Leu Ser Cys Arg Ala Ser Lys Ser Val Ser Thr Ser Ala Tyr Ser
145                 150                 155                 160

Tyr Met His Trp Tyr Gln Gln Lys Pro Gly Gln Ala Pro Arg Leu Leu
                165                 170                 175

Ile Tyr Leu Ala Ser Asn Leu Glu Ser Gly Ile Pro Ala Arg Phe Ser
            180                 185                 190

Gly Ser Gly Ser Gly Thr Asp Phe Thr Leu Thr Ile Ser Ser Leu Glu
            195                 200                 205

Pro Glu Asp Phe Ala Val Tyr Tyr Cys Gln His Ser Arg Glu Leu Pro
            210                 215                 220

Tyr Thr Phe Gly Gln Gly Thr Lys Leu Glu Ile Lys Arg
225                 230                 235

<210> SEQ ID NO 137
<211> LENGTH: 232
<212> TYPE: PRT
<213> ORGANISM: Artificial Sequence
<220> FEATURE:
<223> OTHER INFORMATION: VH-VL(FAP)C13
```

<400> SEQUENCE: 137

```
Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Gly Ile Ser Ala Ser Gly Gly Tyr Ile Asp Tyr Ala Asp Ser Val
    50                  55                  60

Lys Gly Arg Val Thr Ile Ser Arg Asp Asn Ser Lys Asn Met Ala Tyr
65                  70                  75                  80

Leu Gln Met Ser Ser Leu Arg Ala Glu Asp Thr Ala Leu Tyr Tyr Cys
                85                  90                  95

Ala Lys Gly Gly Asn Tyr Gln Met Leu Leu Asp His Trp Gly Gln Gly
            100                 105                 110

Thr Leu Val Thr Val Ser Ser Gly Gly Gly Ser Asp Ile Gln Met
        115                 120                 125

Thr Gln Ser Pro Ser Ser Leu Ser Ala Ser Thr Gly Asp Arg Val Thr
    130                 135                 140

Ile Thr Cys Arg Ala Ser Gln Asp Ile Ser Ser Tyr Leu Ala Trp Tyr
145                 150                 155                 160

Gln Gln Ala Pro Gly Lys Ala Pro His Leu Leu Met Ser Gly Ala Thr
                165                 170                 175

Thr Leu Gln Thr Gly Val Pro Ser Arg Phe Ser Gly Ser Gly Ser Gly
            180                 185                 190

Thr Asp Phe Thr Leu Thr Ile Thr Ser Leu Gln Ser Glu Asp Phe Ala
        195                 200                 205

Thr Tyr Tyr Cys Gln Gln Tyr Tyr Ile Tyr Pro Pro Thr Phe Gly Gln
    210                 215                 220

Gly Thr Arg Val Glu Ile Lys Arg
225                 230
```

<210> SEQ ID NO 138
<211> LENGTH: 239
<212> TYPE: PRT
<213> ORGANISM: Artificial Sequence
<220> FEATURE:
<223> OTHER INFORMATION: VH-VL(FAP)C50

<400> SEQUENCE: 138

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Cys Thr Asp Gly Ser Cys Pro Thr Ile Gly Pro
            100                 105                 110

Gly Pro Asn Trp Gly Gln Gly Thr Leu Val Thr Val Ser Ser Gly Gly
```

-continued

```
            115                 120                 125
Gly Gly Ser Asp Ile Gln Met Thr Gln Ser Pro Ser Ser Leu Ser Ala
        130                 135                 140

Ser Thr Gly Asp Arg Val Thr Ile Thr Cys Arg Ala Ser Gln Asp Ile
145                 150                 155                 160

Ser Ser Tyr Leu Ala Trp Tyr Gln Gln Ala Pro Gly Lys Ala Pro His
                165                 170                 175

Leu Leu Met Ser Gly Ala Thr Thr Leu Gln Thr Gly Val Pro Ser Arg
            180                 185                 190

Phe Ser Gly Ser Gly Ser Gly Thr Asp Phe Thr Leu Thr Ile Thr Ser
        195                 200                 205

Leu Gln Ser Glu Asp Phe Ala Thr Tyr Tyr Cys Gln Gln Tyr Tyr Ile
    210                 215                 220

Tyr Pro Pro Thr Phe Gly Gln Gly Thr Arg Val Glu Ile Lys Arg
225                 230                 235
```